(12) United States Patent
Bebbington et al.

(10) Patent No.: US 10,774,145 B2
(45) Date of Patent: *Sep. 15, 2020

(54) METHODS AND COMPOSITIONS FOR TREATING FIBROTIC DISEASES

(71) Applicant: Allakos Inc., San Carlos, CA (US)

(72) Inventors: Christopher Robert Bebbington, San Mateo, CA (US); Nenad Tomasevic, Foster City, CA (US); Rustom Falahati, Lafayette, CA (US); Bradford Andrew Youngblood, Burlingame, CA (US)

(73) Assignee: Allakos Inc., Redwood city, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/737,270

(22) PCT Filed: Jun. 16, 2016

(86) PCT No.: PCT/US2016/037935
§ 371 (c)(1),
(2) Date: Dec. 15, 2017

(87) PCT Pub. No.: WO2016/205567
PCT Pub. Date: Dec. 22, 2016

(65) Prior Publication Data
US 2018/0179279 A1    Jun. 28, 2018

Related U.S. Application Data

(60) Provisional application No. 62/181,146, filed on Jun. 17, 2015, provisional application No. 62/296,482, filed on Feb. 17, 2016, provisional application No. 62/344,357, filed on Jun. 1, 2016.

(51) Int. Cl.
| | | |
|---|---|---|
| *A61K 39/00* | (2006.01) | |
| *C07K 16/28* | (2006.01) | |
| *A61P 37/06* | (2006.01) | |
| *A61P 11/00* | (2006.01) | |

(52) U.S. Cl.
CPC .......... *C07K 16/2803* (2013.01); *A61P 11/00* (2018.01); *A61P 37/06* (2018.01); *A61K 2039/505* (2013.01); *A61K 2039/572* (2013.01); *C07K 2317/20* (2013.01); *C07K 2317/41* (2013.01); *C07K 2317/52* (2013.01); *C07K 2317/567* (2013.01); *C07K 2317/732* (2013.01); *C07K 2317/75* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| RE30,985 E | 6/1982 | Cartaya |
| 4,419,446 A | 12/1983 | Howley et al. |
| 4,560,655 A | 12/1985 | Baker |
| 4,601,978 A | 7/1986 | Karin |
| 4,657,866 A | 4/1987 | Kumar |
| 4,676,980 A | 6/1987 | Segal et al. |
| 4,767,704 A | 8/1988 | Cleveland et al. |
| 4,816,567 A | 3/1989 | Cabilly et al. |
| 4,927,762 A | 5/1990 | Darfler |
| 4,965,199 A | 10/1990 | Capon et al. |
| 5,122,464 A | 6/1992 | Wilson et al. |
| 5,122,469 A | 6/1992 | Mather et al. |
| 5,264,365 A | 11/1993 | Georgiou et al. |
| 5,500,362 A | 3/1996 | Robinson et al. |
| 5,508,192 A | 4/1996 | Georgiou et al. |
| 5,571,894 A | 11/1996 | Wels et al. |
| 5,587,458 A | 12/1996 | King et al. |
| 5,624,821 A | 4/1997 | Winter et al. |
| 5,639,635 A | 6/1997 | Joly et al. |
| 5,641,870 A | 6/1997 | Rinderknecht et al. |
| 5,648,237 A | 7/1997 | Carter et al. |
| 5,648,260 A | 7/1997 | Winter et al. |
| 5,677,425 A | 10/1997 | Bodmer et al. |

(Continued)

FOREIGN PATENT DOCUMENTS

| | | |
|---|---|---|
| EP | 2465873 A1 | 6/2012 |
| JP | 2003525615 A | 9/2003 |

(Continued)

OTHER PUBLICATIONS

Roger et al. (1994, Int. J. Exp. Path. 75:397-404).*

(Continued)

*Primary Examiner* — Elizabeth C. Kemmerer
(74) *Attorney, Agent, or Firm* — Morrison and Foerster LLP

(57) ABSTRACT

The invention provides methods and compositions for the prevention or treatment of fibrotic diseases such as idiopathic pulmonary fibrosis and pre-fibrotic diseases such as chronic hypersensitivity pneumonitis. In particular, the invention provides methods for the prevention or treatment of fibrotic diseases and pre-fibrotic diseases through administration of antibodies or agonists that bind to human Siglec-8 or compositions comprising said antibodies or agonists. The invention also provides articles of manufacture or kits comprising antibodies or agonists that bind to human Siglec-8 for the prevention or treatment fibrotic diseases such as idiopathic pulmonary fibrosis and pre-fibrotic diseases such as chronic hypersensitivity pneumonitis.

37 Claims, 12 Drawing Sheets

Specification includes a Sequence Listing.

(56) References Cited

U.S. PATENT DOCUMENTS

| | | | |
|---|---|---|---|
| 5,739,277 A | 4/1998 | Presta et al. | |
| 5,821,337 A | 10/1998 | Carter et al. | |
| 5,834,597 A | 11/1998 | Tso et al. | |
| 5,840,523 A | 11/1998 | Simmons et al. | |
| 5,869,046 A | 2/1999 | Presta et al. | |
| 5,885,573 A | 3/1999 | Bluestone et al. | |
| 5,891,693 A | 4/1999 | Bebbington et al. | |
| 6,027,888 A | 2/2000 | Georgiou et al. | |
| 6,083,715 A | 7/2000 | Georgiou et al. | |
| 6,121,022 A | 9/2000 | Presta et al. | |
| 6,165,745 A | 12/2000 | Ward et al. | |
| 6,194,551 B1 | 2/2001 | Idusogie et al. | |
| 6,227,375 B1 | 5/2001 | Powollik et al. | |
| 6,248,516 B1 | 6/2001 | Winter et al. | |
| 6,277,375 B1 | 8/2001 | Ward | |
| 6,602,684 B1 | 8/2003 | Umaña et al. | |
| 6,737,056 B1 | 5/2004 | Presta | |
| 6,821,505 B2 | 11/2004 | Ward | |
| 6,982,321 B2 | 1/2006 | Winter | |
| 7,087,409 B2 | 8/2006 | Barbas et al. | |
| 7,317,091 B2 | 1/2008 | Lazar et al. | |
| 7,335,742 B2 | 2/2008 | Presta | |
| 7,557,191 B2 | 7/2009 | Abrahamson et al. | |
| 7,745,421 B2 | 6/2010 | Bochner et al. | |
| 7,871,612 B2 | 1/2011 | Abrahamson et al. | |
| 7,981,843 B2 | 7/2011 | Flynn et al. | |
| 8,178,512 B2 | 5/2012 | Bochner et al. | |
| 8,197,811 B2 | 6/2012 | Abrahamson et al. | |
| 8,207,305 B2 | 6/2012 | Abrahamson et al. | |
| 8,357,671 B2 | 1/2013 | Paulson et al. | |
| 8,574,907 B2 | 11/2013 | Alley et al. | |
| 9,546,215 B2 | 1/2017 | Bebbington et al. | |
| 10,183,996 B2 * | 1/2019 | Bebbington | C07K 16/2803 |
| 10,604,577 B2 | 3/2020 | Bebbington | |
| 2002/0106738 A1 | 8/2002 | Foussias et al. | |
| 2002/0164328 A1 | 11/2002 | Shinkawa et al. | |
| 2003/0092091 A1 | 5/2003 | Abrahamson et al. | |
| 2003/0115614 A1 | 6/2003 | Kanda et al. | |
| 2003/0157108 A1 | 8/2003 | Presta | |
| 2003/0190311 A1 | 10/2003 | Dall'Acqua et al. | |
| 2004/0093621 A1 | 5/2004 | Shitara et al. | |
| 2004/0109865 A1 | 6/2004 | Niwa et al. | |
| 2004/0110282 A1 | 6/2004 | Kanda et al. | |
| 2004/0110704 A1 | 6/2004 | Yamane et al. | |
| 2004/0132140 A1 | 7/2004 | Satoh et al. | |
| 2005/0014934 A1 | 1/2005 | Hinton et al. | |
| 2005/0123546 A1 | 6/2005 | Umana et al. | |
| 2006/0134098 A1 | 6/2006 | Bebbington et al. | |
| 2007/0134259 A1 | 6/2007 | Bundle et al. | |
| 2007/0264258 A1 | 11/2007 | Abrahamson et al. | |
| 2008/0139485 A1 | 6/2008 | Bochner et al. | |
| 2008/0213212 A1 | 9/2008 | Abrahamson et al. | |
| 2009/0238837 A1 | 9/2009 | Paulson et al. | |
| 2010/0056760 A1 | 3/2010 | Abrahamson et al. | |
| 2011/0046078 A1 | 2/2011 | Bochner et al. | |
| 2011/0059107 A1 | 3/2011 | Allison et al. | |
| 2011/0293631 A1 | 5/2011 | Thumbikat et al. | |
| 2011/0217319 A1 | 9/2011 | Abrahamson et al. | |
| 2012/0214975 A1 | 8/2012 | Sandig et al. | |
| 2015/0203578 A1 | 7/2015 | Bebbington et al. | |
| 2017/0073413 A1 | 3/2017 | Bebbington et al. | |
| 2017/0114138 A1 | 4/2017 | Bebbington et al. | |
| 2017/0209556 A1 | 7/2017 | Bebbington et al. | |
| 2019/0338027 A1 | 11/2019 | Youngblood | |

FOREIGN PATENT DOCUMENTS

| | | |
|---|---|---|
| WO | WO-1987/000195 A1 | 1/1987 |
| WO | WO-1990/003430 A1 | 4/1990 |
| WO | WO-1993/006213 A1 | 4/1993 |
| WO | WO-1993/008829 A1 | 5/1993 |
| WO | WO-1993/016185 A2 | 8/1993 |
| WO | WO-1994/011026 A2 | 5/1994 |
| WO | WO-1994/029351 A2 | 12/1994 |
| WO | WO-1997/030087 A1 | 8/1997 |
| WO | WO-1998/058964 A1 | 12/1998 |
| WO | WO-1999/022764 A1 | 5/1999 |
| WO | WO-1999/051642 A1 | 10/1999 |
| WO | WO-2000/042072 A2 | 7/2000 |
| WO | WO-2000/061739 A1 | 10/2000 |
| WO | WO-2001/029246 A1 | 4/2001 |
| WO | WO-2001/066126 A1 | 9/2001 |
| WO | WO-2003/011878 A2 | 2/2003 |
| WO | WO-2003/084570 A1 | 10/2003 |
| WO | WO-2003/085119 A1 | 10/2003 |
| WO | WO-2004/056312 A2 | 8/2004 |
| WO | WO-2005/035586 A1 | 4/2005 |
| WO | WO-2005/035778 A1 | 4/2005 |
| WO | WO-2005/053742 A1 | 6/2005 |
| WO | WO-2005/116088 A2 | 12/2005 |
| WO | WO-2007/056525 A2 | 5/2007 |
| WO | WO-2008/077546 A1 | 7/2008 |
| WO | WO-2015/089117 A1 | 6/2015 |
| WO | WO-2015/131155 A1 | 9/2015 |
| WO | WO-2017/070527 A1 | 4/2017 |
| WO | WO2018129400 A1 | 7/2018 |
| WO | WO2018204868 A1 | 11/2018 |
| WO | WO2018204871 A1 | 11/2018 |

OTHER PUBLICATIONS

Andersson et al. (2011, Respiratory Research 12:139-151).*
Beckett et al. (2013, J. Allergy Clin. Innnnunol. 131:752-762).*
Villar et al. (Apr. 2015, Critical Care 19:138-146).*
Seibold et al. (1990, Arthritis and Rheumatism 33:1702-1709).*
Almagro, J.C. et al. (Jan. 1, 2008). "Humanization of Antibodies," Frontiers in Bioscience 13:1619-1631.
European Examination Report dated Apr. 1, 2019, for European Patent Application No. 157551755, filed on Aug. 25, 2016, 6 pages_
European Extended Search Report dated Nov. 15, 2018, for European Patent No. 16812473.3, filed on Jan. 10, 2018, 10 pages.
Ishitoya, J. (Sep. 29, 2007). "Eosinophilic Sinusitis/Eosinophilic Otitis Media—Chronic Eosinophilic Inflammation of the Upper Respiratory Tract Which has Been Recently Focused," Japan Medical Journal 4353:.53-57, with English Translation, 17 pages total.
Scordamaglia, F. et al. (Feb. 2008). "Perturbations of Natural Killer Cell Regulatory Functions in Respiratory Allergic Diseases," Journal of Allergy and Clinical Immunology 121(2):479-485.
Takeno, S. et al. (2012). "What is the Difference Between Paranasal Sinus Bronchial Syndrome and Asthma?," Pathology and Treatment of Chronic Sinusitis Associated With Asthma 143:45-53, with English Translation 33 pages total.
Alegre, M-L. et al., "A Non-Activating "Humanized" Anti-CD3 Monoclonal Antibody Retains Immunosuppressive Properties In Vivo", Transplantation, vol. 57, Issue 12, 1994, pp. 1537-1543.
Angal, S. et al., "A Single Amino Acid Substitution Abolishes the Heterogeneity of Chimeric Mouse/human (IgG4) Antibody", Molecular Immunology, vol. 30, Issue 1, Jan. 1993, pp. 105-108.
Arié, J-P. et al., "Chaperone Function of FkpA, A Heat Shock Prolyl Isomerase, in the Periplasm of Escherichia coli", Molecular Microbiology, vol. 39, No. 1, 2001, pp. 199-210.
Armour, K.L. et al., "Recombinant Human IgG Molecules Lacking FcGamma Receptor I Binding and Monocyte Triggering Activities", European Journal of Immunology, vol. 29, 1999, pp. 2613-2624.
Bachmann, Barbara J., "Derivations and Genotypes of Some Mutant Derivatives of Escherichia coli K-12", Cellular and Molecular Biology, vol. 2, 1987, pp. 1190-1219.
Barnes, D. et al., "Methods for Growth of Cultured Cells in Serum-Free Medium", Analytical Biochemistry, vol. 102, 1980, pp. 255-270.
Bass, S. et al., "Hormone Phage: an Enrichment Method for Variant Proteins with Altered Binding Properties", Proteins, vol. 8, 1990, pp. 309-314.
Berges-Gimeno, M.P. et al., "The Natural History and Clinical Characteristics of Asprin-Exacerbaated Respiratory Disease," Annals of Allergy, Asthma & Immunology, vol. 89, Nov. 2002, pp. 474-478.
Boerner, P. et al., "Production of Antigen-specific Human Monoclonal Antibodies from in Vitro-primed Human Splenocytes", The Journal of Immunology, vol. 147, No. 1, Jul. 1, 1991, pp. 86-95.

(56) References Cited

OTHER PUBLICATIONS

Bothmann, H. et al., "The Periplasmic *Escherichia coli* Peptidylprolyl cis,trans-Isomerase FkpA", *The Journal of Biological Chemistry*, vol. 275, No. 22, 2000, pp. 17100-17105.

Brennan, M et al., "Preparation of Bispecific Antibodies by Chemical Recombination of Monoclonal Immunoglobulin G1 Fragments", *Science*, vol. 229, 1985, pp. 81-83.

Brodeur, B.R. et al., "Mouse-Human Myeloma Partners for the Production of Heterohybridomas", in Chapter 4, *Monoclonal Antibody Production Techniques and Applications*, 1987, pp. 51-63.

Brüggermann, M. et al., "Designer Mice: the Production of Human Antibody Repertoires in Transgenic Animals", *The Year in Immunology*, vol. 7, 1993, pp. 33-40.

Brunner, K.T. et al., "Quantitative Assay of the Lytic Action of Immune Lymphoid Cells on 51Cr-Labelled Allogeneic Target Cells in Vitro; Inhibition by Isoantibody and by Drugs", *Immunology*, vol. 14, 1968, pp. 181-196.

Bryson, J.M. et al., "Local and Systemic Eosinophilia in Patients Undergoing Endoscopic Sinus Surgery for Chronic Rhinosinusitis with and Without Polyposis," *Clin. Otolaryngol.* vol. 28, 2003, pp. 55-58.

Carter, P. et al., "High Level *Escherichia coli* Expression and Production of a Bivalent Humanized Antibody Fragment", *Biotechnology*, vol. 10, Feb. 1992, pp. 163-167.

Carter, P. et al., "Humanization of an Anti-p185$^{HER2}$ Antibody for Human Cancer Therapy", *Proceedings of the National Academy of Sciences*, vol. 89, May 1992, pp. 4285-4289.

Casset, F. et al., "A Peptide Mimetic of an Anti-CD4 Monoclonal Antibody by Rational Design," *Biochem. Biophys. Res. Comm.* 2003, 307:198-205.

Chen, J. et al., "Chaperone Activity of DsbC*", *The Journal of Biological Chemistry*, vol. 274, No. 28, 1999, pp. 19601-19605.

Chen, Y. et al., "Selection and Analysis of an Optimized Anti-VEGF Antibody: Crystal Structure of an Affinity-matured Fab in Complex with Antigen", *Journal of Molecular Biology*, vol. 293, 1999, pp. 865-881.

Cheng, M. et al. "NK cell-based Immunotherapy for Malignant Diseases", *Cellular & Molecular Immunology*, vol. 10, 2013, pp. 230-252.

Chothia, C. et al., "Canonical Structures for the Hypervariable Regions of Immunoglobulins", *Journal of Molecular Biology*, vol. 196, Issue 4, Aug. 20, 1987, pp. 901-917.

Clynes, R. et al., "Fc Receptors are Required in Passive and Active Immunity to Melanoma", *Proceedings of the National Academy of Sciences*, vol. 95, Jan. 1998, pp. 652-656.

Cunningham, B.C. et al., "High-Resolution Epitope Mapping of hGH-receptor Interactions by Alanine-Scanning Mutagenesis", *Science*, vol. 244, Jun. 2, 1989, pp. 1081-1085.

Duncan, A.R. et al., "Localization of the Binding Site for the Human High-affinity Fc Receptor on IgG", *Nature*, vol. 332, 1988, pp. 563-564.

Duncan, A.R. et al., "The Binding Site for C1q on IgG", *Nature*, vol. 332, 1988, pp. 738-740.

Eswar, N. et al., "Comparative Protein Structure Modeling Using Modeller", *Current Protocols in Bioinformatics*, Unit-5.6, Oct. 2006, pp. 1-47.

Fairclough, L. et al., "Killer Cells in Chronic Obstructive Pulmonary Disease", *Clinical Science*, vol. 114, 2008, pp. 533-541.

Ferrara, C. et al., "Modulation of Therapeutic Antibody Effector Functions by Glycosylation Engineering: Influence of Golgi Enzyme Localization Domain and Co-Expression of Heterologous β1, 4-N-acetylglucosaminyltransferase III and Golgi α-Mannosidase II", *Biotechnology and Bioengineering*, vol. 93, Issue No. 5, Apr. 5, 2006, pp. 851-861.

Floyd, C. et al., "Siglec-8: A novel Eosinophil-Specific Member of the Immunoglobulin Superfamily", *Journal of Biological Chemistry*, vol. 275, No. 2, 2000, 861-866.

Fokkens, W.J. et al., "European Position Paper on Rhinosinusitis and Nasal Polyps", *EPOS*, vol. 50, Supplemental 23, Mar. 2012, pp. 1-299.

Gevaert, P. et al., "Omalizumab is Effective in Allergic and Nonallergic Patients with Nasal Polyps and Asthma", *The Journal of Allergy and Clinical of Immunology*, vol. 131, No. 1, Jan. 2013, pp. 110-116.

Ghetie, V. et al., "Increasing the Serum Persistence of an Igg Fragment by Random Mutagenesis", *Nat Biotech*, vol. 15, 1997, pp. 637-640.

Goodman, J.W. et al., "Immunoglobulin Proteins", *in Chapter 6, Basic and Clinical Immunology*, 1994, pp. 66-79.

Gotlib, J. et al., "International Working Group-Myeloproliferative Neoplasms Research and Treatment (IWG-MRT) & European Competence Network on Mastocytosis (ECNM) Consensus Response Criteria in Advanced Systemic Mastocytosis", *Blood*, vol. 121, No. 13, Mar. 28, 2013, pp. 2393-2401.

Graham, F.L. et al., "Characteristics of a Human Cell Line Transformed by DNA from Human Adenovirus Type 5", *Journal of General Virology*, vol. 36, 1977, pp. 59-72.

Guhl, S. et al., "Long-Term Cultured Human Skin Mast Cells Are Suitable for Pharmacological Studies of Anti-Allergic Drugs Due to High Responsiveness to FcεRI Cross-Linking", *Bioscience, Biotechnology, and Biochemistry*, vol. 75, No. 2, 2011, pp. 382-384.

Gunten, S. et al., "Intravenous Immunoglobulin Preparations Contain Anti-Siglec-8 Autoantibodies", *Journal of Allergy and Clinical Immunology*, vol. 119, No. 4, 2007, pp. 1005-1011.

Guss, B. et al., "Structure of the IgG-binding Regions of *Streptococcal* Protein G", *The EMBO Journal*, vol. 5, No. 7, 1986, pp. 1567-1575.

Guyer, R.L. et al., "Immunoglobulin Binding by Mouse Intestinal Epithelial Cell Receptors", *The Journal of Immunology*, vol. 117, No. 2, Aug. 1, 1976, pp. 587-593.

Ham, R.G. et al., "Media and Growth Requirements", *Methods in Enzymology*, vol. 58, 1979, pp. 44-93.

Hamers-Casterman, C. et al., "Naturally Occurring Antibodies Devoid of Light Chains", *Nature*, vol. 363, Jun. 3, 1993, pp. 446-448.

Hara, H. et al., "Overproduction of Penicillin-Binding Protein 7 Suppresses Thermosensitive Growth Defect at Low Osmolarity due to an spr Mutation of *Escherichia coli*", *Microbial Drug Resistance*, vol. 2, No. 1, 1996, pp. 63-72.

Harris, W. J., "Production of Humanized Monoclonal Antibodies for in Vivo Imaging and Therapy", *Biochemical Society Transactions*, vol. 23, No. 4, Nov. 1, 1995, pp. 1035-1038.

Hermine, O. et al, "Case-Control Cohort study of Patients' Perceptions of Disability in Mastocytosis", *Plos ONE*, vol. 3, No. 5, 2008, pp. 1-14.

Holm, P. et al., "Functional Mapping and Single Chain Construction of the Anti-Cytokeratin 8 Monoclonal Antibody TS1," *Mol. Immunol.* 2007; 44(6):1075-1084.

Hori, Y.S. et al., "Eosinopenia as A predictive Factor of the Short-Term Risk of Mortality and Infection After Acute Cerebral Infarction", *J. Stroke Cerebrovasc. Dis.* 25(6):1307-1312, (Jun. 2016).

Hu, Y. et al., "Diagnostic Significance of Blood Eosinophil Count in Eosinophilic Chronic Rhinosinusitis With Nasal Polys in Chinese Adults", *Laryngoscope*, vol. 122, Mar. 2012, pp. 498-503.

Hudson, P.J. et al., "Engineered Antibodies", *Nature Medicine*, vol. 9, 2003, pp. 129-134.

Hudson, S.A. et al., "Eosinophil-Selective Binding and Proapoptotic Effect in Vitro pf a Synthetic Siglec-8 Ligand, Polymeric 6'-Sulfated Sialyl Lewis X", *The Journal of Pharmacology and Experimental Therapeutics*, vol. 330, No. 2, 2009, pp. 608-612.

Hudson, S.A. et al., "Developmental, Malignancy-Related, and Cross-Species Analysis of Eosinophil, Mast Cell, and Basophil Siglec-8 Expression", *Journal of Clinical Immunology*, vol. 31, No. 6, Dec. 2011, pp. 1045-1053.

Hurle, M.R. et al., "Protein Engineering Techniques for Antibody Humanization", *Current Opinion in Biotechnology*, vol. 5, Issue 4, Aug. 1994, pp. 428-433.

Hutchins, J.T. et al., "Improved Biodistribution, Tumor Targeting, and reduced Immunogenicity in Mice with a Gamma 4 Variant of Campath-IH", *Proceedings of the National Academy of Sciences*, vol. 92, Dec. 1995, pp. 11980-11984.

(56) References Cited

OTHER PUBLICATIONS

Idusogie, E.E. et al., "Engineered Antibodies with Increased Activity to Recruit Complement", *The Journal of Immunology*, vol. 166, 2001, pp. 2571-2575.

Idusogie, E.E. et al., "Mapping of the C1q Binding Site on Rituxan, A Chimeric Antibody with a Human IgG1 Fc", *The Journal of Immunology*, vol. 164, 2000, pp. 4178-4184.

Jakobovits, A. et al., "Analysis of Homozygous Mutant Chimeric Mice: Deletion of The Immunoglobulin Heavy-chain Joining Region Blocks B-cell Development and Antibody Production", *PNAS, Proceedings of the National Academy of Sciences*, vol. 90, Mar. 1993, pp. 2551-2555.

Jakobovits, A. et al., "Germ-line Transmission and Expression of a Human-derived Yeast Artificial Chromosome", *Nature*, vol. 362, Mar. 18, 1993, pp. 255-258.

Jefferis, R. et al., "Human Immunoglobulin Allotypes",*MABS*, vol. 1, No. 4, Jul./Aug. 2009, pp. 1-7.

Jefferis, R. et al., "Interaction Sites on Human IgG-Fc for FcγR: Current Models", *Immunology Letters*, vol. 82, Issues 1-2, Jun. 3, 2002, pp. 57-65.

Jefferis, R. et al., "Modulation of Fcγr and Human Complement Activation by Igg3-core Oligosaccharide Interactions", *Immunology Letters*, vol. 54, Issues 2-3, Dec. 2, 1996, pp. 101-104.

Jefferis, R. et al., "Recognition Sites on Human Igg for Fcγ Receptors: The Role of Glycosylation", *Immunology Letters*, vol. 44, Issues 2-3, Jan. 2, 1995, pp. 111-117.

Jenkins, C. et al., "Systematic Review of Prevalence of Asprin Induced Astham and its Implications for Clinical Practice" *BMJ, Papers*, 2004, pp. 1-7.

Johnson, G. et al., "The Kabat Database and a Bioinformatics Example", *Antibody Engineering Methods in Molecular Biology™*, vol. 248, 2004, pp. 11-25.

Joly, J.C. et al., "Overexpression of *Escherichia coli* Oxidoreductases Increases Recombinant Insulin Like Growth Factor-I Accumulation", *Proc. Natl. Acad. Sci.*, vol. 95, Mar. 1998, pp. 2773-2777.

Jones, P.T. et al., "Replacing the Complementarity-determining Regions in a Human Antibody with those from a Mouse", *Nature*, vol. 321, May 29, 1986, pp. 522-525.

Kikly, K.K. et al., "Identification of Saf-2, A Novel Siglec Expressed on Eosinophils, Mast Cells, and Basophils", *The Journal of Allergy and Clinical Immunology*, vol. 105, Issue 6, Part 1, 2000, pp. 1093-1100.

Kiladjian, J.-J. et al., "Cytolytic Function and Survival of Natural Killer Cells are Severely Altered in Myelodysplastic Syndromes", *Leukemia*, vol. 20, 2006, pp. 463-470.

Kim, J-K. et al., "Localization of the Site of the Murine IgG1 Molecule that is Involved in Binding to the Murine Intestinal Fc Receptor", *Eur. J. Immunol.*, vol. 24, 1994, pp. 2429-2434.

Kim, J.H. et al., "Natural Killer Cells from Patients with Chronic Rhinosinusitis have Impaired Effector Functions", *Plos One*, vol. 8, No. 10, e-77177, Oct. 2013, pp. 1-9.

Kiwamoto, T. et al., "Siglec-8 as a Drugable Target to Treat Eosinophil and Mast Cell Associated Conditions", *Pharmacology & Therapeutics*, vol. 135, Issue No. 3, Sep. 2012, 22 pages.

Kowalski, Marek L., Aspirin Exacerbated Respiratory Disease (AERD)*, World Allergy Organization, Available at [http://www.worldallergy.org/professional/allergic_diseases_center/aspirin/], 2006, 6 pages.

Kozbor, D. et al., "A Human Hybrid Myeloma for Production of Human Monoclonal Antibodies", *The Journal of Immunology*, vol. 133, No. 6, Dec. 1, 1984, pp. 3001-3005.

Lange, B. et al., "The Sino-Nasal Outcome Test 22 Validated for Danish Patients", *Dan. Med. Bull*, vol. 58, No. 2, Feb. 2011, pp. 1-6.

Lazar, G.A. et al., "Engineered Antibody Fc Variants with Enhanced Effector Function", *PNAS*, vol. 103, No. 11, Mar. 14, 2006, pp. 4005-4010.

Lefranc, Marie-Paule, "IMGT, The International ImMunoGeneTics Database®", *Nucleic Acids Research*, vol. 31, No. 1, 2003, pp. 307-310.

Lichtenfels, R. et al., "CARE-LASS (calcein-release-assay), An Improved Fluorescence-based Test System to Measure Cytotoxic T Lymphocyte Activity", *Journal of Immunological Methods*, vol. 172, Issue 2, Jun. 24, 1994, pp. 227-239.

Lindmark, R. et al., "Binding of Immunoglobulins to Protein A and Immunoglobulin Levels in Mammalian Sera", *Journal of Immunological Methods*, vol. 62, 1983, pp. 1-13.

Lund, J. et al., "Human FcγRI and FcγRII Interact With Distinct but Overlapping Sites on Human IgG", *The Journal of Immunology*, vol. 147, No. 8, Oct. 15, 1991, pp. 2657-2662.

Lund, J. et al., "Multiple Binding Sites on the $C_H2$ Domain of IgG for Mouse FcγRII", *Molecular Immunology*, vol. 29, Issue 1, Jan. 1992, pp. 53-59.

Lund, J. et al., "Oligosaccharide-Protein Interactions in IgG can Modulate Recognition by FcGamma Receptors", *FASEB*, vol. 9, Jan. 1995, pp. 115-119.

Lund, J. et al., "Multiple Interactions of Igg with its Core Oligosaccharide can Modulate Recognition by Complement and Human Fc Gamma Receptor I and Influence the Synthesis of its Oligosaccharide Chains.", *The Journal of Immunology*, vol. 157, No. 11, Dec. 1, 1996, pp. 4963-4969.

MacCallum, A.M. et al. "Antibody-Antigen Interactions: Contact Analysis and Binding Site Topography," *J. Mol. Biol.* 262:732-745, (1996).

Marcondes, A.M. et al., "Dysregulation of IL-32 in Myelodysplastic Syndrome and Chronic Myelomonocytic Leukemia Modulates Apoptosis and Impairs NK Function", *PNAS*, vol. 105, No. 8, Feb. 26, 2008, pp. 2865-2870.

Mather, Jennie P., "Establishment and Characterization of Two Distinct Mouse Testicular Epithelial Cell Lines", *Biology of Reproduction*, vol. 23, 1980, pp. 243-252.

Mather, J.P. et al., "Culture of Testicular Cells in Hormone-Supplemented Serum-Free Medium", *Annals of the New York Academy of Sciences, Testicular Cell Culture*, 1982, pp. 44-68.

Milstein, C. et al., "Hybrid Hybridomas and Their Use in Immunohistochemistry", *Nature*, vol. 305, Oct. 6, 1983, pp. 537-540.

Morimoto, K. et al., "Single-step Purification of F(ab')$_2$ Fragments of Mouse Monoclonal Antibodies (immunoglobulins G1) By Hydrophobic Interaction High Performance Liquid Chromatography Using Tskgel Phenyl-5PW", *Journal of Biochemical and Biophysical Methods*, vol. 24, Issues 1-2, 1992, pp. 107-117.

Morrison, S.L. et al., "Chimeric Human Antibody Molecules: Mouse Antigen-binding Domains with Human Constant Region Domains", *PNAS*, vol. 81, Nov. 1984, pp. 6851-6855.

Mroz, R.M. et al., "Siglec-8 in Induced Sputum of COPD Patients", *Advances in Experimental Medicine and Biology*, vol. 788, 2013, pp. 19-23.

Muroi, A. et al., "The Composite Effect of Transgenic Plant Volatiles for Acquired Immunity to Herbivory Caused by Inter-Plant Communications", Plus One, vol. 6 No. 10, e24594, Oct. 2011, pp. 1-8.

Munson, P.J. et al., "Ligand: A Versatile Computerized Approach for Characterization of Ligand-binding Systems", *Analytical Biochemistry*, vol. 107, Issue 1, Sep. 1, 1980, pp. 220-239.

Nutku, E. et al., "Ligation of Siglec-8: A Selective Mechanism for Induction of Human Eosinophil Apoptosis", *Blood*, vol. 101, No. 12, Jun. 15, 2003, pp. 5014-5020.

Nutku et al. "Mechanism of Siglec-8-induced Human Eosinophil Apoptosis: Role of Caspases and Mitochondrial Injury". *Biochemical and Biophysical Research Communications* vol. 336. No. 3, Oct. 28, 2005, pp. 918-924.

O'Donnell, R. et al. (May 2006). "Inflammatory cells in the airways in COPD." *Thorax J.* vol. 61 No. 5, May 2006, pp. 448-454.

Okazaki, A. et al., "Fucose Depletion from Human IgG1 Oligosaccharide Enhances Binding Enthalpy and Association Rate Between IgG1 and FcγRIIIa", *Journal of Molecular Biology*, vol. 336, 2004, pp. 1239-1249.

O'Reilly, M.R. et al., "Siglecs as Targets for Therapy in Immune Cell Mediated Diseases", *Trends Pharmacol. Sci.*, vol. 30, No. 5, May 2009, pp. 240-248.

Pahl, J. et al., "Tricking the Balance: NK Cells in Anti-Cancer Immunity", *Immunobiology*, 2015, pp. 1-10.

(56) References Cited

OTHER PUBLICATIONS

Patel, A.S. et al., "An Improved Assay for Antibody Dependent Cellular Cytotoxicity Based on Time Resolved Fluorometry", *Journal of Immunological Methods*, vol. 184, Issue 1, Jul. 17, 1995, pp. 29-38.
Patnaik, M.M. et al., "Systemic Mastocytosis: A Concise Clinical and Laboratory Review", *Arch. Pathol. Lab. Med.*, vol. 131, May 2007, pp. 784-791.
Paul, ed., *Fundamental Immunology*, 1993, Raven Press, New York, pp. 292-295.
Pillai, S. et al., "Siglecs and Immune Regulation", *Annual Review of Immunology*, vol. 30, 2012, pp. 357-392.
Plückthun, A., "Antibodies from *Escherichia coli*", in Chapter 11, *The Pharmacology of Monoclonal Antibodies*, 1994, pp. 269-315.
Presta, Leonard G., "Antibody Engineering", *Current Opinion in Structural Biology*, vol. 2, 1992, pp. 593-596.
Presta, L.G. et al., "Humanization of An Antibody Directed against IgE", *The Journal of Immunology*, vol. 151, No. 5, Sep. 1, 1993, pp. 2623-2632.
Presta, L.G. et al., "Engineering Therapeutic Antibodies for Improved Function", *Biochemical Society Transactions*, vol. 30, No. 4, 2002, pp. 487-490.
Prieto, A. et al. "Defective Natural Killer and Phagocytic Activities in Chronic Obstructive Pulmonary Disease are Restored by Glycophosphopeptical (Inmunoferón)", *American Journal of Respiratory and Critical Care Medicine*, vol. 163, 2001, pp. 1578-1583.
Proba, K. et al., "Functional Antibody Single-chain Fragments From The Cytoplasm of *Escherichia coli*: Influence of Thioredoxin Reductase (trxb)", *Gene*, vol. 159, Issue 2, 1995, pp. 203-207.
Rahimi-Rad, M.H. et al., "Eosinopenia as a Marker of Outcome in Acute Exacerbations of Chronic Obstructive Pulmonary Disease," *J. Clin. Med.*, vol. 10, No. 1, 2015, pp. 10-13.
Ramm, R. et al., "The Periplasmic *Escherichia coli* Peptidylprolyl cis,Trans-Isomerase FkpA", *The Journal of Biological Chemistry*, vol. 275, No. 22, 2000, pp. 17106-17113.
Ravetch, J.V. et al., "Fc Receptors", *Annual Review of Immunology*, vol. 9, 1991, pp. 457-492.
Reddy, M.P. et al., "Elimination of Fc Receptor-Dependent Effector Functions of a Modified IgG4 Monoclonal Antibody to Human CD4", *The Journal of Immunology*, vol. 164, 2000, pp. 1925-1933.
Reyes, G.R. et al., "Expression of Human β-Interferon cDNA Under the Control of a Thymidine Kinase Promoter from Herpes Simplex Virus", *Nature*, vol. 297, Jun. 17, 1982, pp. 598-601.
Riechmann, L. et al., "Reshaping Human Antibodies for Therapy", *Nature*, vol. 332, Mar. 24, Mar. 24, 1988, pp. 323-327.
Ripka, J. et al., "Two Chinese Hamster Ovary Glycosylation Mutants Affected in The Conversion of GDP-mannose to GDP-fucose.", *Archives of Biochemistry and Biophysics*, vol. 249, No. 2, Sep. 1986, pp. 533-545.
Ruhno, J. et al., "The Increased Number of Epithelial Mast Cells in Nasal Polyps and Adjacent Turbinates is not Allergy-Dependent", *Allergy*, vol. 45, 1990, pp. 370-374.
Saha, S. et al. (2006). "Eosinophilic Airway Inflammation in COPD." *Int. J. Chron. Obstruct. Pulmon Dis.* vol. 1, No., 2006, pp. 39-47.
Scatchard, G., "The Attractions of Proteins for Small Molecules and Ions", *Annals of the New York Academy of Sciences*, 1949, pp. 660-672.
Settipane, Guy A., "Epidemiology of Nasal Polyps", *Allergy and Asthma Proceedings*, vol. 17, No. 5, Sep.-Oct. 1996, pp. 231-236.
Sheriff, S. et al., "Redefining the Minimal Antigen-binding Fragment", *Nature Structural & Molecular Biology*, vol. 3, No. 9, Sep. 1996, pp. 733-736.
Shi, J. et al., "Characterizing T-Cell Phenotypes in Nasal Polyposis in Chinese Patients", *Journal of Investigational Allergology and Clinical Immunology*, vol. 19, No. 4, 2009, pp. 276-282.
Shields, R.L. et al., "High resolution Mapping of the binding site on Human IgG1 for FcγRI, FcγRII, FcγRIII, and FcRn and deisgn of IgG1 variants with improved binding to the fcγR.", *The Journal of Biological Chemistry.* vol. 276, No. 9, 2001, pp. 6591-6604.

Siebenlist, U. et al., "*E. coli* ENA Polymerase Interacts Homologously with Two Different Promoters", *Cell*, vol. 20, Issue 2, Jun. 1980, pp. 269-281.
Simmons, L.C. et al., "Expression of Full-length Immunoglobulins in *Escherichia coli*: Rapid and Efficient Production of Aglycosylated Antibodies", *Journal of Immunological Methods*, vol. 263, Issues 1-2, May 1, 2002, pp. 133-147.
Sims, M.J. et al., "A Humanized Cd18 Antibody Can Block Function Without Cell Destruction", *The Journal of Immunology*, vol. 151, No. 4, Aug. 15, 1993, pp. 2296-2308.
Song, D.J. et al. "Anti-Siglec-F Antibody Reduces Allergen-Induced Eosinophilic Inflammation and Airway Remodelling," I, 2009, vol. 183, No. 8, pp. 5333-5341.
Spronsen, E. et al., "Evidence-Based Recommendations Regarding the Differential Diagnosis and Assessment of Nasal Congestion: Using the New GRADE System", *Allergy*, vol. 63, 2008, pp. 820-833.
Steinke, J.W. et al., "Interleukin-4 in the Generation of the AERD Phenotype: Implications for Molecular Mechanisms Driving Therapeutic Benefit of Aspirin Desensitization", *Journal of Allergy*, vol. 2012, Issue 182090, 2012, pp. 1-9.
Steinke, J.W. et al., "Prominent Role of IFN-γ in Patients with Aspirin-Exacerbated Respiratory Disease", *Journal of Allergy and Clinical Immunology*, vol. 132, Issue 4, Oct. 2013, pp. 856-865.
Stevenson, D.D. et al., "Pathogenesis of Aspirin-Exacerbated Respiratory Disease", *Clinical Reviews in Allergy and Immunology*, vol. 24, 2003, pp. 169-187.
Stevenson, D.D. et al. "Clinical and Pathologic Perspective on Aspirin Sensitivity and Asthma", *The Journal of Allergy and Clinical Immunology*, vol. 118, No. 4, Oct. 2006, pp. 773-786.
Suresh, M.R. et al., "Bispecific Monoclonal Antibodies from Hybrid Hybridomas", *Methods in Enzymology*, vol. 121, 1986, pp. 210-228.
Szczeklik, Andrzej et al., "Hypersensitivity to Aspirin and Nonsteroidal Anti-Inflammatory Drugs", In: *Middleton's Allergy, 7th Edition*, 2009, pp. 1227-1243.
Szczeklik, Andrzej, "Aspirin-Induced Asthma: A Tribute to John Vane as a Source of Inspiration", *Pharmacological Reports*, vol. 62, 2010, pp. 526-529.
Tanaka, S. et al., "Development of Mature and Functional Human Myeloid subsets in HSC Engrafted NOD/SCID/IL2rγKO Mice", *The Journal of Immunology*, vol. 188, No. 12, Jun. 2012, pp. 6145-6155.
Tashiro, F. et al. "Zearalenone Reductase from Rat Liver," *Journal of Biochemistry* vol. 93 No. 6, (1983), pp. 1557-1566.
Territo, M. "Eosinophilic Disorders," Merck Manual http://www.merckmanuals.com/home/blood-disorders/white-blood-cell-disorders/eosinophilic-disorders, accessed Aug. 2, 2016.
Traunecker, A. et al., "Bispecific Single Chain Molecules (Janusins) Target Cytotoxic Lymphocytes on HIV Infected Cells", *The EMBO Journal*, vol. 10, No. 12, 1991, pp. 3655-3659.
Urlaub, G. et al., "Isolation of Chinese Hamster Cell Mutants Deficient in Dihydrofolate Reductase Activity", *Proceedings of the National Academy of Sciences*, vol. 77, No. 7, Jul. 1980, pp. 4216-4220.
Vajdos, F.F. et al. "Comprehensive Functional Maps of the Antigen-Binding Site of an Anti-ErbB2 Antibody Obtained With Shotgun Scanning Mutagenesis," *J. Mol. Biol.* 2002, vol. 320, No. 2, pp. 415-428.
Valent, Peter, "Diagnostic Evaluation and Classification of Mastocytosis", *Immunol Allergy Clin North Am*, vol. 26, 2006, pp. 515-534.
Valent, P. et al., "Standards and Standardization in Mastocytosis: Consensus Statements on Diagnostics, Treatment Recommendations and Response Criteria", *European Journal of Clinical Investigation*, vol. 37, 2007, pp. 435-453.
Valent, P. et al., "Proposed Diagnostic Algorithm for Patients With Suspected Mastocytosis: A Proposal of the European Competence Network on Mastocytosis", *European Journal of Allergy and Clinical Immunology*, vol. 69, 2014, pp. 1267-1274.
Van Veen, I. H. et al., "Consistency of Sputum Eosinophilia in Difficult-to-Treat Asthma: A 5-year Follow-Up Study", *The Journal of Allergy and Clinical Immunology*, vol. 124, No. 3, Sep. 2009, pp. 615-617.

(56) References Cited

OTHER PUBLICATIONS

Vaswani, S.K. et al., "Humanized Antibodies as Potential Therapeutic Drugs", *Annals of Allergy, Asthma & Immunology*, vol. 81, Issue 2, Aug. 1998, pp. 105-116.
Verhoeyen, M. et al., "Reshaping Human Antibodies: Grafting an Antilysozyme Activity", *Science*, vol. 239, 1988, pp. 1534-1536.
Verstovsek, S. "Advanced Systemic Mastocytosis: The Impact of KIT Mutations in Diagnosis, Treatment and Progression", *European Journal of Haematology*, vol. 90, 2012, pp. 89-98.
Wechsler, M.E. et al., "Novel Targeted Therapies for Eosinophilic Disorders", *Journal of Allergy and Clinical Immunology*, vol. 130, No. 3, Sep. 2012, pp. 563-571.
Xu, D. et al., "In Vitro Characterization of Five Humanized OKT3 Effector Function Variant Antibodies", *Cellular Immunology*, vol. 200, Issue 1, Feb. 25, 2000, pp. 16-26.
Xu, J.L. et al., "Diversity in the CDR3 Region of $V_H$ Is Sufficient for Most Antibody Specificities", *Immunity*, vol. 13, Jul. 2000, pp. 37-45.
Yamane-Ohnuki, N. et al., "Establishment of *FUT8* Knockout Chinese Hamster Ovary Cells: An Ideal Host Cell Line for Producing Completely Defucosylated Antibodies with Enhanced Antibody-Dependent Cellular Cytotoxicity", *Biotechnology and Bioengineering*, vol. 87, Issue No. 5, Sep. 5, 2004, pp. 614-622.
Yaniv, Moshe, "Enhancing Elements for Activation of Eukaryotic Promoters", *Nature*, vol. 297, May 6, 1982, pp. 17-18.
Yansura, D.G. et al., "Nucleotide Sequence Selection for Increased Expression of Heterologous Genes in *Escherichia coli*", *Methods: A Companion to Methods in Enzymol*, 1992, pp. 151-158.
Yokoi, H. et al., "Inhibition of FcεrI-Dependent Mediator Release and Calcium Flux from Human Mast Cells by Sialic Acid-Binding Immunoglobulin-Like Lectin 8 Engagement", *Journal of Allergy and Clinical Immunology*, vol. 121, No. 2, Feb. 2008, pp. 499-505.
Zapata, G. et al., "Engineering Linear F(ab')2 Fragments for Efficient Production in *Escherichia coli* and Enhanced Antiproliferative Activity", *Protein Engineering*, vol. 8, No. 10, 1995, pp. 1057-1062.
Extended European Search Report dated Jun. 29, 2017, for European Patent Application No. 14869424.3, filed on Jun. 24, 2016, 11 pages.
European Partial Search Report dated Aug. 30, 2017, for European Patent Application No. 15755175.5, filed on Aug. 25, 2016, 8 pages.
European Search Report dated Dec. 8, 2017, for European Patent Application No. 15755175.5, filed on Aug. 25, 2016, 15 pages.
Non-Final Office Acttion dated Dec. 26, 2017, for U.S. Appl. No. 15/121,756, filed Aug. 25, 2016, 22 pages.
International Preliminary Report on Patentability received for PCT Patent Application No. PCT/US2014/069409, dated Jun. 23, 2016, 12 pages.
International Preliminary Report on Patentability received for PCT Patent Application No. PCT/US2015/018188, dated Sep. 15, 2016, 8 Pages.
International Preliminary Report on Patentability received for PCT Application No. PCT/US2016/037935, dated Dec. 28, 2017, 11 pages.
International Search Report and Written Opinion received for PCT Application No. PCT/US2016/037935, dated Aug. 10, 2016, 15 pages.
International Search Report and Written Opinion received for PCT Application No. PCT/US2016/058199, dated Jan. 9, 2017, 11 pages.
International Search Report and Written Opinion received for PCT Application No. PCT/US2014/069409, dated Mar. 6, 2015, 19 pages.
International Search Report and Written Opinion received for PCT Application No. PCT/US2015/018188, dated Apr. 28, 2015, 13 pages.
International Search Report and Written Opinion received for PCT Application No. PCT/US2018/012694, dated Jan. 8, 2018, 12 pages.
Clinicaltrials.gov. (Apr. 5, 2018). "A Study to Assess the Efficacy and Safety of AK002 in Subjects With Antihistamine-Resistant Chronic Urticaria, NCT03436797," downloaded from https://clinicaltrials.gov/ct2/history/NCT03436797?V_6=View#StudyPageTop, on Jun. 5, 2019, 8 pages.
European Extended Search Report dated May 15, 2019 for European Patent No. 16858333.4, filed on Apr. 17, 2019, 7 pages.
International Preliminary Report on Patentability receivedfor PCT Application No. PCT/US2016/058199, dated Apr. 24, 2018, 6 pages.
International Preliminary Report on Patentability received for PCT Application No. PCT/US2018/012694, dated Jul. 9, 2019, 6 pages.
International Search Report and Written Opinion received for PCT Application No. PCT/SU2019/030523, dated Jul. 2, 2019, 10 pages.
O'Brien-Ladner, A.R. et al. (1993). "Bleomycin Injury of the Lung in a Mast-Cell-Deficient Model," Agents Actions 39:20-24.
Rasmussen, H. et al. (Feb. 2018). "A Randomized, Double-Blind, Placebo-Controlled, Ascending Dose Phase 1 Study of AK002, A Novel Siglec-8 Selective Monoclonal Antibody, in Healthy Subjects," J. Allergy Clin. Immunol. 141(2):AB403, Abstract No. L15, 1 page.
U.S. Appl. No. 16/610,429, titled "Methods and Compositions for Treating Inflammatory Gastrointestinal Disorders", filed Nov. 1, 2019, for Bebbington et al. (U.S. Patent Application is not submitted herewith pursuant to the waiver of 37 C.F.R. § 1.98(a)(2)(iii) issued by the Office on Sep. 21, 2004.).
U.S. Appl. No. 16/610,80, titled "Methods And Compositions For Treating Allergic Ocular Diseases", filed Nov. 1, 2019, for Bebbington et al. (U.S. Patent Application is not submitted herewith pursuant to the waiver of 37 C.F.R § 1.98(a)(2)(iii) issued by the Office on Sep. 21, 2004.).
U.S. Appl. No. 16/796,795, titled "Methods and Compositions for Treating Systemic Mastocytosis," filed Feb. 20, 2020, for Bebbington et al. (U.S. Patent Application is not submitted herewith pursuant to the waiver of 37 C.F.R. § 1.98(a)(2)(iii) issued by the Office on Sep. 21, 2004.).

\* cited by examiner

METHODS AND COMPOSITIONS FOR TREATING FIBROTIC DISEASES

CROSS REFERENCE TO RELATED APPLICATIONS

This application is a National Phase application under 35 U.S.C. § 371 of International Application No. PCT/US2016/037935, filed Jun. 16, 2016, which claims priority to U.S. Provisional Application Ser. No. 62/181,146, filed on Jun. 17, 2015, U.S. Provisional Application Ser. No. 62/296,482, filed on Feb. 17, 2016, and U.S. Provisional Application Ser. No. 62/344,357, filed on Jun. 1, 2016, the disclosures of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 701712000300SEQLIST.txt, date recorded: Dec. 15, 2017, size: 91 KB).

FIELD OF THE INVENTION

This invention relates to methods for preventing and/or treating fibrotic diseases and pre-fibrotic diseases by administration of antibodies or agonists that bind to human Siglec-8 or compositions comprising said antibodies or agonists.

BACKGROUND OF THE INVENTION

Fibrosis is a condition characterized by excess deposition of extracellular matrix components in an organ or tissue that leads to an accumulation of tough fibrous scar tissue. For example, pulmonary fibrosis is a major type of fibrotic disease that is characterized by an inflammatory response that includes macrophages, neutrophils, lymphocytes, and mast cells. Idiopathic Pulmonary Fibrosis (IPF) is a chronic lung disease with unknown etiology in which normal lung parenchyma is progressively replaced with fibrotic tissue, leading to dyspnea, cough, impaired lung function, and increased mortality. IPF has a poor prognosis, with a median survival of approximately three years from the time of diagnosis, and great associated morbidity, with wide-ranging negative effects on quality of life. Most patients with IPF succumb to respiratory failure. There are several pathogenic events that occur in the development of IPF and several of these events have been targeted by therapeutic agents for the purpose of treating IPF. Therapeutic approaches targeting macrophages, neutrophils or lymphocytes have failed to alter the course of IPF pathogenesis. See Ahluwalia et al., *Am J Respir Crit Care Med.* 190(8):867-78, 2014 and Woodcock et al., F1000*Prime Rep.*, 6:16, 2014 for a review of IPF and available treatments for IPF. Therefore, there remains a need for therapies that can control the activity of immune cells involved in the pathogenesis of fibrotic disease.

The number of mast cells and mast cell mediators are significantly elevated in IPF. Mast cells are the main source of TGF-β, a cytokine that plays a role in the development of fibrosis via stimulation of collagen production by fibroblasts and signaling for differentiation of fibroblasts into myofibroblasts. It has also been shown that mast cell-deficient mice are protected from bleomycin-induced pulmonary fibrosis. See Veerappan et al., *DNA Cell Biol.* 32(4):206-18. Although mast cells appear to be involved in the pathogenesis of IPF, their exact role in the multitude of complex pathogenic events that underlay the development of fibrotic disease remains unclear.

Siglecs (sialic acid-binding immunoglobulin-like lectins) are single-pass transmembrane cell surface proteins found predominantly on leukocytes and are characterized by their specificity for sialic acids attached to cell-surface glycoconjugates. The Siglec family contains at least 15 members that are found in mammals (Pillai et al., *Annu Rev Immunol.*, 30:357-392, 2012). These members include sialoadhesion (Siglec-1), CD22 (Siglec-2), CD33 (Siglec-3), myelin associated glycoprotein (Siglec-4), Siglec-5, OBBP1 (Siglec-6), AIRM1 (Siglec-7), SAF-2 (Siglec-8), and CD329 (Siglec-9). Siglec-8 was first discovered as part of efforts to identify novel human eosinophil proteins. In addition to expression by eosinophils, it is also expressed by mast cells and basophils. Siglec-8 recognizes a sulfated glycan, i.e., 6'-sulfo-sialyl Lewis X or 6'-sulfo-sialyl-N-acetyl-S-lactosamine, and contains an intracellular immunoreceptor tyrosine-based inhibitory motif (ITIM) domain shown to inhibit mast cell function. Siglec-8 has been shown to modulate cellular responses mediated by the IgE pathway but the effect of Siglec-8 activation on non-IgE mediated immune response pathways is unknown.

All references cited herein, including patent applications, patent publications, and scientific literature, are herein incorporated by reference in their entirety, as if each individual reference were specifically and individually indicated to be incorporated by reference.

SUMMARY OF THE INVENTION

Provided herein are methods of using antibodies or agonists that bind to human Siglec-8, or compositions comprising thereof, for the prevention or treatment of fibrotic diseases or pre-fibrotic diseases. Fibrotic diseases include, but are not limited to, pulmonary fibrosis (e.g., idiopathic pulmonary fibrosis), hepatic fibrosis, renal fibrosis (e.g., renal interstitial fibrosis), cardiac fibrosis, spleen fibrosis, ocular fibrosis, mechanical-induced fibrosis (e.g., ventilator-induced pulmonary fibrosis), implant-induced fibrosis, radiation-induced fibrosis, drug-induced fibrosis (e.g., bleomycin-induced pulmonary fibrosis), viral-induced fibrosis, cystic fibrosis, cancer-associated fibrosis, atherosclerosis, bone marrow fibrosis (e.g., myelofibrosis), scleroderma (e.g., systemic sclerosis), mediastinal fibrosis and retroperitoneal cavity fibrosis. Pre-fibrotic diseases include, but are not limited to, bleomycin-induced pneumonitis, chronic hypersensitivity pneumonitis, polycythemia vera, essential thrombocythemia, age-related macular degeneration, diabetic retinopathy, neovascular glaucoma, retinopathy of prematurity, and proliferative vitreoretinopathy.

In one aspect, provided herein is a method for treating or preventing fibrotic disease in an individual comprising administering to the individual an effective amount of an antibody or an agonist that binds to human Siglec-8. In some embodiments, the individual has a fibrotic disease. In some embodiments, the individual has been diagnosed with a fibrotic disease or is at risk of developing the fibrotic disease. In some embodiments herein, the fibrotic disease is selected from the group consisting of: pulmonary fibrosis, hepatic fibrosis, renal fibrosis, cardiac fibrosis, spleen fibrosis, and ocular fibrosis. In a further embodiment, the pulmonary fibrosis is idiopathic pulmonary fibrosis. In some embodiments, the pulmonary fibrosis is associated with chronic obstructive pulmonary disease. In some embodiments herein, the fibrotic disease is selected from the group consisting of: mechanical-induced fibrosis, implant-induced fibrosis, radiation-induced fibrosis, drug-induced fibrosis and viral-induced fibrosis. In a further embodiment, the mechanical induced fibrosis is ventilator-induced pulmonary fibrosis. In yet another further embodiment, the drug-induced fibrosis is bleomycin-induced pulmonary fibrosis. In some embodiments, the fibrotic disease is selected from the group consisting of: cystic fibrosis, cancer-associated fibrosis, atherosclerosis, bone marrow fibrosis, scleroderma, mediastinal fibrosis and retroperitoneal cavity fibrosis. In some embodiments, the scleroderma is systemic sclerosis. In some of the embodiments herein, one or more symptom in the individual with the fibrotic disease is reduced relative to baseline after administration of the antibody or the agonist that binds to human Siglec-8. In a further embodiment, the one or more symptom can be a symptom associated with a fibrotic disease disclosed herein, such as, but not limited to, shortness of breath, dry cough, weight loss, fatigue, malaise, finger or toe clubbing, muscle pain, or joint pain. In some embodiments herein, one or more pulmonary function in the individual with pulmonary fibrosis is increased by at least 5% relative to baseline after administration of the antibody or the agonist that binds to human Siglec-8. In a further embodiment, the one or more pulmonary function is selected from the group consisting of: vital capacity (VC), residual volume (V), forced expiratory volume ($FEV_1$), forced vital capacity (FVC), forced expiratory flow (FEF), peak expiratory flow rate (PEFR), inspiratory reserve volume (IRV), functional residual capacity (FRC), inspirator capacity (IC), total lung capacity (TLC), expiratory reserve volume (ERV), tidal volume (TV) and maximum voluntary ventilation (MVV). In some embodiments, one or more pathologic parameter in the individual with fibrotic disease is reduced by at least 5% relative to baseline after administration of the antibody or the agonist that binds to human Siglec-8. In a further embodiment, the one or more pathologic parameter is selected from the group consisting of: neutrophil influx, number of mast cells, cytokine release, collagen accumulation, fibroblast or myofibroblast infiltration and fibroblastic foci formation. In some embodiments, mast cell activation is reduced in the individual relative to baseline after administration of the antibody or the agonist that binds to human Siglec-8. In any of the embodiments herein, the individual can be a human. In any of the embodiments herein, the antibody can be in a pharmaceutical composition comprising the antibody and a pharmaceutically acceptable carrier. In any of the embodiments herein, the agonist can be in a pharmaceutical composition comprising the agonist and a pharmaceutically acceptable carrier.

In one aspect, provided herein is a method for treating or preventing pre-fibrotic disease in an individual comprising administering to the individual an effective amount of an antibody or an agonist that binds to human Siglec-8. In some embodiments, the individual has a pre-fibrotic disease. In some embodiments, the individual has been diagnosed with a pre-fibrotic disease or is at risk of developing the pre-fibrotic disease. In some embodiments, the pre-fibrotic disease is selected from the group consisting of: bleomycin-induced pneumonitis, chronic hypersensitivity pneumonitis, polycythemia vera, essential thrombocythemia, age-related macular degeneration, diabetic retinopathy, neovascular glaucoma, retinopathy of prematurity, and proliferative vitreoretinopathy. In some of the embodiments herein, one or more symptom in the individual with pre-fibrotic disease is reduced relative to baseline after administration of the antibody or the agonist that binds to human Siglec-8. In a further embodiment, the one or more symptom can be a symptom associated with a pre-fibrotic disease disclosed herein, such as, but not limited to, shortness of breath, dry cough, weight loss, fatigue, malaise, finger or toe clubbing, muscle pain, or joint pain. In some embodiments, one or more pathologic parameter in the individual with pre-fibrotic disease is reduced by at least 5% relative to baseline after administration of the antibody or the agonist that binds to human Siglec-8. In a further embodiment, the one or more pathologic parameter is selected from the group consisting of: neutrophil influx, number of mast cells, cytokine release, collagen accumulation, fibroblast or myofibroblast infiltration and fibroblastic foci formation. In some embodiments, mast cell activation is reduced in the individual relative to baseline after administration of the antibody or the agonist that binds to human Siglec-8. In any of the embodiments herein, the individual can be a human. In any of the embodiments herein, the antibody can be in a pharmaceutical composition comprising the antibody and a pharmaceutically acceptable carrier. In any of the embodiments herein, the agonist can be in a pharmaceutical composition comprising the agonist and a pharmaceutically acceptable carrier.

In another aspect, provided herein is a method for reducing mast cell activation by an agent of a non-IgE mediated cell signaling pathway in an individual comprising administering to the individual an effective amount of an antibody or an agonist that binds to human Siglec-8. In one embodiment, the individual has a fibrotic disease. In some embodiments, the individual has been diagnosed with a fibrotic disease or is at risk of developing the fibrotic disease. In some embodiments herein, the fibrotic disease is selected from the group consisting of: pulmonary fibrosis, hepatic fibrosis, renal fibrosis, cardiac fibrosis, spleen fibrosis, and ocular fibrosis. In a further embodiment, the pulmonary fibrosis is idiopathic pulmonary fibrosis. In some embodiments, the pulmonary fibrosis is associated with chronic obstructive pulmonary disease. In some embodiments herein, the fibrotic disease is selected from the group consisting of: mechanical-induced fibrosis, implant-induced fibrosis, radiation-induced fibrosis, drug-induced fibrosis and viral-induced fibrosis. In a further embodiment, the mechanical induced fibrosis is ventilator-induced pulmonary fibrosis. In yet another further embodiment, the drug-induced fibrosis is bleomycin-induced pulmonary fibrosis. In some embodiments, the fibrotic disease is selected from the group consisting of: cystic fibrosis, cancer-associated fibrosis, atherosclerosis, bone marrow fibrosis, scleroderma, mediastinal fibrosis and retroperitoneal cavity fibrosis. In some embodiments, the scleroderma is systemic sclerosis. In some of the embodiments herein, one or more symptom in the individual with the fibrotic disease is reduced relative to baseline after administration of the antibody or the agonist that binds to human Siglec-8. In a further embodiment, the one or more symptom can be a symptom associated with a fibrotic disease disclosed herein, such as, but not limited to, shortness of breath, dry cough, weight loss, fatigue, malaise, finger or toe clubbing, muscle pain, or joint pain. In some embodiments herein, one or more pulmonary function in the individual with pulmonary fibrosis is increased by at least 5% relative to baseline after administration of the antibody or the agonist that binds to human Siglec-8. In a further embodiment, the one or more pulmonary function is selected from the group consisting of: vital capacity (VC), residual volume (V), forced expiratory volume ($FEV_1$), forced vital capacity (FVC), forced expiratory flow (FEF), peak expiratory flow rate (PEFR), inspiratory reserve volume (IRV), functional residual capacity (FRC), inspirator capacity (IC), total lung capacity (TLC), expiratory reserve volume (ERV), tidal volume (TV) and maximum voluntary ventilation (MVV). In some embodiments, one or more pathologic parameter in the individual with fibrotic disease is reduced by at least 5% relative to baseline after administration of the antibody or the agonist that binds to human Siglec-8. In a further embodiment, the one or more pathologic parameter is selected from the group consisting of: neutrophil influx, number of mast cells, cytokine release, collagen accumulation, fibroblast or myofibroblast infiltration and fibroblastic foci formation. In some of the embodiments herein, the agent of the non-IgE mediated cell signaling pathway is selected from the group consisting of: thymic stromal lymphopoietin (TSLP), Stem cell factor (SCF), Toll-like Receptor 3 (TLR3), Interleukin 33 (IL-33), and complement proteins. In some embodiments, mast cell activation is reduced in the individual relative to baseline after administration of the antibody or the agonist that binds to human Siglec-8. In any of the embodiments herein, the individual can be a human. In any of the embodiments herein, the antibody can be in a pharmaceutical composition comprising the antibody and a pharmaceutically acceptable carrier. In any of the embodiments herein, the agonist can be in a pharmaceutical composition comprising the agonist and a pharmaceutically acceptable carrier.

In another aspect, provided herein is a method for reducing mast cell activation by an agent of a non-IgE mediated cell signaling pathway in an individual comprising administering to the individual an effective amount of an antibody or an agonist that binds to human Siglec-8. In one embodiment, the individual has a pre-fibrotic disease. In some embodiments, the individual has been diagnosed with a pre-fibrotic disease or is at risk of developing the pre-fibrotic disease. In some embodiments, the pre-fibrotic disease is selected from the group consisting of: bleomycin-induced pneumonitis, chronic hypersensitivity pneumonitis, polycythemia vera, essential thrombocythemia, age-related macular degeneration, diabetic retinopathy, neovascular glaucoma, retinopathy of prematurity, and proliferative vitreoretinopathy. In some of the embodiments herein, one or more symptom in the individual with pre-fibrotic disease is reduced relative to baseline after administration of the antibody or the agonist that binds to human Siglec-8. In a further embodiment, the one or more symptom can be a symptom associated with a pre-fibrotic disease disclosed herein, such as, but not limited to, shortness of breath, dry cough, weight loss, fatigue, malaise, finger or toe clubbing, muscle pain, or joint pain. In some embodiments, one or more pathologic parameter in the individual with pre-fibrotic disease is reduced by at least 5% relative to baseline after administration of the antibody or the agonist that binds to human Siglec-8. In a further embodiment, the one or more pathologic parameter is selected from the group consisting of: neutrophil influx, number of mast cells, cytokine release, collagen accumulation, fibroblast or myofibroblast infiltration and fibroblastic foci formation. In some of the embodiments herein, the agent of the non-IgE mediated cell signaling pathway is selected from the group consisting of: thymic stromal lymphopoietin (TSLP), Stem cell factor (SCF), Toll-like Receptor 3 (TLR3), Interleukin 33 (IL-33), and complement proteins. In some embodiments, mast cell activation is reduced in the individual relative to baseline after administration of the antibody or the agonist that binds to human Siglec-8. In any of the embodiments herein, the individual can be a human. In any of the embodiments herein, the antibody can be in a pharmaceutical composition comprising the antibody and a pharmaceutically acceptable carrier. In any of the embodiments herein, the agonist can be in a pharmaceutical composition comprising the agonist and a pharmaceutically acceptable carrier.

In another aspect, provided herein is a composition comprising an antibody or an agonist that binds to human Siglec-8 for use in treating or preventing fibrotic disease in an individual. In some embodiments, the individual has a fibrotic disease. In some embodiments, the individual has been diagnosed with a fibrotic disease or is at risk of developing the fibrotic disease. In some embodiments, the antibody comprises a Fc region and N-glycoside-linked carbohydrate chains linked to the Fc region, wherein less than 50% of the N-glycoside-linked carbohydrate chains contain a fucose residue. In a further embodiment, substantially none of the N-glycoside-linked carbohydrate chains contain a fucose residue. In some embodiments herein, the fibrotic disease is selected from the group consisting of: pulmonary fibrosis, hepatic fibrosis, renal fibrosis, cardiac fibrosis, spleen fibrosis, and ocular fibrosis. In a further embodiment, the pulmonary fibrosis is idiopathic pulmonary fibrosis. In some embodiments, the pulmonary fibrosis is associated with chronic obstructive pulmonary disease. In some embodiments herein, the fibrotic disease is selected from the group consisting of: mechanical-induced fibrosis, implant-induced fibrosis, radiation-induced fibrosis, drug-induced fibrosis and viral-induced fibrosis. In a further embodiment, the mechanical induced fibrosis is ventilator-induced pulmonary fibrosis. In yet another further embodiment, the drug-induced fibrosis is bleomycin-induced pulmonary fibrosis. In some embodiments, the fibrotic disease is selected from the group consisting of: cystic fibrosis, cancer-associated fibrosis, atherosclerosis, bone marrow fibrosis, scleroderma, mediastinal fibrosis and retroperitoneal cavity fibrosis. In some embodiments, the scleroderma is systemic sclerosis. In some of the embodiments herein, one or more symptom in the individual with the fibrotic disease is reduced relative to baseline after administration of the composition comprising the antibody or the agonist that binds to human Siglec-8. In a further embodiment, the one or more symptom can be a symptom associated with a fibrotic disease disclosed herein, such as, but not limited to, shortness of breath, dry cough, weight loss, fatigue, malaise, finger or toe clubbing, muscle pain, or joint pain. In some embodiments herein, one or more pulmonary function in the individual with pulmonary fibrosis is increased by at least 5% relative to baseline after administration of the composition comprising the antibody or the agonist that binds to human Siglec-8. In a further embodiment, the one or more pulmonary function is selected from the group consisting of: vital capacity (VC), residual volume (V), forced expiratory volume (FEV$_1$), forced vital capacity (FVC), forced expiratory flow (FEF), peak expiratory flow rate (PEFR), inspiratory reserve volume (IRV), functional residual capacity (FRC), inspirator capacity (IC), total lung capacity (TLC), expiratory reserve volume (ERV), tidal volume (TV) and maximum voluntary ventilation (MVV). In some embodiments, one or more pathologic parameter in the individual with fibrotic disease is reduced by at least 5% relative to baseline after administration of the composition comprising the antibody or the agonist that binds to human Siglec-8. In a further embodiment, the one or more pathologic parameter is selected from the group consisting of: neutrophil influx, number of mast cells, cytokine release, collagen accumulation, fibroblast or myofibroblast infiltration and fibroblastic foci formation. In some embodiments, mast cell activation is reduced in the individual relative to baseline after administration of the composition comprising the antibody or the agonist that binds to human Siglec-8. In any of the embodiments herein, the individual can be a human. In any of the embodiments herein, the composition can further comprise a pharmaceutically acceptable carrier.

In another aspect, provided herein is a composition comprising an antibody or an agonist that binds to human Siglec-8 for use in treating or preventing pre-fibrotic disease in an individual. In some embodiments, the individual has a pre-fibrotic disease. In some embodiments, the individual has been diagnosed with a pre-fibrotic disease or is at risk of developing the pre-fibrotic disease. In some embodiments, the antibody comprises a Fc region and N-glycoside-linked carbohydrate chains linked to the Fc region, wherein less than 50% of the N-glycoside-linked carbohydrate chains contain a fucose residue. In a further embodiment, substantially none of the N-glycoside-linked carbohydrate chains contain a fucose residue. In some embodiments, the pre-fibrotic disease is selected from the group consisting of: bleomycin-induced pneumonitis, chronic hypersensitivity pneumonitis, polycythemia vera, essential thrombocythemia, age-related macular degeneration, diabetic retinopathy, neovascular glaucoma, retinopathy of prematurity, and proliferative vitreoretinopathy. In some of the embodiments herein, one or more symptom in the individual with pre-fibrotic disease is reduced relative to baseline after administration of the composition comprising the antibody or the agonist that binds to human Siglec-8. In a further embodiment, the one or more symptom can be a symptom associated with a pre-fibrotic disease disclosed herein, such as, but not limited to, shortness of breath, dry cough, weight loss, fatigue, malaise, finger or toe clubbing, muscle pain, or joint pain. In some embodiments, one or more pathologic parameter in the individual with pre-fibrotic disease is reduced by at least 5% relative to baseline after administration of the composition comprising the antibody or the agonist that binds to human Siglec-8. In a further embodiment, the one or more pathologic parameter is selected from the group consisting of: neutrophil influx, number of mast cells, cytokine release, collagen accumulation, fibroblast or myofibroblast infiltration and fibroblastic foci formation. In some embodiments, mast cell activation is reduced in the individual relative to baseline after administration of the composition comprising the antibody or the agonist that binds to human Siglec-8. In any of the embodiments herein, the individual can be a human. In any of the embodiments herein, the composition can further comprise a pharmaceutically acceptable carrier.

In another aspect, provided herein is a composition comprising an antibody or an agonist that binds to human Siglec-8 for use in reducing mast cell activation by an agent of a non-IgE mediated cell signaling pathway in an individual comprising administering to the individual the composition. In some embodiments, the antibody comprises a Fc region and N-glycoside-linked carbohydrate chains linked to the Fc region, wherein less than 50% of the N-glycoside-linked carbohydrate chains contain a fucose residue. In a further embodiment, substantially none of the N-glycoside-linked carbohydrate chains contain a fucose residue. In some embodiments, the individual has a fibrotic disease. In some embodiments, the individual has been diagnosed with a fibrotic disease or is at risk of developing the fibrotic disease. In some embodiments herein, the fibrotic disease is selected from the group consisting of: pulmonary fibrosis, hepatic fibrosis, renal fibrosis, cardiac fibrosis, spleen fibrosis, and ocular fibrosis. In a further embodiment, the pulmonary fibrosis is idiopathic pulmonary fibrosis. In some embodiments, the pulmonary fibrosis is associated with chronic obstructive pulmonary disease. In some embodiments herein, the fibrotic disease is selected from the group consisting of: mechanical-induced fibrosis, implant-induced fibrosis, radiation-induced fibrosis, drug-induced fibrosis and viral-induced fibrosis. In a further embodiment, the mechanical induced fibrosis is ventilator-induced pulmonary fibrosis. In yet another further embodiment, the drug-induced fibrosis is bleomycin-induced pulmonary fibrosis. In some embodiments, the fibrotic disease is selected from the group consisting of: cystic fibrosis, cancer-associated fibrosis, atherosclerosis, bone marrow fibrosis, scleroderma, mediastinal fibrosis and retroperitoneal cavity fibrosis. In some embodiments, the scleroderma is systemic sclerosis. In some of the embodiments herein, one or more symptom in the individual with the fibrotic disease is reduced relative to baseline after administration of the composition comprising the antibody or the agonist that binds to human Siglec-8. In a further embodiment, the one or more symptom can be a symptom associated with a fibrotic disease disclosed herein, such as, but not limited to, shortness of breath, dry cough, weight loss, fatigue, malaise, finger or toe clubbing, muscle pain, or joint pain. In some embodiments herein, one or more pulmonary function in the individual with pulmonary fibrosis is increased by at least 5% relative to baseline after administration of the composition comprising the antibody or the agonist that binds to human Siglec-8. In a further embodiment, the one or more pulmonary function is selected from the group consisting of: vital capacity (VC), residual volume (V), forced expiratory volume ($FEV_1$), forced vital capacity (FVC), forced expiratory flow (FEF), peak expiratory flow rate (PEFR), inspiratory reserve volume (IRV), functional residual capacity (FRC), inspirator capacity (IC), total lung capacity (TLC), expiratory reserve volume (ERV), tidal volume (TV) and maximum voluntary ventilation (MVV). In some embodiments, one or more pathologic parameter in the individual with fibrotic disease is reduced by at least 5% relative to baseline after administration of the composition comprising the antibody or the agonist that binds to human Siglec-8. In a further embodiment, the one or more pathologic parameter is selected from the group consisting of: neutrophil influx, number of mast cells, cytokine release, collagen accumulation, fibroblast or myofibroblast infiltration and fibroblastic foci formation. In some of the embodiments herein, the agent of the non-IgE mediated cell signaling pathway is selected from the group consisting of: thymic stromal lymphopoietin (TSLP), Stem cell factor (SCF), Toll-like Receptor 3 (TLR3), Interleukin 33 (IL-33), and complement proteins. In some embodiments, mast cell activation is reduced in the individual relative to baseline after administration of the composition comprising the antibody or the agonist that binds to human Siglec-8. In any of the embodiments herein, the individual can be a human. In any of the embodiments herein, the composition can further comprise a pharmaceutically acceptable carrier.

In another aspect, provided herein is a composition comprising an antibody or an agonist that binds to human Siglec-8 for use in reducing mast cell activation by an agent of a non-IgE mediated cell signaling pathway in an individual comprising administering to the individual the composition. In some embodiments, the antibody comprises a Fc region and N-glycoside-linked carbohydrate chains linked to the Fc region, wherein less than 50% of the N-glycoside-linked carbohydrate chains contain a fucose residue. In a further embodiment, substantially none of the N-glycosidelinked carbohydrate chains contain a fucose residue. In some embodiments, the individual has a pre-fibrotic disease. In some embodiments, the individual has been diagnosed with a pre-fibrotic disease or is at risk of developing the pre-fibrotic disease. In some embodiments, the pre-fibrotic disease is selected from the group consisting of: bleomycin-induced pneumonitis, chronic hypersensitivity pneumonitis, polycythemia vera, essential thrombocythemia, age-related macular degeneration, diabetic retinopathy, neovascular glaucoma, retinopathy of prematurity, and proliferative vitreoretinopathy. In some of the embodiments herein, one or more symptom in the individual with pre-fibrotic disease is reduced relative to baseline after administration of the composition comprising the antibody or the agonist that binds to human Siglec-8. In a further embodiment, the one or more symptom can be a symptom associated with a pre-fibrotic disease disclosed herein, such as, but not limited to, shortness of breath, dry cough, weight loss, fatigue, malaise, finger or toe clubbing, muscle pain, or joint pain. In some embodiments, one or more pathologic parameter in the individual with pre-fibrotic disease is reduced by at least 5% relative to baseline after administration of the composition comprising the antibody or the agonist that binds to human Siglec-8. In a further embodiment, the one or more pathologic parameter is selected from the group consisting of: neutrophil influx, number of mast cells, cytokine release, collagen accumulation, fibroblast or myofibroblast infiltration and fibroblastic foci formation. In some of the embodiments herein, the agent of the non-IgE mediated cell signaling pathway is selected from the group consisting of: thymic stromal lymphopoietin (TSLP), Stem cell factor (SCF), Toll-like Receptor 3 (TLR3), Interleukin 33 (IL-33), and complement proteins. In some embodiments, mast cell activation is reduced in the individual relative to baseline after administration of the composition comprising the antibody or the agonist that binds to human Siglec-8. In any of the embodiments herein, the individual can be a human. In any of the embodiments herein, the composition can further comprise a pharmaceutically acceptable carrier.

In some aspects, also provided herein is an article of manufacture comprising a medicament comprising an antibody or an agonist that binds to human Siglec-8 and a package insert comprising instructions for administration of the medicament in an individual in need thereof to treat or prevent fibrotic disease. In some embodiments, the individual has a fibrotic disease. In some embodiments, the individual has been diagnosed with a fibrotic disease or is at risk of developing the fibrotic disease. In some embodiments herein, the fibrotic disease is selected from the group consisting of: pulmonary fibrosis, hepatic fibrosis, renal fibrosis, cardiac fibrosis, spleen fibrosis, and ocular fibrosis. In a further embodiment, the pulmonary fibrosis is idiopathic pulmonary fibrosis. In some embodiments, the pulmonary fibrosis is associated with chronic obstructive pulmonary disease. In some embodiments herein, the fibrotic disease is selected from the group consisting of: mechanical-induced fibrosis, implant-induced fibrosis, radiation-induced fibrosis, drug-induced fibrosis and viral-induced fibrosis. In a further embodiment, the mechanical induced fibrosis is ventilator-induced pulmonary fibrosis. In yet another further embodiment, the drug-induced fibrosis is bleomycin-induced pulmonary fibrosis. In some embodiments, the fibrotic disease is selected from the group consisting of: cystic fibrosis, cancer-associated fibrosis, atherosclerosis, bone marrow fibrosis, scleroderma, mediastinal fibrosis and retroperitoneal cavity fibrosis. In some embodiments, the scleroderma is systemic sclerosis. In some of the embodiments herein, the package insert further indicates that the treatment is effective in reducing one or more symptom in the individual with the fibrotic disease relative to baseline after administration of the antibody or the agonist that binds to human Siglec-8. In a further embodiment, the one or more symptom can be a symptom associated with a fibrotic disease disclosed herein, such as, but not limited to, shortness of breath, dry cough, weight loss, fatigue, malaise, finger or toe clubbing, muscle pain, or joint pain. In some embodiments herein, one or more pulmonary function in the individual with pulmonary fibrosis is increased by at least 5% relative to baseline after administration of the antibody or the agonist that binds to human Siglec-8. In a further embodiment, the one or more pulmonary function is selected from the group consisting of: vital capacity (VC), residual volume (V), forced expiratory volume ($FEV_1$), forced vital capacity (FVC), forced expiratory flow (FEF), peak expiratory flow rate (PEFR), inspiratory reserve volume (IRV), functional residual capacity (FRC), inspirator capacity (IC), total lung capacity (TLC), expiratory reserve volume (ERV), tidal volume (TV) and maximum voluntary ventilation (MVV). In some embodiments, one or more pathologic parameter in the individual with fibrotic disease is reduced by at least 5% relative to baseline after administration of the antibody or the agonist that binds to human Siglec-8. In a further embodiment, the one or more pathologic parameter is selected from the group consisting of: neutrophil influx, number of mast cells, cytokine release, collagen accumulation, fibroblast or myofibroblast infiltration and fibroblastic foci formation. In some embodiments, mast cell activation is reduced in the individual relative to baseline after administration of the antibody or the agonist that binds to human Siglec-8. In any of the embodiments herein, the individual can be a human. In any of the embodiments herein, the antibody can be in a pharmaceutical composition comprising the antibody and a pharmaceutically acceptable carrier. In any of the embodiments herein, the agonist can be in a pharmaceutical composition comprising the agonist and a pharmaceutically acceptable carrier.

In some aspects, also provided herein is an article of manufacture comprising a medicament comprising an antibody or an agonist that binds to human Siglec-8 and a package insert comprising instructions for administration of the medicament in an individual in need thereof to treat or prevent pre-fibrotic disease. In some embodiments, the individual has a pre-fibrotic disease. In some embodiments, the individual has been diagnosed with a pre-fibrotic disease or is at risk of developing the pre-fibrotic disease. In some embodiments, the pre-fibrotic disease is selected from the group consisting of: bleomycin-induced pneumonitis, chronic hypersensitivity pneumonitis, polycythemia vera, essential thrombocythemia, age-related macular degeneration, diabetic retinopathy, neovascular glaucoma, retinopathy of prematurity, and proliferative vitreoretinopathy. In some of the embodiments herein, the package insert further indicates that the treatment is effective in reducing one or more symptom in the individual with pre-fibrotic disease relative to baseline after administration of the antibody or the agonist that binds to human Siglec-8. In a further embodiment, the one or more symptom can be a symptom associated with a pre-fibrotic disease disclosed herein, such as, but not limited to, shortness of breath, dry cough, weight loss, fatigue, malaise, finger or toe clubbing, muscle pain, or joint pain. In some embodiments, one or more pathologic parameter in the individual with pre-fibrotic disease is reduced by at least 5% relative to baseline after administration of the antibody or the agonist that binds to human Siglec-8. In a further embodiment, the one or more pathologic parameter is selected from the group consisting of: neutrophil influx, number of mast cells, cytokine release, collagen accumulation, fibroblast or myofibroblast infiltration and fibroblastic foci formation. In some embodiments, mast cell activation is reduced in the individual relative to baseline after administration of the antibody or the agonist that binds to human Siglec-8. In any of the embodiments herein, the individual can be a human. In any of the embodiments herein, the antibody can be in a pharmaceutical composition comprising the antibody and a pharmaceutically acceptable carrier. In any of the embodiments herein, the agonist can be in a pharmaceutical composition comprising the agonist and a pharmaceutically acceptable carrier.

In other aspects, provided herein is a method for treating or preventing fibrotic disease in an individual comprising administering to the individual an effective amount of an agonist that binds to human Siglec-8. In some embodiments, the individual has a fibrotic disease. In some embodiments, the individual has been diagnosed with a fibrotic disease or is at risk of developing the fibrotic disease. In some embodiments herein, the agonist is a 6'-sulfo-sLe$^X$-containing agonist selected from the group consisting of: a 6'-sulfo-sLe$^X$-containing ligand, a 6'-sulfo-sLe$^X$-containing oligosaccharide, a 6'-sulfo-sLe$^X$-containing polypeptide, and a 6'-sulfo-sLe$^X$-containing glycoprotein. In some embodiments, the agonist is an agonist antibody that binds to human Siglec-8.

In yet another aspect, provided herein is a method for treating or preventing pre-fibrotic disease in an individual comprising administering to the individual an effective amount of an agonist that binds to human Siglec-8. In some embodiments, the individual has a pre-fibrotic disease. In some embodiments, the individual has been diagnosed with a pre-fibrotic disease or is at risk of developing the pre-fibrotic disease. In some embodiments herein, the agonist is a 6'-sulfo-sLe$^X$-containing agonist selected from the group consisting of: a 6'-sulfo-sLe$^X$-containing ligand, a 6'-sulfo-sLe$^X$-containing oligosaccharide, a 6'-sulfo-sLe$^X$-containing polypeptide, and a 6'-sulfo-sLe$^X$-containing glycoprotein. In some embodiments, the agonist is an agonist antibody that binds to human Siglec-8.

In yet another aspect, provided herein is a method for reducing mast cell activation by an agent of a non-IgE mediated cell signaling pathway in an individual comprising administering to the individual an effective amount of an agonist that binds to human Siglec-8. In some embodiments, the individual has a fibrotic disease. In some embodiments, the individual has been diagnosed with a fibrotic disease or is at risk of developing the fibrotic disease. In some embodiments, the individual has a pre-fibrotic disease. In some embodiments, the individual has been diagnosed with a pre-fibrotic disease or is at risk of developing the pre-fibrotic disease. In some embodiments herein, the agonist is a 6'-sulfo-sLe$^X$-containing agonist selected from the group consisting of: a 6'-sulfo-sLe$^X$-containing ligand, a 6'-sulfo-sLe$^X$-containing oligosaccharide, a 6'-sulfo-sLe$^X$-containing polypeptide, and a 6'-sulfo-sLe$^X$-containing glycoprotein. In some embodiments, the agonist is an agonist antibody that binds to human Siglec-8.

In any of the embodiments of the methods and compositions for use therein, the antibody can be a monoclonal antibody. In any of the embodiments of the methods and compositions for use therein, the antibody can be an IgG1 antibody. In any of the embodiments of the methods and compositions for use therein, the antibody can be engineered to improve antibody-dependent cell-mediated cytotoxicity (ADCC) activity. In a further embodiment, the antibody comprises at least one amino acid substitution in the Fc region that improves ADCC activity. In any of the embodiments of the methods and compositions for use therein, one or two of the heavy chains of the antibody can be non-fucosylated. In any of the embodiments of the methods and compositions for use therein, the antibody can be a human antibody, a humanized antibody or a chimeric antibody. In any of the embodiments of the methods and compositions for use therein, the antibody can be a murine antibody. In any of the embodiments of the methods and compositions for use therein, the antibody can be an antibody fragment selected from the group consisting of Fab, Fab'-SH, Fv, scFv, and (Fab')$_2$ fragments. In some embodiments, the antibody comprises a heavy chain variable region and a light chain variable region, wherein the heavy chain variable region comprises (i) HVR-H1 comprising the amino acid sequence of SEQ ID NO:61, (ii) HVR-H2 comprising the amino acid sequence of SEQ ID NO:62, and (iii) HVR-H3 comprising the amino acid sequence of SEQ ID NO:63; and/or wherein the light chain variable region comprises (i) HVR-L1 comprising the amino acid sequence of SEQ ID NO:64, (ii) HVR-L2 comprising the amino acid sequence of SEQ ID NO:65, and (iii) HVR-L3 comprising the amino acid sequence of SEQ ID NO:66. In some embodiments, the antibody comprises a heavy chain variable region comprising the amino acid sequence of SEQ ID NO:6; and/or a light chain variable region comprising the amino acid sequence selected from SEQ ID NOs:16 or 21. In some embodiments, the antibody comprises a heavy chain Fc region comprising a human IgG Fc region. In a further embodiment, the human IgG Fc region comprises a human IgG1 or a human IgG4. In a further embodiment, the human IgG4 comprises the amino acid substitution S228P, and wherein the amino acid residues are numbered according to the EU index as in Kabat. In some embodiments, the human IgG1 comprises the amino acid sequence of SEQ ID NO:78. In some embodiments, the human IgG4 comprises the amino acid sequence of SEQ ID NO:79. In some embodiments, the antibody comprises a heavy chain comprising the amino acid sequence of SEQ ID NO:75; and/or a light chain comprising the amino acid sequence SEQ ID NOs:76 or 77. In some embodiments, the antibody comprises a heavy chain variable region and a light chain variable region, wherein the heavy chain variable region comprises (i) HVR-H1 comprising the amino acid sequence of SEQ ID NO:61, (ii) HVR-H2 comprising the amino acid sequence of SEQ ID NO:62, and (iii) HVR-H3 comprising the amino acid sequence selected from SEQ ID NOs:67-70; and/or wherein the light chain variable region comprises (i) HVR-L1 comprising the amino acid sequence of SEQ ID NO:64, (ii) HVR-L2 comprising the amino acid sequence of SEQ ID NO:65, and (iii) HVR-L3 comprising the amino acid sequence of SEQ ID NO:71. In some embodiments, the antibody comprises a heavy chain variable region comprising the amino acid sequence selected from SEQ ID NOs: 11-14; and/or a light chain variable region comprising the amino acid sequence selected from SEQ ID NOs:23-24. In some embodiments, the antibody comprises a heavy chain variable region comprising the amino acid sequence selected from SEQ ID NOs:2-14; and/or a light chain variable region comprising the amino acid sequence selected from SEQ ID NOs: 16-24. In some embodiments, the antibody comprises a heavy chain variable region comprising the amino acid sequence selected from SEQ ID NOs:2-10; and/or a light chain variable region comprising the amino acid sequence selected from SEQ ID NOs: 16-22. In some embodiments, the antibody comprises: (a) heavy chain variable region comprising: (1) an HC-FR1 comprising the amino acid sequence selected from SEQ ID NOs:26-29; (2) an HVR-H1 comprising the amino acid sequence of SEQ ID NO:61; (3) an HC-FR2 comprising the amino acid sequence selected from SEQ ID NOs:31-36; (4) an HVR-H2 comprising the amino acid sequence of SEQ ID NO:62; (5) an HC-FR3 comprising the amino acid sequence selected from SEQ ID NOs:38-43; (6) an HVR-H3 comprising the amino acid sequence of SEQ ID NO:63; and (7) an HC-FR4 comprising the amino acid sequence selected from SEQ ID NOs:45-46, and/or (b) a light chain variable region comprising: (1) an LC-FR1 comprising the amino acid sequence selected from SEQ ID NOs:48-49; (2) an HVR-L1 comprising the amino acid sequence of SEQ ID NO:64; (3) an LC-FR2 comprising the amino acid sequence selected from SEQ ID NOs:51-53; (4) an HVR-L2 comprising the amino acid sequence of SEQ ID NO:65; (5) an LC-FR3 comprising the amino acid sequence selected from SEQ ID NOs:55-58; (6) an HVR-L3 comprising the amino acid sequence of SEQ ID NO:66; and (7) an LC-FR4 comprising the amino acid sequence of SEQ ID NO:60. In some embodiments, the antibody comprises: (a) heavy chain variable region comprising: (1) an HC-FR1 comprising the amino acid sequence of SEQ ID NO:26; (2) an HVR-H1 comprising the amino acid sequence of SEQ ID NO:61; (3) an HC-FR2 comprising the amino acid sequence of SEQ ID NO:34; (4) an HVR-H2 comprising the amino acid sequence of SEQ ID NO:62; (5) an HC-FR3 comprising the amino acid sequence of SEQ ID NO:38; (6) an HVR-H3 comprising the amino acid sequence of SEQ ID NO:63; and (7) an HC-FR4 comprising the amino acid sequence of SEQ ID NOs:45; and/or (b) a light chain variable region comprising: (1) an LC-FR1 comprising the amino acid sequence of SEQ ID NO:48; (2) an HVR-L1 comprising the amino acid sequence of SEQ ID NO:64; (3) an LC-FR2 comprising the amino acid sequence of SEQ ID NO:51; (4) an HVR-L2 comprising the amino acid sequence of SEQ ID NO:65; (5) an LC-FR3 comprising the amino acid sequence of SEQ ID NO:55; (6) an HVR-L3 comprising the amino acid sequence of SEQ ID NO:66; and (7) an LC-FR4 comprising the amino acid sequence of SEQ ID NO:60. In some embodiments, the antibody comprises: (a) heavy chain variable region comprising: (1) an HC-FR1 comprising the amino acid sequence of SEQ ID NO:26; (2) an HVR-H1 comprising the amino acid sequence of SEQ ID NO:61; (3) an HC-FR2 comprising the amino acid sequence of SEQ ID NO:34; (4) an HVR-H2 comprising the amino acid sequence of SEQ ID NO:62; (5) an HC-FR3 comprising the amino acid sequence of SEQ ID NO:38; (6) an HVR-H3 comprising the amino acid sequence of SEQ ID NO:63; and (7) an HC-FR4 comprising the amino acid sequence of SEQ ID NOs:45; and/or (b) a light chain variable region comprising: (1) an LC-FR1 comprising the amino acid sequence of SEQ ID NO:48; (2) an HVR-L1 comprising the amino acid sequence of SEQ ID NO:64; (3) an LC-FR2 comprising the amino acid sequence of SEQ ID NO:51; (4) an HVR-L2 comprising the amino acid sequence of SEQ ID NO:65; (5) an LC-FR3 comprising the amino acid sequence of SEQ ID NO:58; (6) an HVR-L3 comprising the amino acid sequence of SEQ ID NO:66; and (7) an LC-FR4 comprising the amino acid sequence of SEQ ID NO:60. In some embodiments, the antibody comprises a heavy chain variable region comprising (i) HVR-H1 comprising the amino acid sequence of SEQ ID NO:88, (ii) HVR-H2 comprising the amino acid sequence of SEQ ID NO:91, and (iii) HVR-H3 comprising the amino acid sequence of SEQ ID NO:94; and/or a light chain variable region comprising (i) HVR-L1 comprising the amino acid sequence of SEQ ID NO:97, (ii) HVR-L2 comprising the amino acid sequence of SEQ ID NO:100, and (iii) HVR-L3 comprising the amino acid sequence of SEQ ID NO:103. In some embodiments, the antibody comprises a heavy chain variable region comprising (i) HVR-H1 comprising the amino acid sequence of SEQ ID NO:89, (ii) HVR-H2 comprising the amino acid sequence of SEQ ID NO:92, and (iii) HVR-H3 comprising the amino acid sequence of SEQ ID NO:95; and/or a light chain variable region comprising (i) HVR-L1 comprising the amino acid sequence of SEQ ID NO:98, (ii) HVR-L2 comprising the amino acid sequence of SEQ ID NO:101, and (iii) HVR-L3 comprising the amino acid sequence of SEQ ID NO:104. In some embodiments, the antibody comprises a heavy chain variable region comprising (i) HVR-H1 comprising the amino acid sequence of SEQ ID NO:90, (ii) HVR-H2 comprising the amino acid sequence of SEQ ID NO:93, and (iii) HVR-H3 comprising the amino acid sequence of SEQ ID NO:96; and/or a light chain variable region comprising (i) HVR-L1 comprising the amino acid sequence of SEQ ID NO:99, (ii) HVR-L2 comprising the amino acid sequence of SEQ ID NO:102, and (iii) HVR-L3 comprising the amino acid sequence of SEQ ID NO:105. In some embodiments, the antibody comprises a heavy chain variable region comprising the amino acid sequence of SEQ ID NO:106; and/or a light chain variable region comprising the amino acid sequence of SEQ ID NO:109. In some embodiments, the antibody comprises a heavy chain variable region comprising the amino acid sequence of SEQ ID NO:107; and/or a light chain variable region comprising the amino acid sequence of SEQ ID NO:110. In some embodiments, the antibody comprises a heavy chain variable region comprising the amino acid sequence of SEQ ID NO:108; and/or a light chain variable region comprising the amino acid sequence of SEQ ID NO:111.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

BRIEF DESCRIPTION OF THE DRAWINGS

FIG. 2A) Experiment 1 and FIG. 2B)

Experiment 2 are duplicate experiments except Experiment 2 includes a group of mice treated with m2E2 Depleting antibody. BAL indicates bronchoalveolar lavage; (1) Isotype indicates murine IgG1 isotype control antibody; (2) m2E2 Depleting indicates a murine monoclonal anti-Siglec-8 antibody with a murine IgG2a isotype that kills eosinophils and mast cells by ADCC activity; (3) m2E2 Inhibitory indicates a murine monoclonal anti-Siglec-8 antibody with a murine IgG1 isotype that kills eosinophils and inhibits mast cell activity; and (4) Naive indicates Siglec-8 transgenic mice that were not administered an antibody or bleomycin. p-values were determined by comparing the mouse IgG1 isotype control antibody study group to the m2E2 Depleting antibody study group, the m2E2 Inhibitory antibody study group or the naive study group.

Figure 3:
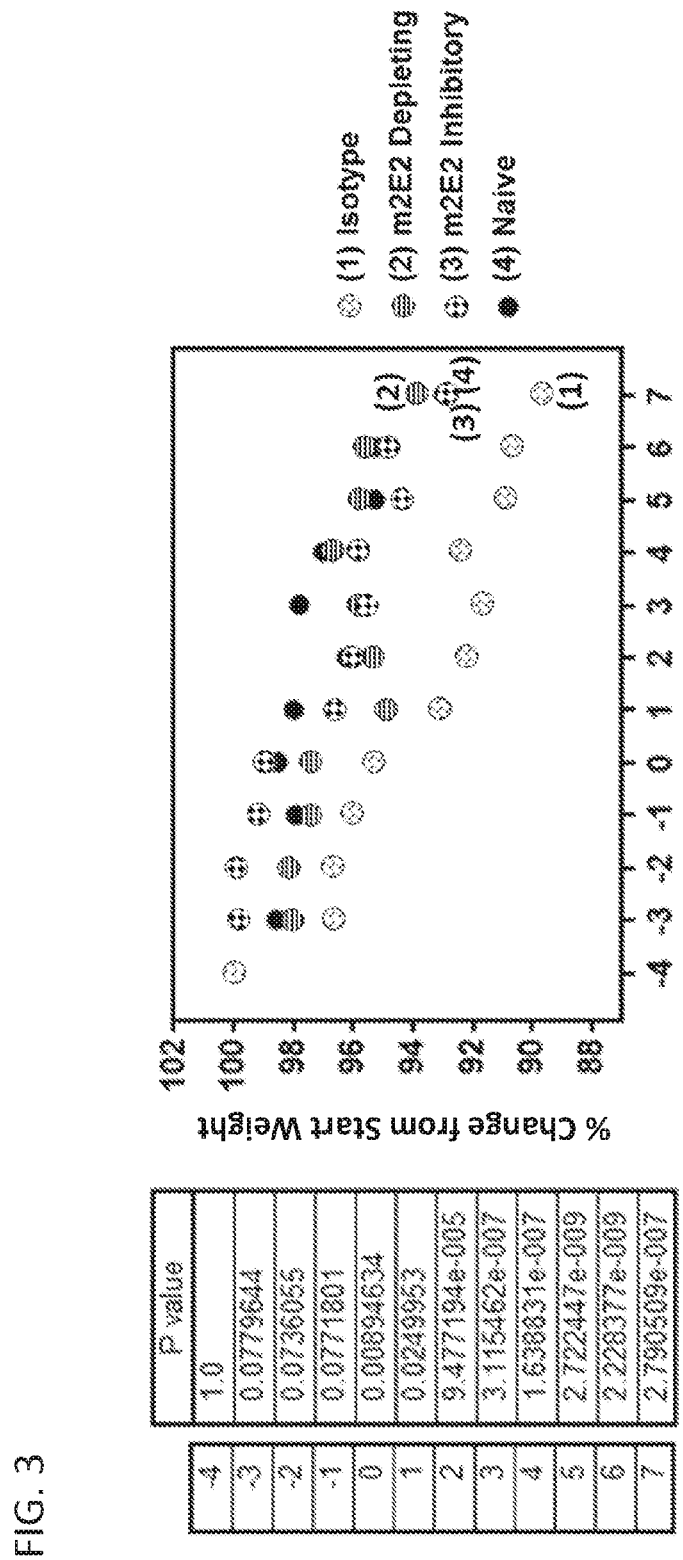

FIG. 3 is a graph showing that anti-Siglec-8 antibodies protect Siglec-8 transgenic mice from bleomycin-induced weight loss. (1) Isotype indicates murine IgG1 isotype control antibody; (2) m2E2 Depleting indicates a murine monoclonal anti-Siglec-8 antibody with a murine IgG2a isotype that kills eosinophils and mast cells by ADCC activity; (3) m2E2 Inhibitory indicates a murine monoclonal anti-Siglec-8 antibody with a murine IgG1 isotype that kills eosinophils and inhibits mast cell activity; and (4) Naive indicates Siglec-8 transgenic mice that were not administered an antibody or bleomycin. p-values were determined by comparing the mouse IgG1 isotype control antibody study group to the m2E2 Depleting antibody study group.

Figure 4:
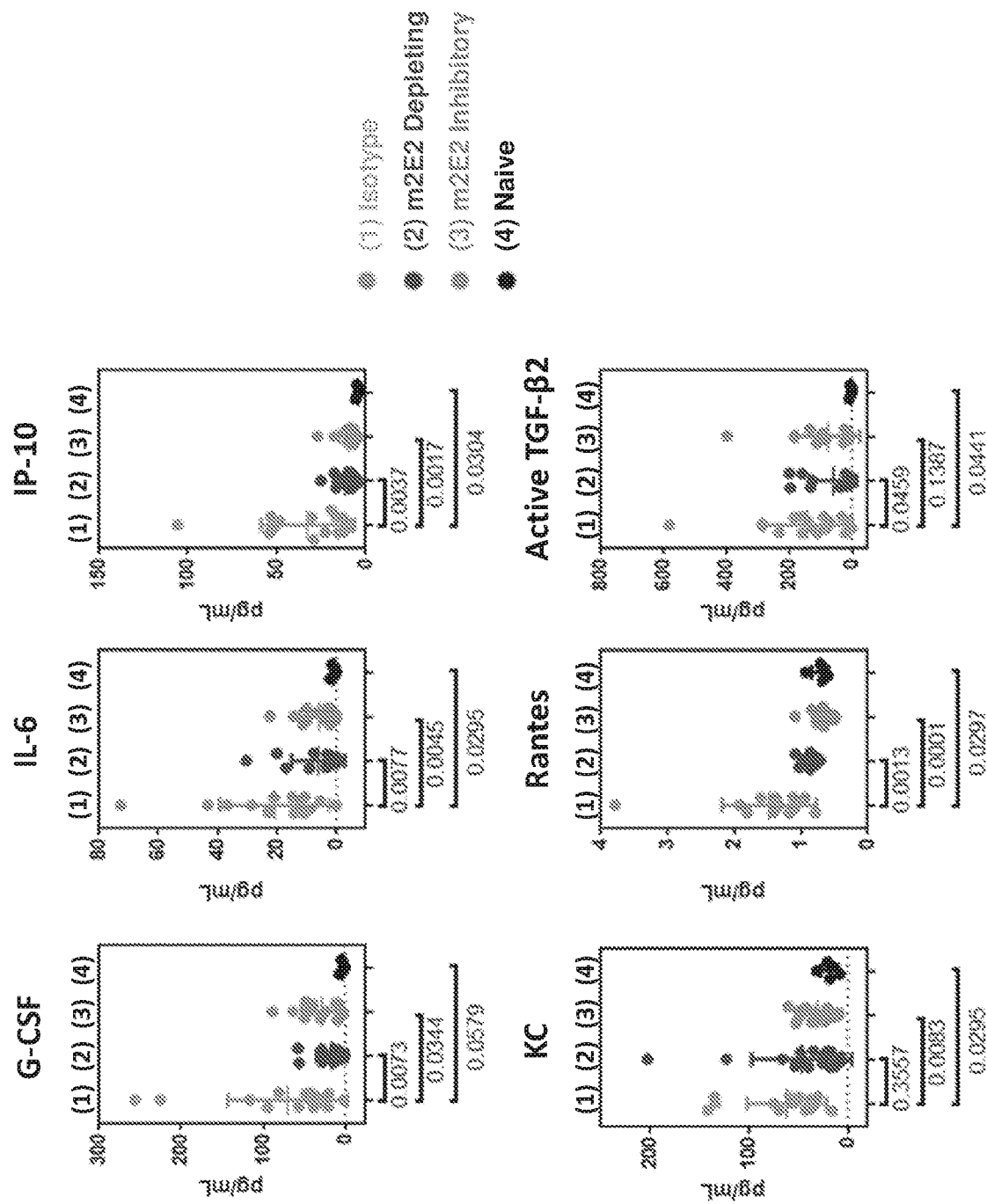

FIG. 4 is a graph showing inhibition of elevated cytokines in the bronchoalveolar lavage fluid after bleomycin-induced lung fibrosis in Siglec-8 transgenic mice due to treatment with anti-Siglec-8 antibodies. (1) Isotype indicates murine IgG1 isotype control antibody; (2) m2E2 Depleting indicates a murine monoclonal anti-Siglec-8 antibody with a murine IgG2a isotype that kills eosinophils and mast cells by ADCC activity; (3) m2E2 Inhibitory indicates a murine monoclonal anti-Siglec-8 antibody with a murine IgG1 isotype that kills eosinophils and inhibits mast cell activity; and (4) Naive indicates Siglec-8 transgenic mice that were not administered an antibody or bleomycin. p-values were determined by comparing the mouse IgG1 isotype control antibody study group to the m2E2 Depleting antibody study group, the m2E2 Inhibitory antibody study group or the naive study group. G-CSF indicates granulocyte colony-stimulating factor; IL-6 indicates interleukin-6; IP-10 indicates interferon gamma-induced protein 10; KC indicates keratinocyte-derived cytokine; RANTES indicates regulated on activation normal T cell expressed and secreted protein; and active TGF-$\beta$ indicates transforming growth factor-$\beta$ in active form.

Figure 5:
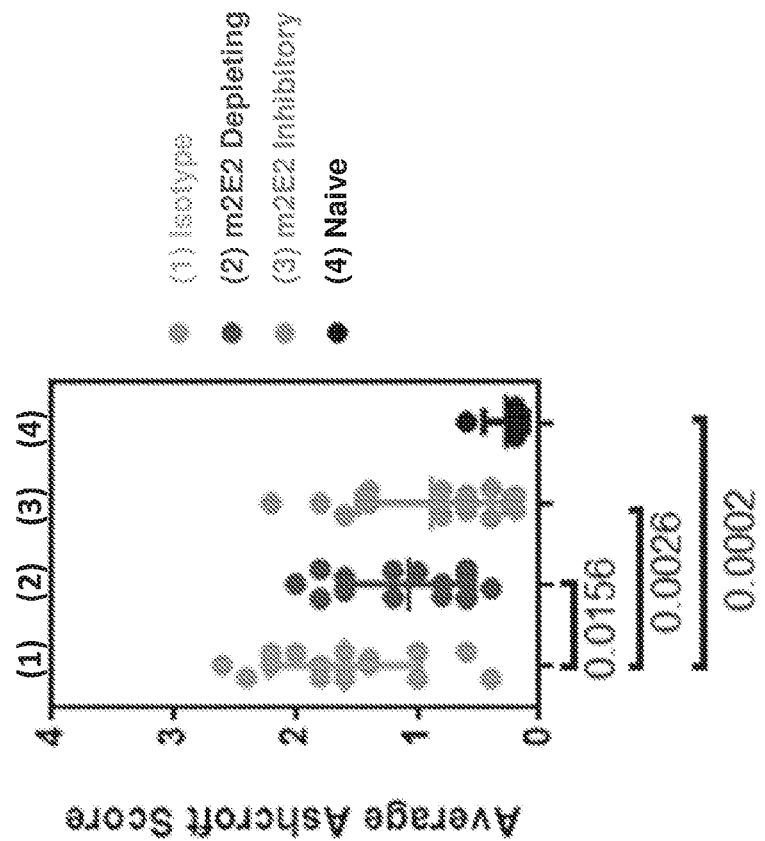

FIG. 5 is a graph showing reduction of an Ashcroft score from lungs of Siglec-8 transgenic mice with bleomycin-induced lung fibrosis due to treatment with anti-Siglec-8 antibodies. (1) Isotype indicates murine IgG1 isotype control antibody; (2) m2E2 Depleting indicates a murine monoclonal anti-Siglec-8 antibody with a murine IgG2a isotype that kills eosinophils and mast cells by ADCC activity; (3) m2E2 Inhibitory indicates a murine monoclonal anti-Siglec-8 antibody with a murine IgG1 isotype that kills eosinophils and inhibits mast cell activity; and (4) Naive indicates Siglec-8 transgenic mice that were not administered an antibody or bleomycin. p-values were determined by comparing the mouse IgG1 isotype control antibody study group to the m2E2 Depleting antibody study group, the m2E2 Inhibitory antibody study group or the naive study group.

Figure 6:
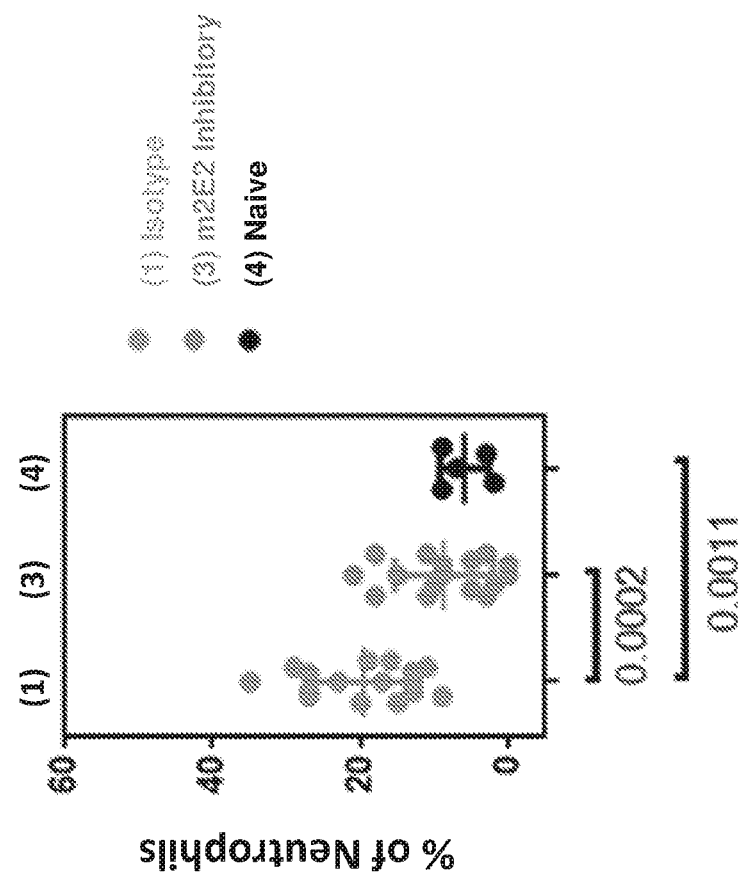

FIG. 6 is a graph showing inhibition of neutrophil influx into the bronchoalveolar space in Siglec-8 transgenic mice with bleomycin-induced lung fibrosis due to therapeutic treatment with anti-Siglec-8 antibodies. (1) Isotype indicates murine IgG1 isotype control antibody; (3) m2E2 Inhibitory indicates a murine monoclonal anti-Siglec-8 antibody with a murine IgG1 isotype that kills eosinophils and inhibits mast cell activity; and (4) Naive indicates Siglec-8 transgenic mice that were not administered an antibody or bleomycin. p-values were determined by comparing the mouse IgG1 isotype control antibody study group to the m2E2 Inhibitory antibody study group or the naive study group. % of neutrophils indicates the percentage of neutrophils relative to the total number of leukocytes in the sample.

Figure 7:
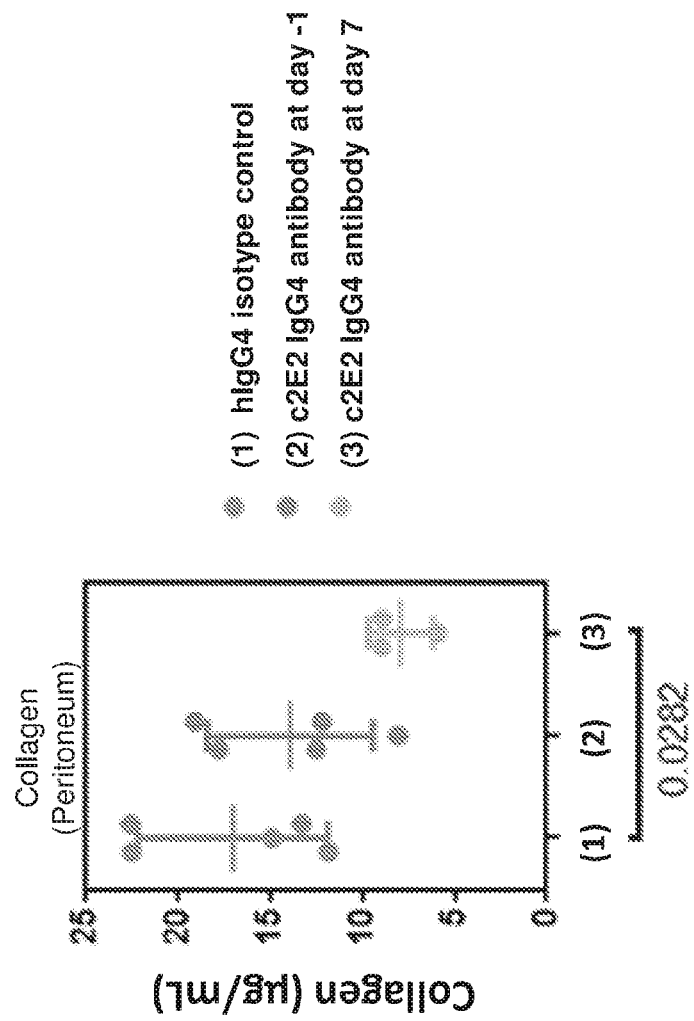

FIG. 7 is a graph showing prevention and inhibition of collagen deposition in humanized mice with foreign body-induced fibrosis in peritoneum due to treatment with anti-Siglec-8 antibodies. (1) hIgG4 isotype control indicates human IgG4 isotype control antibody; (2) c2E2 IgG4 antibody at day −1 indicates a chimeric monoclonal anti-Siglec-8 antibody with a human IgG4 isotype and murine 2E2 variable domains that was dosed one day prior to implantation of beads; (3) c2E2 IgG4 antibody at day 7 indicates a chimeric monoclonal anti-Siglec-8 antibody with a human IgG4 isotype and murine 2E2 variable domains that was dosed seven days after the implantation of beads. p-values were determined by comparing the human IgG4 isotype control antibody study group to the c2E2 IgG4 antibody study groups.

Figure 8:
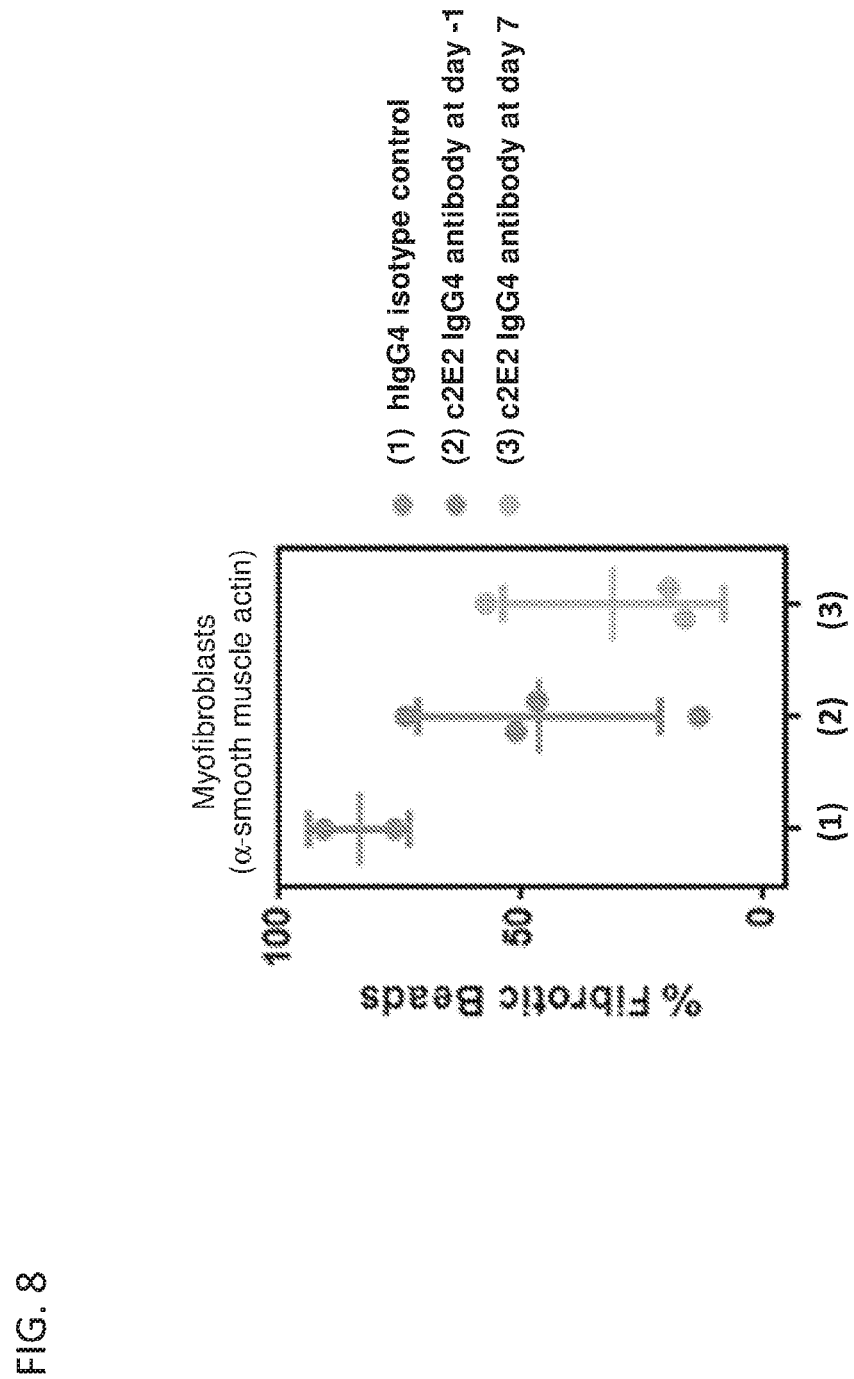

FIG. 8 is a graph showing prevention and inhibition of myofibroblasts accumulation in humanized mice with foreign body-induced fibrosis in peritoneum due to treatment with anti-Siglec-8 antibodies. (1) hIgG4 isotype control indicates human IgG4 isotype control antibody; (2) c2E2 IgG4 antibody at day −1 indicates a chimeric monoclonal anti-Siglec-8 antibody with a human IgG4 isotype and murine 2E2 variable domains that was dosed one day prior to implantation of beads; (3) c2E2 IgG4 antibody at day 7 indicates a chimeric monoclonal anti-Siglec-8 antibody with a human IgG4 isotype and murine 2E2 variable domains that was dosed seven days after the implantation of beads. $\alpha$-smooth muscle actin is a marker for myofibroblasts. % Fibrotic Beads indicates the number of recovered polystyrene beads associated with myofibroblasts.

Figure 9:
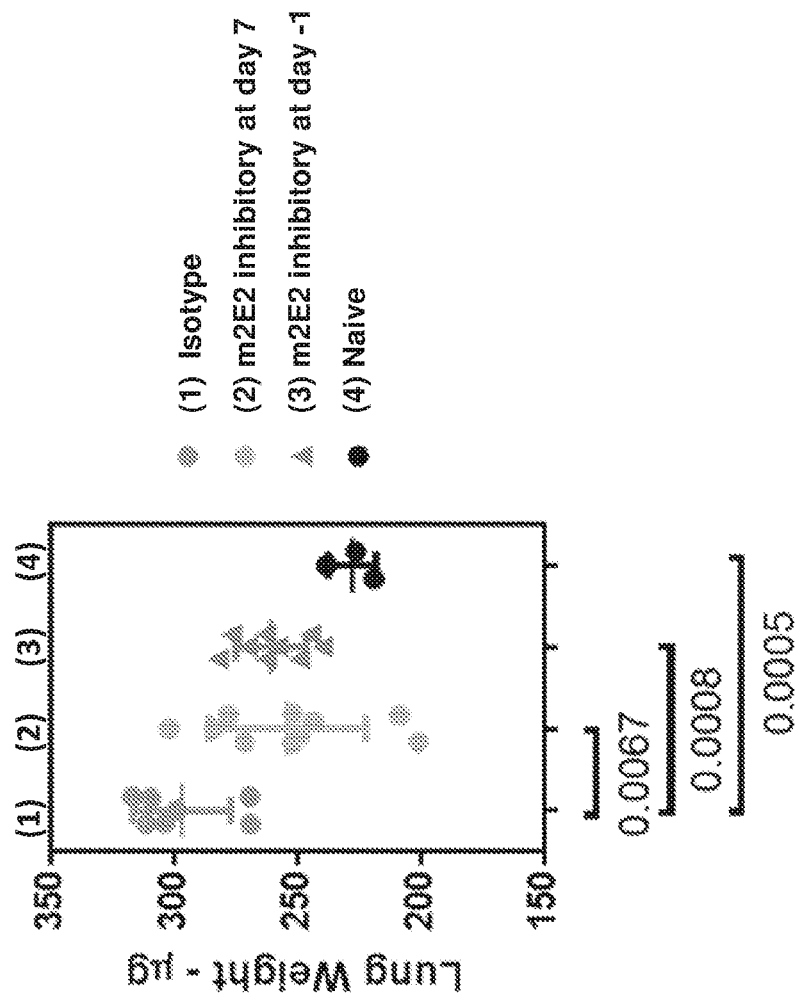

FIG. 9 is a graph showing decreased lung weights in Siglec-8 transgenic mice with bleomycin-induced cutaneous fibrosis that were treated with anti-Siglec-8 antibodies. (1) Isotype indicates murine IgG1 isotype control antibody; (2) m2E2 inhibitory at day 7 indicates a murine monoclonal anti-Siglec-8 antibody with a murine IgG1 isotype that kills eosinophils and inhibits mast cell activity. Mice were dosed starting 7 days after initial bleomycin administration; (3) m2E2 inhibitory at day −1 indicates a murine monoclonal anti-Siglec-8 antibody with a murine IgG1 isotype that kills eosinophils and inhibits mast cell activity. Mice were dosed starting 1 day before initial bleomycin administration; and (4) Naive indicates Siglec-8 transgenic mice that were not administered an antibody or bleomycin. p-values were determined by comparing the mouse IgG1 isotype control antibody study group to the m2E2 inhibitory antibody study group treated at day 7, the m2E2 inhibitory antibody study group treated at day −1 or the naive study group.

Figure 10A:
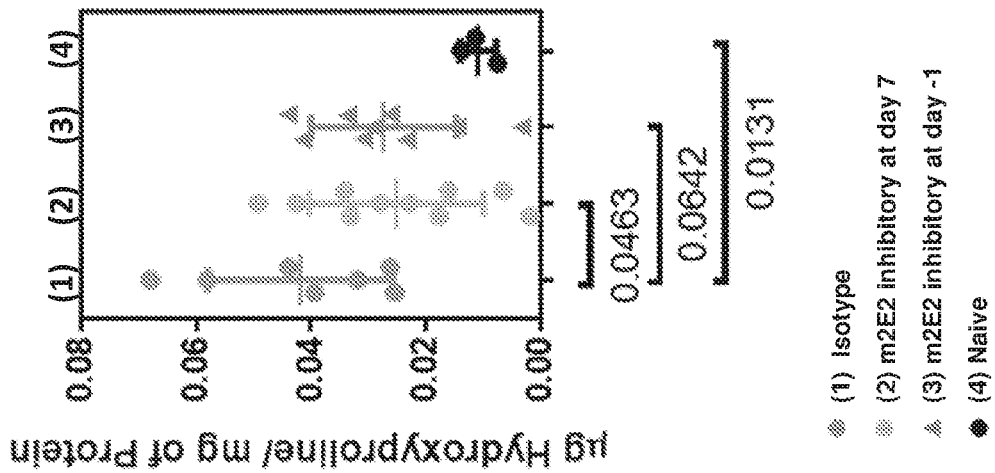
Figure 10B:
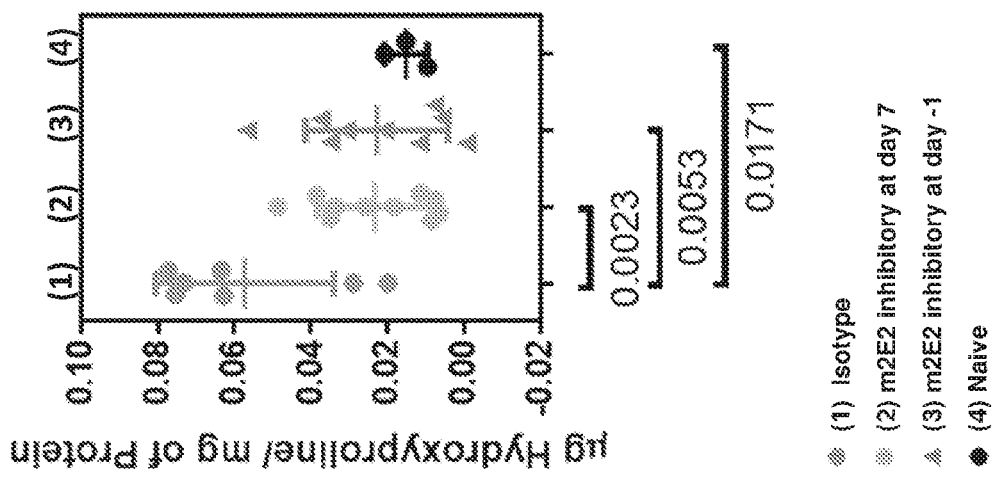

FIGS. 10A and 10B is a series of graphs showing prevention of hydroxyproline accumulation in the skin and lungs of Siglec-8 transgenic mice with bleomycin-induced cutaneous fibrosis due to treatment an anti-Siglec-8 antibody. FIG. 10A) is a graph showing decreased hydroxyproline accumulation in the lung, whereas FIG. 10B) is showing decreased hydroxyproline in the skin of Siglec-8 transgenic mice with bleomycin-induced cutaneous fibrosis. (1) Isotype indicates murine IgG1 isotype control antibody; (2) m2E2 inhibitory at day 7 indicates a murine monoclonal anti-Siglec-8 antibody with a murine IgG1 isotype that kills eosinophils and inhibits mast cell activity. Mice were dosed starting 7 days after initial bleomycin administration; (3) m2E2 inhibitory at day −1 indicates a murine monoclonal anti-Siglec-8 antibody with a murine IgG1 isotype that kills eosinophils and inhibits mast cell activity. Mice were dosed starting 1 day before initial bleomycin administration; and (4) Naive indicates Siglec-8 transgenic mice that were not administered an antibody or bleomycin. p-values were determined by comparing the mouse IgG1 isotype control antibody study group to the m2E2 inhibitory antibody study group treated at day 7, the m2E2 inhibitory antibody study group treated at day −1 or the naive study group.

Figure 11A:
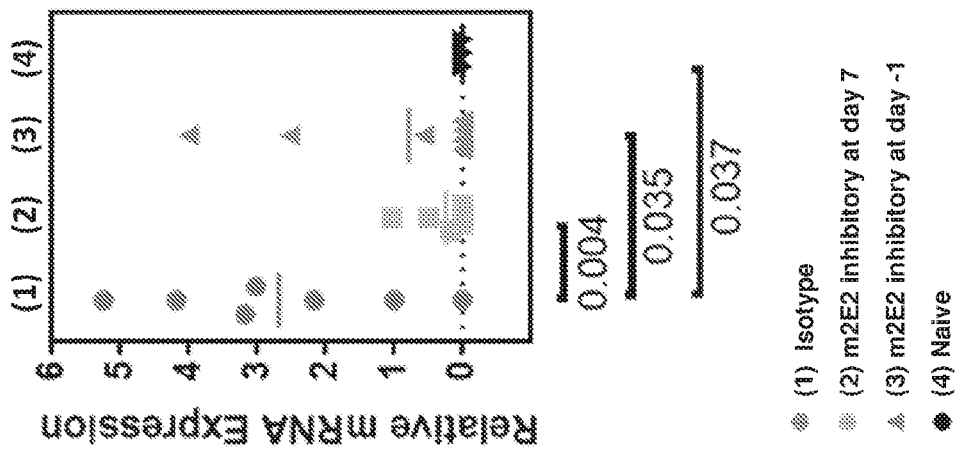
Figure 11B:
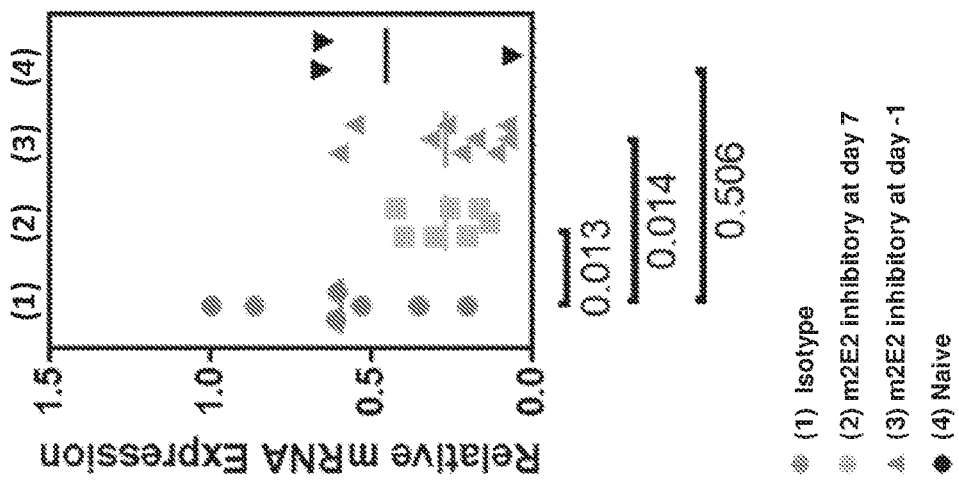

FIGS. 11A and 11B is a series of graphs showing decreased expression of pro-fibrotic mediators in the skin lesion due to treatment with an anti-Siglec-8 antibody in Siglec-8 transgenic mice with bleomycin-induced cutaneous fibrosis. FIG. 11A is a graph showing decreased TGFβ RNA expression and FIG. 11B is a graph showing decreased IL-13 RNA expression in the skin following m2E2 treatment in bleomycin-induced cutaneous fibrosis. IL-13 indicates Interleukin-13; TGFβ indicates transforming growth factor beta; (1) Isotype indicates murine IgG1 isotype control antibody; (2) m2E2 inhibitory at day 7 indicates a murine monoclonal anti-Siglec-8 antibody with a murine IgG1 isotype that kills eosinophils and inhibits mast cell activity. Mice were dosed starting 7 days after initial bleomycin administration; (3) m2E2 inhibitory at day −1 indicates a murine monoclonal anti-Siglec-8 antibody with a murine IgG1 isotype that kills eosinophils and inhibits mast cell activity. Mice were dosed starting 1 day before initial bleomycin administration; and (4) Naive indicates Siglec-8 transgenic mice that were not administered an antibody or bleomycin. p-values were determined by comparing the mouse IgG1 isotype control antibody study group to the m2E2 inhibitory antibody study group treated at day 7, the m2E2 inhibitory antibody study group treated at day −1 or the naive study group.

Figure 12:
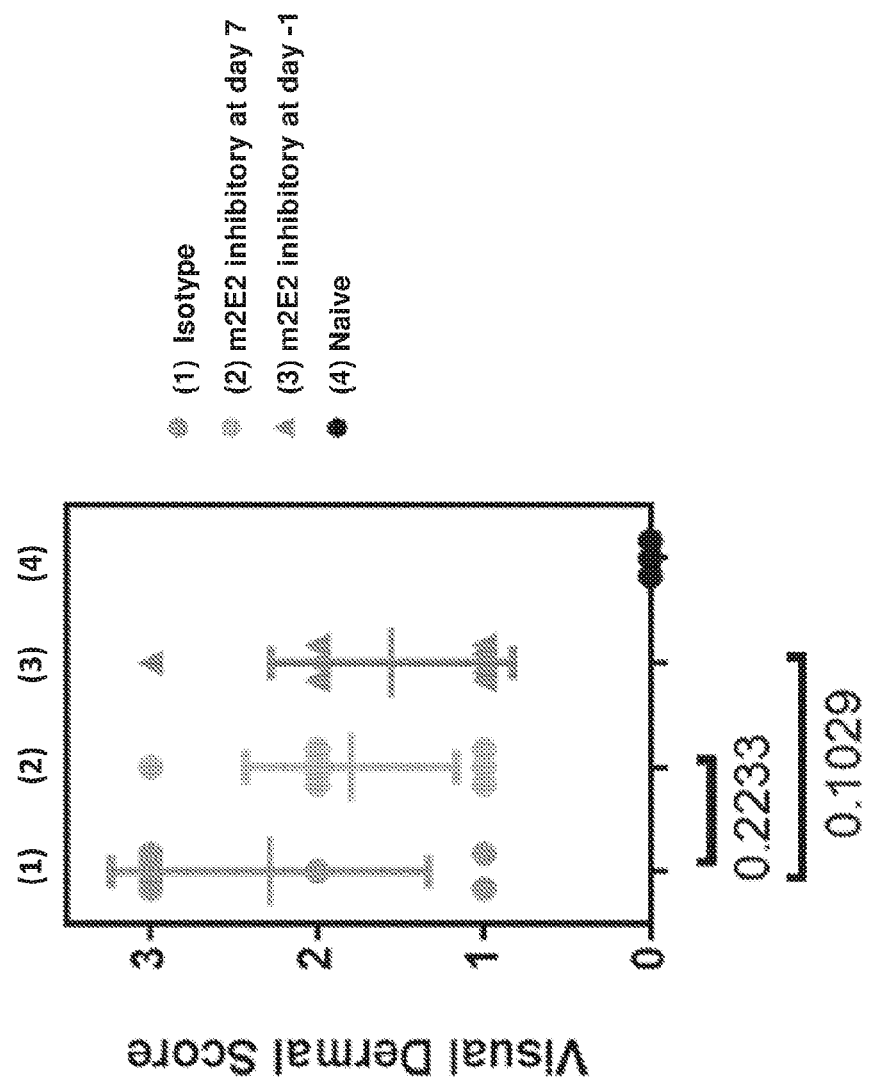

FIG. 12 is a graph showing a decreased trend in the visual dermal score in Siglec-8 transgenic mice with bleomycin-induced cutaneous fibrosis that were treated with anti-Siglec-8 antibodies. (1) Isotype indicates murine IgG1 isotype control antibody; (2) m2E2 inhibitory at day 7 indicates a murine monoclonal anti-Siglec-8 antibody with a murine IgG1 isotype that kills eosinophils and inhibits mast cell activity. Mice were dosed starting 7 days after initial bleomycin administration; (3) m2E2 inhibitory at day −1 indicates a murine monoclonal anti-Siglec-8 antibody with a murine IgG1 isotype that kills eosinophils and inhibits mast cell activity. Mice were dosed starting 1 day before initial bleomycin administration; and (4) Naive indicates Siglec-8 transgenic mice that were not administered an antibody or bleomycin. p-values were determined by comparing the mouse IgG1 isotype control antibody study group to the m2E2 inhibitory antibody study group treated at day 7, the m2E2 inhibitory antibody study group treated at day −1 or the naive study group.

DETAILED DESCRIPTION

I. Definitions

Before describing the invention in detail, it is to be understood that this invention is not limited to particular compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the invention described herein include "comprising," "consisting," and "consisting essentially of" aspects and embodiments.

The term "antibody" includes polyclonal antibodies, monoclonal antibodies (including full length antibodies which have an immunoglobulin Fc region), antibody compositions with polyepitopic specificity, multispecific antibodies (e.g., bispecific antibodies, diabodies, and single-chain antibody molecules, as well as antibody fragments (e.g., Fab, F(ab')$_2$, and Fv). The term "immunoglobulin" (Ig) is used interchangeably with "antibody" herein.

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_H$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., *Basic and Clinical Immunology*, 8th Edition, Daniel P. Sties, Abba I. Terr and Tristram G. Parsolw (eds), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the CH sequence and function, e.g., humans express the following subclasses: IgG1, IgG2, IgG3, IgG4, IgA1 and IgA2. IgG1 antibodies can exist in multiple polymorphic variants termed allotypes (reviewed in Jefferis and Lefranc 2009. *mAbs* Vol 1 Issue 41-7) any of which are suitable for use in the invention. Common allotypic variants in human populations are those designated by the letters a, f, n, z.

An "isolated" antibody is one that has been identified, separated and/or recovered from a component of its production environment (e.g., naturally or recombinantly). In some embodiments, the isolated polypeptide is free of association with all other components from its production environment. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In some embodiments, the polypeptide is purified: (1) to greater than 95% by weight of antibody as determined by, for example, the Lowry method, and in some embodiments, to greater than 99% by weight; (1) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or silver stain. Isolated antibody includes the antibody in situ within recombinant cells since at least one component of the antibody's natural environment will not be present. Ordinarily, however, an isolated polypeptide or antibody is prepared by at least one purification step.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. In some embodiments, monoclonal antibodies have a C-terminal cleavage at the heavy chain and/or light chain. For example, 1, 2, 3, 4, or 5 amino acid residues are cleaved at the C-terminus of heavy chain and/or light chain. In some embodiments, the C-terminal cleavage removes a C-terminal lysine from the heavy chain. In some embodiments, monoclonal antibodies have an N-terminal cleavage at the heavy chain and/or light chain. For example, 1, 2, 3, 4, or 5 amino acid residues are cleaved at the N-terminus of heavy chain and/or light chain. In some embodiments, monoclonal antibodies are highly specific, being directed against a single antigenic site. In some embodiments, monoclonal antibodies are highly specific, being directed against multiple antigenic sites (such as a bispecific antibody or a multispecific antibody). The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method, recombinant DNA methods, phage-display technologies, and technologies for producing human or human-like antibodies in animals that have parts or all of the human immunoglobulin loci or genes encoding human immunoglobulin sequences.

The term "naked antibody" refers to an antibody that is not conjugated to a cytotoxic moiety or radiolabel.

The terms "full-length antibody," "intact antibody" or "whole antibody" are used interchangeably to refer to an antibody in its substantially intact form, as opposed to an antibody fragment. Specifically whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., Protein Eng. 8(10): 1057-1062 [1995]); single-chain antibody molecules and multispecific antibodies formed from antibody fragments.

Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. In some embodiments, the sFv polypeptide further comprises a polypeptide linker between the $V_H$ and $V_L$ domains which enables the sFv to form the desired structure for antigen binding. For a review of the sFv, see Pluckthun in *The Pharmacology of Monoclonal Antibodies*, vol. 113, Rosenburg and Moore eds., Springer-Verlag, New York, pp. 269-315 (1994).

"Functional fragments" of the antibodies of the invention comprise a portion of an intact antibody, generally including the antigen binding or variable region of the intact antibody or the Fv region of an antibody which retains or has modified FcR binding capability. Examples of antibody fragments include linear antibody, single-chain antibody molecules and multispecific antibodies formed from antibody fragments.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is (are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA,* 81:6851-6855 (1984)). Chimeric antibodies of interest herein include PRIMATIZED® antibodies wherein the antigen-binding region of the antibody is derived from an antibody produced by, e.g., immunizing macaque monkeys with an antigen of interest. As used herein. "humanized antibody" is used as a subset of "chimeric antibodies."

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from an HVR of the recipient are replaced by residues from an HVR of a non-human species (donor antibody) such as mouse, rat, rabbit or non-human primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. In some embodiments, the number of these amino acid substitutions in the FR are no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al. *Nature* 321:522-525 (1986); Riechmann et al. *Nature* 332: 323-329 (1988); and Presta, *Curr. Op. Struct. Biol.* 2:593-596 (1992). See also, for example, Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409. In some embodiments, humanized antibodies are directed against a single antigenic site. In some embodiments, humanized antibodies are directed against multiple antigenic sites. An alternative humanization method is described in U.S. Pat. No. 7,981, 843 and U.S. Patent Application Publication No. 2006/0134098.

The "variable region" or "variable domain" of an antibody refers to the amino-terminal domains of the heavy or light chain of the antibody. The variable domains of the heavy chain and light chain may be referred to as "VH" and "VL", respectively. These domains are generally the most variable parts of the antibody (relative to other antibodies of the same class) and contain the antigen binding sites.

The term "hypervariable region," "HVR," or "HV," when used herein refers to the regions of an antibody-variable domain that are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al. *Immunity* 13:37-45 (2000); Johnson and Wu in *Methods in Molecular Biology* 248:1-25 (Lo, ed., Human Press, Totowa, N.J., 2003)). Indeed, naturally occurring camelid antibodies consisting of a heavy chain only are functional and stable in the absence of light chain. See, e.g., Hamers-Casterman et al., *Nature* 363:446-448 (1993) and Sheriff et al., *Nature Struct. Biol.* 3:733-736 (1996).

A number of HVR delineations are in use and are encompassed herein. The HVRs that are Kabat complementarity-determining regions (CDRs) are based on sequence variability and are the most commonly used (Kabat et al., *Sequences of Proteins of Immunological Interest,* 5$^{th}$ Ed. Public Health Service, National Institute of Health, Bethesda, Md. (1991)). Chothia HVRs refer instead to the location of the structural loops (Chothia and Lesk *J. Mol. Biol.* 196:901-917 (1987)). The "contact" HVRs are based on an analysis of the available complex crystal structures. The residues from each of these HVRs are noted below.

| Loop | Kabat | Chothia | Contact |
|---|---|---|---|
| L1 | L24-L34 | L26-L34 | L30-L36 |
| L2 | L50-L56 | L50-L56 | L46-L55 |
| L3 | L89-L97 | L91-L96 | L89-L96 |
| H1 | H31-H35B | H26-H32 | H30-H35B (Kabat Numbering) |
| H1 | H31-H35 | H26-H32 | H30-H35 (Chothia Numbering) |
| H2 | H50-H65 | H53-H56 | H47-H58 |
| H3 | H95-H102 | H95-H102 | H93-H101 |

Unless otherwise indicated, the variable-domain residues (HVR residues and framework region residues) are numbered according to Kabat et al., supra.

"Framework" or "FR" residues are those variable-domain residues other than the HVR residues as herein defined.

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

An "acceptor human framework" for the purposes herein is a framework comprising the amino acid sequence of a VL or VH framework derived from a human immunoglobulin framework or a human consensus framework. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For example, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

An antibody that "binds to", "specifically binds to" or is "specific for" a particular a polypeptide or an epitope on a particular polypeptide is one that binds to that particular polypeptide or epitope on a particular polypeptide without substantially binding to any other polypeptide or polypeptide epitope. In some embodiments, binding of an anti-Siglec-8 antibody described herein (e.g., an antibody that binds to human Siglec-8) to an unrelated non-Siglec-8 polypeptide is less than about 10% of the antibody binding to Siglec-8 as measured by methods known in the art (e.g., enzyme-linked immunosorbent assay (ELISA)). In some embodiments, an antibody that binds to a Siglec-8 (e.g., an antibody that binds to human Siglec-8) has a dissociation constant (Kd) of ≤1 µM, ≤100 nM, ≤10 nM, ≤2 nM, ≤1 nM, ≤0.7 nM, ≤0.6 nM, ≤0.5 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

The term "anti-Siglec-8 antibody" or "an antibody that binds to human Siglec-8" refers to an antibody that binds to a polypeptide or an epitope of human Siglec-8 without substantially binding to any other polypeptide or epitope of an unrelated non-Siglec-8 polypeptide.

The term "Siglec-8" as used herein refers to a human Siglec-8 protein. The term also includes naturally occurring variants of Siglec-8, including splice variants or allelic variants. The amino acid sequence of an exemplary human Siglec-8 is shown in SEQ ID NO:72. The amino acid sequence of another exemplary human Siglec-8 is shown in SEQ ID NO:73. In some embodiments, a human Siglec-8 protein comprises the human Siglec-8 extracellular domain fused to an immunoglobulin Fc region. The amino acid sequence of an exemplary human Siglec-8 extracellular domain fused to an immunoglobulin Fc region is shown in SEQ ID NO:74. The amino acid sequence underlined in SEQ ID NO:74 indicates the Fc region of the Siglec-8 Fc fusion protein amino acid sequence.

Human Siglec-8 Amino Acid Sequence
(SEQ ID NO: 72)
GYLLQVQELVTVQEGLCVHVPCSFSYPQDGWTDSDPVHGYWFRAGDRPYQ

DAPVATNNPDREVQAETQGRFQLLGDIWSNDCSLSIRDARKRDKGSYFFR

LERGSMKWSYKSQLNYKTKQLSVFVTALTHRPDILILGTLESGHSRNLTC

SVPWACKQGTPPMISWIGASVSSPGPTTARSSVLTLTPKPQDHGTSLTCQ

VTLPGTGVTTTSTVRLDVSYPPWNLTMTVFQGDATASTALGNGSSLSVLE

GQSLRLVCAVNSNPPARLSWTRGSLTLCPSRSSNPGLLELPRVHVRDEGE

FTCRAQNAQGSQHISLSLSLQNEGTGTSRPVSQVTLAAVGGAGATALAFL

SFCIIFIIVRSCRKKSARPAAGVGDTGMEDAKAIRGSASQGPLTESWKDG

NPLKKPPPAVAPSSGEEGELHYATLSFHKVKPQDPQGQEATDSEYSEIKI

HKRETAETQACLRNHNPSSKEVRG

Human Siglec-8 Amino Acid Sequence
(SEQ ID NO: 73)
GYLLQVQELVTVQEGLCVHVPCSFSYPQDGWTDSDPVHGYWFRAGDRPYQ

DAPVATNNPDREVQAETQGRFQLLGDIWSNDCSLSIRDARKRDKGSYFFR

LERGSMKWSYKSQLNYKTKQLSVFVTALTHRPDILILGTLESGHPRNLTC

SVPWACKQGTPPMISWIGASVSSPGPTTARSSVLTLTPKPQDHGTSLTCQ

VILPGTGVITTSTVRLDVSYITWNLTMTVFQGDATASTALGNGSSLSVLE

GQSLRINCAVNSNPPARLSWTRGSLTLCPSRSSNPGILELPRVHVRDEGE

FTCRAQNAQGSQHISLSLSLQNEGTGTSRPVSQVTLAAVGGAGATALAFL

SFCIIFIIVRSCRIKSARPAAGVGDTOMEDAKAIROSASQGPLTESWKDG

NPLKKPPPAVAPSSGEEGELHYATLSFHKVKPQDPQGQEATDSEYSEIKI

HKRETAETQACLRNHNPSSKEVRG

Siglec-8 Pc Fusion Protein Amino Acid Sequence
(SEQ ID NO: 74)
GYLLQVQELVTVQEGLCVHVPCSFSYPQDGWTDSDPVHGYWFRAGDRPYQ

DAPVATNNPDREVQAETQGRFQLLGDIWSNDCSISIRDARKRDKGSYFFR

LERGSMICWSYKSQLNYKTKQLSVFWALTHRPDILILGTLESGHSRNLTC

SVPWACKQGTPPMISWIGASVSSPGPTTARSSVETLTPKPQDHGTSLTCQ

VTLPGTGVTTTSTVRLDVSYPPWNLTMTVFQGDATASTALGNGSSLSVLE

GQSLRLVCAVNSNPPARLSWTRGSLTLCPSRSSNPGLLELPRVHVRDEGE

FTCRAQNAQGSQHISLSLSLQNEGTGTSRPVSQVTLAAVGGIEGR<u>SDKTH

TCPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKVS

NKALPAPIEKTISKAKGQPREPQVYTLPPSREEMTKNQVSLTCLVKGFYP

SDIAVEWESNGQPENNYKTTPPVLDSDGSFFLYSKLTVDKSRWQQGNVFS

CSVMHEALHNHYTQKSLSLSPGK</u>

Antibodies that "induce apoptosis" or are "apoptotic" are those that induce programmed cell death as determined by standard apoptosis assays, such as binding of annexin V, fragmentation of DNA, cell shrinkage, dilation of endoplasmic reticulum, cell fragmentation, and/or formation of membrane vesicles (called apoptotic bodies). For example, the apoptotic activity of the anti-Siglec-8 antibodies (e.g., an antibody that binds to human Siglec-8) of the present invention can be showed by staining cells with annexin V.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g. B cell receptors); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., natural killer (NK) cells, neutrophils and macrophages) enable these cytotoxic effector cells to bind specifically to an antigen-bearing target cell and subsequently kill the target cell with cytotoxins. The antibodies "arm" the cytotoxic cells and are required for killing of the target cell by this mechanism. The primary cells for mediating ADCC. NK cells, express FcγRIII only, whereas monocytes express FcγRI, FcγRII and FcγRIII. Fc expression on hematopoietic cells is summarized in Table 3 on page 464 of Ravetch and Kinet, *Annu. Rev. Immunol.* 9: 457-92 (1991). In some embodiments, an anti-Siglec-8 antibody (e.g., an antibody that binds to human Siglec-8) described herein enhances ADCC. To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and natural killer (NK) cells. Alternatively, or additionally, ADCC activity of the molecule of interest may be assessed in vivo, e.g., in an animal model such as that disclosed in Clynes et al., *PNAS USA* 95:652-656 (1998). Other Fc variants that alter ADCC activity and other antibody properties include those disclosed by Ghetie et al., Nat Biotech. 15:637-40, 1997; Duncan et al, Nature 332:563-564, 1988; Lund et al., J. Immunol 147:2657-2662, 1991; Lund et al, Mol Immunol 29:53-59, 1992; Alegre et al, Transplantation 57:1537-1543, 1994; Hutchins et al., Proc Natl. Acad Sci USA 92:11980-11984, 1995; Jefferis et al, Immunol Lett. 44:111-117, 1995; Lund et al., FASEB J9:115-119, 1995; Jefferis et al, Immunol Lett 54:101-104, 1996; Lund et al, J Immunol 157:4963-4969, 1996; Armour et al., Eur J Immunol 29:2613-2624, 1999; Idusogie et al, J Immunol 164:4178-4184, 200; Reddy et al, J Immunol 164:1925-1933, 2000; Xu et al., Cell Immunol 200:16-26, 2000; Idusogie et al, J Immunol 166: 2571-2575, 2001; Shields et al., J Biol Chem 276:6591-6604, 2001; Jefferis et al, Immunol Lett 82:57-65. 2002; Presta et al., Biochem Soc Trans 30:487-490, 2002; Lazar et al., Proc. Natl. Acad. Sci. USA 103:4005-4010, 2006; U.S. Pat. Nos. 5,624,821; 5,885,573; 5,677,425; 6,165,745; 6,277,375; 5,869,046; 6,121,022; 5,624,821; 5,648,260; 6,194,551; 6,737,056; 6,821,505; 6,277,375; 7,335,742; and 7,317,091.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. Suitable native-sequence Fc regions for use in the antibodies of the invention include human IgG1, IgG2, IgG3 and IgG4. A single amino acid substitution (S228P according to Kabat numbering; designated IgG4Pro) may be introduced to abolish the heterogeneity observed in recombinant IgG4 antibody. See Angal, S. et al. (1993) Mol Immunol 30, 105-108.

"Non-fucosylated" or "fucose-deficient" antibody refers to a glycosylation antibody variant comprising an Fc region wherein a carbohydrate structure attached to the Fc region has reduced fucose or lacks fucose. In some embodiments, an antibody with reduced fucose or lacking fucose has improved ADCC function. Non-fucosylated or fucose-deficient antibodies have reduced fucose relative to the amount of fucose on the same antibody produced in a cell line. In some embodiments, a non-fucosylated or fucose-deficient antibody composition contemplated herein is a composition wherein less than about 50% of the N-linked glycans attached to the Fc region of the antibodies in the composition comprise fucose.

The terms "fucosylation" or "fucosylated" refers to the presence of fucose residues within the oligosaccharides attached to the peptide backbone of an antibody. Specifically, a fucosylated antibody comprises α (1,6)-linked fucose at the innermost N-acetylglucosamine (GlcNAc) residue in one or both of the N-linked oligosaccharides attached to the antibody Fc region, e.g. at position Asn 297 of the human IgG1 Fc domain (EU numbering of Fc region residues). Asn297 may also be located about ±3 amino acids upstream or downstream of position 297, i.e. between positions 294 and 300, due to minor sequence variations in immunoglobulins.

The "degree of fucosylation" is the percentage of fucosylated oligosaccharides relative to all oligosaccharides identified by methods known in the art e.g., in an N-glycosidase F treated antibody composition assessed by matrix-assisted laser desorption-ionization time-of-flight mass spectrometry (MALDI TOF MS). In a composition of a "fully fucosylated antibody" essentially all oligosaccharides comprise fucose residues, i.e. are fucosylated. In some embodiments, a composition of a fully fucosylated antibody has a degree of fucosylation of at least about 90%. Accordingly, an individual antibody in such a composition typically comprises fucose residues in each of the two N-linked oligosaccharides in the Fc region. Conversely, in a composition of a "fully non-fucosylated" antibody essentially none of the oligosaccharides are fucosylated, and an individual antibody in such a composition does not contain fucose residues in either of the two N-linked oligosaccharides in the Fc region. In some embodiments, a composition of a fully non-fucosylated antibody has a degree of fucosylation of less than about 10%. In a composition of a "partially fucosylated antibody" only part of the oligosaccharides comprise fucose. An individual antibody in such a composition can comprise fucose residues in none, one or both of the N-linked oligosaccharides in the Fc region, provided that the composition does not comprise essentially all individual antibodies that lack fucose residues in the N-linked oligosaccharides in the Fe region, nor essentially all individual antibodies that contain fucose residues in both of the N-linked oligosaccharides in the Fc region. In one embodiment, a composition of a partially fucosylated antibody has a degree of fucosylation of about 10% to about 80% (e.g., about 50% to about 80%, about 60% to about 80%, or about 70% to about 80%).

"Binding affinity" as used herein refers to the strength of the non-covalent interactions between a single binding site of a molecule (e.g., an antibody) and its binding partner (e.g., an antigen). In some embodiments, the binding affinity of an antibody for a Siglec-8 (which may be a dimer, such as the Siglec-8-Fc fusion protein described herein) can generally be represented by a dissociation constant (Kd). Affinity can be measured by common methods known in the art, including those described herein.

"Binding avidity" as used herein refers to the binding strength of multiple binding sites of a molecule (e.g., an antibody) and its binding partner (e.g., an antigen).

An "isolated" nucleic acid molecule encoding the antibodies herein is a nucleic acid molecule that is identified and separated from at least one contaminant nucleic acid molecule with which it is ordinarily associated in the environment in which it was produced. In some embodiments, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "pharmaceutical formulation" refers to a preparation that is in such form as to permit the biological activity of the active ingredient to be effective, and that contains no additional components that are unacceptably toxic to an individual to which the formulation would be administered. Such formulations are sterile.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin. gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

As used herein, the term "treatment" or "treating" refers to clinical intervention designed to alter the natural course of the individual or cell being treated during the course of clinical pathology. Desirable effects of treatment include decreasing the rate of disease progression, ameliorating or palliating the disease state, and remission or improved prognosis. An individual is successfully "treated", for example, if one or more symptoms associated with a disorder (e.g., a fibrotic disease) are mitigated or eliminated. For example, an individual is successfully "treated" if treatment results in increasing the quality of life of those suffering from a disease, decreasing the dose of other medications required for treating the disease, reducing the frequency of recurrence of the disease, lessening severity of the disease, delaying the development or progression of the disease, and/or prolonging survival of individuals.

As used herein, "in conjunction with" refers to administration of one treatment modality in addition to another treatment modality. As such, "in conjunction with" refers to administration of one treatment modality before, during or after administration of the other treatment modality to the individual.

As used herein, the term "prevention" or "preventing" includes providing prophylaxis with respect to occurrence or recurrence of a disease in an individual. An individual may be predisposed to, susceptible to a disorder, or at risk of developing a disorder, but has not yet been diagnosed with the disorder. In some embodiments, anti-Siglec-8 antibodies (e.g., an antibody that binds to human Siglec-8) described herein are used to delay development of a disorder (e.g. a fibrotic disease).

As used herein, an individual "at risk" of developing a disorder (e.g., a fibrotic disease) may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of the disease (e.g., a fibrotic disease), as known in the art. An individual having one or more of these risk factors has a higher probability of developing the disorder than an individual without one or more of these risk factors.

An "effective amount" refers to at least an amount effective, at dosages and for periods of time necessary, to achieve the desired or indicated effect, including a therapeutic or prophylactic result. An effective amount can be provided in one or more administrations. A "therapeutically effective amount" is at least the minimum concentration required to effect a measurable improvement of a particular disorder. A therapeutically effective amount herein may vary according to factors such as the disease state, age, sex, and weight of the patient, and the ability of the antibody to elicit a desired response in the individual. A therapeutically effective amount may also be one in which any toxic or detrimental effects of the antibody are outweighed by the therapeutically beneficial effects. A "prophylactically effective amount" refers to an amount effective, at the dosages and for periods of time necessary, to achieve the desired prophylactic result. Typically but not necessarily, since a prophylactic dose is used in individuals prior to or at the earlier stage of disease, the prophylactically effective amount can be less than the therapeutically effective amount.

"Chronic" administration refers to administration of the medicament(s) in a continuous as opposed to acute mode, so as to maintain the initial therapeutic effect (activity) for an extended period of time. "Intermittent" administration is treatment that is not consecutively done without interruption, but rather is cyclic in nature.

As used herein, an "individual" or a "subject" is a mammal. A "mammal" for purposes of treatment includes humans, domestic and farm animals, and zoo, sports, or pet animals, such as dogs, horses, rabbits, cattle, pigs, hamsters, gerbils, mice, ferrets, rats, cats, etc. In some embodiments, the individual or subject is a human.

II. Compositions and Methods

A. Methods of the Invention

Provided herein are methods for treating or preventing a fibrotic disease (e.g., idiopathic pulmonary fibrosis) in an individual comprising administering to the individual an effective amount of an antibody described herein that binds to human Siglec-8 (e.g., an anti-Siglec-8 antibody), or compositions thereof. Also provided herein are methods for treating or preventing a fibrotic disease (e.g., idiopathic pulmonary fibrosis) in an individual comprising administering to the individual an effective amount of an agonist described herein that binds to human Siglec-8 (e.g., a 6'-sulfo-sLe$^X$-containing agonist or agonist antibodies), or compositions thereof. In some embodiments, the individual (e.g., a human) has been diagnosed with a fibrotic disease (e.g., idiopathic pulmonary fibrosis) or is at risk of developing the fibrotic disease. Non-limiting examples of fibrotic diseases that are treatable with the antibodies and agonists, and compositions thereof, of the present invention include pulmonary fibrosis (e.g., idiopathic pulmonary fibrosis), hepatic fibrosis (e.g., cirrhosis), renal fibrosis (e.g., renal interstitial fibrosis), cardiac fibrosis (e.g., endomyocardial fibrosis and atrial fibrosis), spleen fibrosis, ocular fibrosis, mechanical-induced fibrosis (e.g., ventilator-induced pulmonary fibrosis), implant-induced fibrosis, radiation-induced fibrosis, drug-induced fibrosis (e.g., bleomycin-induced pulmonary fibrosis), viral-induced fibrosis, cystic fibrosis, cancer-associated fibrosis, atherosclerosis, bone marrow fibrosis (e.g., myelofibrosis), scleroderma (e.g., systemic sclerosis), mediastinal fibrosis and retroperitoneal cavity fibrosis. In some embodiments, the fibrotic disease is a mast cell-mediated disorder.

Also provided herein are methods for treating or preventing a pre-fibrotic disease (e.g., chronic hypersensitivity pneumonitis) in an individual comprising administering to the individual an effective amount of an antibody described herein that binds to human Siglec-8 (e.g., an anti-Siglec-8 antibody), or compositions thereof. Also provided herein are methods for treating or preventing a pre-fibrotic disease (e.g., chronic hypersensitivity pneumonitis) in an individual comprising administering to the individual an effective amount of an agonist described herein that binds to human Siglec-8 (e.g., a 6'-sulfo-sLe$^X$-containing agonist or agonist antibodies), or compositions thereof. In some embodiments, the individual (e.g., a human) has been diagnosed with a pre-fibrotic disease (e.g., chronic hypersensitivity pneumonitis) or is at risk of developing a fibrotic disease (e.g. idiopathic pulmonary fibrosis). Non-limiting examples of pre-fibrotic diseases that are treatable with the antibodies and agonists, and compositions thereof, of the present invention include bleomycin-induced pneumonitis, chronic hypersensitivity pneumonitis, polycythemia vera, essential thrombocythemia, age-related macular degeneration, diabetic retinopathy, neovascular glaucoma, retinopathy of prematurity, and proliferative vitreoretinopathy. In some embodiments, the pre-fibrotic disease is a mast cell-mediated disorder.

Fibrotic disease is characterized by excessive connective tissue accumulation and tissue contraction that can lead to progressive deterioration in the normal structure and function of organs and tissues. Fibrotic disease generally arises due to a normal wound-healing process that has gone awry. After tissue injury, the normal wound-healing process involves epithelial and/or endothelial cells which release inflammatory mediators that initiate an antifibrinolytic-coagulation cascade, which triggers blood clot formation. This is followed by an inflammatory and proliferative phase, wherein leukocytes are recruited and then activated and induced to proliferate by chemokines and growth factors. The activated leukocytes secrete profibrotic cytokines such as IL-13 and TGF-β. Stimulated epithelial cells, endothelial cells, and myofibroblasts also produce matrix metalloproteinases (MMPs), and additional cytokines and chemokines that recruit and activate neutrophils, macrophages, T cells, B cells, and eosinophils, which are important components of reparative tissue. Shortly after the initial inflammatory phase, myofibroblasts produce extracellular matrix (ECM) components, and endothelial cells form new blood vessels. In the subsequent remodeling phase, the activated myofibroblasts stimulate wound contraction. Collagen fibers also become more organized, blood vessels are restored to normal, scar tissue is eliminated, and epithelial and/or endothelial cells divide and migrate over the basal layers to regenerate the epithelium or endothelium, respectively, restoring the damaged tissue to its normal appearance. In the case of chronic wounds, this normal wound-healing process is disrupted. Persistent inflammation, tissue necrosis, and infection lead to chronic myofibroblast activation and excessive accumulation of ECM components, which promotes the formation of a fibrotic scar. See Wynn T. A., *J Clin Invest.*, 2007, 114(3):524-529. There are many fibrotic diseases of the organs and tissues that are caused by a variety of injuries. Injuries that lead to fibrosis include, but are not limited to, infection by an infectious agent (e.g., bacteria, virus, fungi and multicellular parasites), mechanical stress (e.g., respiratory ventilator), exposure to environmental agents (e.g., dust, mold, asbestos, etc.), radiation exposure, drug exposure (e.g., chemotherapeutic drugs), and pre-fibrotic diseases that are characterized by chronic injury that leads to abnormal wound healing of tissues and/or organs. Although the there are various types of fibrotic diseases, they all contain a common hallmark of disease that is well known to one of skill in the art, accumulation of excess ECM components. See Wynn et al. *Nature Medicine*, 2012, 18:1028-1040.

In some embodiments, provided herein is a method for treating or preventing fibrotic disease of an organ in an individual comprising administering to the individual an effective amount of an antibody (e.g., an anti-Siglec-8 antibody) or an agonist (e.g., a 6'-sulfo-sLe$^X$-containing agonist) that binds to human Siglec-8. In some embodiments, the fibrotic disease of an organ is selected from the group consisting of: pulmonary fibrosis, hepatic fibrosis, renal fibrosis, cardiac fibrosis, spleen fibrosis, and ocular fibrosis. In some embodiments, the pulmonary fibrosis is, but is not limited to, idiopathic pulmonary fibrosis (IPF), idiopathic nonspecific interstitial pneumonitis (NSIP), cryptogenic organizing pneumonia (COP), Hamman-Rich syndrome (also known as acute interstitial pneumonia), lymphocytic interstitial pneumonitis (LIP), respiratory bronchiolitis interstitial lung disease, desquamative interstitial pneumonitis or idiopathic lymphoid interstitial pneumonia, or idiopathic pleuroparenchymal fibroelastosis. In some embodiments, the pulmonary fibrosis is idiopathic pulmonary fibrosis. In some embodiments, the pulmonary fibrosis is associated with chronic obstructive pulmonary disease. In some embodiments, the hepatic fibrosis is, but is not limited to, cirrhosis, alcohol-induced hepatic fibrosis, hepatitis C virus (HCV)-induced hepatic fibrosis, hepatitis B virus (HBV)-induced fibrosis, or nonalcoholic steatohepatitis. In some embodiments, the renal fibrosis is, but is not limited to, renal interstitial fibrosis or glomerulosclerosis. In some embodiments, the cardiac fibrosis is, but is not limited to, endomyocardial fibrosis or atrial fibrosis.

In some embodiments, provided herein is a method for treating or preventing fibrotic disease induced by an environmental agent in an individual comprising administering to the individual an effective amount of an antibody (e.g. an anti-Siglec-8 antibody) or an agonist (e.g., a 6'-sulfo-sLe$^X$-containing agonist) that binds to human Siglec-8. In some embodiments, the fibrotic disease induced by an environmental agent is selected from the group consisting of: mechanical-induced fibrosis, implant-induced fibrosis, radiation-induced fibrosis, drug-induced fibrosis, and viral-induced fibrosis. In some embodiments, the mechanical-induced fibrosis is, but is not limited to, ventilator-induced pulmonary fibrosis. In some embodiments, the drug-induced fibrosis is, but is not limited to, bleomycin-induced pulmonary fibrosis, methotrexate-induced fibrosis, and cyclophosphamide-induced fibrosis, amiodarone-induced fibrosis, propranolol-induced fibrosis, nitrofurantoin-induced fibrosis, and sulfasalazine-induced fibrosis. In some embodiments, the viral-induced fibrosis is, but is not limited to, HCV-induced fibrosis. HBV-induced fibrosis, TT virus-induced fibrosis, adenovirus-induced fibrosis, human cytomegalovirus-induced fibrosis, and Epstein-Barr virus-induced fibrosis.

In some embodiments, provided herein is a method for treating or preventing fibrotic disease in an individual comprising administering to the individual an effective amount of an antibody (e.g., an anti-Siglec-8 antibody) or an agonist (e.g., a 6'-sulfo-sLe$^x$-containing agonist) that binds to human Siglec-8. In some embodiments herein, the fibrotic disease is selected from the group consisting of: cystic fibrosis, cancer-associated fibrosis, atherosclerosis, bone marrow fibrosis, scleroderma, mediastinal fibrosis and retroperitoneal cavity fibrosis. In some embodiments, the fibrotic disease is associated with a cancer (i.e., a cancer-associated fibrosis). In some embodiments, the cancer is, but is not limited to, sarcomas such as fibrosarcoma, malignant fibrous histiocytoma, liposarcoma, rhabdomyosarcoma, leiomyosarcoma, angiosarcoma, Kaposi's sarcoma, lymphangiosarcoma, synovial sarcoma, chondrosarcoma, and osteosarcoma, brain tumor, head and neck carcinoma, breast carcinoma, lung carcinoma, esophageal carcinoma, stomach carcinoma, duodenal carcinoma, appendiceal carcinoma, colon carcinoma, rectal carcinoma, hepatic carcinoma, pancreatic carcinoma, gallbladder carcinoma, bile duct carcinoma, anal carcinoma, kidney carcinoma, ureteral carcinoma, bladder carcinoma, prostate carcinoma, penile carcinoma, testicular carcinoma, uterine carcinoma, ovarian carcinoma, vulvar carcinoma, vaginal carcinoma, and skin carcinoma and, furthermore, leukemia, or malignant lymphoma. In some embodiments, the cancer-associated fibrosis is present at, but not limited to, the brain, head and neck, breast, limbs, lung, heart, thymus, esophagus, stomach, small intestine (duodenum, jejunum, ileum), large intestine (colon, cecum, appendix, rectum), liver, pancreas, gallbladder, anus, kidney, ureter, bladder, prostate, penis, testis, uterus, ovary, vulva, vagina, skin, striated muscle, smooth muscle, synovial membrane, cartilage, bone, thyroid, adrenal gland, peritoneum, mesentery, bone marrow, blood, vascular system, lymphatic system such as lymph nodes, or lymphatic fluid. See U.S. Pat. No. 8,686,052. In some embodiments, the fibrotic disease is a bone marrow fibrosis. In a further embodiment, the bone marrow fibrosis is, but is not limited to, myelofibrosis. In some embodiments, the fibrotic disease is scleroderma. In a further embodiment, the scleroderma is localized scleroderma or systemic scleroderma. In a further embodiment, the scleroderma is, but is not limited to, systemic morphea, linear scleroderma, systemic sclerosis, limited scleroderma or diffuse scleroderma. In some embodiments, the fibrotic disease is Dupuytren's contracture.

Types of fibrotic disease and methods of diagnosing fibrotic disease are well known to one of skill in the art. For example, symptoms of idiopathic pulmonary fibrosis (IPF) include, but are not limited to, shortness of breath, dry cough, weight loss, fatigue, malaise, muscle pain, joint pain, and finger and toe clubbing. IPF disease progression can be monitored with techniques such as high-resolution CT (HRCT) scanning. In a diagnosis by HRCT, the presence of the following characteristics is noted: (1) presence of reticular abnormality and/or traction bronchiectasis with basal and peripheral predominance; (2) presence of honeycombing with basal and peripheral predominance; and (3) absence of atypical features such as micronodules, peribronchovascular nodules, consolidation, isolated (non-honeycomb) cysts, ground glass attenuation (or, if present, is less extensive than reticular opacity), and mediastinal adenopathy (or, if present, is not extensive enough to be visible on chest x-ray). A diagnosis of definite IPF is made if characteristics (1), (2), and (3) are met. A diagnosis of probable IPF is made if characteristics (1) and (3) are met. Pulmonary function can also be monitored in IPF patients to determine progression of disease. Pulmonary function values are well known in the art. The following is an example of pulmonary function values that may be used. The values include, but are not limited to, vital capacity (VC), residual volume (V), forced expiratory volume ($FEV_1$), forced vital capacity (FVC), forced expiratory flow (FEF), peak expiratory flow rate (PEFR), inspiratory reserve volume (IRV), functional residual capacity (FRC), inspirator capacity (IC), total lung capacity (TLC), expiratory reserve volume (ERV), tidal volume (TV) and maximum voluntary ventilation (MVV). $FEV_1$ measures the volume of air exhaled over a pre-determined period of time by a forced expiration immediately after a full inspiration. FVC measures the total volume of air exhaled immediately after a full inspiration. FEF measures the volume of air exhaled during a FVC divided by the time in seconds. PEFR measures the maximum flow rate during a forced exhale starting from full inspiration. V is the volume of air remaining in the lungs after a full expiration. Lung volumes are usually reduced as IPF progresses. Lung volumes can be measured by determining functional residual capacity (FRC), total lung capacity (TLC), and residual value (V). Patients with IPF also develop more rapid shallow breaths as the diseases progresses, and therefore the work of breathing is increased. Expiratory flow rates, forced expiratory volume ($FEV_1$), and forced vital capacity (FVC) are often decreased because of the reduction in lung volume, but the $FEV_1$-to-FVC ration is maintained or increased in IPF. Gas exchange at rest and during exercise as well as pulmonary hemodynamics can also be pulmonary functions that are tested to diagnose and monitor IPF. See *American Journal of Respiratory and Critical Care Medicine,* 2000, 161(2):646-664; Travis et al., *Am J Respir Crit Care Med,* 2013, 188(6):733-748; and U.S. Pat. No. 8,247,379.

As another example of fibrotic disease, pulmonary fibrosis can be associated with chronic obstructive pulmonary disease (COPD). COPD is characterized by the presence of chronic bronchitis and/or emphysema. Lung tissue remodeling in COPD involves processes such as epithelial disruption, smooth muscle hypertrophy, smooth muscle hyperplasia, airway wall fibrosis, and alveolar destruction. See Salazar et al., *Lung,* 2011, 189(2):101-109. In addition to some individuals with COPD having fibrosis due to lung tissue remodeling, a subpopulation of individuals with COPD can also have pulmonary fibrosis. For example, idiopathic pulmonary fibrosis (IPF) is now recognized to co-exist with COPD with a recent study finding the prevalence of IPF in people with COPD is as high as 6%. See Divo et al., *Am J Respir Crit Care Med.,* 2012, 186(2):155-161. Variants of pulmonary fibrosis associated with emphysema have also been described, also known as combined pulmonary fibrosis and emphysema (CPFE), which is characterized by extertional dyspnea, upper-lobe emphysema and lower-lobe fibrosis, preserved lung volume, diminished capacity of gas exchange and poor survival. See Cottin et al., *Eur. Respir. J.,* 2005, 26(4):586-593.

As another representative example of fibrotic disease, hepatic fibrosis can be diagnosed by assessing liver enzyme levels that have been traditionally used to assess liver disease, such as serum alanine aminotransferase (ALT) and aspartate amino transferase (AST). An AST/ALT (AAR) ration of >1 is predictive of cirrhosis. See Bataller et al., *J Clin Invest.,* 2005, 115(2):209-218.

In another example, in cardiac fibrosis, fibrotic tissues accumulate in the heart and blood vessels as a result of hypertension, hypertensive heart disease, atherosclerosis, and myocardial infarction. These cardiovascular diseases all exhibit an accumulation of extracellular matrix or fibrotic deposition which results in stiffening of the vasculature and stiffening of the cardiac tissue itself. Typically the symptoms of cardiac fibrosis relate to the specific chambers and valves where the disease is most extensive. Symptoms of cardiac fibrosis include, but are not limited to, lower extremity swelling, increasing abdominal girth, dyspnea, fatigue, nausea, chest pain, palpitations and fainting. See U.S. Pat. No. 8,461,303.

In another example of fibrotic disease, individuals may require mechanical ventilation to improve oxygenation and facilitate organ repair when recovering from illnesses such as sepsis, acute lung injury and acute respiratory distress syndrome. Evidence from experimental and clinical studies suggests that mechanical ventilation can cause lung fibrosis. There is a need to prevent or treat pulmonary fibrosis associated with mechanical ventilation. Mechanical, drug (e.g., bleomycin), and radiation-induced fibrosis exhibit similar cellular mechanisms, namely activated myofibroblasts which produce collagen. This indicates that a therapeutic agent that can effectively treat drug-induced fibrosis can be effective for treating mechanical-induced fibrosis and radiation-induced fibrosis. See Cabrera-Benitez et al., *Anesthesiology,* 2014, 121:189-198; Villar et al., *Critical Care,* 2015, 19:138; and Schaefer et al., *Eur Respir Rev.,* 2011, 20(120):85-97.

In another example of fibrotic disease, implant-induced fibrosis occurs when an implant is placed in the body and encounters a foreign body response from the surrounding host tissue. The response is characterized by the infiltration of inflammatory cells to the area to destroy or remove the implant, followed by the repair and regeneration of injured tissue. If the implant cannot be removed, the inflammatory response persists until the implant becomes encapsulated in a layer of fibrotic connective tissue that shields it from the immune system. Fibrosis due to the implant or fibrous encapsulation of the implant can compromise the efficiency of the implant and can lead to implant failure. See Rolfe B. et al., Regenerative Medicine and Tissue Engineering-Cells and Biomaterials, *InTech,* 2011, pages 551-568. In some embodiments, implant-induced fibrosis occurs in an individual after the individual has been implanted with an implant during a medical procedure. In some embodiments, implant-induced fibrosis occurs in an individual after the individual has been implanted with an implant during a cosmetic procedure. An implant contemplated herein includes, but is not limited to, an implant used for cosmetic surgery (e.g., breast augmentation, breast reconstruction, etc.), joint replacement surgery (e.g. hip joint replacement, knee joint replacement, shoulder joint replacement, ankle joint replacement, etc.), hernia repair surgery, graft surgery (e.g., artificial vascular graft surgery, skin graft surgery, etc.), stent placement, organ transplant surgery, neurosurgery, heart surgery, or any other medical surgery. An implant contemplated herein also includes, but is not limited to, an orthopedic implant, a dental implant, a breast implant, a chin implant, a cheek implant, a buttock implant, nose implant, penile implant, a pacemaker, a suture, a graft (e.g., a vascular graft, skin graft, a bone graft, etc.), a heart valve, intraocular lens, a controlled drug delivery device, a biosensor, a stent (e.g., gastrointestinal stent, tracheal stent, bronchial stent, urinary stent, ear stent, nose stent, etc.), a surgical mesh or film, a biomaterial, a medical device, a catheter, glaucoma drainage device, a pressure monitor device, contraceptive implant, an artificial joint, an organ transplant (e.g., kidney transplant, lung transplant, heart transplant, etc.) or any other medical implant or cosmetic implant. In some embodiments, the graft is an autograft, an isograft, an allograft or a xenograft. In some embodiments, the antibody (e.g., an anti-Siglec-8 antibody) or an agonist (e.g., a 6'-sulfo-sLe$^X$-containing agonist) that binds to human Siglec-8 contemplated herein can be administered to an individual before and/or after implantation of an implant contemplated herein in the individual. In some embodiments, the antibody (e.g., an anti-Siglec-8 antibody) or an agonist (e.g., a 6'-sulfo-sLe$^X$-containing agonist) that binds to human Siglec-8 contemplated herein can be administered to an individual during implantation of an implant contemplated herein in the individual. In some embodiments, the antibody (e.g., an anti-Siglec-8 antibody) or an agonist (e.g., a 6'-sulfo-sLe$^X$-containing agonist) that binds to human Siglec-8 contemplated herein can be administered to an individual at about the same time the individual is implanted with an implant contemplated herein. In some embodiments, an implant contemplated herein can be coated with the antibody (e.g., an anti-Siglec-8 antibody) or an agonist (e.g., a 6'-sulfo-sLe$^X$-containing agonist) that binds to human Siglec-8. In some embodiments, an implant contemplated herein can be embedded with the antibody (e.g., an anti-Siglec-8 antibody) or an agonist (e.g., a 6'-sulfo-sLe$^X$-containing agonist) that binds to human Siglec-8.

In another example of fibrotic disease, scleroderma is an autoimmune, rheumatic, and chronic disease that affects the body by hardening of connective tissue, such as in the skin, fingers or toes, digestive system, heart, lungs and kidneys. There are two major types of scleroderma, localized scleroderma and systemic scleroderma. Skin lesions appear in both types of scleroderma and appear in different shapes and colors. Skin lesions are considered to be a part of the skin that has an abnormal growth or appearance compared to the skin around it. Morphea, a form of localized scleroderma, is characterized by waxy patches on the skin of various sizes and color. Linear scleroderma, also a form of localized scleroderma, starts as a streak or line of hardened waxy skin, usually on an arm, leg or head and neck area. In systemic sclerosis, hardening of connective tissue can occur in the internal systems of the body and result in major organ dysfunction. Limited scleroderma or diffuse scleroderma are two types of systemic sclerosis and are based on the extent of skin tightening. See LeRoy et al., *J Rheumatol.,* 1988, 15:202-205. In limited scleroderma, skin tightening is confined to the fingers, hands, and forearms distal to the elbows, with or without tightening of skin of the feet and of the legs distal to the knees. In diffuse disease, the skin of the proximal extremities and trunk is also involved. Symptoms of scleroderma can include, but are not limited to, joint pain, skin rashes, swollen blood vessels in the skin, skin ulcers, weight loss, tightened and hardened fingers, acid reflux, chronic cough, difficulty swallowing, dry mouth, fatigue, headache, joint stiffness, sensitivity to cold, or shortness of breath. In some of the embodiments herein, the fibrotic disease is scleroderma. In a further embodiment, the scleroderma is localized scleroderma or systemic scleroderma. In another further embodiment, the scleroderma is, but is not limited to, systemic morphea, linear scleroderma, systemic sclerosis, limited scleroderma or diffuse scleroderma.

In some embodiments, provided herein is a method for treating or preventing pre-fibrotic disease in an individual comprising administering to the individual an effective amount of an antibody (e.g., an anti-Siglec-8 antibody) or an agonist (e.g., a 6'-sulfo-sLe$^X$-containing agonist) that binds to human Siglec-8. In some embodiments, the pre-fibrotic disease is bleomycin-induced pneumonitis. In some embodiments, the pre-fibrotic disease is chronic hypersensitivity pneumonitis. In some embodiments, the pre-fibrotic disease is polycythemia vera. In some embodiments, the pre-fibrotic disease is essential thrombocythemia. In some embodiments, the pre-fibrotic disease is a pre-fibrotic disease of the eye. In some embodiments, the pre-fibrotic disease is selected from the group consisting of: age-related macular degeneration, diabetic retinopathy, neovascular glaucoma, retinopathy of prematurity, and proliferative vitreoretinopathy.

Types of pre-fibrotic disease and methods of diagnosing pre-fibrotic disease are well known to one of skill in the art. Pre-fibrotic disease as contemplated herein includes a disease that results in an individual to be more susceptible to or be at risk of developing a fibrotic disease, such as a fibrotic disease contemplated herein. For example, chronic hypersensitivity pneumonitis is a pre-fibrotic disease in which lungs become inflamed from breathing in foreign substances such as mold, dust, and chemicals. Symptoms of chronic hypersensitivity pneumonitis include, but are not limited to, cough, shortness of breath, fatigue, weight loss, and finger or toe clubbing. Chronic hypersensitivity pneumonitis can cause long-term lung damage such as pulmonary fibrosis.

In another example of pre-fibrotic disease, polycythemia vera is a pre-fibrotic disease of the bone marrow that leads to an abnormal increase in the number of blood cells. Symptoms of polycythemia vera include, but are not limited to, trouble breathing when lying down, dizziness, excess bleeding, full feeling in the left upper abdomen due to enlarged spleen, headache, itchiness, red skin coloring, shortness of breath, bluish skin color, fatigue, red skin spots, vision problems, and phlebitis. A complication of polycythemia vera is the development of the fibrotic disease, myelofibrosis, a progressive bone marrow disorder that results in bone marrow scarring, severe anemia, and enlargement of liver and spleen.

In another representative example of pre-fibrotic disease, essential thrombocythemia is a pre-fibrotic disease in which the body produces too many blood platelets. Symptoms of essential thrombocythemia include, but are not limited to, headache, dizziness, chest pain, weakness, fainting, temporary vision changes, numbness or tingling of the hands and feet, pain in hands and feet, mildly enlarged spleen, nosebleeds, bruising, bleeding from mouth and gums, and bloody stool. A complication of essential thrombocythemia is the development of the fibrotic disease, myelofibrosis.

The retina of the eye consists of multiple layers of neurons, blood vessels, ECM, and various resident and transient cells such as glial cells and monocytes. The vascular supply of the retina consists of the retinal blood vessels and the choriocapillaris. The photoreceptors are in the outermost portion of the neurosensory retina and rest on a monolayer of cells, the retinal pigmented epithelium (RPE). The RPE rests on a collagenous basement membrane (Bruch membrane), and directly beneath this structure flows the choriocapillaris, providing blood supply for the outer third of the retina. Diseases that lead to vision loss can be as a result of abnormalities in the retinal or choroidal vasculature. These diseases, characterized by macula edema, retinal and vitreous hemorrhage, and fibrovascular scarring, include age-related macular degeneration, diabetic retinopathy, neovascular glaucoma, retinopathy of prematurity, and neovascular glaucoma. The final common pathophysiological denominator in all of these diseases is the retinal response to injury, with chronic wound healing leading to fibrosis. See Friedlander, M., *J Clin Invest.*, 2007, 117(3):576-586.

Methodologies and assays known in the art and described herein can be used for assessment of any fibrotic disease (e.g., idiopathic pulmonary fibrosis) or any pre-fibrotic disease described herein (e.g., chronic hypersensitivity pneumonitis) or symptom of a fibrotic disease or a pre-fibrotic disease described herein.

In some embodiments of the methods provided herein, the method further comprises a step of diagnosing an individual (e.g., a patient) with a fibrotic disease (e.g., idiopathic pulmonary fibrosis), selecting an individual (e.g., a patient) with a fibrotic disease (e.g., idiopathic pulmonary fibrosis) for treatment, and/or determining if an individual (e.g., a patient) has a fibrotic disease (e.g., idiopathic pulmonary fibrosis). In some embodiments, the method further comprises a step of diagnosing an individual with a fibrotic disease, selecting an individual with a fibrotic disease for treatment, and/or determining if an individual has a fibrotic disease before treating or preventing a fibrotic disease (e.g., idiopathic pulmonary fibrosis) in the individual, wherein the method comprises administering an effective amount of an antibody (e.g., an anti-Siglec-8 antibody) or an agonist (e.g., a 6'-sulfo-sLe$^X$-containing agonist) that binds to human Siglec-8. In some embodiments, the method further comprises a step of diagnosing an individual with a fibrotic disease, selecting an individual with a fibrotic disease for treatment, and/or determining if an individual has a fibrotic disease after treating or preventing a fibrotic disease (e.g., idiopathic pulmonary fibrosis) in the individual, wherein the method comprises administering an effective amount of an antibody (e.g., an anti-Siglec-8 antibody) or an agonist (e.g., a 6'-sulfo-sLe$^X$-containing agonist) that binds to human Siglec-8.

In some embodiments of the methods provided herein, the method further comprises a step of diagnosing an individual (e.g. a patient) with a pre-fibrotic disease (e.g., chronic hypersensitivity pneumonitis), selecting an individual (e.g., a patient) with a pre-fibrotic disease (e.g., chronic hypersensitivity pneumonitis) for treatment, and/or determining if an individual (e.g., a patient) has a pre-fibrotic disease (e.g., chronic hypersensitivity pneumonitis). In some embodiments, the method further comprises a step of diagnosing an individual with a pre-fibrotic disease, selecting an individual with a pre-fibrotic disease for treatment, and/or determining if an individual has a pre-fibrotic disease before treating or preventing a pre-fibrotic disease (e.g., chronic hypersensitivity pneumonitis) in the individual, wherein the method comprises administering an effective amount of an antibody (e.g., an anti-Siglec-8 antibody) or an agonist (e.g., a 6'-sulfo-sLe$^X$-containing agonist) that binds to human Siglec-8. In some embodiments, the method further comprises a step of diagnosing an individual with a pre-fibrotic disease, selecting an individual with a pre-fibrotic disease for treatment, and/or determining if an individual has a pre-fibrotic disease after treating or preventing a pre-fibrotic disease (e.g., chronic hypersensitivity pneumonitis) in the individual, wherein the method comprises administering an effective amount of an antibody (e.g., an anti-Siglec-8 antibody) or an agonist (e.g., a 6'-sulfo-sLe$^X$-containing agonist) that binds to human Siglec-8.

In some embodiments, provided herein is a method for treating or preventing a fibrotic disease (e.g., idiopathic pulmonary fibrosis) in an individual comprising administering to the individual an effective amount of an antibody (e.g., an anti-Siglec-8 antibody) or an agonist (e.g., a 6'-sulfo-sLe$^X$-containing agonist) that binds to human Siglec-8. In some embodiments, the fibrotic disease is selected from the group consisting of: pulmonary fibrosis, hepatic fibrosis, renal fibrosis, cardiac fibrosis, spleen fibrosis, and ocular fibrosis. In some embodiments, the pulmonary fibrosis is idiopathic pulmonary fibrosis. In some embodiments, the pulmonary fibrosis is associated with chronic obstructive pulmonary disease. In some embodiments, the fibrotic disease is selected from the group consisting of: mechanical-induced fibrosis, implant-induced fibrosis, radiation-induced fibrosis, drug-induced fibrosis, and viral-induced fibrosis. In some embodiments, the mechanical-induced fibrosis is ventilator-induced pulmonary fibrosis. In some embodiments, the drug-induced fibrosis is bleomycin-induced pulmonary fibrosis. In some embodiments, the fibrotic disease is selected from the group consisting of: cystic fibrosis, cancer-associated fibrosis, atherosclerosis, bone marrow fibrosis, scleroderma, mediastinal fibrosis and retroperitoneal cavity fibrosis. In some embodiments, the bone marrow fibrosis is myelofibrosis. In some embodiments, the scleroderma is systemic fibrosis. In some embodiments, the scleroderma is systemic sclerosis. In some of the embodiments herein, one or more symptom in an individual with fibrotic disease (e.g., idiopathic pulmonary fibrosis) is reduced or improved (e.g., a reference value) relative to baseline after administration of the antibody (e.g., an anti-Siglec-8 antibody) or the agonist (e.g. a 6'-sulfo-sLe$^X$-containing agonist) that binds to human Siglec-8. In a further embodiment, the one or more symptom can be a symptom associated with a fibrotic disease disclosed herein, such as, but not limited to, shortness of breath, dry cough, weight loss, fatigue, malaise, finger or toe clubbing, muscle pain, or joint pain. In some embodiments, one or more pulmonary function in the individual with pulmonary fibrosis (e.g., idiopathic pulmonary fibrosis) is increased by at least 5% (e.g., a reference value) relative to baseline after administration of the antibody (e.g., an anti-Siglec-8 antibody) or the agonist (e.g., a 6'-sulfo-sLe$^X$-containing agonist) that binds to human Siglec-8. In a further embodiment, the one or more pulmonary function is selected from the group consisting of: vital capacity (VC), residual volume (V), forced expiratory volume (FEV$_1$), forced vital capacity (FVC), forced expiratory flow (FEF), peak expiratory flow rate (PEFR), inspiratory reserve volume (IRV), functional residual capacity (FRC), inspirator capacity (IC), total lung capacity (TLC), expiratory reserve volume (ERV), tidal volume (TV) and maximum voluntary ventilation (MVV). In some embodiments, one or more pathologic parameter in the individual with fibrotic disease (e.g., idiopathic pulmonary fibrosis) is reduced by at least 5% (e.g., a reference value) relative to baseline after administration of the antibody (e.g., an anti-Siglec-8 antibody) or the agonist (e.g., a 6'-sulfo-sLe$^X$-containing agonist) that binds to human Siglec-8. In a further embodiment, the one or more pathologic parameter is selected from the group consisting of: neutrophil influx, number of mast cells, cytokine release, collagen accumulation, fibroblast or myofibroblast infiltration and fibroblastic foci formation. In some embodiments herein, the individual is a human. In some of the embodiments herein, the antibody is in a pharmaceutical composition comprising the antibody and a pharmaceutically acceptable carrier. In some of the embodiments herein, the agonist is in a pharmaceutical composition comprising the agonist and a pharmaceutically acceptable carrier.

In some embodiments, provided herein is a method for treating or preventing a pre-fibrotic disease (e.g., chronic hypersensitivity pneumonitis) in an individual comprising administering to the individual an effective amount of an antibody (e.g., an anti-Siglec-8 antibody) or an agonist (e.g. a 6'-sulfo-sLe$^X$-containing agonist) that binds to human Siglec-8. In some embodiments, the pre-fibrotic disease is selected from the group consisting of: bleomycin-induced pneumonitis, chronic hypersensitivity pneumonitis, polycythemia vera, essential thrombocythemia, age-related macular degeneration, diabetic retinopathy, neovascular glaucoma, retinopathy of prematurity, and proliferative vitreoretinopathy. In some embodiments, the pre-fibrotic disease is bleomycin-induced pneumonitis. In some embodiments, the pre-fibrotic disease is chronic hypersensitivity pneumonitis. In some of the embodiments herein, one or more symptom in an individual with pre-fibrotic disease (e.g. chronic hypersensitivity pneumonitis) is reduced or improved (e.g., a reference value) relative to baseline after administration of the antibody (e.g., an anti-Siglec-8 antibody) or the agonist (e.g., a 6'-sulfo-sLe$^X$-containing agonist) that binds to human Siglec-8. In a further embodiment, the one or more symptom can be a symptom associated with a pre-fibrotic disease disclosed herein, such as, but not limited to, shortness of breath, dry cough, weight loss, fatigue, malaise, finger or toe clubbing, muscle pain, or joint pain. In some embodiments, one or more pathologic parameter in the individual with pre-fibrotic disease (e.g., chronic hypersensitivity pneumonitis) is reduced by at least 5% (e.g., a reference value) relative to baseline after administration of the antibody (e.g., an anti-Siglec-8 antibody) or the agonist (e.g., a 6'-sulfo-sLe$^X$-containing agonist) that binds to human Siglec-8. In a further embodiment, the one or more pathologic parameter is selected from the group consisting of: neutrophil influx, number of mast cells, cytokine release, collagen accumulation, fibroblast or myofibroblast infiltration and fibroblastic foci formation. In some embodiments herein, the individual is a human. In some of the embodiments herein, the antibody is in a pharmaceutical composition comprising the antibody and a pharmaceutically acceptable carrier. In some of the embodiments herein, the agonist is in a pharmaceutical composition comprising the agonist and a pharmaceutically acceptable carrier.

The terms "baseline" or "baseline value" used interchangeably herein can refer to a measurement or characterization of a symptom (e.g., cytokine release, collagen accumulation, neutrophil influx, etc.) before the administration of the therapy (e.g., an anti-Siglec-8 antibody) or at the beginning of administration of the therapy. The baseline value can be compared to a reference value in order to determine the reduction or improvement of a symptom of a fibrotic disease or a pre-fibrotic disease contemplated herein. The terms "reference" or "reference value" used interchangeably herein can refer to a measurement or characterization of a symptom after administration of the therapy (e.g., an anti-Siglec-8 antibody). The reference value can be measured one or more times during a dosage regimen or treatment cycle or at the completion of the dosage regimen or treatment cycle. A "reference value" can be an absolute value; a relative value; a value that has an upper and/or lower limit; a range of values; an average value; a median value; a mean value; or a value as compared to a baseline value. Similarly, a "baseline value" can be an absolute value; a relative value; a value that has an upper and/or lower limit; a range of values; an average value; a median value; a mean value; or a value as compared to a reference value. The reference value and/or baseline value can be obtained from one individual, from two different individuals or from a group of individuals (e.g., a group of two, three, four, five or more individuals). For example, an individual with a fibrotic disease (e.g., idiopathic pulmonary fibrosis) can have a reduced level of collagen accumulation after administration of the antibody that binds to human Siglec-8 (e.g., a reference value) as compared to the level of collagen accumulation before or at the beginning of administration of the antibody that binds to human Siglec-8 in the individual (e.g., a baseline value). In another example, an individual with a fibrotic disease (e.g., idiopathic pulmonary fibrosis) can have a reduced level of collagen accumulation after administration of the antibody that binds to human Siglec-8 (e.g., a reference value) as compared to the level of collagen accumulation before or at the beginning of administration of the antibody that binds to human Siglec-8 in a different individual (e.g., a baseline value). In yet another example, an individual with a fibrotic disease (e.g., idiopathic pulmonary fibrosis) can have a reduced level of collagen accumulation after administration of the antibody that binds to human Siglec-8 (e.g. a reference value) as compared to the level of collagen accumulation before or at the beginning of administration of the antibody that binds to human Siglec-8 in a group of individuals (e.g., a baseline value). In another example, a group of individuals with a fibrotic disease (e.g., idiopathic pulmonary fibrosis) can have a reduced level of collagen accumulation after administration of the antibody that binds to human Siglec-8 (e.g., a reference value) as compared to the level of collagen accumulation before or at the beginning of administration of the antibody that binds to human Siglec-8 in a group of individuals (e.g., a baseline value). In any of the embodiments herein, the baseline value can be obtained from one individual, from two different individuals or from a group of individuals (e.g., a group of two, three, four, five or more individuals) that are not treated with an antibody that binds to human Siglec-8.

Mast cells play a role in both allergic immune responses (e.g., an IgE mediated cell signaling pathway) and non-allergic cellular functions (e.g., a non-IgE mediated cell signaling pathway). Non-IgE mediated mast cell functions include the regulation of epithelial function (e.g., secretion and epithelial permeability), smooth-muscle function (e.g., peristalsis and bronchioconstriction), endothelial functions (e.g. blood flow, coagulation and vascular permeability), neuronal functions and other tissue functions (e.g., wound healing and fibrosis). These functions are mediated by a variety of cell signaling agents (i.e., an agent of the non-IgE mediated cell signaling pathway) such as growth factors, tissue factors, infectious agents, neuropeptides, and protein antigens. See Bischoff et al., Nature Reviews Immunology, 2007, 7:93-104. A method of treatment contemplated herein is a method for reducing mast cell activation by an agent of a non-IgE mediated cell signaling pathway in an individual with an antibody or agonist described herein that binds to human Siglec-8, or compositions thereof. In some of the embodiments herein, the agent of the non-IgE mediated cell signaling pathway is selected from the group consisting of: thymic stromal lymphopoietin (TSLP), Stem cell factor (SCF), Toll-like Receptor 3 (TLR3), Interleukin 33 (IL-33), and complement proteins. In some embodiments, mast cell activation is reduced in the individual relative to baseline after administration of the antibody or the agonist that binds to human Siglec-8. In some embodiments, the individual has a fibrotic disease described herein. In some embodiments, the fibrotic disease is selected from the group consisting of: pulmonary fibrosis, hepatic fibrosis, renal fibrosis, cardiac fibrosis, spleen fibrosis, and ocular fibrosis. In a further embodiment, the pulmonary fibrosis is idiopathic pulmonary fibrosis. In some embodiments, the pulmonary fibrosis is associated with chronic obstructive pulmonary disease. In some embodiments herein, the fibrotic disease is selected from the group consisting of: mechanical-induced fibrosis, implant-induced fibrosis, radiation-induced fibrosis, drug-induced fibrosis and viral-induced fibrosis. In a further embodiment, the mechanical induced fibrosis is ventilator-induced pulmonary fibrosis. In yet another further embodiment, the drug-induced fibrosis is bleomycin-induced pulmonary fibrosis. In some embodiments, the fibrotic disease is selected from the group consisting of: cystic fibrosis, cancer-associated fibrosis, atherosclerosis, bone marrow fibrosis, scleroderma, mediastinal fibrosis and retroperitoneal cavity fibrosis. In some embodiments, the scleroderma is systemic sclerosis. In some embodiments, the individual has a pre-fibrotic disease described herein. In some embodiments, the pre-fibrotic disease is selected from the group consisting of: bleomycin-induced pneumonitis, chronic hypersensitivity pneumonitis, polycythemia vera, essential thrombocythemia, age-related macular degeneration, diabetic retinopathy, neovascular glaucoma, retinopathy of prematurity, and proliferative vitreoretinopathy.

In some embodiments, an individual described herein is administered an effective amount of an antibody or agonist that binds to human Siglec-8, or compositions thereof, for depletion or reduction of eosinophils (e.g., eosinophils expressing Siglec-8). In some embodiments, the anti-Siglec-8 antibody depletes or reduces at least about 20%, about 30%, about 40%, about 50%, about 60%, about 70%, about 80%, about 90% or about 100% of the eosinophils (e.g. eosinophils expressing Siglec-8) in a sample obtained from the subject as compared to a baseline level before treatment. In some embodiments, the anti-Siglec-8 antibody depletes or reduces at least about 20% of the eosinophils (e.g., eosinophils expressing Siglec-8) in a sample obtained from the subject as compared to a baseline level before treatment. In some embodiments, the depletion or reduction of eosinophils is measured by comparing the eosinophil population number in a sample (e.g., a tissue sample or a biological fluid sample) from an individual after treatment with the antibody or agonist to the eosinophil population number in a sample from an individual before treatment with the antibody or agonist. In some embodiments, the depletion or reduction of eosinophils is measured by comparing the eosinophil population number in a sample (e.g., a tissue sample or a biological fluid sample) from an individual after treatment with the antibody or agonist to the eosinophil population number in a sample from another individual without the antibody treatment or the agonist treatment or average eosinophil population number in samples from individuals without the antibody treatment or the agonist treatment. In some embodiments, the sample is a tissue sample (e.g., a skin sample, a lung sample, a bone marrow sample, etc.). In some embodiments herein, the antibody depletes eosinophils in a tissue sample (e.g., a lung sample). In some embodiments, the sample is a biological fluid sample (e.g., a blood sample, a bronchoalveolar lavage sample, etc.). In some embodiments herein, the antibody depletes eosinophils in a biological fluid sample (e.g., a bronchoalveolar lavage sample). In some embodiments of the methods herein, the effective amount of an antibody or agonist that binds to human Siglec-8, or compositions thereof, induces apoptosis of activated eosinophils. Eosinophils can be activated or sensitized by cytokines or hormones such as, but not limited to, IL-5, GM-CSF, IL-33, IFN-γ, TNF-α, and leptin. In some embodiments of the methods herein, the effective amount of an antibody or agonist described herein that binds to human Siglec-8, or compositions thereof, induces apoptosis of resting eosinophils. In some embodiments, the effective amount of an antibody or agonist described herein that binds to human Siglec-8, or compositions thereof, has antibody-dependent cell-mediated cytotoxicity (ADCC) activity against eosinophils. In some embodiments, the effective amount of an antibody or agonist described herein that binds to human Siglec-8, or compositions thereof, prevents or reduces eosinophil production of inflammatory mediators. Exemplary inflammatory mediators include, but are not limited to, reactive oxygen species, granule proteins (e.g., eosinophil cationic protein, major basic protein, eosinophil-derived neurotoxin, eosinophil peroxidase, etc.), lipid mediators (e.g., PAF, PGE1, PGE2, etc.), enzymes (e.g., elastase), growth factors (e.g., VEGF, PDGF, TGF-α, TGF-β, etc.), chemokines (e.g., RANTES. MCP-1, MCP-3, MCP4, eotaxin, etc.) and cytokines (e.g., L-3, IL-5, IL-10, IL-13, IL-15, IL-33, TNF-α, etc.).

In some embodiments, an individual described herein is administered an effective amount of an antibody or agonist that binds to human Siglec-8, or compositions thereof, for depletion or reduction of mast cells. In some embodiments, the depletion or reduction of mast cells is measured by comparing the mast cell population number in a sample (e.g., a tissue sample or a biological fluid sample) from an individual after treatment with the antibody or agonist to the mast cell population number in a sample from an individual before treatment with the antibody or agonist. In some embodiments, the depletion or reduction of mast cells is measured by comparing the mast cell population number in a sample (e.g., a tissue sample or a biological fluid sample) from an individual after treatment with the antibody or agonist to the mast cell population number in a sample from another individual without the antibody treatment or agonist treatment or average mast cell population number in samples from individuals without the antibody treatment or agonist treatment. In some embodiments, the sample is a tissue sample (e.g., a skin sample, a lung sample, a bone marrow sample, etc.). In some embodiments, the sample is a biological fluid sample (e.g., a blood sample, a bronchoalveolar lavage sample, etc.). In some embodiments, the effective amount of an antibody or agonist described herein that binds to human Siglec-8, or compositions thereof, has antibody-dependent cell-mediated cytotoxicity (ADCC) activity against mast cells. In some embodiments, depletion or reduction of mast cells is the reduction or prevention of preformed or newly formed inflammatory mediators produced from mast cells. Exemplary inflammatory mediators include, but are not limited to, histamine, N-methyl histamine, enzymes (e.g. tryptase, chymase, cathespin G, carboxypeptidase, etc.), lipid mediators (e.g., prostaglandin D2, prostaglandin E2, leukotriene B4, leukotriene C4, platelet-activating factor, 11-beta-prostaglandin F2, etc.), chemokines (e.g., CCL2, CCL3, CCL4, CCL11 (i.e., eotaxin), CXCL1, CXCL2, CXCL3, CXCL10, etc.), and cytokines (e.g., IL-3, IL-4, IL-5, IL-15, IL-33, GM-CSF, TNF, etc.).

In some embodiments, an individual described herein is administered an effective amount of an antibody or agonist that binds to human Siglec-8, or compositions thereof, for depleting mast cells expressing Siglec-8, wherein the anti-Siglec-8 antibody kills mast cells expressing Siglec-8 by ADCC activity. In some embodiments, the anti-Siglec-8 antibody depletes at least about 20%, about 30%, about 40%, about 50%, about 60%, about 70%, about 80%, about 90% or about 100% of the mast cells expressing Siglec-8 in a sample obtained from the subject as compared to a baseline level before treatment. In some embodiments, the anti-Siglec-8 antibody depletes at least about 20% of the mast cells expressing Siglec-8 in a sample obtained from the subject as compared to a baseline level before treatment. In some embodiments, the depletion or killing of mast cells is measured by comparing the mast cell population number in a sample (e.g. a tissue sample or a biological fluid sample) from a subject after treatment with the antibody to the mast cell population number in a sample from a subject before treatment with the antibody. In some embodiments, the depletion or killing of mast cells is measured by comparing the mast cell population number in a sample (e.g., a tissue sample or a biological fluid sample) from a subject after treatment with the antibody to the mast cell population number in a sample from another subject without the antibody treatment or average mast cell population number in samples from subjects without the antibody treatment. In some embodiments, the sample is a tissue sample (e.g., a skin sample, a lung sample, a bone marrow sample, etc.). In some embodiments, the sample is a biological fluid sample (e.g., a blood sample, a bronchoalveolar lavage sample, etc.). In some embodiments, the anti-Siglec-8 antibody has been engineered to improve ADCC activity. In some embodiments, the anti-Siglec-8 antibody comprises at least one amino acid substitution in the Fc region that improves ADCC activity. In some embodiments, at least one or two of the heavy chains of the antibody is non-fucosylated. In some embodiments, depletion or killing of mast cells is the reduction or prevention of preformed or newly formed inflammatory mediators produced from mast cells. Exemplary inflammatory mediators include, but are not limited to, histamine, N-methyl histamine, enzymes (e.g., tryptase, chymase, cathespin G, carboxypeptidase, etc.), lipid mediators (e.g., prostaglandin D2, prostaglandin E2, leukotriene B4, leukotriene C4, platelet-activating factor, 11-beta-prostaglandin F2, etc.), chemokines (e.g., CCL2, CCL3, CCL4, CCL11 (i.e., eotaxin), CXCL1, CXCL2. CXCL3, CXCL10, etc.), and cytokines (e.g., IL-3, IL-4, IL-5, IL-13, IL-15, IL-33, GM-CSF, TNF, etc.).

In some embodiments, an individual described herein is administered an effective amount of an antibody or agonist that binds to human Siglec-8, or compositions thereof, for the inhibition of mast cell-mediated activity. In some embodiments, the inhibition of mast cell-mediated activity is measured by comparing the mast cell-mediated activity in a sample (e.g., a tissue sample or a biological fluid sample) from an individual after treatment with the antibody or agonist to the mast cell-mediated activity in a sample from an individual before treatment with the antibody or agonist. In some embodiments, the inhibition of mast cell-mediated activity is measured by comparing the mast cell-mediated activity in a sample (e.g. a tissue sample or a biological fluid sample) from an individual after treatment with the antibody or agonist to the mast cell-mediated activity in a sample from another individual without the antibody treatment or agonist treatment or average mast cell-mediated activity in samples from individuals without the antibody treatment or agonist treatment. In some embodiments, the sample is a tissue sample (e.g., a skin sample, a lung sample, a bone marrow sample, etc.). In some embodiments, the sample is a biological fluid sample (e.g., a blood sample, a bronchoalveolar lavage sample, etc.). In some embodiments, inhibition of mast cell-mediated activity is the inhibition of mast cell degranulation. In some embodiments, inhibition of mast cell-mediated activity is the inhibition of neutrophil influx to sites of fibrotic disease. In some embodiments, inhibition of mast cell-mediated activity is the inhibition of collagen accumulation at sites of fibrotic disease. In some embodiments, inhibition of mast cell-mediated activity is the inhibition of cytokine release at sites of fibrotic disease. In some embodiments, inhibition of mast cell-mediated activity is the reduction in the number of mast cells in the individual. In some embodiments, inhibition of mast cell-mediated activity is the inhibition of release of preformed or newly formed inflammatory mediators from mast cells. Exemplary inflammatory mediators include, but are not limited to, histamine, N-methyl histamine, enzymes (e.g. tryptase, chymase, cathespin G, carboxypeptidase, etc.), lipid mediators (e.g., prostaglandin D2, prostaglandin E2, leukotriene B4, leukotriene C4, platelet-activating factor, 11-beta-prostaglandin F2, etc.), chemokines (e.g., CCL2, CCL3, CCL4, CCL11 (i.e., eotaxin), CXCL1, CXCL2, CXCL3, CXCL10, etc.), and cytokines (e.g., IL-3, IL-4, IL-5, IL-13, IL-15, IL-33, GM-CSF, TNF, etc.).

For the prevention or treatment of disease, the appropriate dosage of an active agent, will depend on the type of disease to be treated, as defined above, the severity and course of the disease, whether the agent is administered for preventive or therapeutic purposes, previous therapy, the individual's clinical history and response to the agent, and the discretion of the attending physician. The agent is suitably administered to the individual at one time or over a series of treatments. In some embodiments of the methods described herein, an interval between administrations of an anti-Siglec-8 antibody (e.g., an antibody that binds to human Siglec-8) or agonist described herein is about one month or longer. In some embodiments, the interval between administrations is about two months, about three months, about four months, about five months, about six months or longer. As used herein, an interval between administrations refers to the time period between one administration of the antibody or agonist and the next administration of the antibody or agonist. As used herein, an interval of about one month includes four weeks. Accordingly, in some embodiments, the interval between administrations is about four weeks, about five weeks, about six weeks, about seven weeks, about eight weeks, about nine weeks, about ten weeks, about eleven weeks, about twelve weeks, about sixteen weeks, about twenty weeks, about twenty four weeks, or longer. In some embodiments, the interval between administrations is about one day, about two days, about three days, about four days, about five days, about five days, about seven days or longer. In some embodiments, the treatment includes multiple administrations of the antibody or agonist, wherein the interval between administrations may vary. For example, the interval between the first administration and the second administration is about one month, and the intervals between the subsequent administrations are about three months. In some embodiments, the interval between the first administration and the second administration is about one month, the interval between the second administration and the third administration is about two months, and the intervals between the subsequent administrations are about three months. In some embodiments, an anti-Siglec-8 antibody described herein (e.g., an antibody that binds to human Siglec-8) or agonist described herein is administered at a flat dose. In some embodiments, an anti-Siglec-8 antibody described herein (e.g., an antibody that binds to human Siglec-8) or agonist described herein is administered to an individual at a dosage from about 0.1 mg to about 1800 mg per dose. In some embodiments, the anti-Siglec-8 antibody (e.g., an antibody that binds to human Siglec-8) or agonist is administered to an individual at a dosage of about any of 0.1 mg, 0.5 mg, 1 mg, 5 mg, 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1100 mg, 1200 mg, 1300 mg, 1400 mg, 1500 mg, 1600 mg, 1700 mg, and 1800 mg per dose. In some embodiments, an anti-Siglec-8 antibody described herein (e.g., an antibody that binds to human Siglec-8) or agonist described herein is administered to an individual at a dosage from about 150 mg to about 450 mg per dose. In some embodiments, the anti-Siglec-8 antibody (e.g., an antibody that binds to human Siglec-8) or agonist is administered to an individual at a dosage of about any of 150 mg, 200 mg, 250 mg, 300 mg, 350 mg, 400 mg, and 450 mg per dose. In some embodiments, an anti-Siglec-8 antibody described herein (e.g., an antibody that binds to human Siglec-8) or agonist described herein is administered to an individual at a dosage from about 0.1 mg/kg to about 20 mg/kg per dose. In some embodiments, an anti-Siglec-8 antibody described herein (e.g., an antibody that binds to human Siglec-8) or agonist described herein is administered to an individual at a dosage from about 0.01 mg/kg to about 10 mg/kg per dose. In some embodiments, an anti-Siglec-8 antibody described herein (e.g., an antibody that binds to human Siglec-8) or agonist described herein is administered to a subject at a dosage from about 0.1 mg/kg to about 10 mg/kg or about 1.0 mg/kg to about 10 mg/kg. In some embodiments, an anti-Siglec-8 antibody described herein is administered to a subject at a dosage of about any of 0.1 mg/kg, 0.5 mg/kg, 1.0 mg/kg, 1.5 mg/kg, 2.0 mg/kg, 2.5 mg/kg, 3.0 mg/kg, 3.5 mg/kg, 4.0 mg/kg, 4.5 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg, 9.5 mg/kg, or 10.0 mg/kg. Any of the dosing frequency described above may be used. Any dosing frequency described above may be used in the methods or uses of the compositions described herein. Efficacy of treatment with an antibody described herein (e.g., an antibody that binds to human Siglec-8) or agonist described herein can be assessed using any of the methodologies or assays described herein at intervals ranging between every week and every three months. In some embodiments of the methods described herein, efficacy of treatment (e.g., reduction or improvement of one or more symptom) is assessed about every one month, about every two months, about every three months, about every four months, about every five months, about every six months or longer after administration of an antibody or agonist that binds to human Siglec-8. In some embodiments of the methods described herein, efficacy of treatment (e.g. reduction or improvement of one or more symptom) is assessed about every one week, about every two weeks, about every three weeks, about every four weeks, about every five weeks, about every six weeks, about every seven weeks, about every eight weeks, about every nine weeks, about every ten weeks, about every eleven weeks, about every twelve weeks, about every sixteen weeks, about every twenty weeks, about every twenty four weeks, or longer. In some embodiments of the methods described herein, efficacy of treatment (e.g., reduction or improvement of one or more symptom) is assessed about every day, about every two days, about every three days, about every four days, about every five days, about every six days, about every seven days or longer.

Agonists of Siglec-8

In one aspect, the present invention provides for agonists for use in any of the methods herein. In some embodiments, an agonist is an agent that binds to Siglec-8 expressed on eosinophils and induces apoptosis of eosinophils in vitro or in vivo. In some embodiments, an agonist is an agent that binds to Siglec-8 expressed on mast cells and inhibits activation of mast cells in vitro or in vivo. In some embodiments, an agonist is an agent that binds to Siglec-8 expressed on mast cells and depletes or reduces the number of mast cells in vitro or in vivo. In some embodiments, the agonist is an agonist antibody. In some embodiments, the agonist antibody (e.g., antibody 2E2 provide herein) crosslinks Siglec-8 expressed by eosinophils and induces activation of one or more caspases (e.g., caspase-8, caspase-3, and caspase-9) in eosinophils and/or loss of mitochondrial membrane potential. See Nutku et al., *Biochem Biophys Res Commun.*, 336:918-924, 2005. Siglec-8 binds to the glycan 6'-sulfo-sialyl Lewis X (also referred to herein as 6'-sulfo-sLe$^X$) and engagement to this glycan induces apoptosis of Siglec-8 expressing cells (e.g., eosinophils). See Hudson et al., *J Pharmacol Exp Ther.* 330(2):608-12, 2009. In some embodiments herein, an agonist of Siglec-8 is a molecule having a 6'-sulfo-sLe$^X$ attached or linked to a molecule (e.g., a polymer, an oligosaccharide, a polypeptide, a glycoprotein, etc.). In some embodiments herein, the agonist is a 6'-sulfo-sLe$^X$-containing agonist molecule (e.g., a 6'-sulfo-sLe$^X$-containing ligand, a 6'-sulfo-sLe$^X$-containing oligosaccharide, a 6'-sulfo-sLe$^X$-containing polypeptide, and a 6'-sulfo-sLe$^X$-containing glycoprotein).

Agonists may be identified from a variety of sources, for example, cells, cell-free preparations, chemical libraries, and natural product mixtures. Such agonists may be natural or modified substrates, ligands, receptors, oligonucleotides, polypeptides, or antibodies that contain the glycan 6'-sulfo-sLe$^X$ and bind to Siglec-8, or may be structural or functional mimetics thereof. Structural or functional mimetics of such natural or modified substrates, ligands, receptors, oligonucleotides, or antibodies that contain the glycan 6'-sulfo-sLe$^X$ are referred to herein as a "6'-sulfo-sLe$^X$-containing glycomimetic." See Coligan et al., Current Protocols in Immunology 1(2): Chapter 5, 1991. For example, a 6'-sulfo-sLe$^X$-containing glycomimetic may be a synthetic polymer-based ligand decorated with 6'-sulfo-sLe$^X$ that structurally or functionally mimics the activity of the natural ligand of Siglec-8. See Hudson et al. J Pharmacol Exp Ther., 330(2): 608-12, 2009 for examples of glycomimetics contemplated herein. Other examples of potential agonists include antibodies or, in some cases, oligonucleotides or polypeptides which are closely related to the natural ligand of Siglec-8, or small molecules which bind to Siglec-8. Synthetic compounds that mimic the conformation and desirable features of a particular polysaccharide ligand (e.g., a 6'-sulfo-sLe$^X$-containing ligand) that binds to Siglec-8, and preferably avoid at least some undesirable features (such as low binding affinity, short half-life in vivo, and the like) of the original polysaccharide ligand of interest (e.g., a 6'-sulfo-sLe$^X$-containing ligand), are referred to herein as "mimetics". See U.S. Pat. No. 8,178,512 for examples of mimetics contemplated herein.

In some aspects, an agonist that binds to human Siglec-8 (e.g., 6'-sulfo-sLeX-containing agonist or an antibody) described herein induces apoptosis of eosinophils. Apoptosis of eosinophils can be assessed by methods well known in the art. See Hudson et al., *J Pharmacol Exp Ther.*, 330(2):608-12, 2009 and Nutku et al., *Biochem Biophys Res Commun.*, 336:918-924, 2005. For example, human eosinophils are isolated from peripheral blood, purified, and cultured for 24 or 72 hours in IL-5 followed by incubation with the agonist that binds to human Siglec-8 for an additional 24 hours. Cell survival is then assessed by flow cytometric analysis after labeling with annexin-V and propidium iodide. Agonist activity may also be assessed using by detecting activation of caspases (e.g., caspase-8, caspase-3, and caspase-9) in eosinophils and/or loss of mitochondrial membrane potential in eosinophils. These assays are described in Nutku et al., *Biochem Biophys Res Commun.*, 336:918-924, 2005.

Antibodies

In one aspect, the invention provides isolated antibodies that bind to a human Siglec-8 (e.g., an agonist antibody that binds to human Siglec-8). In some embodiments, an anti-Siglec-8 antibody described herein has one or more of the following characteristics: (1) binds a human Siglec-8; (2) binds to an extracellular domain of a human Siglec-8; (3) binds a human Siglec-8 with a higher affinity than mouse antibody 2E2 and/or mouse antibody 2C4; (4) binds a human Siglec-8 with a higher avidity than mouse antibody 2E2 and/or mouse antibody 2C4; (5) has a Tm of about 70° C.-72° C. or higher in a thermal shift assay; (6) has a reduced degree of fucosylation or is non-fucosylated; (7) binds a human Siglec-8 expressed on eosinophils and induces apoptosis of eosinophils: (8) binds a human Siglec-8 expressed on mast cells and depletes or reduces the number of mast cells; (9) binds a human Siglec-8 expressed on mast cells and inhibits FcεRI-dependent activities of mast cells (e.g., histamine release, PGD2 release, Ca2+ flux, and/or β-hexosaminidase release, etc.); (10) has been engineered to improve ADCC activity; and (11) binds a human Siglec-8 expressed on mast cells and inhibits the activation of mast cells by an agent of a non-IgE mediated cell signaling pathway (e.g., complement proteins).

In one aspect, the invention provides antibodies that bind to a human Siglec-8. In some embodiments, the human Siglec-8 comprises an amino acid sequence of SEQ ID NO:72. In some embodiments, the human Siglec-8 comprises an amino acid sequence of SEQ ID NO:73. In some embodiments, an antibody described herein binds to a human Siglec-8 expressed on eosinophils and induces apoptosis of eosinophils. In some embodiments, an antibody described herein binds to a human Siglec-8 expressed on mast cells and depletes or reduces the number of mast cells. In some embodiments, an antibody described herein binds to a human Siglec-8 expressed on mast cells and inhibits mast cell-mediated activity. In some embodiments, an antibody described herein binds to a human Siglec-8 expressed on mast cells and reduces mast cell activation by an agent of a non-IgE mediated immune response pathway. In a further embodiment, the agent of the non-IgE mediated cell signaling pathway is selected from the group consisting of: thymic stromal lymphopoietin (TSLP), Stem cell factor (SCF), Toll-like Receptor 3 (TLR3), Interleukin 33 (IL-33), and complement proteins.

In one aspect, an anti-Siglec-8 antibody described herein is a monoclonal antibody. In one aspect, an anti-Siglec-8 antibody described herein is an antibody fragment (including antigen-binding fragment), e.g., a Fab, Fab'-SH, Fv, scFv, or (Fab')2 fragment. In one aspect, an anti-Siglec-8 antibody described herein is a chimeric, humanized, or human antibody. In one aspect, any of the anti-Siglec-8 antibodies described herein are purified.

In one aspect, anti-Siglec-8 antibodies that compete with murine 2E2 antibody and murine 2C4 antibody binding to Siglec-8 are provided. Anti-Siglec-8 antibodies that bind to the same epitope as murine 2E2 antibody and murine 2C4 antibody are also provided. Murine antibodies to Siglec-8, 2E2 and 2C4 antibody are described in U.S. Pat. Nos. 8,207,305; 8,197,811, 7,871,612, and 7,557,191.

In one aspect, anti-Siglec-8 antibodies that compete with any anti-Siglec-8 antibody described herein (e.g., HEKA, HEKF, 1C3, 1H10, 4F11) for binding to Siglec-8 are provided. Anti-Siglec-8 antibodies that bind to the same epitope as any anti-Siglec-8 antibody described herein (e.g., HEKA, HEKF, 1C3, 1H10, 4F11) are also provided.

In one aspect of the invention, polynucleotides encoding anti-Siglec-8 antibodies are provided. In certain embodiments, vectors comprising polynucleotides encoding anti-Siglec-8 antibodies are provided. In certain embodiments, host cells comprising such vectors are provided. In another aspect of the invention, compositions comprising anti-Siglec-8 antibodies or polynucleotides encoding anti-Siglec-8 antibodies are provided. In certain embodiments, a composition of the invention is a pharmaceutical formulation for the treatment of a fibrotic disease (e.g., idiopathic pulmonary fibrosis) or pre-fibrotic disease (e.g., chronic hypersensitivity pneumonitis), such as those enumerated herein. In certain embodiments, a composition of the invention is a pharmaceutical formulation for the prevention of a fibrotic disease (e.g., idiopathic pulmonary fibrosis) or pre-fibrotic disease (e.g., chronic hypersensitivity pneumonitis), such as those enumerated herein.

In one aspect, provided herein is an anti-Siglec-8 antibody comprising 1, 2, 3, 4, 5, or 6 of the HVR sequences of the murine antibody 2C4. In one aspect, provided herein is an anti-Siglec-8 antibody comprising 1, 2, 3, 4, 5, or 6 of the HVR sequences of the murine antibody 2E2. In some embodiments, the HVR is a Kabat CDR or a Chothia CDR.

In one aspect, provided herein is an anti-Siglec-8 antibody comprising 1, 2, 3, 4, 5, or 6 of the HVR sequences of the murine antibody 1C3. In one aspect, provided herein is an anti-Siglec-8 antibody comprising 1, 2, 3, 4, 5, or 6 of the HVR sequences of the murine antibody 4F11. In one aspect, provided herein is an anti-Siglec-8 antibody comprising 1, 2, 3, 4, 5, or 6 of the HVR sequences of the murine antibody 1H10. In some embodiments, the HVR is a Kabat CDR or a Chothia CDR.

In one aspect, provided herein is an isolated anti-Siglec-8 antibody that binds to human Siglec-8 and non-human primate Siglec-8. In some embodiments, the antibody that binds to a human Siglec-8 and a non-human primate Siglec-8, binds to an epitope in Domain 1 of human Siglec-8. In some embodiments, the antibody that binds to a human Siglec-8 and a non-human primate Siglec-8, binds to an epitope in Domain 3 of human Siglec-8. In some embodiments, the antibody that binds to a human Siglec-8 and a non-human primate Siglec-8 is a humanized antibody, a chimeric antibody, or a human antibody. In some embodiments, the antibody that binds to a human Siglec-8 and a non-human primate Siglec-8 is a murine antibody. In some embodiments, the antibody that binds to a human Siglec-8 and a non-human primate Siglec-8 is a human IgG1 antibody.

In one aspect, provided herein is an anti-Siglec-8 antibody comprising a heavy chain variable region and a light chain variable region, wherein the heavy chain variable region comprises (i) HVR-H1 comprising the amino acid sequence of SEQ ID NO:61. (ii) HVR-H2 comprising the amino acid sequence of SEQ ID NO:62, and (iii) HVR-H3 comprising the amino acid sequence of SEQ ID NO:63; and/or wherein the light chain variable region comprises (i) HVR-L1 comprising the amino acid sequence of SEQ ID NO:64, (ii) HVR-L2 comprising the amino acid sequence of SEQ ID NO:65, and (iii) HVR-L3 comprising the amino acid sequence of SEQ ID NO:66.

In one aspect, provided herein is an anti-Siglec-8 antibody comprising a heavy chain variable region and a light chain variable region, wherein the heavy chain variable region comprises (i) HVR-H1 comprising the amino acid sequence of SEQ ID NO:61. (ii) HVR-H2 comprising the amino acid sequence of SEQ ID NO:62, and (iii) HVR-H3 comprising the amino acid sequence selected from SEQ ID NOs:67-70; and/or wherein the light chain variable region comprises (i) HVR-L1 comprising the amino acid sequence of SEQ ID NO:64. (ii) HVR-L2 comprising the amino acid sequence of SEQ ID NO:65, and (iii) HVR-L3 comprising the amino acid sequence of SEQ ID NO:66.

In one aspect, provided herein is an anti-Siglec-8 antibody comprising a heavy chain variable region and a light chain variable region, wherein the heavy chain variable region comprises (i) HVR-H1 comprising the amino acid sequence of SEQ ID NO:61, (ii) HVR-H2 comprising the amino acid sequence of SEQ ID NO:62, and (iii) HVR-H3 comprising the amino acid sequence of SEQ ID NO:63; and/or wherein the light chain variable region comprises (i) HVR-L1 comprising the amino acid sequence of SEQ ID NO:64, (ii) HVR-L2 comprising the amino acid sequence of SEQ ID NO:65, and (iii) HVR-L3 comprising the amino acid sequence of SEQ ID NO:71.

In another aspect, provided herein is an anti-Siglec-8 antibody comprising a heavy chain variable region and a light chain variable region, wherein the heavy chain variable region comprises (i) HVR-H1 comprising the amino acid sequence of SEQ ID NO:61, (ii) HVR-H2 comprising the amino acid sequence of SEQ ID NO:62, and (iii) HVR-H3 comprising the amino acid sequence selected from SEQ ID NOs:67-70; and/or wherein the light chain variable region comprises (i) HVR-L1 comprising the amino acid sequence of SEQ ID NO:64. (ii) HVR-L2 comprising the amino acid sequence of SEQ ID NO:65, and (iii) HVR-L3 comprising the amino acid sequence of SEQ ID NO:71.

In another aspect, provided herein is an anti-Siglec-8 antibody comprising a heavy chain variable region and a light chain variable region, wherein the heavy chain variable region comprises (i) HVR-H1 comprising the amino acid sequence of SEQ ID NO:88, (ii) HVR-H2 comprising the amino acid sequence of SEQ ID NO:91, and (iii) HVR-H3 comprising the amino acid sequence of SEQ ID NO:94; and/or a light chain variable region comprising (i) HVR-L1 comprising the amino acid sequence of SEQ ID NO:97, (ii) HVR-L2 comprising the amino acid sequence of SEQ ID NO:100, and (iii) HVR-L3 comprising the amino acid sequence of SEQ ID NO:103.

In another aspect, provided herein is an anti-Siglec-8 antibody comprising a heavy chain variable region and a light chain variable region, wherein the heavy chain variable region comprises (i) HVR-H1 comprising the amino acid sequence of SEQ ID NO:89, (ii) HVR-H2 comprising the amino acid sequence of SEQ ID NO:92, and (iii) HVR-H3 comprising the amino acid sequence of SEQ ID NO:95; and/or a light chain variable region comprising (i) HVR-L1 comprising the amino acid sequence of SEQ ID NO:98, (ii) HVR-L2 comprising the amino acid sequence of SEQ ID NO:101, and (iii) HVR-L3 comprising the amino acid sequence of SEQ ID NO:104.

In another aspect, provided herein is an anti-Siglec-8 antibody comprising a heavy chain variable region and a light chain variable region, wherein the heavy chain variable region comprises (i) HVR-H1 comprising the amino acid sequence of SEQ ID NO:90, (ii) HVR-H2 comprising the amino acid sequence of SEQ ID NO:93, and (iii) HVR-H3 comprising the amino acid sequence of SEQ ID NO:96; and/or a light chain variable region comprising (i) HVR-L1 comprising the amino acid sequence of SEQ ID NO:99, (ii) HVR-L2 comprising the amino acid sequence of SEQ ID NO:102, and (iii) HVR-L3 comprising the amino acid sequence of SEQ ID NO:105.

An anti-Siglec-8 antibody described herein may comprise any suitable framework variable domain sequence, provided that the antibody retains the ability to bind human Siglec-8. As used herein, heavy chain framework regions are designated "HC-FR1-FR4," and light chain framework regions are designated "LC-FR1-FR4." In some embodiments, the anti-Siglec-8 antibody comprises a heavy chain variable domain framework sequence of SEQ ID NO:26, 34, 38, and 45 (HC-FR1, HC-FR2, HC-FR3, and HC-FR4, respectively). In some embodiments, the anti-Siglec-8 antibody comprises a light chain variable domain framework sequence of SEQ ID NO:48, 51, 55, and 60 (LC-FR1, LC-FR2, LC-FR3, and LC-FR4, respectively). In some embodiments, the anti-Siglec-8 antibody comprises a light chain variable domain framework sequence of SEQ ID NO:48, 51, 58, and 60 (LC-FR1, LC-FR2, LC-FR3, and LC-FR4, respectively).

In one embodiment, an anti-Siglec-8 antibody comprises a heavy chain variable domain comprising a framework sequence and hypervariable regions, wherein the framework sequence comprises the HC-FR1-HC-FR4 sequences SEQ ID NOs:26-29 (HC-FR1), SEQ ID NOs:31-36 (HC-FR2), SEQ ID NOs:38-43 (HC-FR3), and SEQ ID NOs:45 or 46 (HC-FR4), respectively; the HVR-H1 comprises the amino acid sequence of SEQ ID NO:61; the HVR-H2 comprises the amino acid sequence of SEQ ID NO:62; and the HVR-H3 comprises an amino acid sequence of SEQ ID NO:63. In one embodiment, an anti-Siglec-8 antibody comprises a heavy chain variable domain comprising a framework sequence and hypervariable regions, wherein the framework sequence comprises the HC-FR1-HC-FR4 sequences SEQ ID NOs:26-29 (HC-FR1), SEQ ID NOs:31-36 (HC-FR2), SEQ ID NOs:38-43 (HC-FR3), and SEQ ID NOs:45 or 46 (HC-FR4), respectively; the HVR-H1 comprises the amino acid sequence of SEQ ID NO:61; the HVR-H2 comprises the amino acid sequence of SEQ ID NO:62; and the HVR-H3 comprises an amino acid sequence selected from SEQ ID NOs:67-70. In one embodiment, an anti-Siglec-8 antibody comprises a light chain variable domain comprising a framework sequence and hypervariable regions, wherein the framework sequence comprises the LC-FR1-LC-FR4 sequences SEQ ID NOs:48 or 49 (LC-FR1), SEQ ID NOs: 51-53 (LC-FR2), SEQ ID NOs:55-58 (LC-FR3), and SEQ ID NO:60 (LC-FR4), respectively; the HVR-L1 comprises the amino acid sequence of SEQ ID NO:64; the HVR-L2 comprises the amino acid sequence of SEQ ID NO:65; and the HVR-L3 comprises an amino acid sequence of SEQ ID NO:66. In one embodiment, an anti-Siglec-8 antibody comprises a light chain variable domain comprising a framework sequence and hypervariable regions, wherein the framework sequence comprises the LC-FR1-LC-FR4 sequences SEQ ID NOs:48 or 49 (LC-FR1), SEQ ID NOs:51-53 (LC-FR2), SEQ ID NOs:55-58 (LC-FR3), and SEQ ID NO:60 (LC-FR4), respectively; the HVR-L1 comprises the amino acid sequence of SEQ ID NO:64; the HVR-L2 comprises the amino acid sequence of SEQ ID NO:65; and the HVR-L3 comprises an amino acid sequence of SEQ ID NO:71. In one embodiment of these antibodies, the heavy chain variable domain comprises an amino acid sequence selected from SEQ ID NOs:2-10 and the light chain variable domain comprises and amino acid sequence selected from SEQ ID NOs: 16-22. In one embodiment of these antibodies, the heavy chain variable domain comprises an amino acid sequence selected from SEQ ID NOs:2-10 and the light chain variable domain comprises and amino acid sequence selected from SEQ ID NOs:23 or 24. In one embodiment of these antibodies, the heavy chain variable domain comprises an amino acid sequence selected from SEQ ID NOs:11-14 and the light chain variable domain comprises and amino acid sequence selected from SEQ ID NOs: 16-22. In one embodiment of these antibodies, the heavy chain variable domain comprises an amino acid sequence selected from SEQ ID NOs:11-14 and the light chain variable domain comprises and amino acid sequence selected from SEQ ID NOs:23 or 24. In one embodiment of these antibodies, the heavy chain variable domain comprises an amino acid sequence of SEQ ID NO:6 and the light chain variable domain comprises and amino acid sequence of SEQ ID NO:16. In one embodiment of these antibodies, the heavy chain variable domain comprises an amino acid sequence of SEQ ID NO:6 and the light chain variable domain comprises and amino acid sequence of SEQ ID NO:21.

In some embodiments, the heavy chain HVR sequences comprise the following:

```
a) HVR-H1
(IYGAH (SEQ ID NO: 61));

b) HVR-H2
(VIWAGGSTNYNSALMS (SEQ ID NO: 62));
and c) HVR-H3
(DGSSPYYYSMEY (SEQ ID NO: 63);

DGSSPYYYGMEY (SEQ ID NO: 67);

DGSSPYYYSMDY (SEQ ID NO: 68);

DGSSPYYYSMEV (SEQ ID NO: 69);
or

DGSSPYYYGMDV (SEQ ID NO: 70)).
```

In some embodiments, the heavy chain HVR sequences comprise the following:

```
a) HVR-H1
(SYAMS (SEQ ID NO: 88);

DYYMY (SEQ ID NO: 89);
or

SSWMN (SEQ ID NO: 90));

b) HVR-H2
(IISSGGSYTYYSDSVKG (SEQ ID NO: 91);

RIAPEDGDTEYAPKFQG (SEQ ID NO: 92);
or

QIYPGDDYTNYNGKFKG (SEQ ID NO: 93));
and
```

-continued c) HVR-H3
(HETAQAAWFAY (SEQ ID NO: 94);

EGNYYGSSILDY (SEQ ID NO: 95);
or

LGPYGPFAD (SEQ ID NO: 96)).

In some embodiments, the heavy chain FR sequences comprise the following:

a) HC-FR1
(EVQLVESGGGLVQPGGSLRLSCAASGFSLT (SEQ ID NO: 26);

EVQLVESGGGLVQPGGSLRLSCAVSGFSLT (SEQ ID NO: 27);

QVQLQESGPGLVKPSETLSLTCTVSGGSIS (SEQ ID NO: 28);
or

QVQLQESGPGLVKPSETLSLTCTVSGFSLT (SEQ ID NO: 29));

b) HC-FR2
(WVRQAPGKGLEWVS (SEQ ID NO: 31);

WVRQAPGKGLEWLG (SEQ ID NO: 32);

WVRQAPGKGLEWLS (SEQ ID NO: 33);

WVRQAPGKGLEWVG (SEQ ID NO: 34);

WIRQPPGKGLEWIG (SEQ ID NO: 35);
or

WVRQPPGKGLEWLG (SEQ ID NO: 36));

c) HC-FR3
(RETISKDNSKNTVYLQMNSLRAEDTAVYYCAR (SEQ ID NO: 38);

RESISKDNSKNTVYLQMNSLRAEDTAVYYCAR (SEQ ID NO: 39);

RLTISKDNSKNTVYLQMNSLRAEDTAVYYCAR (SEQ ID NO: 40);

RFSISKDNSKNTVYLQMNSLRAEDTAVYYCAR (SEQ ID NO: 41):

RVTISVDTSKNQFSLKLSSVTAADTAVYYCAR (SEQ ID NO: 42);
or

RESISKDNSKNQVSLKLSSVTAADTAVYYCAR (SEQ ID NO: 43));
and d) HC-FR4
(WGQGTTVTVSS (SEQ ID NO: 45);
or

WGQGTLVTVSS (SEQ ID NO: 46)).

In some embodiments, the light chain HVR sequences comprise the following:

a) HVR-L1
(SATSSVSYMH (SEQ ID NO: 64));

b) HVR-L2
(STSNLAS (SEQ ID NO: 65));
and c) HVR-L3
(QQRSSYPFT (SEQ ID NO: 66);
or

QQRSSYPYT (SEQ ID NO: 71)).

In some embodiments, the light chain HVR sequences comprise the following:

a) HVR-L1
(SASSSVSYMH (SEQ ID NO: 97);

RASQDITNYLN (SEQ ID NO: 98);
or

SASSSVSYMY (SEQ ID NO: 99));

b) HVR-L2
(DTSKLAY (SEQ ID NO: 100);

FTSRLHS (SEQ ID NO: 101);
or

DTSSLAS (SEQ ID NO: 102));
and c) HVR-L3
(QQWSSNPPT (SEQ ID NO: 103);

QQGNTLPWT (SEQ ID NO: 104);
or

QQWNSDPYT (SEQ ID NO: 105)).

In some embodiments, the heavy chain FR sequences comprise the following:

a) LC-FR1
(EIVLTQSPATLSLSPGERATLSC (SEQ ID NO: 48);
or

EIILTQSPATLSLSPGERATLSC (SEQ ID NO: 49));

b) LC-FR2
(WFQQKPGQAPRLLIY (SEQ ID NO: 51);

WFQQKPGQAPRLWIY (SEQ ID NO: 52);
or

WYQQKPGQAPRLLIY (SEQ ID NO: 53));

c) LC-FR3
(GIPARFSGSGSGTDFTLTISSLEPEDFAVYYC (SEQ ID NO: 55);

GVPARFSGSGSGTDYTLTISSLEPEDFAVYYC (SEQ ID NO: 56);

GVPARFSGSGSGTDFTLTISSLEPEDFAVYYC (SEQ ID NO: 57);
or

GIPARFSGSGSGTDYTLTISSLEPEDFAVYYC (SEQ ID NO: 58));
and d) LC-FR4
(FGPGTKLDIK (SEQ ID NO: 60)).

In some embodiments, provided herein is an anti-Siglec-8 antibody (e.g., a humanized anti-Siglec-8) antibody that binds to human Siglec-8, wherein the antibody comprises a heavy chain variable region and a light chain variable region, wherein the antibody comprises:
  (a) heavy chain variable domain comprising:
    (1) an HC-FR1 comprising the amino acid sequence selected from SEQ ID NOs:26-29;
    (2) an HVR-H1 comprising the amino acid sequence of SEQ ID NO:61
    (3) an HC-FR2 comprising the amino acid sequence selected from SEQ ID NOs:31-36;
    (4) an HVR-H2 comprising the amino acid sequence of SEQ ID NO:62;
    (5) an HC-FR3 comprising the amino acid sequence selected from SEQ ID NOs:38-43;
    (6) an HVR-H3 comprising the amino acid sequence of SEQ ID NO:63; and
    (7) an HC-FR4 comprising the amino acid sequence selected from SEQ ID NOs:45-46, and/or (b) a light chain variable domain comprising:
(1) an LC-FR comprising the amino acid sequence selected from SEQ ID NOs:48-49;
(2) an HVR-L1 comprising the amino acid sequence of SEQ ID NO:64;
(3) an LC-FR2 comprising the amino acid sequence selected from SEQ ID NOs:51-53;
(4) an HVR-L2 comprising the amino acid sequence of SEQ ID NO:65;
(5) an LC-FR3 comprising the amino acid sequence selected from SEQ ID NOs:55-58;
(6) an HVR-L3 comprising the amino acid sequence of SEQ ID NO:66; and
(7) an LC-FR4 comprising the amino acid sequence of SEQ ID NO:60.

In one aspect, provided herein is an anti-Siglec-8 antibody comprising a heavy chain variable domain selected from SEQ ID NOs:2-10 and/or comprising a light chain variable domain selected from SEQ ID NOs: 16-22. In one aspect, provided herein is an anti-Siglec-8 antibody comprising a heavy chain variable domain selected from SEQ ID NOs: 2-10 and/or comprising a light chain variable domain selected from SEQ ID NO:23 or 24. In one aspect, provided herein is an anti-Siglec-8 antibody comprising a heavy chain variable domain selected from SEQ ID NOs: 11-14 and/or comprising a light chain variable domain selected from SEQ ID NOs: 16-22. In one aspect, provided herein is an anti-Siglec-8 antibody comprising a heavy chain variable domain selected from SEQ ID NOs: 11-14 and/or comprising a light chain variable domain selected from SEQ ID NO:23 or 24. In one aspect, provided herein is an anti-Siglec-8 antibody comprising a heavy chain variable domain of SEQ ID NO:6 and/or comprising a light chain variable domain selected from SEQ ID NO:16 or 21.

In one aspect, provided herein is an anti-Siglec-8 antibody comprising a heavy chain variable domain selected from SEQ ID NOs:106-108 and/or comprising a light chain variable domain selected from SEQ ID NOs: 109-111. In one aspect, provided herein is an anti-Siglec-8 antibody comprising a heavy chain variable domain of SEQ ID NO:106 and/or comprising a light chain variable domain of SEQ ID NO:109. In one aspect, provided herein is an anti-Siglec-8 antibody comprising a heavy chain variable domain of SEQ ID NO:107 and/or comprising a light chain variable domain of SEQ ID NO:110. In one aspect, provided herein is an anti-Siglec-8 antibody comprising a heavy chain variable domain of SEQ ID NO:108 and/or comprising a light chain variable domain of SEQ ID NO:111.

In some embodiments, provided herein is an anti-Siglec-8 antibody comprising a heavy chain variable domain comprising an amino acid sequence having at least 90%, 91%, 92%, 93%, 94%, 95%, 96%, 97%, 98%, or 99% sequence identity to an amino acid sequence selected from SEQ ID NOs:2-14. In some embodiments, provided herein is an anti-Siglec-8 antibody comprising a heavy chain variable domain comprising an amino acid sequence having at least 90%, 91%, 92%, 93%, 94%, 95%, 96%, 97%, 98%, or 99% sequence identity to an amino acid sequence selected from SEQ ID NOs:106-108. In some embodiments, an amino acid sequence having at least 90%, 91%, 92%, 93%, 94%, 95%, 96%, 97%, 98%, or 99% sequence identity contains substitutions, insertions, or deletions relative to the reference sequence, but an antibody comprising that amino acid sequence retains the ability to bind to human Siglec-8. In some embodiments, the substitutions, insertions, or deletions (e.g., 1, 2, 3, 4, or 5 amino acids) occur in regions outside the HVRs (i.e., in the FRs). In some embodiments, an anti-Siglec-8 antibody comprises a heavy chain variable domain comprising an amino acid sequence of SEQ ID NO:6. In some embodiments, an anti-Siglec-8 antibody comprises a heavy chain variable domain comprising an amino acid sequence selected from SEQ ID NOs: 106-108.

In some embodiments, provided herein is an anti-Siglec-8 antibody comprising a light chain variable domain comprising an amino acid sequence having at least 90%, 91%, 92%, 93%, 94%, 95%, 96%, 97%, 98%, or 99% sequence identity to an amino acid sequence selected from SEQ ID NOs: 16-24. In some embodiments, provided herein is an anti-Siglec-8 antibody comprising a light chain variable domain comprising an amino acid sequence having at least 90%, 91%, 92%, 93%, 94%, 95%, 96%, 97%, 98%, or 99% sequence identity to an amino acid sequence selected from SEQ ID NOs:109-111. In some embodiments, an amino acid sequence having at least 90%, 91%, 92%, 93%, 94%, 95%, 96%, 97%, 98%, or 99% sequence identity contains substitutions, insertions, or deletions relative to the reference sequence, but an antibody comprising that amino acid sequence retains the ability to bind to human Siglec-8. In some embodiments, the substitutions, insertions, or deletions (e.g., 1, 2, 3, 4, or 5 amino acids) occur in regions outside the HVRs (i.e., in the FRs). In some embodiments, an anti-Siglec-8 antibody comprises a light chain variable domain comprising an amino acid sequence of SEQ ID NO:16 or 21. In some embodiments, an anti-Siglec-8 antibody comprises a heavy chain variable domain comprising an amino acid sequence selected from SEQ ID NOs:109-111.

In one aspect, the invention provides an anti-Siglec-8 antibody comprising (a) one, two, or three VH HVRs selected from those shown in Table 2 and/or (b) one, two, or three VL HVRs selected from those shown in Table 2.

In one aspect, the invention provides an anti-Siglec-8 antibody comprising (a) one, two, or three VH HVRs selected from those shown in Table 5 and/or (b) one, two, or three VL HVRs selected from those shown in Table 5.

In one aspect, the invention provides an anti-Siglec-8 antibody comprising (a) one, two, three or four VH FRs selected from those shown in Table 3 and/or (b) one, two, three or four VL FRs selected from those shown in Table 3.

In some embodiments, provided herein is an anti-Siglec-8 antibody comprising a heavy chain variable domain and/or a light chain variable domain of an antibody shown in Table 4, for example, HAKA antibody, HAKB antibody, HAKC antibody, etc.

TABLE 2

Amino acid sequences of HVRs of antibodies

| Antibody Chain | HVR1 | HVR2 | HVR3 |
| --- | --- | --- | --- |
| 2E2 antibody | | | |
| Heavy chain | IYGAH<br>SEQ ID NO: 61 | VIWAGGSTNYNSALMS<br>SEQ ID NO: 62 | DGSSPYYYSMEY<br>SEQ ID NO: 63 |

TABLE 2-continued

Amino acid sequences of HVRs of antibodies

| Antibody Chain | HVR1 | HVR2 | HVR3 |
| --- | --- | --- | --- |
| Light chain | SATSSVSYMH SEQ ID NO: 64 | STSNLAS SEQ ID NO: 65 | QQRSSYPFT SEQ ID NO: 66 |

Humanized Heavy Chain Variants 2E2 RHA, 2E2 RHB, 2E2 RHC, 2E2 RHD, 2E2 RHE, 2E2 RHF, 2E2 RHG, 2E2 RHA2, and 2E2 RHB2

| | | | |
| --- | --- | --- | --- |
| Heavy chain | IYGAH SEQ ID NO: 61 | VIWAGGSTNYNSALMS SEQ ID NO: 62 | DGSSPYYYSMEY SEQ ID NO: 63 |

Humanized Light Chain Variants 2E2 RKA, 2E2 RKB, 2E2 RKC, 2E2 RKD, 2E2 RKE, 2E2 RKF, and 2E2 RKG

| | | | |
| --- | --- | --- | --- |
| Light chain | SATSSVSYMH SEQ ID NO: 64 | STSNLAS SEQ ID NO: 65 | QQRSSYPFT SEQ ID NO: 66 |

Humanized Heavy Chain Variants 2E2 RHE S-G, 2E2 RHE E-D, 2E2 RHE Y-V and 2E2 RHE triple

| | | | |
| --- | --- | --- | --- |
| 2E2 RHE S-G | IYGAH SEQ ID NO: 61 | VIWAGGSTNYNSALMS SEQ ID NO: 62 | DGSSPYYYGMEY SEQ ID NO: 67 |
| 2E2 RHE E-D | IYGAH SEQ ID NO: 61 | VIWAGGSTNYNSALMS SEQ ID NO: 62 | DGSSPYYYSMDY SEQ ID NO: 68 |
| 2E2 RHE Y-V | IYGAH SEQ ID NO: 61 | VIWAGGSTNYNSALMS SEQ ID NO: 62 | DGSSPYYYSMEV SEQ ID NO: 69 |
| 2E2 RHE triple | IYGAH SEQ ID NO: 61 | VIWAGGSTNYNSALMS SEQ ID NO: 62 | DGSSPYYYGMDV SEQ ID NO: 70 |

Humanized Light Chain Variants 2E2 RKA F-Y and 2E2 RKF F-Y

| | | | |
| --- | --- | --- | --- |
| 2E2 RKA F-Y | SATSSVSYMH SEQ ID NO: 64 | STSNLAS SEQ ID NO: 65 | QQRSSYPYT SEQ ID NO: 71 |
| 2E2 RKF F-Y | SATSSVSYMH SEQ ID NO: 64 | STSNLAS SEQ ID NO: 65 | QQRSSYPYT SEQ ID NO: 71 |

TABLE 3

Amino acid sequences of FRs of antibodies

| | FR1 | FR2 | FR3 | FR4 |
| --- | --- | --- | --- | --- |
| Heavy Chain | | | | |
| 2E2 | QVQLKESGPGLVAPS QSLSITCTVSGFSLT (SEQ ID NO: 25) | WVRQPPGKGLEWLG (SEQ ID NO: 30) | RLSISKDNSKSQVFL KINSLQTDDTALYYC AR (SEQ ID NO: 37) | WGQGTSVTVSS (SEQ ID NO: 44) |
| 2E2 RHA | EVQLVESGGGLVQPG GSLRLSCAASGFSLT (SEQ ID NO: 26) | WVRQAPGKGLEWVS (SEQ ID NO: 31) | RFTISKDNSKNTVYL QMNSLRAEDTAVYYC AR (SEQ ID NO: 38) | WGQGTTVTVSS (SEQ ID NO: 45) |
| 2E2 RHB | EVQLVESGGGLVQPG GSLRLSCAVSGFSLT (SEQ ID NO: 27) | WVRQAPGKGLEWLG (SEQ ID NO: 32) | RLSISKDNSKNIVYL QMNSLRAEDTAVYYC AR (SEQ ID NO: 39) | WGQGTTVTVSS (SEQ ID NO: 45) |
| 2E2 RHC | EVQLVESGGGLVQPG GSLRLSCAVSGFSLT (SEQ ID NO: 27) | WVRQAPGKGLEWVS (SEQ ID NO: 31) | RFTISKDNSKNTVYL QMNSLRAEDTAVYYC AR (SEQ ID NO: 38) | WGQGTTVTVSS (SEQ ID NO: 45) |
| 2E2 RHD | EVQLVESGGGLVQPG GSLRLSCAASGFSLT (SEQ ID NO: 26) | WVRQAPGKGLEWLS (SEQ ID NO: 33) | RFTISKDNSKNTVYL QMNSLRAEDTAVYYC AR (SEQ ID NO: 38) | WGQGTTVTVSS (SEQ ID NO: 45) |

TABLE 3-continued

Amino acid sequences of FRs of antibodies

| | FR1 | FR2 | FR3 | FR4 |
|---|---|---|---|---|
| 2E2 RHE | EVQLVESGGGLVQPG GSLRLSCAASGFSLT (SEQ ID NO: 26) | WVRQAPGKGLEWVG (SEQ ID NO: 34) | RFTISKDNSKNTVYL QMNSLRAEDTAVYYC AR (SEQ ID NO: 38) | WGQGTTVTVSS (SEQ ID NO: 45) |
| 2E2 RHF | EVQLVESGGGLVQPG GSLRLSCAASGFSLT (SEQ ID NO: 26) | WVRQAPGKGLEWVS (SEQ ID NO: 31) | RLTISKDNSKNTVYL QMNSLRAEDTAVYYC AR (SEQ ID NO: 40) | WGQGTTVTVSS (SEQ ID NO: 45) |
| 2E2 RHG | EVQLVESGGGLVQPG GSLRLSCAASGFSLT (SEQ ID NO: 26) | WVRQAPGKGLEWVS (SEQ ID NO: 31) | RFSISKDNSKNTVYL QMNSLRAEDTAVYYC AR (SEQ ID NO: 41) | WGQGTTVTVSS (SEQ ID NO: 45) |
| 2E2 RHA2 | QVQLQESGPGLVKPS ETLSLTCTVSGGSIS (SEQ ID NO: 28) | WIRQPPGKGLEWIG (SEQ ID NO: 35) | RVTISVDTSKNQFSL KLSSVTAADTAVYYC AR (SEQ ID NO: 42) | WGQGTLVTVSS (SEQ ID NO: 46) |
| 2E2 RHB2 | QVQLQESGPGLVKPS ETLSLTCTVSGFSLT (SEQ ID NO: 29) | WVRQPPGKGLEWLG (SEQ ID NO: 36) | RLSISKDNSKNQVSL KLSSVTAADTAVYYC AR (SEQ ID NO: 43) | WGQGTLVTVSS (SEQ ID NO: 46) |
| 2E2 RHE S-G | EVQLVESGGGLVQPG GSLRLSCAASGFSLT (SEQ ID NO: 26) | WVRQAPGKGLEWVG (SEQ ID NO: 34) | RFTISKDNSKNTVYL QMNSLRAEDTAVYYC AR (SEQ ID NO: 38) | WGQGTTVTVSS (SEQ ID NO: 45) |
| 2E2 RHE E-D | EVQLVESGGGLVQPG GSLRLSCAASGFSLT (SEQ ID NO: 26) | WVRQAPGKGLEWVG (SEQ ID NO: 34) | RFTISKDNSKNTVYL QMNSLRAEDTAVYYC AR (SEQ ID NO: 38) | WGQGTTVTVSS (SEQ ID NO: 45) |
| 2E2 RHE Y-V | EVQLVESGGGLVQPG GSLRLSCAASGFSLT (SEQ ID NO: 26) | WVRQAPGKGLEWVG (SEQ ID NO: 34) | RFTISKDNSKNTVYL QMNSLRAEDTAVYYC AR (SEQ ID NO: 38) | WGQGTTVTVSS (SEQ ID NO: 45) |
| 2E2 RHE triple | EVQLVESGGGLVQPG GSLRLSCAASGFSLT (SEQ ID NO: 26) | WVRQAPGKGLEWVG (SEQ ID NO: 34) | RFTISKDNSKNTVYL QMNSLRAEDTAVYYC AR (SEQ ID NO: 38) | WGQGTTVTVSS (SEQ ID NO: 45) |

| Light Chain | | | | |
|---|---|---|---|---|
| 2E2 | QIILTQSPAIMSASP GEKVSITC (SEQ ID NO: 47) | WFQQKPGTSPKLWIY (SEQ ID NO: 50) | GVPVRFSGSGSGTSY SLTISRMEAEDAATY YC (SEQ ID NO: 54) | FGSGTKLEIK (SEQ ID NO: 59) |
| RKA | EIVLTQSPATLSLSP GERATLSC (SEQ ID NO: 48) | WFQQKPGQAPRLLIY (SEQ ID NO: 51) | GIPARFSGSGSGTDF TLTISSLEPEDFAVY YC (SEQ ID NO: 55) | FGPGTKLDIK (SEQ ID NO: 60) |
| RKB | EIILTQSPATLSLSP GERATLSC (SEQ ID NO: 49) | WFQQKPGQAPRLWIY (SEQ ID NO: 52) | GVPARFSGSGSGTDY TLTISSLEPEDFAVY YC (SEQ ID NO: 56) | FGPGTKLDIK (SEQ ID NO: 60) |
| RKC | EIILTQSPATLSLSP GERATLSC (SEQ ID NO: 49) | WFQQKPGQAPRLLIY (SEQ ID NO: 51) | GIPARFSGSGSGTDF TLTISSLEPEDFAVY YC (SEQ ID NO: 55) | FGPGTKLDIK (SEQ ID NO: 60) |
| RKD | EIVLTQSPATLSLSP GERATLSC (SEQ ID NO: 48) | WFQQKPGQAPRLWIY (SEQ ID NO: 52) | GIPARFSGSGSGTDF TLTISSLEPEDFAVY YC (SEQ ID NO: 55) | FGPGTKLDIK (SEQ ID NO: 60) |

TABLE 3-continued

Amino acid sequences of FRs of antibodies

| | FR1 | FR2 | FR3 | FR4 |
|---|---|---|---|---|
| RKE | EIVLTQSPATLSLSPGERATLSC (SEQ ID NO: 48) | WFQQKPGQAPRLLIY (SEQ ID NO: 51) | GVPARFSGSGSGTDFTLTISSLEPEDFAVYYC (SEQ ID NO: 57) | FGPGTKLDIK (SEQ ID NO: 60) |
| RKF | EIVLTQSPATLSLSPGERATLSC (SEQ ID NO: 48) | WFQQKPGQAPRLLIY (SEQ ID NO: 51) | GIPARFSGSGSGTDYTLTISSLEPEDFAVYYC (SEQ ID NO: 58) | FGPGTKLDIK (SEQ ID NO: 60) |
| RKG | EIVLTQSPATLSLSPGERATLSC (SEQ ID NO: 48) | WYQQKPGQAPRLLIY (SEQ ID NO: 53) | GIPARESGSGSGTDFTLTISSLEPEDFAVYYC (SEQ ID NO: 55) | FGPGTKLDIK (SEQ ID NO: 60) |
| RKA F-Y | EIVLTQSPATLSLSPGERATLSC (SEQ ID NO: 48) | WFQQKPGQAPRLLIY (SEQ ID NO: 51) | GIPARFSGSGSGTDFTLTISSLEPEDFAVYYC (SEQ ID NO: 55) | FGPGTKLDIK (SEQ ID NO: 60) |
| RKF F-Y | EIVLTQSPATLSLSPGERATLSC (SEQ ID NO: 48) | WFQQKPGQAPRLLIY (SEQ ID NO: 51) | GIPARFSGSGSGTDYTLTISSLEPEDFAVYYC (SEQ ID NO: 58) | FGPGTKLDIK (SEQ ID NO: 60) |

TABLE 4

Amino acid sequences of variable regions of antibodies

| Antibody Name | Variable Heavy Chain | Variable Light Chain |
|---|---|---|
| ch2C4 | ch2C4 VH | ch2C4 VK |
| ch2E2 | ch2E2 VH (SEQ ID NO: 1) | ch2E2 VK (SEQ ID NO: 15) |
| cVHKA | ch2E2 VH (SEQ ID NO: 1) | 2E2 RKA (SEQ ID NO: 16) |
| cVHKB | ch2E2 VH (SEQ ID NO: 1) | 2E2 RKB (SEQ ID NO: 17) |
| HAcVK | 2E2 RHA (SEQ ID NO: 2) | ch2E2 VK (SEQ ID NO: 15) |
| HBcVK | 2E2 RHB (SEQ ID NO: 3) | ch2E2 VK (SEQ ID NO: 15) |
| HAKA | 2E2 RHA (SEQ ID NO: 2) | 2E2 RKA (SEQ ID NO: 16) |
| HAKB | 2E2 RHA (SEQ ID NO: 2) | 2E2 RKB (SEQ ID NO: 17) |
| HAKC | 2E2 RHA (SEQ ID NO: 2) | 2E2 RKC (SEQ ID NO: 18) |
| HAKD | 2E2 RHA (SEQ ID NO: 2) | 2E2 RKD (SEQ ID NO: 19) |
| HAKE | 2E2 RHA (SEQ ID NO: 2) | 2E2 RKE (SEQ ID NO: 20) |
| HAKF | 2E2 RHA (SEQ ID NO: 2) | 2E2 RKF (SEQ ID NO: 21) |
| HAKG | 2E2 RHA (SEQ ID NO: 2) | 2E2 RKG (SEQ ID NO: 22) |
| HBKA | 2E2 RHB (SEQ ID NO: 3) | 2E2 RKA (SEQ ID NO: 16) |
| HBKB | 2E2 RHB (SEQ ID NO: 3) | 2E2 RKB (SEQ ID NO: 17) |
| HBKC | 2E2 RHB (SEQ ID NO: 3) | 2E2 RKC (SEQ ID NO: 18) |
| HBKD | 2E2 RHB (SEQ ID NO: 3) | 2E2 RKD (SEQ ID NO: 19) |
| HBKE | 2E2 RHB (SEQ ID NO: 3) | 2E2 RKE (SEQ ID NO: 20) |
| HBKF | 2E2 RHB (SEQ ID NO: 3) | 2E2 RKF (SEQ ID NO: 21) |
| HBKG | 2E2 RHB (SEQ ID NO: 3) | 2E2 RKG (SEQ ID NO: 22) |
| HCKA | 2E2 RHC (SEQ ID NO: 4) | 2E2 RKA (SEQ ID NO: 16) |
| HCKB | 2E2 RHC (SEQ ID NO: 4) | 2E2 RKB (SEQ ID NO: 17) |
| HCKC | 2E2 RHC (SEQ ID NO: 4) | 2E2 RKC (SEQ ID NO: 18) |
| HCKD | 2E2 RHC (SEQ ID NO: 4) | 2E2 RKD (SEQ ID NO: 19) |
| HCKE | 2E2 RHC (SEQ ID NO: 4) | 2E2 RKE (SEQ ID NO: 20) |
| HCKF | 2E2 RHC (SEQ ID NO: 4) | 2E2 RKF (SEQ ID NO: 21) |
| HCKG | 2E2 RHC (SEQ ID NO: 4) | 2E2 RKG (SEQ ID NO: 22) |
| HDKA | 2E2 RHD (SEQ ID NO: 5) | 2E2 RKA (SEQ ID NO: 16) |
| HDKB | 2E2 RHD (SEQ ID NO: 5) | 2E2 RKB (SEQ ID NO: 17) |
| HDKC | 2E2 RHD (SEQ ID NO: 5) | 2E2 RKC (SEQ ID NO: 18) |
| HDKD | 2E2 RHD (SEQ ID NO: 5) | 2E2 RKD (SEQ ID NO: 19) |
| HDKE | 2E2 RHD (SEQ ID NO: 5) | 2E2 RKE (SEQ ID NO: 20) |
| HDKF | 2E2 RHD (SEQ ID NO: 5) | 2E2 RKF (SEQ ID NO: 21) |
| HDKG | 2E2 RHD (SEQ ID NO: 5) | 2E2 RKG (SEQ ID NO: 22) |
| HEKA | 2E2 RHE (SEQ ID NO: 6) | 2E2 RKA (SEQ ID NO: 16) |
| HEKB | 2E2 RHE (SEQ ID NO: 6) | 2E2 RKB (SEQ ID NO: 17) |
| HEKC | 2E2 RHE (SEQ ID NO: 6) | 2E2 RKC (SEQ ID NO: 18) |
| HEKD | 2E2 RHE (SEQ ID NO: 6) | 2E2 RKD (SEQ ID NO: 19) |
| HEKE | 2E2 RHE (SEQ ID NO: 6) | 2E2 RKE (SEQ ID NO: 20) |
| HEKF | 2E2 RHE (SEQ ID NO: 6) | 2E2 RKF (SEQ ID NO: 21) |
| HEKG | 2E2 RHE (SEQ ID NO: 6) | 2E2 RKG (SEQ ID NO: 22) |

TABLE 4-continued

Amino acid sequences of variable regions of antibodies

| Antibody Name | Variable Heavy Chain | Variable Light Chain |
| --- | --- | --- |
| HFKA | 2E2 RHF (SEQ ID NO: 7) | 2E2 RKA (SEQ ID NO: 16) |
| HFKB | 2E2 RHF (SEQ ID NO: 7) | 2E2 RKB (SEQ ID NO: 17) |
| HFKC | 2E2 RHF (SEQ ID NO: 7) | 2E2 RKC (SEQ ID NO: 18) |
| HFKD | 2E2 RHF (SEQ ID NO: 7) | 2E2 RKD (SEQ ID NO: 19) |
| HFKE | 2E2 RHF (SEQ ID NO: 7) | 2E2 RKE (SEQ ID NO: 20) |
| HFKF | 2E2 RHF (SEQ ID NO: 7) | 2E2 RKF (SEQ ID NO: 21) |
| HFKG | 2E2 RHF (SEQ ID NO: 7) | 2E2 RKG (SEQ ID NO: 22) |
| HGKA | 2E2 RHG (SEQ ID NO: 8) | 2E2 RKA (SEQ ID NO: 16) |
| HGKB | 2E2 RHG (SEQ ID NO: 8) | 2E2 RKB (SEQ ID NO: 17) |
| HGKC | 2E2 RHG (SEQ ID NO: 8) | 2E2 RKC (SEQ ID NO: 18) |
| HGKD | 2E2 RHG (SEQ ID NO: 8) | 2E2 RKD (SEQ ID NO: 19) |
| HGKE | 2E2 RHG (SEQ ID NO: 8) | 2E2 RKE (SEQ ID NO: 20) |
| HGKF | 2E2 RHG (SEQ ID NO: 8) | 2E2 RKF (SEQ ID NO: 21) |
| HGHG | 2E2 RHG (SEQ ID NO: 8) | 2E2 RKG (SEQ ID NO: 22) |
| HA2KA | 2E2 RHA2 (SEQ ID NO: 9) | 2E2 RKA (SEQ ID NO: 16) |
| HA2KB | 2E2 RHA2 (SEQ ID NO: 9) | 2E2 RKB (SEQ ID NO: 17) |
| HB2KA | 2E2 RHB2 (SEQ ID NO: 10) | 2E2 RKA (SEQ ID NO: 16) |
| HB2KB | 2E2 RHB2 (SEQ ID NO: 10) | 2E2 RKB (SEQ ID NO: 17) |
| HA2KF | 2E2 RHA2 (SEQ ID NO: 9) | 2E2 RKF (SEQ ID NO: 21) |
| HB2KF | 2E2 RHB2 (SEQ ID NO: 10) | 2E2 RKF (SEQ ID NO: 21) |
| HA2KC | 2E2 RHA2 (SEQ ID NO: 9) | 2E2 RKC (SEQ ID NO: 18) |
| HA2KD | 2E2 RHA2 (SEQ ID NO: 9) | 2E2 RKD (SEQ ID NO: 19) |
| HA2KE | 2E2 RHA2 (SEQ ID NO: 9) | 2E2 RKE (SEQ ID NO: 20) |
| HA2KF | 2E2 RHA2 (SEQ ID NO: 9) | 2E2 RKF (SEQ ID NO: 21) |
| HA2KG | 2E2 RHA2 (SEQ ID NO: 9) | 2E2 RKG (SEQ ID NO: 22) |
| HB2KC | 2E2 RHB2 (SEQ ID NO: 10) | 2E2 RKC (SEQ ID NO: 18) |
| HB2KD | 2E2 RHB2 (SEQ ID NO: 10) | 2E2 RKD (SEQ ID NO: 19) |
| HB2KE | 2E2 RHB2 (SEQ ID NO: 10) | 2E2 RKE (SEQ ID NO: 20) |
| HA2KFmut | 2E2 RHA2 (SEQ ID NO: 9) | 2E2 RKF F-Y mut (SEQ ID NO: 24) |
| HB2KFmut | 2E2 RHB2 (SEQ ID NO: 10) | 2E2 RKF F-Y mut (SEQ ID NO: 24) |
| HEKAmut | 2E2 RHE (SEQ ID NO: 6) | 2E2 RKA F-Y mut (SEQ ID NO: 23) |
| HEKFmut | 2E2 RHE (SEQ ID NO: 6) | 2E2 RKF F-Y mut (SEQ ID NO: 24) |
| HAKFmut | 2E2 RHA (SEQ ID NO: 2) | 2E2 RKF F-Y mut (SEQ ID NO: 24) |
| HBKFmut | 2E2 RHB (SEQ ID NO: 3) | 2E2 RKF F-Y mut (SEQ ID NO: 24) |
| HCKFmut | 2E2 RHC (SEQ ID NO: 4) | 2E2 RKF F-Y mut (SEQ ID NO: 24) |
| HDKFmut | 2E2 RHD (SEQ ID NO: 5) | 2E2 RKF F-Y mut (SEQ ID NO: 24) |
| HFKFmut | 2E2 RHF (SEQ ID NO: 7) | 2E2 RKF F-Y mut (SEQ ID NO: 24) |
| HGKFmut | 2E2 RHG (SEQ ID NO: 8) | 2E2 RKF F-Y mut (SEQ ID NO: 24) |
| RHE Y-VKA | 2E2 RHE Y-V (SEQ ID NO: 13) | 2E2 RKA (SEQ ID NO: 16) |
| RHE Y-VKB | 2E2 RHE Y-V (SEQ ID NO: 13) | 2E2 RKB (SEQ ID NO: 17) |
| RHE Y-VKC | 2E2 RHE Y-V (SEQ ID NO: 13) | 2E2 RKC (SEQ ID NO: 18) |
| RHE Y-VKD | 2E2 RHE Y-V (SEQ ID NO: 13) | 2E2 RKD (SEQ ID NO: 19) |
| RHE Y-VKE | 2E2 RHE Y-V (SEQ ID NO: 13) | 2E2 RKE (SEQ ID NO: 20) |
| RHE Y-VKF | 2E2 RHE Y-V (SEQ ID NO: 13) | 2E2 RKF (SEQ ID NO: 21) |
| RHE Y-VKG | 2E2 RHE Y-V (SEQ ID NO: 13) | 2E2 RKG (SEQ ID NO: 22) |
| RHE E-DKA | 2E2 RHE E-D (SEQ ID NO: 12) | 2E2 RKA (SEQ ID NO: 16) |
| RHE E-DKB | 2E2 RHE E-D (SEQ ID NO: 12) | 2E2 RKB (SEQ ID NO: 17) |
| RHE E-DKC | 2E2 RHE E-D (SEQ ID NO: 12) | 2E2 RKC (SEQ ID NO: 18) |
| RHE E-DKD | 2E2 RHE E-D (SEQ ID NO: 12) | 2E2 RKD (SEQ ID NO: 19) |
| RHE E-DKE | 2E2 RHE E-D (SEQ ID NO: 12) | 2E2 RKE (SEQ ID NO: 20) |
| RHE E-DKF | 2E2 RHE E-D (SEQ ID NO: 12) | 2E2 RKF (SEQ ID NO: 21) |
| RHE E-DKG | 2E2 RHE E-D (SEQ ID NO: 12) | 2E2 RKG (SEQ ID NO: 22) |
| RHE E-DKFmut | 2E2 RHE E-D (SEQ ID NO: 12) | 2E2 RKF F-Y mut (SEQ ID NO: 24) |
| RHE S-GKA | 2E2 RHE S-G (SEQ ID NO: 11) | 2E2 RKA (SEQ ID NO: 16) |
| RHE S-GKB | 2E2 RHE S-G (SEQ ID NO: 11) | 2E2 RKB (SEQ ID NO: 17) |
| RHE S-GKC | 2E2 RHE S-G (SEQ ID NO: 11) | 2E2 RKC (SEQ ID NO: 18) |
| RHE S-GKD | 2E2 RHE S-G (SEQ ID NO: 11) | 2E2 RKD (SEQ ID NO: 19) |
| RHE S-GKE | 2E2 RHE S-G (SEQ ID NO: 11) | 2E2 RKE (SEQ ID NO: 20) |
| RHE S-GKF | 2E2 RHE S-G (SEQ ID NO: 11) | 2E2 RKF (SEQ ID NO: 21) |
| RHE S-GKG | 2E2 RHE S-G (SEQ ID NO: 11) | 2E2 RKG (SEQ ID NO: 22) |
| RHE Triple-KA | 2E2 RHE triple (SEQ ID NO: 14) | 2E2 RKA (SEQ ID NO: 16) |
| RHE Triple-KB | 2E2 RHE triple (SEQ ID NO: 14) | 2E2 RKB (SEQ ID NO: 17) |
| RHE Triple-KC | 2E2 RHE triple (SEQ ID NO: 14) | 2E2 RKC (SEQ ID NO: 18) |
| RHE Triple-KD | 2E2 RHE triple (SEQ ID NO: 14) | 2E2 RKD (SEQ ID NO: 19) |
| RHE Triple-KE | 2E2 RHE triple (SEQ ID NO: 14) | 2E2 RKE (SEQ ID NO: 20) |
| RHE Triple-KF | 2E2 RHE triple (SEQ ID NO: 14) | 2E2 RKF (SEQ ID NO: 21) |
| RHE Triple-KG | 2E2 RHE triple (SEQ ID NO: 14) | 2E2 RKG (SEQ ID NO: 22) |
| RHE Triple-KFmut | 2E2 RHE triple (SEQ ID NO: 14) | 2E2 RKF F-Y mut (SEQ ID NO: 24) |
| RHE Y-VKFmut | 2E2 RHE Y-V (SEQ ID NO: 13) | 2E2 RKF F-Y mut (SEQ ID NO: 24) |
| RHE E-DKFmut | 2E2 RHE E-D (SEQ ID NO: 12) | 2E2 RKF F-Y mut (SEQ ID NO: 24) |

TABLE 5

Amino acid sequences of HVRs from murine 1C3, 1H10, and 4F11 antibodies

| Antibody | Chain | HVR1 | HVR2 | HVR3 |
|---|---|---|---|---|
| 1C3 | Heavy Chain | SYAMS<br>SEQ ID NO: 88 | IISSGGSYTYYSDSVKG<br>SEQ ID NO: 91 | HETAQAAWFAY<br>SEQ ID NO: 94 |
| 1H10 | Heavy Chain | DYYMY<br>SEQ ID NO: 89 | RIAPEDGDTEYAPKFQG<br>SEQ ID NO: 92 | EGNYYGSSILDY<br>SEQ ID NO: 95 |
| 4F11 | Heavy Chain | SSWMN<br>SEQ ID NO: 90 | QIYPGDDYTNYNGKFKG<br>SEQ ID NO: 93 | LGPYGPFAD<br>SEQ ID NO: 96 |
| 1C3 | Light Chain | SASSSVSYMH<br>SEQ ID NO: 97 | DTSKLAY<br>SEQ ID NO: 100 | QQWSSNPPT<br>SEQ ID NO: 103 |
| 1H10 | Light Chain | RASQDITNYLN<br>SEQ ID NO: 98 | FTSRLHS<br>SEQ ID NO: 101 | QQGNTLPWT<br>SEQ ID NO: 104 |
| 4F11 | Light Chain | SASSSVSYMY<br>SEQ ID NO: 99 | DTSSLAS<br>SEQ ID NO: 102 | QQWNSDPYT<br>SEQ ID NO: 105 |

There are five classes of immunoglobulins: IgA, IgD, IgE, IgG and IgM, having heavy chains designated α, δ, ε, γ and μ, respectively. The γ and α classes are further divided into subclasses e.g., humans express the following subclasses: IgG1, IgG2, IgG3, IgG4, IgA1 and IgA2. IgG1 antibodies can exist in multiple polymorphic variants termed allotypes (reviewed in Jefferis and Lefranc 2009. mAbs Vol 1 Issue 41-7) any of which are suitable for use in some of the embodiments herein. Common allotypic variants in human populations are those designated by the letters a, f, n, z or combinations thereof. In any of the embodiments herein, the antibody may comprise a heavy chain Fc region comprising a human IgG Fc region. In further embodiments, the human IgG Fc region comprises a human IgG1 or IgG4. In some embodiments, the human IgG4 comprises the amino acid substitution S228P, wherein the amino acid residues are numbered according to the EU index as in Kabat. In some embodiments, the human IgG1 comprises the amino acid sequence of SEQ ID NO:78. In some embodiments, the human IgG4 comprises the amino acid sequence of SEQ ID NO:79.

In some embodiments, provided herein is an anti-Siglec-8 antibody comprising a heavy chain comprising the amino acid sequence of SEQ ID NO:75; and/or a light chain comprising the amino acid sequence selected from SEQ ID NOs:76 or 77. In some embodiments, the antibody may comprise a heavy chain comprising the amino acid sequence of SEQ ID NO:87; and/or a light chain comprising the amino acid sequence of SEQ ID NO:76. In some embodiments, the anti-Siglec-8 antibody depletes mast cells and inhibits mast cell activation. In some embodiments, the anti-Siglec-8 antibody depletes activated eosinophils and inhibits mast cell activation. In some embodiments, the anti-Siglec-8 antibody induces apoptosis of activated eosinophils. In some embodiments, the anti-Siglec-8 antibody induces apoptosis of resting eosinophils. In some embodiments herein, the antibody depletes eosinophils in a tissue (e.g., nasal polyps). In some embodiments herein, the antibody depletes eosinophils in a biological fluid (e.g., blood).

1. Antibody Affinity

In some aspects, an anti-Siglec-8 antibody described herein binds to human Siglec-8 with about the same or higher affinity and/or higher avidity as compared mouse antibody 2E2 and/or mouse antibody 2C4. In certain embodiments, an anti-Siglec-8 antibody provided herein has a dissociation constant (Kd) of ≤1 μM, ≤150 nM, ≤100 nM, ≤50 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g. from $10^{-9}$ M to $10^{-13}$ M). In some embodiments, an anti-Siglec-8 antibody described herein binds to human Siglec-8 at about 1.5-fold, about 2-fold, about 3-fold, about 4-fold, about 5-fold, about 6-fold, about 7-fold, about 8-fold, about 9-fold or about 10-fold higher affinity than mouse antibody 2E2 and/or mouse antibody 2C4. In some embodiments herein, the anti-Siglec-8 antibody comprises a heavy chain variable region comprising the amino acid sequence of SEQ ID NO:6; and/or a light chain variable region comprising the amino acid sequence selected from SEQ ID NOs: 16 or 21.

In one embodiment, the binding affinity of the anti-Siglec-8 antibody can be determined by a surface plasmon resonance assay. For example, the Kd or Kd value can be measured by using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore® Inc.) are activated with N-ethyl-N'-(3-dimethylaminopropyl)-carbodiimide hydrochloride (EDC) and N-hydroxysuccinimide (NHS) according to the supplier's instructions. Capture antibodies (e.g. anti-human-Fc) are diluted with 10 mM sodium acetate, pH 4.8, before injection at a flow rate of 30 μl/minute and further immobilized with an anti-Siglec-8 antibody. For kinetics measurements, two-fold serial dilutions of dimeric Siglec-8 are injected in PBS with 0.05% Tween 20 (PBST) at 25° C. at a flow rate of approximately 25 μl/min. Association rates (kon) and dissociation rates (koff) are calculated using a simple one-to-one Langmuir binding model (BIAcore® Evaluation Software version 3.2) by simultaneously fitting the association and dissociation sensorgrams. The equilibrium dissociation constant (Kd) is calculated as the ratio koff/kon. See, e.g., Chen, Y., et al., (1999) J. Mol. Biol. 293:865-881.

In another embodiment, biolayer interferometry may be used to determine the affinity of anti-Siglec-8 antibodies against Siglec-8. In an exemplary assay, Siglec-8-Fc tagged protein is immobilized onto anti-human capture sensors, and incubated with increasing concentrations of mouse, chimeric, or humanized anti-Siglec-8 Fab fragments to obtain affinity measurements using an instrument such as, for example, the Octet Red 384 System (ForteBio).

The binding affinity of the anti-Siglec-8 antibody can, for example, also be determined by the Scatchard analysis described in Munson et al., *Anal. Biochem.*, 107:220 (1980) using standard techniques well known in the relevant art. See also Scatchard. G., *Ann. N.Y. Acad. Sci.* 51:660 (1947).

1. Antibody Avidity

In one embodiment, the binding avidity of the anti-Siglec-8 antibody can be determined by a surface plasmon resonance assay. For example, the Kd or Kd value can be measured by using a BIAcore T100. Capture antibodies (e.g., goat-anti-human-Fc and goat-anti-mouse-Fc) are immobilized on a CM5 chip. Flow-cells can be immobilized with anti-human or with anti-mouse antibodies. The assay is conducted at a certain temperature and flow rate, for example, at 25° C. at a flow rate of 30 1l/min. Dimeric Siglec-8 is diluted in assay buffer at various concentrations, for example, at a concentration ranging from 15 nM to 1.88 pM. Antibodies are captured and high performance injections are conducted, followed by dissociations. Flow cells are regenerated with a buffer, for example, 50 mM glycine pH 1.5. Results are blanked with an empty reference cell and multiple assay buffer injections, and analyzed with 1:1 global fit parameters.

2. Competition Assays

Competition assays can be used to determine whether two antibodies bind the same epitope by recognizing identical or sterically overlapping epitopes or one antibody competitively inhibits binding of another antibody to the antigen. These assays are known in the art. Typically, antigen or antigen expressing cells is immobilized on a multi-well plate and the ability of unlabeled antibodies to block the binding of labeled antibodies is measured. Common labels for such competition assays are radioactive labels or enzyme labels. In some embodiments, an anti-Siglec-8 antibody described herein competes with a 2E2 antibody described herein, for binding to the epitope present on the cell surface of a cell (e.g., an eosinophil or a mast cell). In some embodiments, an anti-Siglec-8 antibody described herein competes with an antibody comprising a heavy chain variable domain comprising the amino acid sequence of SEQ ID NO:1, and a light chain variable region comprising the amino acid sequence of SEQ ID NO:15, for binding to the epitope present on the cell surface of a cell (e.g., an eosinophil or a mast cell). In some embodiments, an anti-Siglec-8 antibody described herein competes with a 2C4 antibody described herein, for binding to the epitope present on the cell surface of a cell (e.g., an eosinophil or a mast cell). In some embodiments, an anti-Siglec-8 antibody described herein competes with an antibody comprising a heavy chain variable domain comprising the amino acid sequence of SEQ ID NO:2 (as found in U.S. Pat. No. 8,207,305), and a light chain variable region comprising the amino acid sequence of SEQ ID NO:4 (as found in U.S. Pat. No. 8,207,305), for binding to the epitope present on the cell surface of a cell (e.g., an eosinophil or a mast cell).

3. Thermal Stability

In some aspects, an anti-Siglec-8 described herein has a melting temperature (Tm) of at least about 70° C., at least about 71° C., or at least about 72° C. in a thermal shift assay. In an exemplary thermal shift assay, samples comprising a humanized anti-Siglec-8 antibody are incubated with a fluorescent dye (Sypro Orange) for 71 cycles with 1° C. increase per cycle in a qPCR thermal cycler to determine the Tm. In some embodiments herein, the anti-Siglec-8 antibody has a similar or higher Tm as compared to mouse 2E2 antibody and/or mouse 2C4 antibody. In some embodiments herein, the anti-Siglec-8 antibody comprises a heavy chain variable region comprising the amino acid sequence of SEQ ID NO:6; and/or a light chain variable region comprising the amino acid sequence selected from SEQ ID NOs: 16 or 21. In some embodiments, the anti-Siglec-8 antibody has the same or higher Tm as compared to a chimeric 2C4 antibody. In some embodiments, the anti-Siglec-8 antibody has the same or higher Tm as compared to an antibody having a heavy chain comprising the amino acid sequence of SEQ ID NO:84 and a light chain comprising the amino acid sequence of SEQ ID NO:85.

4. Biological Activity Assays

In some aspects, an anti-Siglec-8 antibody described herein induces apoptosis of eosinophils. In some other aspects, an anti-Siglec-8 antibody described herein depletes mast cells. Assays for assessing apoptosis of cells are well known in the art, for example staining with Annexin V and the TUNEL assay. In an exemplary cell apoptosis assay, fresh buffy coat from a blood sample is resuspended in media and plated in a 96-well U-bottom plate. A series of serial 5-fold dilutions of anti-Siglec-8 antibody is added to each well and the plate is incubated at 37° C. at 5% $CO_2$ for greater than four hours. The cells are fixed with paraformaldehyde diluted in PBS and stained with conjugated antibodies specific for eosinophils for detection using a microscope. The eosinophil population in the total peripheral blood leukocytes is evaluated when the buffy coat is incubated in the presence of the anti-Siglec-8 antibody as compared to when the buffy coat is not incubated in the presence of the anti-Siglec-8 antibody. In another exemplary assay, eosinophils purified from a blood sample (e.g., Miltenyi Eosinophil Isolation Kit) are resuspended in media and cultured in the presence or absence of IL-5 overnight. The cultured eosinophils are subsequently harvested by centrifugation, resuspended in media, and plated in a 96-well U-bottom plate. A series of serial 5-fold dilutions of anti-Siglec-8 antibody is added to each well and the plate is incubated at 37° C. at 5% $CO_2$ for greater than four hours. The cells are fixed and stained with Annexin-V using standard techniques well known in the art the number of eosinophils is detected using a microscope. The eosinophil population in the sample is evaluated when the purified cells are incubated in the presence of the anti-Siglec-8 antibody as compared to when the purified cells are not incubated in the presence of the anti-Siglec-8 antibody.

In some aspects, an anti-Siglec-8 antibody described herein induces ADCC activity. In some other aspects, an anti-Siglec-8 antibody described herein kills mast cells expressing Siglec-8 by ADCC activity. In some embodiments, a composition comprises non-fucosylated (i.e., afucosylated) anti-Siglec-8 antibodies. In some embodiments, a composition comprising non-fucosylated anti-Siglec-8 antibodies described herein enhances ADCC activity as compared to a composition comprising partially fucosylated anti-Siglec-8 antibodies. Assays for assessing ADCC activity are well known in the art and described herein. In an exemplary assay, to measure ADCC activity, effector cells and target cells are used. Examples of effector cells include natural killer (NK) cells, large granular lymphocytes (LGL), lymphokine-activated killer (LAK) cells and PBMC comprising NK and LGL, or leukocytes having Fc receptors on the cell surfaces, such as neutrophils, eosinophils and macrophages. The target cell is any cell which expresses on the cell surface antigens that antibodies to be evaluated can recognize. An example of such a target cell is an eosinophil which expresses Siglec-8 on the cell surface. Another example of such a target cell is a mast cell which expresses Siglec-8 on the cell surface. Target cells are labeled with a reagent that enables detection of cytolysis. Examples of reagents for labeling include a radio-active substance such as sodium chromate ($Na_2$ $^{51}CrO_4$). See, e.g., Immunology, 14, 181 (1968); *J. Immunol. Methods.*, 172, 227 (1994); and *J. Immunol. Methods.*, 184, 29 (1995).

In some aspects, an anti-Siglec-8 antibody described herein inhibits mast cell-mediated activities. Mast cell tryptase has been used as a biomarker for total mast cell number and activation. For example, total and active tryptase as well as histamine, N-methyl histamine, and 11-beta-prostaglandin F2 can be measured in blood or urine to assess the reduction in mast cells. See, e.g., U.S. Patent Application Publication No. US 20110293631 for an exemplary mast cell activity assay. In an exemplary assay to assess ADCC and apoptotic activity of anti-Siglec-8 antibodies on mast cells, human mast cells are isolated from human tissues according to published protocols (Guhl et al., *Biosci. Biotechnol. Biochem.*, 2011, 75:382-384; Kulka et al., *In Current Protocols in Immunology*, 2001, (John Wiley & Sons, Inc.)) or differentiated from human hematopoietic stem cells, for example as described by Yokoi et al., *J Allergy Clin Immunol.*, 2008, 121:499-505. Purified mast cells are resuspended in Complete RPMI medium in a sterile 96-well U-bottom plate and incubated in the presence or absence of anti Siglec-8 antibodies for 30 minutes at concentrations ranging between 0.0001 ng/ml and 10 µg/ml. Samples are incubated for a further 4 to 16 hours with and without purified natural killer (NK) cells or fresh PBL to induce ADCC. Cell-killing by apoptosis or ADCC is analyzed by flow cytometry using fluorescent conjugated antibodies to detect mast cells (CD117 and FcεR1) and Annexin-V and 7AAD to discriminate live and dead or dying cells. Annexin-V and 7AAD staining are performed according to manufacturer's instructions.

In some aspects, an anti-Siglec-8 antibody described herein inhibits neutrophil influx to sites of fibrotic disease (e.g., pulmonary fibrosis). Bleomycin is a glycopeptide antitumor antibiotic and antiviral drug. Bleomycin acts by induction of DNA strand breaks. The most serious complication of bleomycin is pulmonary fibrosis and impaired lung function. A well-known animal model of pulmonary fibrosis is generated by a single intratracheal or intranasal delivery of bleomycin to the lungs of a rodent (e.g., a mouse or a rat). Administration of bleomycin generally results in dose-dependent damage to the lung, characterized by inflammatory cell infiltrates, collagen accumulation, and parenchymal consolidation. The lungs are generally studied 7 to 14 days following a single administration of bleomycin. See Mouratis et al., *Curr Opin Pulm Med.*, 2011, 17(5):355-61. In an exemplary assay, transgenic rodents expressing human Siglec-8 on eosinophils, mast cells, and basophils and with bleomycin-induced pulmonary fibrosis are treated with an anti-Siglec-8 antibody described herein at a dosage regimen of interest. Bronchoalveolar lavage (BAL) fluid is harvested from the treated rodents and processed for leukocyte evaluation. The BAL fluid is centrifuged and cell pellet is resuspended in an appropriate lysing buffer to lyse the red blood cells. Phosphate buffered saline (PBS) supplemented with Fetal Bovine Serum (FBS) is added to stop the lysis reaction before centrifuging the sample again to obtain a leukocyte pellet. The number of leukocytes are counted using a hemocytometer and the trypan blue exclusion method as described herein.

In some aspects, an anti-Siglec-8 antibody described herein prevents collagen accumulation at sites of fibrotic disease (e.g., pulmonary fibrosis In an exemplary assay, transgenic rodents expressing human Siglec-8 on eosinophils, mast cells, and basophils and with bleomycin-induced pulmonary fibrosis are treated with an anti-Siglec-8 antibody described herein at a dosage regimen of interest. Bronchoalveolar lavage (BAL) fluid is harvested from the treated rodents and processed for collagen evaluation. The BAL fluid is centrifuged and the supernatant is analyzed for collagen using a collagen assay such as Sircol™ Collagen Assay (Biocolor Life Science Assays, United Kingdom).

Antibody Preparation

The antibody described herein (e.g., an antibody that binds to human Siglec-8) is prepared using techniques available in the art for generating antibodies, exemplary methods of which are described in more detail in the following sections.

1. Antibody Fragments

The present invention encompasses antibody fragments. Antibody fragments may be generated by traditional means, such as enzymatic digestion, or by recombinant techniques. In certain circumstances there are advantages of using antibody fragments, rather than whole antibodies. For a review of certain antibody fragments, see Hudson et al. (2003) *Nat. Med.* 9:129-134.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., Science, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form $F(ab')_2$ fragments (Carter et al., Bio/Technology 10: 163-167 (1992)). According to another approach, $F(ab')_2$ fragments can be isolated directly from recombinant host cell culture. Fab and $F(ab')_2$ fragment with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See WO 93/16185; U.S. Pat. Nos. 5,571,894; and 5,587,458. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See Antibody Engineering, ed. Borrebaeck, supra. The antibody fragment may also be a "linear antibody", e.g., as described in U.S. Pat. No. 5,641,870, for example. Such linear antibodies may be monospecific or bispecific.

2. Humanized Antibodies

The invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter (Jones et al. (1986) *Nature* 321:522-525; Riechmann et al. (1988) *Nature* 332:323-327; Verhoeyen et al. (1988) *Science* 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies can be important to reduce antigenicity. According to the so-called "best-fit" method, the sequence of the variable domain of a rodent (e.g., mouse) antibody is screened against the entire library of known human variable-domain sequences. The human sequence which is closest to that of the rodent is then accepted as the human framework for the humanized antibody (Sims et al. (1993) J. Immunol. 151: 2296; Chothia et al. (1987) J. Mol. Biol. 196:901. Another method uses a particular framework derived from the consensus sequence of all human antibodies of a particular subgroup of light or heavy chains. The same framework may be used for several different humanized antibodies (Carter et al. (1992) Proc. Natl. Acad. Sci. USA, 89:4285; Presta et al. (1993) J. Immunol., 151:2623.

It is further generally desirable that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those, skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

3. Human Antibodies

Human anti-Siglec-8 antibodies of the invention can be constructed by combining Fv clone variable domain sequence(s) selected from human-derived phage display libraries with known human constant domain sequences(s). Alternatively, human monoclonal anti-Siglec-8 antibodies of the invention can be made by the hybridoma method. Human myeloma and mouse-human heteromyeloma cell lines for the production of human monoclonal antibodies have been described, for example, by Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).

It is possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90: 2551 (1993); Jakobovits et al., Nature, 362: 255 (1993); Bruggermann et al., Year in Immunol., 7: 33 (1993).

Gene shuffling can also be used to derive human antibodies from non-human (e.g., rodent) antibodies, where the human antibody has similar affinities and specificities to the starting non-human antibody. According to this method, which is also called "epitope imprinting", either the heavy or light chain variable region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e., the epitope governs the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

4. Bispecific Antibodies

Bispecific antibodies are monoclonal antibodies that have binding specificities for at least two different antigens. In certain embodiments, bispecific antibodies are human or humanized antibodies. In certain embodiments, one of the binding specificities is for Siglec-8 and the other is for any other antigen. In certain embodiments, bispecific antibodies may bind to two different epitopes of Siglec-8. Bispecific antibodies may also be used to localize cytotoxic agents to cells which express Siglec-8. Bispecific antibodies can be prepared as full length antibodies or antibody fragments (e.g. F(ab')$_2$ bispecific antibodies).

Methods for making bispecific antibodies are known in the art. See Milstein and Cuello. Nature, 305: 537 (1983), WO 93/08829 published May 13, 1993, and Traunecker et al., EMBO J., 10: 3655 (1991). For further details of generating bispecific antibodies see, for example, Suresh et al., Methods in Enzymology, 121:210 (1986). Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking method. Suitable cross-linking agents are well known in the art, and are disclosed in U.S. Pat. No. 4,676,980, along with a number of cross-linking techniques.

5. Single-Domain Antibodies

In some embodiments, an antibody of the invention is a single-domain antibody. A single-domain antibody is a single polypeptide chain comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1). In one embodiment, a single-domain antibody consists of all or a portion of the heavy chain variable domain of an antibody.

6. Antibody Variants

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) Science, 244: 1081-1085. Here, a residue or group of target residues are identified (e.g., charged residues such as arg, asp, his, lys, and glu) and replaced by a neutral or negatively charged amino acid (e.g., alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme or a polypeptide which increases the serum half-life of the antibody.

In some embodiments, monoclonal antibodies have a C-terminal cleavage at the heavy chain and/or light chain. For example, 1, 2, 3, 4, or 5 amino acid residues are cleaved at the C-terminus of heavy chain and/or light chain. In some embodiments, the C-terminal cleavage removes a C-terminal lysine from the heavy chain. In some embodiments, monoclonal antibodies have an N-terminal cleavage at the heavy chain and/or light chain. For example, 1, 2, 3, 4, or 5 amino acid residues are cleaved at the N-terminus of heavy chain and/or light chain. In some embodiments, truncated forms of monoclonal antibodies can be made by recombinant techniques.

In certain embodiments, an antibody of the invention is altered to increase or decrease the extent to which the antibody is glycosylated. Glycosylation of polypeptides is typically either N-linked or O-linked. N-linked refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition or deletion of glycosylation sites to the antibody is conveniently accomplished by altering the amino acid sequence such that one or more of the above-described tripeptide sequences (for N-linked glycosylation sites) is created or removed. The alteration may also be made by the addition, deletion, or substitution of one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fucose attached to an Fc region of the antibody are described in US Pat Appl No US 2003/0157108 (Presta, L.). See also US 2004/0093621 (Kyowa Hakko Kogyo Co., Ltd). Antibodies with a bisecting N-acetylglucosamine (GlcNAc) in the carbohydrate attached to an Fc region of the antibody are referenced in WO 2003/011878, Jean-Mairet et al. and U.S. Pat. No. 6,602,684, Umana et al. Antibodies with at least one galactose residue in the oligosaccharide attached to an Fc region of the antibody are reported in WO 1997/30087, Patel et al. See, also, WO 1998/58964 (Raju. S.) and WO 1999/22764 (Raju, S.) concerning antibodies with altered carbohydrate attached to the Fc region thereof. See also US 2005/0123546 (Umana et al.) on antigen-binding molecules with modified glycosylation.

In certain embodiments, a glycosylation variant comprises an Fc region, wherein a carbohydrate structure attached to the Fc region lacks fucose. Such variants have improved ADCC function. Optionally, the Fc region further comprises one or more amino acid substitutions therein which further improve ADCC, for example, substitutions at positions 298, 333, and/or 334 of the Fc region (Eu numbering of residues). Examples of publications related to "defucosylated" or "fucose-deficient" antibodies include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; Okazaki et al. J. Mol. Biol. 336:1239-1249 (2004); Yamane-Ohnuki et al. Biotech. Bioeng. 87: 614 (2004). Examples of cell lines producing defucosylated antibodies include Lec13 CHO cells deficient in protein fucosylation (Ripka et al. Arch. Biochem. Biophys. 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (Yamane-Ohnuki et al. Biotech. Bioeng. 87: 614 (2004)), and cells overexpressing β1,4-N-acetylglycosminyltransferase III (GnT-III) and Golgi μ-mannosidase II (ManII).

Antibodies are contemplated herein that have reduced fucose relative to the amount of fucose on the same antibody produced in a wild-type CHO cell. For example, the antibody has a lower amount of fucose than it would otherwise have if produced by native CHO cells (e.g., a CHO cell that produce a native glycosylation pattern, such as, a CHO cell containing a native FUT8 gene). In certain embodiments, an anti-Siglec-8 antibody provided herein is one wherein less than about 50%, 40%, 30%, 20%, 10%, 5% or 1% of the N-linked glycans thereon comprise fucose. In certain embodiments, an anti-Siglec-8 antibody provided herein is one wherein none of the N-linked glycans thereon comprise fucose, i.e. wherein the antibody is completely without fucose, or has no fucose or is non-fucosylated or is afucosylated. The amount of fucose can be determined by calculating the average amount of fucose within the sugar chain at Asn297, relative to the sum of all glycostructures attached to Asn297 (e.g., complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. In some embodiments, at least one or two of the heavy chains of the antibody is non-fucosylated.

In one embodiment, the antibody is altered to improve its serum half-life. To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule (US 2003/0190311. U.S. Pat. Nos. 6,821,505; 6,165,745; 5,624,821; 5,648,260; 6,165,745; 5,834,597).

Another type of variant is an amino acid substitution variant. These variants have at least one amino acid residue in the antibody molecule replaced by a different residue. Sites of interest for substitutional mutagenesis include the hypervariable regions, but FR alterations are also contemplated. Conservative substitutions are shown in Table 1 under the heading of "preferred substitutions." If such substitutions result in a desirable change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation. (b) the charge or hydrophobicity of the molecule at the target site, or c) the bulk of the side chain. Amino acids may be grouped according to similarities in the properties of their side chains (in A. L. Lehninger, in Biochemistry, second ed., pp. 73-75, Worth Publishers, New York (1975)):

(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His (H)

Alternatively, naturally occurring residues may be divided into groups based on common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg:
(5) residues that influence chain orientation: Gly, Pro:
(6) aromatic: Trp, Tyr, Phe.

Non-conservative substitutions will entail exchanging a member of one of these classes for another class. Such substituted residues also may be introduced into the conservative substitution sites or, into the remaining (non-conserved) sites.

One type of substitutional variant involves substituting one or more hypervariable region residues of a parent antibody (e.g., a humanized or human antibody). Generally, the resulting variant(s) selected for further development will have modified (e.g., improved) biological properties relative to the parent antibody from which they are generated. A convenient way for generating such substitutional variants involves affinity maturation using phage display. Briefly, several hypervariable region sites (e.g., 6-7 sites) are mutated to generate all possible amino acid substitutions at each site. The antibodies thus generated are displayed from filamentous phage particles as fusions to at least part of a phage coat protein (e.g., the gene III product of M13) packaged within each particle. The phage-displayed variants are then screened for their biological activity (e.g., binding affinity). In order to identify candidate hypervariable region sites for modification, scanning mutagenesis (e.g., alanine scanning) can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to techniques known in the art, including those elaborated herein. Once such variants are generated, the panel of variants is subjected to screening using techniques known in the art, including those described herein, and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of antibodies of the invention, thereby generating an Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions including that of a hinge cysteine. In some embodiments, the Fc region variant comprises a human IgG4 Fc region. In a further embodiment, the human IgG4 Fc region comprises the amino acid substitution S228P, wherein the amino acid residues are numbered according to the EU index as in Kabat.

In accordance with this description and the teachings of the art, it is contemplated that in some embodiments, an antibody of the invention may comprise one or more alterations as compared to the wild type counterpart antibody, e.g. in the Fc region. These antibodies would nonetheless retain substantially the same characteristics required for therapeutic utility as compared to their wild type counterpart. For example, it is thought that certain alterations can be made in the Fc region that would result in altered (i.e., either improved or diminished) C1q binding and/or Complement Dependent Cytotoxicity (CDC), e.g., as described in WO99/51642. See also Duncan & Winter Nature 322:738-40 (1988); U.S. Pat. Nos. 5,648,260; 5,624,821; and WO94/29351 concerning other examples of Fc region variants. WO0/42072 (Presta) and WO 2004/056312 (Lowman) describe antibody variants with improved or diminished binding to FcRs. The content of these patent publications are specifically incorporated herein by reference. See, also, Shields et al. J. Biol. Chem. 9(2): 6591-6604 (2001). Antibodies with increased half-lives and improved binding to the neonatal Fc receptor (FcRn), which is responsible for the transfer of maternal IgGs to the fetus (Guyer et al. J. Immunol. 117:587 (1976) and Kim et al., J. Immunol. 24:249 (1994)), are described in US2005/0014934A1 (Hinton et al.). These antibodies comprise an Fc region with one or more substitutions therein which improve binding of the Fc region to FcRn. Polypeptide variants with altered Fc region amino acid sequences and increased or decreased C1q binding capability are described in U.S. Pat. No. 6,194,551 B1, WO99/51642. The contents of those patent publications are specifically incorporated herein by reference. See, also, Idusogie et al. *J. Immunol.* 164: 4178-4184 (2000).

7. Vectors, Host Cells, and Recombinant Methods

For recombinant production of an antibody of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, host cells are of either prokaryotic or eukaryotic (generally mammalian) origin. It will be appreciated that constant regions of any isotype can be used for this purpose, including IgG, IgM, IgA, IgD, and IgE constant regions, and that such constant regions can be obtained from any human or animal species.

Generating Antibodies Using Prokaryotic Host Cells:

a) Vector Construction

Polynucleotide sequences encoding polypeptide components of the antibody of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes-encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as *E. coli* LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the j-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the E. coli trxB-strains) provide cytoplasm conditions that are favorable for disulfide bond formation, thereby permitting proper folding and assembly of expressed protein subunits. Proba and Pluckthun Gene, 159:203 (1995).

Antibodies of the invention can also be produced by using an expression system in which the quantitative ratio of expressed polypeptide components can be modulated in order to maximize the yield of secreted and properly assembled antibodies of the invention. Such modulation is accomplished at least in part by simultaneously modulating translational strengths for the polypeptide components.

One technique for modulating translational strength is disclosed in Simmons et al., U.S. Pat. No. 5,840,523. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence. In certain embodiments, changes in the nucleotide sequence are silent. Alterations in the TIR can include, for example, alterations in the number or spacing of Shine-Dalgarno sequences, along with alterations in the signal sequence. One method for generating mutant signal sequences is the generation of a "codon bank" at the beginning of a coding sequence that does not change the amino acid sequence of the signal sequence (i.e., the changes are silent). This can be accomplished by changing the third nucleotide position of each codon: additionally, some amino acids, such as leucine, serine, and arginine, have multiple first and second positions that can add complexity in making the bank. This method of mutagenesis is described in detail in Yansura et al. (1992) METHODS: A Companion to Methods in Enzymol. 4:151-158.

In one embodiment, a set of vectors is generated with a range of TIR strengths for each cistron therein. This limited set provides a comparison of expression levels of each chain as well as the yield of the desired antibody products under various TIR strength combinations. TIR strengths can be determined by quantifying the expression level of a reporter gene as described in detail in Simmons et al. U.S. Pat. No. 5,840,523. Based on the translational strength comparison, the desired individual TIRs are selected to be combined in the expression vector constructs of the invention.

Prokaryotic host cells suitable for expressing antibodies of the invention include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium*, *Serratia marcescans*, *Klebsiella*, *Proteus*, *Shigella*, *Rhizobia*, *Vitreoscilla*, or *Paracoccus*. In one embodiment, gram-negative cells are used. In one embodiment, *E. coli* cells are used as hosts for the invention. Examples of *E. coli* strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ(nmpc-fepE) degP41 kanR (U.S. Pat. No. 5,639,635). Other strains and derivatives thereof, such as *E. coli* 294 (ATCC 31,446), *E. coli* B, *E. coli* λ 1776 (ATCC 31.537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E. coli*, *Serratia*, or *Salmonella* species can be suitably used as the host when well known plasmids such as pBR322, pBR325, pACYC 177, or pKN410 are used to supply the replicon. Typically the host cell should secrete minimal amounts of proteolytic enzymes, and additional protease inhibitors may desirably be incorporated in the cell culture.

b) Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extra-chromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. In certain embodiments, for E. coli growth, growth temperatures range from about 20° C. to about 39° C.; from about 25° C. to about 37° C.; or about 30° C. The pH of the medium may be any pH ranging from about 5 to about 9, depending mainly on the host organism. In certain embodiments, for E. coli, the pH is from about 6.8 to about 7.4, or about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. In certain embodiments, the phosphate-limiting medium is the C.R.A.P. medium (see, e.g., Simmons et al., J. Immunol. Methods (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, and in certain embodiments, about 1,000 to 100,000 liters of capacity. These fermentors use agitator impellers to distribute oxygen and nutrients, especially glucose. Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) J. Biol. Chem. 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun (2000) J. Biol. Chem. 275: 17106-17113; Arie et al. (2001) Mol. Microbiol. 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP. Tsp, Protease I, Protease Mi, Protease V, Protease VI and combinations thereof. Some E. coli protease-deficient strains are available and described in, for example. Joly et al. (1998), supra; Georgiou et al., U.S. Pat. No. 5,264,365; Georgiou et al., U.S. Pat. No. 5,508,192; Hara et al., Microbial Drug Resistance, 2:63-72 (1996).

In one embodiment, E. coli strains deficient for proteolytic enzymes and transformed with plasmids overexpressing one or more chaperone proteins are used as host cells in the expression system of the invention.

c) Antibody Purification

In one embodiment, the antibody protein produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the antibody products of the invention. Protein A is a 41 kD cell wall protein from Staphylococcus aureus which binds with a high affinity to the Fc region of antibodies. Lindmark et al (1983) J. Immunol. Meth. 62:1-13. The solid phase to which Protein A is immobilized can be a column comprising a glass or silica surface, or a controlled pore glass column or a silicic acid column. In some applications, the column is coated with a reagent, such as glycerol, to possibly prevent non-specific adherence of contaminants.

As the first step of purification, a preparation derived from the cell culture as described above can be applied onto a Protein A immobilized solid phase to allow specific binding of the antibody of interest to Protein A. The solid phase would then be washed to remove contaminants non-specifically bound to the solid phase. Finally the antibody of interest is recovered from the solid phase by elution.

Generating Antibodies Using Eukaryotic Host Cells:

A vector for use in a eukaryotic host cell generally includes one or more of the following non-limiting components: a signal sequence, an origin of replication, one or more marker genes, an enhancer element, a promoter, and a transcription termination sequence.

a) Signal Sequence Component

A vector for use in a eukaryotic host cell may also contain a signal sequence or other polypeptide having a specific cleavage site at the N-terminus of the mature protein or polypeptide of interest. The heterologous signal sequence selected may be one that is recognized and processed (i.e., cleaved by a signal peptidase) by the host cell. In mammalian cell expression, mammalian signal sequences as well as viral secretory leaders, for example, the herpes simplex gD signal, are available. The DNA for such a precursor region is ligated in reading frame to DNA encoding the antibody.

b) Origin of Replication

Generally, an origin of replication component is not needed for mammalian expression vectors. For example, the SV40 origin may typically be used only because it contains the early promoter.

c) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, primate metallothionein genes, adenosine deaminase, ornithine decarboxylase, etc.

For example, in some embodiments, cells transformed with the DHFR selection gene are first identified by culturing all of the transformants in a culture medium that contains methotrexate (Mtx), a competitive antagonist of DHFR. In some embodiments, an appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199. Host cells may include NS0, CHOK1, CHOK1SV or derivatives, including cell lines deficient in glutamine synthetase (GS). Methods for the use of GS as a selectable marker for mammalian cells are described in U.S. Pat. Nos. 5,122,464 and 5,891,693.

d) Promoter Component

Expression and cloning vectors usually contain a promoter that is recognized by the host organism and is operably linked to nucleic acid encoding a polypeptide of interest (e.g., an antibody). Promoter sequences are known for eukaryotes. For example, virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. In certain embodiments, any or all of these sequences may be suitably inserted into eukaryotic expression vectors.

Transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982), describing expression of human β-interferon cDNA in mouse cells under the control of a thymidine kinase promoter from herpes simplex virus. Alternatively, the Rous Sarcoma Virus long terminal repeat can be used as the promoter.

e) Enhancer Element Component

Transcription of DNA encoding an antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the human cytomegalovirus early promoter enhancer, the mouse cytomegalovirus early promoter enhancer, the polyoma enhancer on the late side of the replication origin, and adenovirus enhancers. See also Yaniv, Nature 297:17-18 (1982) describing enhancer elements for activation of eukaryotic promoters. The enhancer may be spliced into the vector at a position 5' or 3' to the antibody polypeptide-encoding sequence, but is generally located at a site 5' from the promoter.

f) Transcription Termination Component

Expression vectors used in eukaryotic host cells may also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

g) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/−DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; CHOK1 cells, CHOK1SV cells or derivatives and a human hepatoma line (Hep G2).

Host cells are transformed with the above-described-expression or cloning vectors for antibody production and cultured in conventional nutrient media modified as appropriate for inducing promoters, selecting transformants, or amplifying the genes encoding the desired sequences.

h) Culturing the Host Cells

The host cells used to produce an antibody of this invention may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other supplements may also be included at appropriate concentrations that would be known to those skilled in the art. The culture conditions, such as temperature, pH, and the like, are those previously used with the host cell selected for expression, and will be apparent to the ordinarily skilled artisan.

i) Purification of Antibody

When using recombinant techniques, the antibody can be produced intracellularly, or directly secreted into the medium. If the antibody is produced intracellularly, as a first step, the particulate debris, either host cells or lysed fragments, may be removed, for example, by centrifugation or ultrafiltration. Where the antibody is secreted into the medium, supernatants from such expression systems may be first concentrated using a commercially available protein concentration filter, for example, an Amicon or Millipore Pellicon ultrafiltration unit. A protease inhibitor such as PMSF may be included in any of the foregoing steps to inhibit proteolysis, and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a convenient technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Methods 62:1-13 (1983)). Protein G is recommended for all mouse isotypes and for human γ3 (Guss et al., EMBO J. 5:15671575 (1986)). The matrix to which the affinity ligand is attached may be agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to further purification, for example, by low pH hydrophobic interaction chromatography using an elution buffer at a pH between about 2.5-4.5, performed at low salt concentrations (e.g., from about 0-0.25M salt).

In general, various methodologies for preparing antibodies for use in research, testing, and clinical use are well-established in the art, consistent with the above-described methodologies and/or as deemed appropriate by one skilled in the art for a particular antibody of interest.

Production of Non-Fucosylated Antibodies

Provided herein are methods for preparing antibodies with a reduced degree of fucosylation. For example, methods contemplated herein include, but are not limited to, use of cell lines deficient in protein fucosylation (e.g. Lec13 CHO cells, alpha-1,6-fucosyltransferase gene knockout CHO cells, cells overexpressing β1,4-N-acetylglycosminyltransferase III and further overexpressing Golgi μ-mannosidase II, etc.), and addition of a fucose analog(s) in a cell culture medium used for the production of the antibodies. See Ripka et al. Arch. Biochem. Biophys. 249:533-545 (1986); US Pat Appl No US 2003/0157108 A1. Presta, L; WO 2004/056312 A1: Yamane-Ohnuki et al. Biotech. Bioeng. 87: 614 (2004); and U.S. Pat. No. 8,574,907. Additional techniques for reducing the fucose content of antibodies include Glymaxx technology described in U.S. Patent Application Publication No. 2012/0214975. Additional techniques for reducing the fucose content of antibodies also include the addition of one or more glycosidase inhibitors in a cell culture medium used for the production of the antibodies. Glycosidase inhibitors include α-glucosidase I, α-glucosidase II, and α-mannosidase I. In some embodiments, the glycosidase inhibitor is an inhibitor of α-mannosidase I (e.g., kifunensine).

As used herein, "core fucosylation" refers to addition of fucose ("fucosylation") to N-acetylglucosamine ("GlcNAc") at the reducing terminal of an N-linked glycan. Also provided are antibodies produced by such methods and compositions thereof.

In some embodiments, fucosylation of complex N-glycoside-linked sugar chains bound to the Fc region (or domain) is reduced. As used herein, a "complex N-glycoside-linked sugar chain" is typically bound to asparagine 297 (according to the number of Kabat), although a complex N-glycoside linked sugar chain can also be linked to other asparagine residues. A "complex N-glycoside-linked sugar chain" excludes a high mannose type of sugar chain, in which only mannose is incorporated at the non-reducing terminal of the core structure, but includes 1) a complex type, in which the non-reducing terminal side of the core structure has one or more branches of galactose-N-acetylglucosamine (also referred to as "gal-GlcNAc") and the non-reducing terminal side of Gal-GlcNAc optionally has a sialic acid, bisecting N-acetylglucosamine or the like; or 2) a hybrid type, in which the non-reducing terminal side of the core structure has both branches of the high mannose N-glycoside-linked sugar chain and complex N-glycoside-linked sugar chain.

In some embodiments, the "complex N-glycoside-linked sugar chain" includes a complex type in which the non-reducing terminal side of the core structure has zero, one or more branches of galactose-N-acetylglucosamine (also referred to as "gal-GlcNAc") and the non-reducing terminal side of Gal-GlcNAc optionally further has a structure such as a sialic acid, bisecting N-acetylglucosamine or the like.

According to the present methods, typically only a minor amount of fucose is incorporated into the complex N-glycoside-linked sugar chain(s). For example, in various embodiments, less than about 60%, less than about 50%, less than about 40%, less than about 30%, less than about 20%, less than about 15%, less than about 10%, less than about 5%, or less than about 1% of the antibody has core fucosylation by fucose in a composition. In some embodiments, substantially none (i.e., less than about 0.5%) of the antibody has core fucosylation by fucose in a composition. In some embodiments, more than about 40%, more than about 50%, more than about 60%, more than about 70%, more than about 80%, more than about 90%, more than about 91%, more than about 92%, more than about 93%, more than about 94%, more than about 95%, more than about 96%, more than about 97%, more than about 98%, or more than about 99% of the antibody is nonfucosylated in a composition.

In some embodiments, provided herein is an antibody wherein substantially none (i.e., less than about 0.5%) of the N-glycoside-linked carbohydrate chains contain a fucose residue. In some embodiments, provided herein is an antibody wherein at least one or two of the heavy chains of the antibody is non-fucosylated.

As described above, a variety of mammalian host-expression vector systems can be utilized to express an antibody. In some embodiments, the culture media is not supplemented with fucose. In some embodiments, an effective amount of a fucose analog is added to the culture media. In this context, an "effective amount" refers to an amount of the analog that is sufficient to decrease fucose incorporation into a complex N-glycoside-linked sugar chain of an antibody by at least about 10%, at least about 20%, at least about 30%, at least about 40% or at least about 50%. In some embodiments, antibodies produced by the instant methods comprise at least about 10%, at least about 20%, at least about 30%, at least about 40% or at least about 50% non-core fucosylated protein (e.g., lacking core fucosylation), as compared with antibodies produced from the host cells cultured in the absence of a fucose analog.

The content (e.g., the ratio) of sugar chains in which fucose is not bound to N-acetylglucosamine in the reducing end of the sugar chain versus sugar chains in which fucose is bound to N-acetylglucosamine in the reducing end of the sugar chain can be determined, for example, as described in the Examples. Other methods include hydrazinolysis or enzyme digestion (see, e.g., *Biochemical Experimentation Methods* 23: Method for Studying Glycoprotein Sugar Chain (Japan Scientific Societies Press), edited by Reiko Takahashi (1989)), fluorescence labeling or radioisotope labeling of the released sugar chain and then separating the labeled sugar chain by chromatography. Also, the compositions of the released sugar chains can be determined by analyzing the chains by the HPAEC-PAD method (see, e.g., *J. Liq Chromatogr.* 6:1557 (1983)). (See generally U.S. Patent Application Publication No. 2004/0110282.).

B. Compositions of the Invention

In some aspects, also provided herein are compositions (e.g., pharmaceutical compositions) comprising any of the anti-Siglec-8 antibodies described herein (e.g. an antibody that binds to Siglec-8) or agonists described herein. In some aspects, provided herein is a composition comprising an anti-Siglec-8 antibody described herein, wherein the antibody comprises a Fc region and N-glycoside-linked carbohydrate chains linked to the Fc region, wherein less than about 50% of the N-glycoside-linked carbohydrate chains contain a fucose residue. In some embodiments, the antibody comprises a Fc region and N-glycoside-linked carbohydrate chains linked to the Fc region, wherein less than about 45%, about 40%, about 35%, about 30%, about 25%, about 20%, or about 15% of the N-glycoside-linked carbohydrate chains contain a fucose residue. In some aspects, provided herein is a composition comprising an anti-Siglec-8 antibody described herein, wherein the antibody comprises a Fc region and N-glycoside-linked carbohydrate chains linked to the Fc region, wherein substantially none of the N-glycoside-linked carbohydrate chains contain a fucose residue.

Therapeutic formulations are prepared for storage by mixing the active ingredient having the desired degree of purity with optional pharmaceutically acceptable carriers, excipients or stabilizers (*Remington: The Science and Practice of Pharmacy,* 20th Ed., Lippincott Williams & Wiklins, Pub., Gennaro Ed., Philadelphia, Pa. 2000). Acceptable carriers, excipients, or stabilizers are nontoxic to recipients at the dosages and concentrations employed, and include buffers, antioxidants including ascorbic acid, methionine, Vitamin E, sodium metabisulfite; preservatives, isotonicifiers, stabilizers, metal complexes (e.g., Zn-protein complexes); chelating agents such as EDTA and/or non-ionic surfactants.

Buffers can be used to control the pH in a range which optimizes the therapeutic effectiveness, especially if stability is pH dependent. Buffers can be present at concentrations ranging from about 50 mM to about 250 mM. Suitable buffering agents for use with the present invention include both organic and inorganic acids and salts thereof. For example, citrate, phosphate, succinate, tartrate, fumarate, gluconate, oxalate, lactate, acetate. Additionally, buffers may be comprised of histidine and trimethylamine salts such as Tris.

Preservatives can be added to prevent microbial growth, and are typically present in a range from about 0.2%-1.0% (w/v). Suitable preservatives for use with the present invention include octadecyldimethylbenzyl ammonium chloride; hexamethonium chloride; benzalkonium halides (e.g., chloride, bromide, iodide), benzethonium chloride; thimerosal, phenol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" can be present to adjust or maintain the tonicity of liquid in a composition. When used with large, charged biomolecules such as proteins and antibodies, they are often termed "stabilizers" because they can interact with the charged groups of the amino acid side chains, thereby lessening the potential for inter and intra-molecular interactions. Tonicity agents can be present in any amount between about 0.1% to about 25% by weight or between about 1 to about 5% by weight, taking into account the relative amounts of the other ingredients. In some embodiments, tonicity agents include polyhydric sugar alcohols, trihydric or higher sugar alcohols, such as glycerin, erythritol, arabitol, xylitol, sorbitol and mannitol.

Additional excipients include agents which can serve as one or more of the following: (1) bulking agents, (2) solubility enhancers, (3) stabilizers and (4) and agents preventing denaturation or adherence to the container wall. Such excipients include: polyhydric sugar alcohols (enumerated above); amino acids such as alanine, glycine, glutamine, asparagine, histidine, arginine, lysine, ornithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, α-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

Non-ionic surfactants or detergents (also known as "wetting agents") can be present to help solubilize the therapeutic agent as well as to protect the therapeutic protein against agitation-induced aggregation, which also permits the formulation to be exposed to shear surface stress without causing denaturation of the active therapeutic protein or antibody. Non-ionic surfactants are present in a range of about 0.05 mg/ml to about 1.0 mg/ml or about 0.07 mg/ml to about 0.2 mg/ml. In some embodiments, non-ionic surfactants are present in a range of about 0.001% to about 0.1% w/v or about 0.01% to about 0.1% w/v or about 0.01% to about 0.025% w/v.

Suitable non-ionic surfactants include polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl celluose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

In order for the formulations to be used for in vivo administration, they must be sterile. The formulation may be rendered sterile by filtration through sterile filtration membranes. The therapeutic compositions herein generally are placed into a container having a sterile access port, for example, an intravenous solution bag or vial having a stopper pierceable by a hypodermic injection needle.

The route of administration is in accordance with known and accepted methods, such as by single or multiple bolus or infusion over a long period of time in a suitable manner, e.g., injection or infusion by subcutaneous, intravenous, intraperitoneal, intramuscular, intraarterial, intralesional or intraarticular routes, topical administration, inhalation or by sustained release or extended-release means.

The formulation herein may also contain more than one active compound as necessary for the particular indication being treated, preferably those with complementary activities that do not adversely affect each other. Alternatively, or in addition, the composition may comprise a cytotoxic agent, cytokine or growth inhibitory agent. Such molecules are suitably present in combination in amounts that are effective for the purpose intended.

III. Articles of Manufacture or Kits

In another aspect, an article of manufacture or kit is provided which comprises an anti-Siglec-8 antibody described herein (e.g., an antibody that binds human Siglec-8) or an agonist described herein. The article of manufacture or kit may further comprise instructions for use of the antibody or agonist in the methods of the invention. Thus, in certain embodiments, the article of manufacture or kit comprises instructions for the use of an anti-Siglec-8 antibody or agonist that binds to human Siglec-8 in methods for treating or preventing a fibrotic disease (e.g., idiopathic pulmonary fibrosis) and/or a pre-fibrotic disease (e.g., chronic hypersensitivity pneumonitis) in an individual comprising administering to the individual an effective amount of an anti-Siglec-8 antibody or agonist that binds to human Siglec-8.

In certain embodiments, the article of manufacture comprises a medicament comprising an antibody or agonist that binds to human Siglec-8 and a package insert comprising instructions for administration of the medicament in an individual in need thereof to treat or prevent a fibrotic disease selected from the group consisting of: pulmonary fibrosis, hepatic fibrosis, renal fibrosis, cardiac fibrosis, spleen fibrosis, and ocular fibrosis. In some embodiments, the pulmonary fibrosis is idiopathic pulmonary fibrosis. In some embodiments, the pulmonary fibrosis is associated with chronic obstructive pulmonary disease. In certain embodiments, the article of manufacture comprises a medicament comprising an antibody or agonist that binds to human Siglec-8 and a package insert comprising instructions for administration of the medicament in an individual in need thereof to treat or prevent a fibrotic disease is selected from the group consisting of: mechanical-induced fibrosis, implant-induced fibrosis, radiation-induced fibrosis, drug-induced fibrosis and viral-induced fibrosis. In some embodiments, the mechanical induced fibrosis is ventilator-induced pulmonary fibrosis. In some embodiments, the drug-induced fibrosis is bleomycin-induced pulmonary fibrosis. In certain embodiments, the article of manufacture comprises a medicament comprising an antibody or agonist that binds to human Siglec-8 and a package insert comprising instructions for administration of the medicament in an individual in need thereof to treat or prevent a fibrotic disease is selected from the group consisting of: cystic fibrosis, cancer-associated fibrosis, atherosclerosis, bone marrow fibrosis, scleroderma, mediastinal fibrosis and retroperitoneal cavity fibrosis. In some embodiments, the package insert further indicates that the treatment is effective in reducing one or more symptom (such as one or more symptom described herein) in the individual with fibrotic disease (e.g., idiopathic pulmonary fibrosis) relative to baseline after administration of the antibody or agonist that binds to human Siglec-8.

In certain embodiments, the article of manufacture comprises a medicament comprising an antibody or agonist that binds to human Siglec-8 and a package insert comprising instructions for administration of the medicament in an individual in need thereof to treat or prevent a pre-fibrotic disease is selected from the group consisting of: bleomycin-induced pneumonitis, chronic hypersensitivity pneumonitis, polycythemia vera, essential thrombocythemia, age-related macular degeneration, diabetic retinopathy, neovascular glaucoma, retinopathy of prematurity, and proliferative vitreoretinopathy. In some embodiments, the package insert further indicates that the treatment is effective in reducing one or more symptom (such as one or more symptom described herein) in the individual with pre-fibrotic disease (e.g., chronic hypersensitivity pneumonitis) relative to baseline after administration of the antibody or agonist that binds to human Siglec-8. In certain embodiments, the individual is a human.

The article of manufacture or kit may further comprise a container. Suitable containers include, for example, bottles, vials (e.g., dual chamber vials), syringes (such as single or dual chamber syringes) and test tubes. The container may be formed from a variety of materials such as glass or plastic. The container holds the formulation.

The article of manufacture or kit may further comprise a label or a package insert, which is on or associated with the container, may indicate directions for reconstitution and/or use of the formulation. The label or package insert may further indicate that the formulation is useful or intended for subcutaneous, intravenous, or other modes of administration for treating or preventing a fibrotic disease (e.g., idiopathic pulmonary fibrosis) and/or a pre-fibrotic disease (e.g., chronic hypersensitivity pneumonitis) in an individual. The container holding the formulation may be a single-use vial or a multi-use vial, which allows for repeat administrations of the reconstituted formulation. The article of manufacture or kit may further comprise a second container comprising a suitable diluent. The article of manufacture or kit may further include other materials desirable from a commercial, therapeutic, and user standpoint, including other buffers, diluents, filters, needles, syringes, and package inserts with instructions for use.

In a specific embodiment, the present invention provides kits for a single dose-administration unit. Such kits comprise a container of an aqueous formulation of therapeutic antibody, including both single or multi-chambered pre-filled syringes. Exemplary pre-filled syringes are available from Vetter GmbH, Ravensburg, Germany.

The present invention also provides an anti-Siglec-8 antibody described herein (e.g., an antibody that binds human Siglec-8) or an agonist that binds to human Siglec-8 in combination with one or more medicament (e.g., a second medicament) for treating or preventing a fibrotic disease (e.g., idiopathic pulmonary fibrosis) and/or a pre-fibrotic disease (e.g., chronic hypersensitivity pneumonitis) in an individual. In some embodiments, the article of manufacture or kit herein optionally further comprises a container comprising a second medicament, wherein the anti-Siglec-8 antibody or agonist is a first medicament, and which article or kit further comprises instructions on the label or package insert for treating the individual with the second medicament, in an effective amount.

In another embodiment, provided herein is an article of manufacture or kit comprising the formulations described herein for administration in an auto-injector device. An auto-injector can be described as an injection device that upon activation, will deliver its contents without additional necessary action from the patient or administrator. They are particularly suited for self-medication of therapeutic formulations when the delivery rate must be constant and the time of delivery is greater than a few moments.

It is understood that the aspects and embodiments described herein are for illustrative purposes only and that various modifications or changes in light thereof will be suggested to persons skilled in the art and are to be included within the spirit and purview of this application and scope of the appended claims.

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

EXAMPLES

Example 1: Activity of Anti-Siglec-8 Antibodies in a Mouse Model of Human Fibrosis Bleomycin-induced pulmonary fibrosis is an experimental model of human fibrosis. The activity of anti-Siglec-8 antibodies in a bleomycin-induced pulmonary fibrosis model was investigated in a Siglec-8 transgenic mouse in which human Siglec-8 was selectively expressed on the surface of mast cells, eosinophils and basophils. The m2E2 depleting antibody is a murine monoclonal anti-Siglec-8 antibody with a murine IgG2a isotype that kills eosinophils and mast cells by ADCC activity. The m2E2 inhibitory antibody is a murine monoclonal anti-Siglec-8 antibody with a murine IgG1 isotype that kills eosinophils and inhibits mast cell activity.

Siglec-8 transgenic mice were administered 3 mg/kg of a murine anti-Siglec-8 antibody (m2E2 depleting antibody or m2E2 inhibitory antibody) or murine IgG1 isotype control antibody via intraperitoneal injection for a total of three times. The first administration of the antibody occurred four days before bleomycin administration (Day −4), the second administration was on the same day as bleomycin administration (Day 0), and the third administration was four days after bleomycin administration (Day 4). Oropharyngeal administration of 1.5 U/kg bleomycin occurred four days after the first administration of the indicated anti-Siglec-8 antibody or isotype control antibody. A control group of mice (naive) that were not administered an antibody or bleomycin was used for subsequent analysis. The weight of Siglec-8 transgenic mice with bleomycin-induced lung fibrosis treated with isotype control antibody, m2E2 depleting antibody, or m2E2 inhibitory antibody and of untreated Siglec-8 transgenic mice without bleomycin-induced lung fibrosis was monitored over the course of the study. Bronchoalveolar lavage (BAL) fluid was harvested from the treated mice seven days after administration of bleomycin and processed for collagen, leukocyte, cell differential, and cytokine evaluation. The BAL fluid was centrifuged at 1,000 rpm at 4° C. for 5 minutes and the supernatant was transferred for subsequent use. The BAL cell pellet was resuspended in 2 mL of 1×BD Pharm Lyse™ Lysing Buffer (BD Biosciences) to lyse the red blood cells. Phosphate buffered saline (PBS) supplemented with 2% Fetal Bovine Serum (FBS) was added to stop the lysis reaction before centrifuging the cells again at 1,000 rpm. The cells were transferred for subsequent use.

Figure 1:
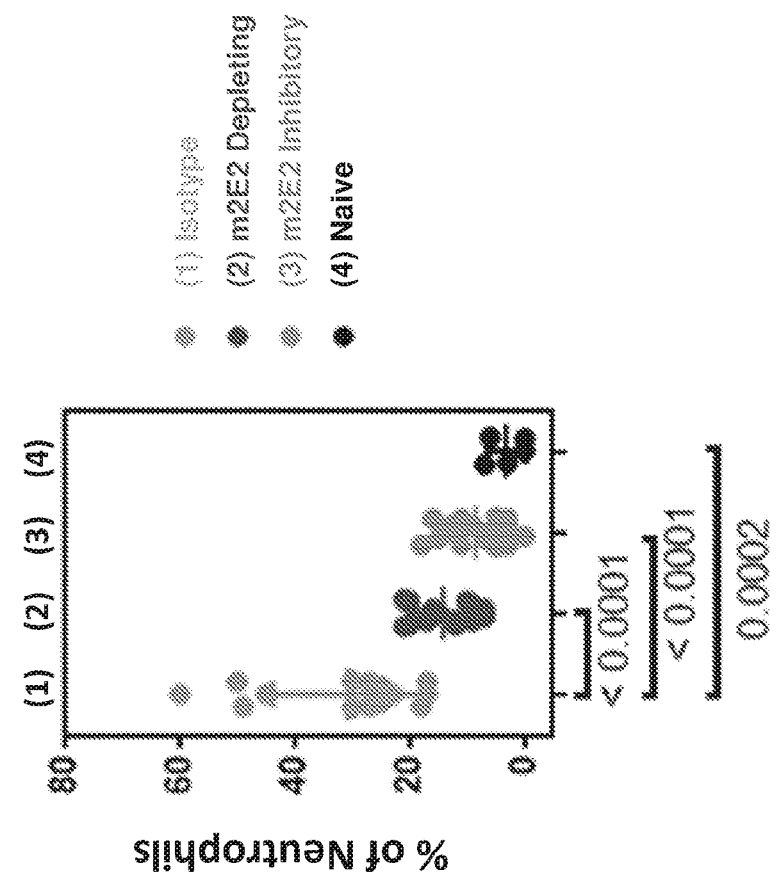
FIG. 1 is a graph showing inhibition of neutrophil influx into the bronchoalveolar space in Siglec-8 transgenic mice with bleomycin-induced lung fibrosis due to treatment with anti-Siglec-8 antibodies. (1) Isotype indicates murine IgG1 isotype control antibody; (2) m2E2 Depleting indicates a murine monoclonal anti-Siglec-8 antibody with a murine IgG2a isotype that kills eosinophils and mast cells by ADCC activity; (3) m2E2 Inhibitory indicates a murine monoclonal anti-Siglec-8 antibody with a murine IgG1 isotype that kills eosinophils and inhibits mast cell activity; and (4) Naive indicates Siglec-8 transgenic mice that were not administered an antibody or bleomycin. p-values were determined by comparing the mouse IgG1 isotype control antibody study group to the m2E2 Depleting antibody study group, the m2E2 Inhibitory antibody study group or the naive study group. % of neutrophils indicates the percentage of neutrophils relative to the total number of leukocytes in the sample.

Leukocytes in the cell pellet sample from BAL fluid were counted using a hemocytometer and the trypan blue exclusion method to monitor dead and live cells. Cytospins were prepared from the cell pellet sample of BAL fluid, differentially stained with Giemsa stain and enumerated under high power magnification for a differential count of nucleated BAL immune cells (i.e., neutrophils, macrophages, monocytes, lymphocytes, and eosinophils) based on visual cell morphology. Both murine m2E2 depleting antibody and murine m2E2 inhibitory antibody significantly inhibited neutrophil influx into the bronchoalveolar space of Siglec-8 transgenic mice with bleomycin-induced lung fibrosis as compared to Siglec-8 transgenic mice with bleomycin-induced lung fibrosis that received the isotype control antibody (FIG. 1).

Figure 2A:
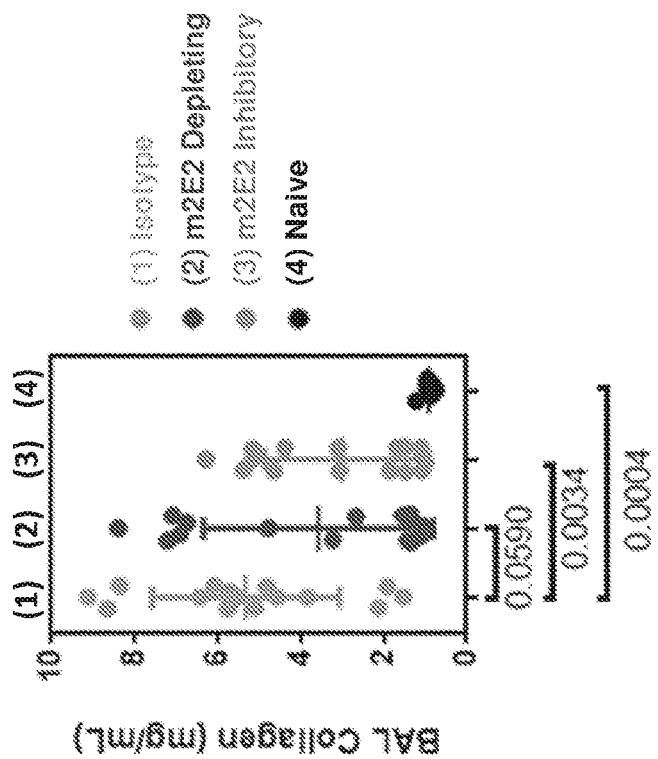
FIGS. 2A and 2B is a series of graphs showing prevention of collagen accumulation in Siglec-8 transgenic mice with bleomycin-induced lung fibrosis due to treatment with anti-Siglec-8 antibodies.
Figure 2B:
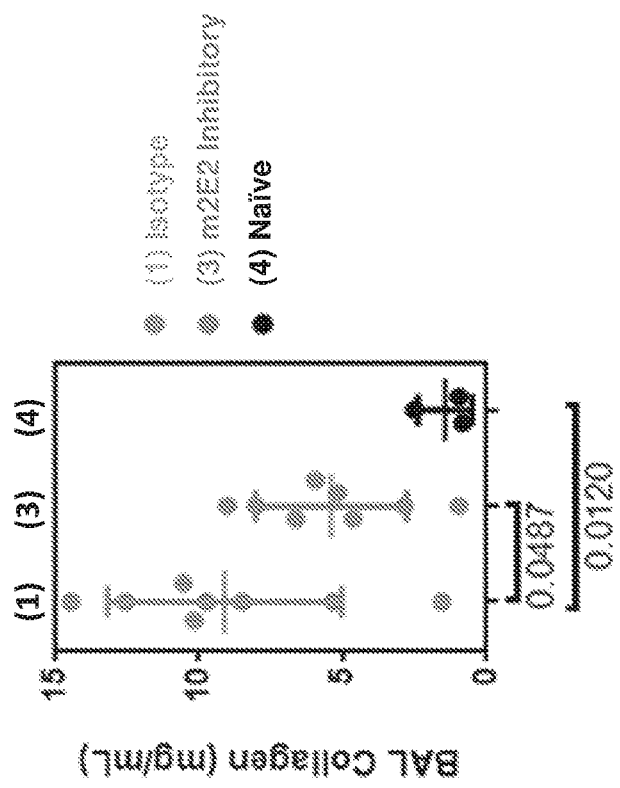

For collagen quantification, a 160 µl sample of the BAL supernatant was analyzed using the Sircol™ Collagen Assay (Biocolor Life Science Assays, United Kingdom). Both murine m2E2 depleting antibody and murine m2E2 inhibitory antibody prevented collagen accumulation in the bronchoalveolar space of Siglec-8 transgenic mice with bleomycin-induced lung fibrosis as compared to Siglec-8 transgenic mice with bleomycin-induced lung fibrosis that received the isotype control antibody (FIG. 2A and FIG. 2B).

Siglec-8 transgenic mice with bleomycin-induced lung fibrosis experienced weight loss over the course of the study (FIG. 3). However, administration of murine m2E2 depleting antibody or murine m2E2 inhibitory antibody significantly protected Siglec-8 transgenic mice from bleomycin-induced weight loss (FIG. 3). The weight change in anti-Siglec-8 antibody treated mice with bleomycin-induced pulmonary fibrosis was comparable to the weight change in untreated mice without bleomycin-induced lung fibrosis (FIG. 3).

For cytokine analysis, a 160 µl sample of the supernatant from the BAL fluid sample was analyzed using a Luminex® Cytokine mouse 32-plex panel (a panel that was designed for quantifying cytokines, chemokines and growth factors in serum, plasma, and tissue culture supernatant; Life Technologies, CA), a latent TGF-β precursor forms panel, and a TGF-β active forms panel for quantification. Both murine m2E2 depleting antibody and murine m2E2 inhibitory antibody inhibited cytokine release in bronchoalveolar fluid of Siglec-8 transgenic mice with bleomycin-induced lung fibrosis as compared to Siglec-8 transgenic mice with bleomycin-induced lung fibrosis that received the isotype control antibody (FIG. 4).

Following BAL harvest, lungs were inflated by approximately 0.5 mL of 10% neutral buffered formalin (NBF) for histopathological analysis. Microscope fields of lungs from each mouse were given an Ashcroft score (graded on a scale from 0 to 8) by a veterinary pathologist based on the degree of fibrosis in lung specimens (FIG. 5). See Ashcroft et al., *J. Clin. Pathol.*, 1998, 41:467-470 for a description of Ashcroft scoring.

Example 2: Anti-Siglec-8 Antibody Treatment in a Mouse Model of Human Fibrosis

Treatment of Siglec-8 transgenic mice exhibiting bleomycin-induced pulmonary fibrosis with anti-Siglec-8 antibodies was investigated. Siglec-8 transgenic mice selectively expressed human Siglec-8 on the surface of mast cells, eosinophils and basophils. The m2E2 inhibitory antibody is a murine monoclonal anti-Siglec-8 antibody with a murine IgG1 isotype that kills activated eosinophils and inhibits mast cell activity.

Siglec-8 transgenic mice were administered 3 mg/kg of a murine anti-Siglec-8 antibody (m2E2 inhibitory antibody) or murine IgG1 isotype control antibody via intraperitoneal injection. The first administration of the m2E2 inhibitory antibody or isotype control antibody was given three days after oropharyngeal administration of 1.5 U/kg bleomycin (Day 3). A control group of mice (naive) that were not administered an antibody or bleomycin was used for subsequent analysis. BAL fluid was harvested from the treated mice seven days after administration of bleomycin and processed for collagen, leukocyte, and cell differential evaluation. The BAL fluid was centrifuged at 1,000 rpm at 4° C. for 5 minutes and the supernatant was transferred for subsequent use. The BAL cell pellet was resuspended in 2 mL of 1×BD Pharm Lyse™ Lysing Buffer (BD Biosciences) to lyse the red blood cells. Phosphate buffered saline (PBS) supplemented with 2% Fetal Bovine Serum (FBS) was added to stop the lysis reaction before centrifuging the cells again at 1,000 rpm. The cells were transferred for subsequent use.

Leukocytes in the cell pellet sample from BAL fluid were counted using a hemocytometer and the trypan blue exclusion method to monitor dead and live cells. Cytospins were prepared from the cell pellet sample of BAL fluid, differentially stained with Giemsa stain and enumerated under high power magnification for a differential count of nucleated BAL immune cells (i.e., neutrophils, macrophages, monocytes, lymphocytes, and eosinophils) based on visual cell morphology. Administration of murine m2E2 inhibitory antibody significantly inhibited neutrophil influx into the bronchoalveolar space of Siglec-8 transgenic mice with bleomycin-induced lung fibrosis as compared to Siglec-8 transgenic mice with bleomycin-induced lung fibrosis that received the isotype control antibody (FIG. 6).

For collagen quantification, a 160 µl sample of the supernatant is analyzed using the Sircol™ Collagen Assay (Biocolor Life Science Assays, United Kingdom).

For cytokine analysis, a 160 µl sample of the supernatant from the BAL fluid sample is analyzed using a Luminex® Cytokine mouse 32-plex panel (a panel that was designed for quantifying cytokines, chemokines and growth factors in serum, plasma, and tissue culture supernatant; Life Technologies, CA), a latent TGF-β precursor forms panel, and a TGF-β active forms panel for quantification.

Following BAL harvest, lungs are inflated by approximately 0.5 mL of 10% neutral buffered formalin (NBF) for histopathological analysis. Microscope fields of lungs from each mouse are given an Ashcroft score (graded on a scale from 0 to 8) by a veterinary pathologist based on the degree of fibrosis in lung specimens. See Ashcroft et al., *J. Clin. Pathol.*, 1998, 41:467-470 for a description of Ashcroft scoring.

The weight of Siglec-8 transgenic mice with bleomycin-induced lung fibrosis treated with isotype control antibody or m2E2 inhibitory antibody and of untreated Siglec-8 transgenic mice without bleomycin-induced lung fibrosis is monitored over the course of the study.

Example 3: Activity of Anti-Siglec-8 Antibodies in a Humanized Mouse Model of Implant-Induced Fibrosis Immunodeficient mice capable of generating abundant human mast cells after engraftment with human hematopoietic stem cells (HSC) have been described (Tanaka et al., *J Immunol.*, 2012, 188(12):6145-55). The mouse strain designated NSG-SGM3 (The Jackson Laboratory) is a derivative of the nonobese diabetic/severe combined immunodeficiency (NOD SCID) mouse with a deletion of the IL-2 receptor gamma-chain gene (NSG mouse). NSG-SGM3 mice are additionally transgenic for 3 human cytokines (stem cell factor [SCF], IL-3, and GM-CSF) to facilitate engraftment with human hematopoietic stem cells. Upon engraftment of NSG-SGM3 mice, human CD34+ cells generate human eosinophils and enhanced numbers of human mast cells. Both cell types in engrafted NSG-SGM3 mice express Siglec-8 at levels comparable to the levels on the corresponding cell types isolated from human peripheral blood and tissues. Thus, these mice provide a model for evaluation of activity of anti-Siglec-8 antibodies in vivo.

In order to evaluate the effect of anti-Siglec-8 antibodies on fibrosis induced by implanted objects, polystyrene beads were implanted in these humanized mice and development of fibrosis was monitored after prophylactic or therapeutic treatment with anti-Siglec-8 antibodies.

Materials and Methods

Polystyrene beads of 500 µm mean diameter where purchased from Phosphorex (Hopkinton, Mass.) and implanted in humanized mice. See Veish et al., Nat. Mater., 2015, 14:643-651 for a description of polystyrene bead implantation in mice. Humanized mice were anesthetized and their abdomens were shaved and sterilized. A 0.5 mm incision was made along the midline of the abdomen and the peritoneal lining was exposed using blunt dissection. The peritoneal wall was then grasped with forceps and a 0.5-1 mm incision was made along the linea alba. Polystyrene beads suspended in PBS were then loaded into a sterile pipette and implanted into the peritoneal cavity through the incision. The incision was closed using 5-0 taper-tipped polydioxanone (PDS II) absorbable sutures and the skin closed over the incision using a wound clip and tissue glue. One day prior to implantation of polystyrene beads (day −1) or seven days after implantation of polystyrene beads (day 7), 100 µg of anti-Siglec-8 antibody (c2E2 IgG4) or isotype matched control human antibody (hIgG4) was administered via intraperitoneal injection every 4 days (q4d) until termination of the 14 day study. Accordingly, 100 µg of c2E2 IgG4 was administered on day −1, 3, 7 and 11 for the prophylactic treatment study group (n=5 mice) or administered on day 7 and 11 for the therapeutic treatment study group (n=5 mice). 100 µg of hIgG4 was administered on day −1, 3, 7 and 11 for the control study group (n=5 mice). The c2E2 IgG4 antibody is a chimeric monoclonal anti-Siglec-8 antibody with a human IgG4 isotype and murine 2E2 variable domains.

The mice were euthanized at day 14 of the study. A 5 ml volume of ice cold PBS was first injected in order to perform a peritoneal lavage to rinse out and collect free-floating intraperitoneal cells. An incision was then made along the abdomen skin and peritoneal wall and Krebs buffer was used to wash out polystyrene beads from the abdomen and into petri dishes for collection. After all the beads were washed out or manually retrieved if fibrosed directly to intraperitoneal tissues, the collected beads were transferred into 50 mL conical tubes for downstream processing before imaging. After peritoneal lavage and bead retrieval, remaining fibrosed intraperitoneal tissues were also excised for analysis. The polystyrene beads and tissues recovered from the peritoneal cavity were gently washed using Krebs buffer and transferred to petri dishes for phase contrast microscopy. Collagen quantification was performed on a fraction of peritoneal lavage supernatants (supernatant remaining after removal of beads and tissue) using a Bicolor Sircol Soluble Collagen Assay.

Alpha smooth muscle actin was quantified using anti-mouse alpha smooth muscle actin antibody (Sigma Aldrich, St. Louis Mo.). Immunofluorescence imaging was used to determine cell populations attached to beads as described in Veish et al., Nat. Mater., 2015, 14:643-651. Materials retrieved from the mice were fixed overnight using 4% paraformaldehyde at 4° C. Polystyrene beads and the associated cells where washed twice with Krebs buffer, permeabilized for 30 min using a 0.1% Triton X100 solution, and blocked for 1 hour using a 1% bovine serum albumin (BSA) solution. Next, the beads were incubated for 1 hour in an immunostaining cocktail solution consisting of DAPI (500 nM) and anti-mouse alpha smooth muscle actin antibody (1:200 dilution) in BSA. After staining, the beads were washed three times with a 0.1% Tween 20 solution and maintained in a 50% glycerol solution. The beads were then transferred to glass bottom dishes and imaged using a Nikon Eclipse Ti series microscope. Images were further analyzed with Nikon Elements image analysis software.

Results

Sterile polystyrene beads implanted into the peritoneum of humanized mice for 14 days induced fibrosis as shown by an increase in collagen deposition (FIG. 7) and accumulation of bead-associated myofibroblasts (FIG. 8). Prophylactic treatment of humanized mice with anti-Siglec-8 antibody one day before bead implantation markedly reduced collagen deposition and accumulation of myofibroblasts on the beads. Anti-Siglec-8 antibody treatment also inhibited collagen deposition and accumulation of myofibroblasts in humanized mice treated with the antibody 7 days after bead implantation.

Example 4: Activity of Anti-Siglec-8 Antibodies in a Mouse Model of Scleroderma and Systemic Fibrosis Subcutaneous administration of bleomycin provides an experimental model of scleroderma, including systemic sclerosis. Mice treated with bleomycin via the subcutaneous route develop fibrosis of both the skin and lungs. The activity of anti-Siglec-8 antibodies in a bleomycin-induced cutaneous fibrosis model was investigated in Siglec-8 transgenic mice in which human Siglec-8 is selectively expressed on the surface of mast cells, eosinophils and basophils.

Siglec-8 transgenic mice were administered 3 mg/kg of murine IgG1 isotype control antibody or murine anti-Siglec-8 antibody (m2E2 IgG1 antibody also known as m2E2 inhibitory antibody) via intraperitoneal injection for a total of six doses in a therapeutic study group (Day +7) or eight doses in a prophylactic study group (Day −1). For the prophylactic study group, the administration of the antibody occurred one day before bleomycin administration (Day −1), and was subsequently administered on Days 3, 7, 11, 15, 19, 23, and 27 after the initial bleomycin administration. For the therapeutic study group, the administration of the antibody occurred on the seventh day after the initial bleomycin administration (Day 7), and was subsequently administered on Days 11, 15, 19, 23, and 27. 0.1 IU bleomycin per mouse was administered subcutaneously on Day 0 and every two days until Day 28 on the back of each mouse. A control group of mice (naive) that were not administered an antibody or bleomycin was used for subsequent analysis. The lung weight of Siglec-8 transgenic mice with bleomycin-induced cutaneous fibrosis treated with isotype control antibody or m2E2 inhibitory antibody was monitored for thirty days after bleomycin administration (Day 30). Untreated Siglec-8 transgenic mice without bleomycin-induced cutaneous fibrosis were monitored during this 30 day monitoring period. At Day 30, a portion of the lungs and skin from lesions of Siglec-8 transgenic mice were processed for analysis of levels of hydroxyproline, a component of collagen, using a BioVision Kit according to the manufacturer's instructions. The remaining lesional skin was processed for RNA extraction using an RNeasy Kit (Qiagen) and reversed transcribed into cDNA using a High Capacity cDNA Kit (Applied Biosystems) according to the manufacturer's instructions. Scientific photographs of bleomycin-induced cutaneous lesions were taken fifteen days (Day 15), twenty days (Day 20), twenty-five days (Day 25) and thirty-days (Day 30) after initial bleomycin administration. A visual dermal score was calculated from photographs in the Siglec-8 transgenic mice with bleomycin-induced cutaneous fibrosis treated with isotype control antibody or m2E2 inhibitory antibody and of untreated Siglec-8 transgenic mice without bleomycin-induced cutaneous fibrosis.

Siglec-8 transgenic mice with bleomycin-induced cutaneous fibrosis experienced increased lung weights after 30 days of the initial bleomycin administration (Day 30). Administration of m2E2 inhibitory antibody significantly protected and inhibited Siglec-8 transgenic mice from lung weight gain compared to Siglec-8 transgenic mice with bleomycin-induced cutaneous fibrosis that received isotype control antibody (FIG. 9). For hydroxyproline quantification, a portion of Siglec-8 transgenic mice lungs and skin were homogenized according to manufacturer's instructions (BioVision). A reduction of hydroxyproline was observed with administration of m2E2 inhibitory antibody in both lungs and skin compared to Siglec-8 transgenic mice with bleomycin-induced cutaneous fibrosis treated with isotype control antibody (FIG. 10A and FIG. 10B). The reduction of hydroxyproline in anti-Siglec-8 antibody treated mice was comparable to the hydroxyproline quantity observed in untreated mice without bleomycin-induced cutaneous fibrosis. For gene expression analysis, cDNA derived from skin of Siglec-8 transgenic mice in bleomycin-induced cutaneous fibrosis was used for quantitative PCR (qPCR) (BioRad) analysis of the pro-fibrotic mediators, interleukin-13 (IL-13) and transforming growth factor beta (TGFβ) using pre-designed, gene-specific primers. Murine m2E2 inhibitory antibody significantly inhibited the expression of both IL-13 and TGFβ in the bleomycin-induced skin lesions compared to Siglec-8 transgenic mice with bleomycin-induced cutaneous fibrosis that received isotype control antibody (FIG. 11A and FIG. 11B).

Bleomycin-induced skin lesions were visually quantified for fibrosis and given a score of one through three based on fibrotic severity of the skin lesion (one being less severe, three being most severe). Siglec-8 transgenic mice with bleomycin-induced cutaneous fibrosis treated with m2E2 inhibitory antibody had lower visual dermal scores as compared to Siglec-8 transgenic mice with bleomycin-induced cutaneous fibrosis that received isotype control antibody (FIG. 12).

SEQUENCES

Amino acid sequence of mouse 2E2 heavy chain variable domain
(SEQ ID NO: 1)
QVQLKESGPGLVAPSQSLSITCTVSGFSLTIYGAHWVRQPPGKGLEW

LGVIWAGGSTNYNSALMSRLSISKDNSKSQVFLKINSLQTDDTALYY

CARDGSSPYYYSMEYWGQGTSVTVSS

Amino acid sequence of 2E2 RHA heavy chain variable domain
(SEQ ID NO: 2)
EVQLVESGGGLVQPGGSLRLSCAASGESLTINGAHWVRQAPGKGLEW

VSVIWAGGSTNYNSALMSRFTISKDNSKNTVYLQMNSLRAEDTAVYY

CARDGSSPYYYSMEYWGQGTTVTVSS

SEQUENCES

Amino acid sequence of 2E2 RHB heavy chain variable domain
(SEQ ID NO: 3)
EVQLVESGGGLVQPGGSLRLSCAVSGFSLTTYGAHWVRQAPGKGLEW

LGVIWAGGSTNYNSALMSRLSISKDNSKNTVYLQMNSLRAEDTAVYY

CARDGSSPYYYSMEYWGQGTTVTVSS

Amino acid sequence of 2E2 RHC heavy chain variable domain
(SEQ ID NO: 4)
EVQLVESGGGLVQPGGSLRLSCAVSGFSLTIYGAHWVRQAPGKGLEW

VSVIWAGGSTNYNSALMSRFTISKDNSKNTVYLQMNSLRAEDTAVYY

CARDGSSPYYYSMEYWGQGTTVTVSS

Amino acid sequence of 2E2 RHD heavy chain variable domain
(SEQ ID NO: 5)
EVQLVESGGGLVQPGGSLRLSCAASGESLTINGAHWVRQAPGKGLEW

LSVIWAGGSTNYNSALMSRFTISKDNSKNTVYLQMNSLRAEDTAVYY

CARDGSSPYYYSMEYWGQGTTVTVSS

Amino acid sequence of 2E2 RHE heavy chain variable domain
(SEQ ID NO: 6)
EVQLVESGGGLVQPGGSLRLSCAASGFSLTTYGAHWVRQAPGKGLEW

VGVIWAGGSTNYNSALMSRFTISKDNSKNTVYLQMNSLRAEDTAVYY

CARDGSSPYYYSMEYWGQGTTVTVSS

Amino acid sequence of 2E2 RHF heavy chain variable domain
(SEQ ID NO: 7)
EVQLVESGGGLVQPGGSLRLSCAASGFSLTIYGAHWVRQAPGKGLEW

VSVIWAGGSTNYNSALMSRLTISKDNSKNTVYLQMNSLRAEDTAVYY

CARDGSSPYYYSMEYWGQGTTVTVSS

Amino acid sequence of 2E2 RHG heavy chain variable domain
(SEQ ID NO: 8)
EVQLVESGGGINQPGGSLRLSCAASGFSLTIYHAHWVRQAPGKGLEW

VSVIWAGGSTNYNSALMSRFSISKDNSKNTVYLQMNSLRAEDTAVYY

CARDGSSPYYYSMEYWGQGTTVTVSS

Amino acid sequence of 2E2 RHA2 heavy chain variable domain
(SEQ ID NO: 9)
QVQLQESGPGINKPSETLSLTCTVSGGSISIYGAHWIRQPPGKGLEW

IGVIWAGGSTNYNSALMSRVTISVDTSKNQFSLKLSSVTAADTAVYY

CARDGSSPYYYSMEYWGQGTLNTVSS

Amino acid sequence of 2E2 RHB2 heavy chain variable domain
(SEQ ID NO: 10)
QVQLQESGPGLVKPSETLSLTCTVSGFSLTIYGAHWVRQPPGKGLEW

LGVIWAGGSTNYNSALMSRLSISKDNSKNQVSLKLSSVTAADTAVYY

CARDGSSPYYYSMEYWGQGTLVTVSS

SEQUENCES

Amino acid sequence of 2E2 RHE S-G mutant
heavy chain variable domain
(SEQ ID NO: 11)
EVQLVESGGGLVQPGGSLRLSCAASGFSLTIYGAHWVRQAPGKGLEW

VGVIWAGGSTNYNSALMSRFTISKDNSKNTVYLQMNSLRAEDTAVYY

CARDGSSPYYYGMEYWGQGTTVTVSS

Amino acid sequence of 2E2 RHE E-D heavy
chain variable domain
(SEQ ID NO: 12)
EVQLVESGGGLVQPGGSLRLSCAASGESLTIYGAHWVRQAPGKGLEW

VGVIWAGGSTNYNSALMSRFTISKDNSKNTVYLQMNSLRAEDTAVYY

CARDGSSPYYYSMDYWGQGTTVTVSS

Amino acid sequence of 2E2 RHE Y-V heavy
chain variable domain
(SEQ ID NO: 13)
EVQLVESGGGLVQPGGSLRLSCAASGFSLTIYGAHWVRQAPGKGLEW

VGVIWAGGSTNYNSALMSRFTISKDNSKNTVYLQMNSLRAEDTAVYY

CARDGSSPYYYSMEVWGQGTTVTVSS

Amino acid sequence of 2E2 RHE triple mutant
heavy chain variable domain
(SEQ ID NO: 14)
EVQLVESGGGLVQPGGSLRLSCAASGFSLTIYGAHWVRQAPGKGLEW

VGVIWAGGSTNYNSALMSRFTISKDNSKNTVYLQMNSLRAEDTAVYY

CARDGSSPYYYGMDVWGQGTTVTVSS

Amino acid sequence of mouse 2E2 light chain
variable domain
(SEQ ID NO: 15)
QIILTQSPAIMSASPGEKVSITCSATSSVSYMHWFQQKPGTSPKLWI

YSTSNLASGVPVRFSGSGSGTSYSLTISRMEAEDAATYYCQQRSSYP

FTFGSGTKLEIK

Amino acid sequence of 2E2 RKA light chain
variable domain
(SEQ ID NO: 16)
EIVLTQSPATLSLSPGERATLSCSATSSVSYMHWFQQKPGQAPRLLI

YSTSNLASGIPARFSGSGSGTDFTLTISSLEPEDFAVYYCQQRSSYP

FTFGPGTKLDIK

Amino acid sequence of 2E2 RKB light chain
variable domain
(SEQ ID NO: 17)
EIILTQSPATLSLSPGERATLSCSATSSVSYMHWFQQKPGQAPRLWI

YSTSNIASGVPARFSGSGSGTDYTLTISSLEPEDFAVYYCQQRSSYP

FTFGPGTKLDIK

Amino acid sequence of 2E2 RKC light chain
variable domain
(SEQ ID NO: 18)
EIILTQSPATLSLSPGERATLSCSATSSVSYMHWFQQKPGQAPRLLI

YSTSNLASGIPARFSGSGSGTDFTLTISSLEPEDFAVYYCQQRSSYP

FTFGPGTKLDIK

Amino acid sequence of 2E2 RKD light chain
variable domain
(SEQ ID NO: 19)
EIVLTQSPATLSLSPGERATLSCSATSSVSYMHWFQQKPGQAPRLWI

YSTSNLASGIPARFSGSGSGTDETLTISSLEPEDFAVVYCQQRSSYP

FTFGPGTKLDIK

Amino acid sequence of 2E2 RKE light chain
variable domain
(SEQ ID NO: 20)
EIVLTQSPATLSLSPGERATLSCSATSSVSYMHWFQQKPGQAPRLLI

YSTSNLASGVPARFSGSGSGTDFTLTISSLEPEDFAVYYCQQRSSYP

FTFGPGTKLDIK

Amino acid sequence of 2E2 RKF light chain
variable domain
(SEQ ID NO: 21)
EIVLTQSPATLSLSPGERATLSCSATSSVSYMHWFQQKPGQAPRLLI

YSTSNLASGIPARFSGSGSGTDYTLTISSLEPEDFAVYYCQQRSSYP

FTFGPGTKLDIK

Amino acid sequence of 2E2 RKG light chain
variable domain
(SEQ ID NO: 22)
EIVLTQSPATLSLSPGERATLSCSATSSVSYMHWYQQKPGQAPRLLI

YSTSNLASGIPARFSGSGSGTDFTLTISSLEPEDFAVYYCQQRSSYP

FTFGPGTKLDIK

Amino acid sequence of 2E2 RKA F-Y mutant light
chain variable domain
(SEQ ID NO: 23)
EIVLTQSPATLSLSPGERATLSCSATSSVSYMHWFQQKPGQAPRLLI

YSTSNLASGIPARFSGSGSGTDFTLTISSLEPEDFAVYYCQQRSSYP

YTFGPGTKLDIK

Amino acid sequence of 2E2 RKF F-Y mutant light
chain variable domain
(SEQ ID NO: 24)
EIVLTQSPATLSLSPGERATLSCSATSSVSYMHWFQQKPGQAPRLLI

YSTSNLASGIPARFSGSGSGTDYTLTISSLEPEDFAVYYCQQRSSYP

YTFGPGTKLDIK

Amino acid sequence of HEKA IgG1 heavy chain
and HEKF IgG1 heavy chain
(SEQ ID NO: 75)
EVQLVESGGGLVQPGGSLRLSCAASGFSLTIYGAHWVRQAPGKGLEW

VGVIWAGGSTNYNSALMSRFTISKDNSKNTVYLQMNSLRAEDTAVYY

CARDGSSPYYYSMEYWGQGTTVTVSSASTKGPSVFPLAPSSKSTSGG

TAALGCLVKDYFPEPVTVSWNSGALTSGVHTFPAVLQSSGLYSLSSV

VTVPSSSLGTQTYICNVNHKPSNTKVDKRVEPKSCDKTHTCPPCPAP

ELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNK

ALPAPIEKTISKAKGQPREPQVYTLPPSREEMTKNQVSLTCLVKGFY

PSDIAVEWESNGQPENNYKTTPPVLDSDGSFFLYSKLTVDKSRWQQG

NVFSCSVMHEALHNHYTQKSLSLSPG

SEQUENCES

Amino acid sequence of HEKA kappa light chain
(SEQ ID NO: 76)
EIVLTQSPATLSLSPGERATLSCSATSSVSYMHWFQQKPGQAPRLLI
YSTSNLASGIPARFSGSGSGTDFTLTISSLEPEDFAVYYCQQRSSYP
FTFGPGTKLDIKRTVAAPSVFIFPPSDEQLKSGTASVVCLLNNFYPR
EAKVQWKVDNALQSGNSQESVTEQDSKDSTYSLSSTLTLSKADYEKH
KVYACEVTHQGLSSPVTKSFNRGEC Amino acid sequence of HEKF kappa light chain
(SEQ ID NO: 77)
EIVLTQSPATLSLSPGERATLSCSATSSVSYMHWFQQKPGQAPRLLI
YSTSNLASGIPARFSGSGSGTDYTLTISSLEPEDFAVYYCQQRSSYP
FTFGPGTKLDIKRTVAAPSVFIFPPSDEQLKSGTASVVCLLNNFYPR
EAKVQWKVDNALQSGNSQESVTEQDSKDSTYSLSSTLTLSKADYEKH
KVYACEVTHQGLSSPVTKSFNRGEC Amino acid sequence of IgG1 heavy chain
constant region (IgG4 contains a S228P mutation)
(SEQ ID NO: 78)
ASTKGPSVFPLAPSSKSTSGGTAALGCLNKDYFPEPVTVSWNSGALT
SGVHTFPAVLQSSGLYSLSSVVTVPSSSLGTQTYICNVNHKPSNTKV
DKRVEPKSCDKTHTCPPCPAPELLGGPSVFLFPPKPKDTLMISRTPE
VTCVVVDVSHEDPEVKFNWYVDGVEVHNAKTKPREEQYNSTYRVVSV
LTVLFIQDWLNGKEYKCKVSNKALPAPIEKTISKAKGQPREPQVYTL
PPSREEMTKNQVSLTCLVKGFYPSDIAVEWESNGQPENNYKTTPPVL
DSDGSFFLYSKLTVDKSRWQQGNVFSCSVMHEALHNHYTQKSLSLSP
G Amino acid sequence of IgG4 heavy chain
constant region
(SEQ ID NO: 79)
ASTKGPSVFPLAPCSRSTSESTAALGCLNKDYFPEPVTVSWNSGALT
SGVHTFPAVLQSSGLYSLSSVVTVPSSSLGTKTYTCNVDHKPSNTKV
DKRVESKYGPPCPPCPAPEFLGGPSVFLFPPKPKDTLMISRTPEVTC
VVVDVSQEDPEVQFNWYVDGVEVHNAKTKPREEQFNSTYRVVSVLTV
LHQDWLNGKEYKCKVSNKGLPSSIEKTISKAKGQPREPQVYTLPPSQ
EEMTKNQVSLTCLVKGFYPSDIAVEWESNGQPENNYKTTPPVLDSDG
SFFLYSRLTVDKSRWQEGNVESCSVMHEALHNHYTQKSLSLSLG Amino acid sequence of Ig kappa light chain
constant region
(SEQ ID NO: 80)
RTVAAPSVFIFPPSDEQLKSGTASVVCLLNNFYPREAKVQWKVDNAL
QSGNSQESVTEQDSKDSTYSLSSTLTLSKADYEKHKVYACEVTHQGL
SSPVTKSENRGEC Amino acid sequence of murine 2C4 and 2E2 IgG1
heavy chain
(SEQ ID NO: 81)
QVQLKRASGPGLVAPSQSLSITCTVSGFSLTIYGAHWVRQPPGKGLE
WLGVIWAGGSTNYNSALMSRLSISKDNSKSQVFLKINSLQTDDTALY WARDGSSPYYYSMEYWGQGTSVTVSSAKTTPPSVYPLAPGSAAQTNS
MVTLGCLNKGYFPEPVTVTWNSGSLSSGVIITFPAVLESDLYTLSSS
VTVPSSPRPSETVTCNVAHPASSTKVDKKIVPRDCGCKPCICTVPEV
SSVFIFPPKPKDVLTITLTPKVFCVVVDISKDDPEVQFSWFVDDVEV
HTAQTQPREEQFNSTERSVSELPIMHQDWLNGKEFKCRVNSAAFPAP
IEKTISKTKGRPKAPQVYTIPPPKEQMAKDKVSLTCMITDFFPEDIT
VEWQWNGQPAENYKNTQPIMNTNGSYFVYSKLNVQKSNWEAGNTFTC
SVLHEGLHNHHTEKSLSHSPG Amino acid sequence of murine 2C4 kappa light
chain
(SEQ ID NO: 82)
EIILTQSPAIMSASPGEKVSITCSATSSVSYMHWFQQKPGTSPKLWF
YSTSNLASGVPVRFSGSGSGTSYSLTISRMEAEDAATYYCQQRSSYP
FTFGSGTKLEIKADAAPTVSIFPPSSEQLTSGGASVVCFLNNFYPKD
INVKWKIDGSERQNGVLNSWTDQDSKDSTYSMSSTLTLTKDEYERHN
SYTCEATHKTSTSPIVKSFNRNEC Amino acid sequence of murine 2E2 kappa light
chain
(SEQ ID NO: 83)
QIILTQSPAIMSASPGEKVSITCSATSSVSYMHWFQQKPGTSPKLWI
YSTSNLASGVPVRFSGSGSGTSYSLTISRMEAEDAATYYCQQRSSYP
FTFGSGTKLEIKADAAPTVSIPPPSSEQLTSGGASVVCFLNNFYPKD
INVKWKIDGSERQNGVLNSWTDQDSKDSTYSMSSTLTLTKDEYERHN
SYTCEATHKTSTSPIVKSENRNEC Amino acid sequence of chimeric 2C4 and 2E2
IgG1 heavy chain
(SEQ ID NO: 84)
QVQLKRASGPGLVAPSQSLSITCTVSGFSLTIYGAHWVRQPPGKGLE
WLGVIWAGGSTNYNSALMSRLSISKDNSKSQVFLKINSLQTDDTALY
YCARDGSSPYYYSMEYWGQGTSVTVSSASTKGPSVFPLAPSSKSTSG
GTAALGCLVKDYFPEPVTVSWNSGALTSGVHTFPAVLQSSGLYSLSS
VVTVPSSSLGTQTYICNVNHKPSNTKVDKRVEPKSCDKTHTCPPCPA
PELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSN
KALPAPIEKTISKAKGQPREPQVYTLPPSREEMTKNQVSLTCLVKGF
YPSDIAVEWESNGQPENNYKTTPPVLDSDGSFFLYSKLTVDKSRWQQ
GNVFSCSVMHEALHNHYTQKSLSLSPG Amino acid sequence of chimeric 2C4 kappa light
chain
(SEQ ID NO: 85)
EIILTQSPAIMSASPGEKVSITCSATSSVSYMHWFQQKPGTSPKLWI
YSTSNLASGVPVRFSGSGSGTSYSLTISRMEAEDAATYYCQQRSSYP
FTFGSGTKLEIKRTVAAPSVFIFPPSDEQLKSGTASVVCLLNNFYPR
EAKVQWKVDNALQSGNSQESVTEQDSKDSTYSLSSTLTLSKADYEKH
KVYACEVTHQGLSSPVTKSFNRGEC

SEQUENCES

Amino acid sequence of chimeric 2E2 kappa light chain
(SEQ ID NO: 86)
QIILTQSPAIMSASPGEKVSITCSATSSVSYMHWFQQKPGTSPKLWI

YSTSNLASGVPVRFSGSGSGTSYSLTISRMEAEDAATYYCQQRSSYP

FTFGSGTKLEIKRTVAAPSVFIFPPSDEQLKSGTASVVCLLNNFYPR

EAKVQWKVDNALQSGNSQESVTEQDSKDSTYSLSSTLTLSKADYEKH

KVYACEVTHQGLSSPVTKSFNRGEC

Amino acid sequence of HEKA IgG4 heavy chain (IgG4 contains a S228P mutation)
(SEQ ID NO: 87)
EVQLVESGGGLVQPGGSLRLSCAASGFSLTIYGAHWVRQAPGKGLEW

VGVIWAGGSTNYNSALMSRFTISKDNSKNTVYLQMNSLRAEDTAVYY

CARDGSSPYYYSMEYWGQGTTVTVSSASTKGPSVFPLAPCSRSTSES

TAALGCLVKDYFPEPVTVSWNSGALTSGVHTFPAVLQSSGLYSLSSV

VTVPSSSLGTKTYTCNVDHKPSNTKVDKRVESKYGPPCPPCPAPEFL

GGPSVFLFPPKPKDTLMISRTPEVTCVVVDVSQEDPEVQFNWYVDGV

EVHNAKTKPREEQFNSTYRVVSVLTVLHQDWLNGKEYKCKVSNKGLP

SSIEKTISKAKGQPREPQVYTLPPSQEEMTKNQVSLTCLVKGFYPSD

IAVEWESNGQPENNYKTTPPVLDSDGSFFLYSRLTVDKSRWQEGNVF

SCSVMHEALHNHYTQKSLSLSLG

Amino acid sequence of mouse 1C3 heavy chain variable domain (underlined residues comprise CDRs H1 and H2 according to Chothia numbering)
(SEQ ID NO: 106)
EVQVVESGGDLVKSGGSLKLSCAAS<u>GFPFSSY</u>AMSWVRQTPDKRLEW VAII<u>SSGGSY</u>TYYSDSVKGRFTISRDNAKNTLYLQMSSLKSEDTAMY

YCARHETAQAAWFAYWGQGTLVTVSA

Amino acid sequence of mouse 1H10 heavy chain variable domain (underlined residues comprise CDRs H1 and H2 according to Chothia numbering)
(SEQ ID NO: 107)
EVQLQQSGAELVRPGASVKLSCTAS<u>GFNIKDY</u>YMYWVKQRPEQGLEW IGRI<u>APEDGD</u>TEYAPKFQGKATVTADTSSNTAYLHLSSLTSEDTAVY

YCTTEGNYYGSSILDYWGQGTTLTVSS

Amino acid sequence of mouse 4F11 heavy chain variable domain (underlined residues comprise CDRs H1 and H2 according to Chothia numbering)
(SEQ ID NO: 108)
QVQLQQSGAELVKPGASVKISCKAS<u>GYAFRSS</u>WMNWVKQRPGKGLEW IGQI<u>YPGDDY</u>TNYNGKFKGKVTLTADRSSSTAYMQLSSLTSEDSAVY

FCARLGPYGPFADWGQGTLVTVSA

Amino acid sequence of mouse 1C3 light chain variable domain
(SEQ ID NO: 109)
QIVLTQSPAIMSASPGEKVTMTCSASSSVSYMHWYQQKSGTSPKRWI

YDTSKLAYGVPARFSGSGSGTSYSLTISSMEAEDAATYYCQQWSSNP

PTFGGGTKLEIK

Amino acid sequence of mouse 1H10 light chain variable domain
(SEQ ID NO: 110)
DIQMTQTTSSLSASLGDRVTISCRASQDITNYLNWYQQKPDGTVKLL

IYFTSRLHSGVPSRFSGSGSGTDYSLTISNLEQEDIATYFCQQGNTL

PWTFGGGTKLEIK

Amino acid sequence of mouse 4F11 light chain variable domain
(SEQ ID NO: 111)
QIVLTQSPAIVSASPGEKVTMTCSASSSVSYMYWYQQRPGSSPRLLI

YDTSSLASGVPVRFSGSGSGTSYSLTISRIESEDAANYYCQQWNSDP

YTFGGGTKLEIK

---

What is claimed is:

1. A method for treating or preventing fibrotic disease in an individual comprising administering to the individual an effective amount of an antibody that binds to human Siglec-8; wherein the antibody comprises a heavy chain variable region and a light chain variable region, wherein the heavy chain variable region comprises the amino acid sequence of SEQ ID NO:6; wherein the light chain variable region comprises the amino acid sequence of SEQ ID NO:16 or 21; and wherein the fibrotic disease is selected from the group consisting of: pulmonary fibrosis, hepatic fibrosis, renal fibrosis, cardiac fibrosis, spleen fibrosis, ocular fibrosis, mechanical-induced fibrosis, implant-induced fibrosis, radiation-induced fibrosis, drug-induced fibrosis, viral-induced fibrosis, cystic fibrosis, cancer-associated fibrosis, atherosclerosis, bone marrow fibrosis, scleroderma, mediastinal fibrosis, retroperitoneal cavity fibrosis, and Dupuytren's contracture.

2. The method of claim 1, wherein the pulmonary fibrosis is idiopathic pulmonary fibrosis.

3. The method of claim 1, wherein the pulmonary fibrosis is associated with chronic obstructive pulmonary disease.

4. The method of claim 1, wherein the mechanical induced fibrosis is ventilator-induced pulmonary fibrosis.

5. The method of claim 1, wherein the drug-induced fibrosis is bleomycin-induced pulmonary fibrosis.

6. The method of claim 1, wherein the scleroderma is systemic sclerosis.

7. The method of claim 1, wherein one or more symptom in the individual with the fibrotic disease is reduced relative to baseline after administration of the antibody that binds to human Siglec-8.

8. The method of claim 1, wherein one or more pulmonary function in the individual with pulmonary fibrosis is increased by at least 5% relative to baseline after administration of the antibody that binds to human Siglec-8.

9. The method of claim 8, wherein the one or more pulmonary function is selected from the group consisting of: vital capacity (VC), residual volume (V), forced expiratory volume (FEV1), forced vital capacity (FVC), forced expiratory flow (FEF), peak expiratory flow rate (PEFR), inspiratory reserve volume (IRV), functional residual capacity (FRC), inspirator capacity (IC), total lung capacity (TLC), expiratory reserve volume (ERV), tidal volume (TV) and maximum voluntary ventilation (MVV).

10. The method of claim 1, wherein one or more pathologic parameter in the individual with fibrotic disease is reduced by at least 5% relative to baseline after administration of the antibody that binds to human Siglec-8.

11. The method of claim 10, wherein the one or more pathologic parameter is selected from the group consisting of: neutrophil influx, number of mast cells, cytokine release, collagen accumulation, fibroblast or myofibroblast infiltration and fibroblastic foci formation.

12. The method of claim 1, wherein mast cell activation is reduced in the individual relative to baseline after administration of the antibody that binds to human Siglec-8.

13. The method of claim 1, wherein the antibody is a monoclonal antibody.

14. The method of claim 1, wherein the antibody has been engineered to improve antibody-dependent cell-mediated cytotoxicity (ADCC) activity.

15. The method of claim 14, wherein the antibody comprises at least one amino acid substitution in the Fc region that improves ADCC activity.

16. The method of claim 1, wherein at least one or two of the heavy chains of the antibody is non-fucosylated.

17. The method of claim 1, wherein the antibody comprises a heavy chain Fc region comprising a human IgG Fc region.

18. The method of claim 17, wherein the human IgG Fc region comprises a human IgG1 or a human IgG4 Fc region.

19. The method of claim 18, wherein the human IgG4 Fc region comprises the amino acid substitution S228P, and wherein the amino acid residues are numbered according to the EU index as in Kabat.

20. The method of claim 1, wherein the antibody comprises a heavy chain comprising the amino acid sequence of SEQ ID NO:87; and a light chain comprising the amino acid sequence of SEQ ID NO:76.

21. The method of claim 1, wherein the individual is a human.

22. The method of claim 1, wherein the antibody is in a pharmaceutical composition comprising the antibody and a pharmaceutically acceptable carrier.

23. The method of claim 1, wherein the antibody is administered to the individual by intravenous infusion.

24. The method of claim 1, wherein the antibody is administered to the individual by subcutaneous injection.

25. The method of claim 18, wherein the human IgG1 Fc region is non-fucosylated.

26. A method for treating or preventing fibrotic disease in an individual comprising administering to the individual an effective amount of a composition comprising an antibody that binds to human Siglec-8; wherein the antibody comprises a heavy chain variable region and a light chain variable region, wherein the heavy chain variable region comprises the amino acid sequence of SEQ ID NO:6; wherein the light chain variable region comprises the amino acid sequence of SEQ ID NO:16 or 21; and wherein the fibrotic disease is selected from the group consisting of: pulmonary fibrosis, hepatic fibrosis, renal fibrosis, cardiac fibrosis, spleen fibrosis, ocular fibrosis, mechanical-induced fibrosis, implant-induced fibrosis, radiation-induced fibrosis, drug-induced fibrosis, viral-induced fibrosis, cystic fibrosis, cancer-associated fibrosis, atherosclerosis, bone marrow fibrosis, scleroderma, mediastinal fibrosis, retroperitoneal cavity fibrosis, and Dupuytren's contracture.

27. The method of claim 26, wherein the antibody comprises a Fc region and N-glycoside-linked carbohydrate chains linked to the Fc region, wherein less than 50% of the N-glycoside-linked carbohydrate chains of the antibody in the composition contain a fucose residue.

28. The method of claim 26, wherein substantially none of the N-glycoside-linked carbohydrate chains of the antibody in the composition contain a fucose residue.

29. The method of claim 1, wherein the antibody comprises a heavy chain comprising the amino acid sequence of SEQ ID NO:75 and a light chain comprising the amino acid sequence selected from SEQ ID NO:76.

30. The method of claim 1, wherein the antibody comprises a heavy chain comprising the amino acid sequence of SEQ ID NO:75 and a light chain comprising the amino acid sequence selected from SEQ ID NO:77.

31. The method of claim 1, wherein the heavy chain variable region comprises the amino acid sequence of SEQ ID NO:6 and the light chain variable region comprises the amino acid sequence of SEQ ID NO:16.

32. The method of claim 1, wherein the heavy chain variable region comprises the amino acid sequence of SEQ ID NO:6 and the light chain variable region comprises the amino acid sequence of SEQ ID NO:21.

33. The method of claim 26, wherein the heavy chain variable region comprises the amino acid sequence of SEQ ID NO:6 and the light chain variable region comprises the amino acid sequence of SEQ ID NO:16.

34. The method of claim 26, wherein the heavy chain variable region comprises the amino acid sequence of SEQ ID NO:6 and the light chain variable region comprises the amino acid sequence of SEQ ID NO:21.

35. The method of claim 26, wherein the antibody comprises a heavy chain comprising the amino acid sequence of SEQ ID NO:75 and a light chain comprising the amino acid sequence selected from SEQ ID NO:76.

36. The method of claim 26, wherein the antibody comprises a heavy chain comprising the amino acid sequence of SEQ ID NO:75 and a light chain comprising the amino acid sequence selected from SEQ ID NO:77.

37. The method of claim 26, wherein the antibody comprises a heavy chain comprising the amino acid sequence of SEQ ID NO:87; and a light chain comprising the amino acid sequence of SEQ ID NO:76.

\* \* \* \* \*

SEQUENCE LISTING

```
<160> NUMBER OF SEQ ID NOS: 111

<210> SEQ ID NO 1
<211> LENGTH: 120
<212> TYPE: PRT
<213> ORGANISM: Artificial Sequence
<220> FEATURE:
<223> OTHER INFORMATION: Synthetic Construct

<400> SEQUENCE: 1

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ile Tyr
            20                  25                  30

Gly Ala His Trp Val Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Lys Ser Gln Val Phe Leu
```

```
                65                  70                  75                  80
Lys Ile Asn Ser Leu Gln Thr Asp Thr Ala Leu Tyr Tyr Cys Ala
                    85                  90                  95

Arg Asp Gly Ser Ser Pro Tyr Tyr Tyr Ser Met Glu Tyr Trp Gly Gln
                100                 105                 110

Gly Thr Ser Val Thr Val Ser Ser
        115                 120
```

<210> SEQ ID NO 2
<211> LENGTH: 120
<212> TYPE: PRT
<213> ORGANISM: Artificial Sequence
<220> FEATURE:
<223> OTHER INFORMATION: Synthetic Construct

<400> SEQUENCE: 2

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
                20                  25                  30

Gly Ala His Trp Val Arg Gln Ala Pro Gly Lys Gly Leu Glu Trp Val
            35                  40                  45

Ser Val Ile Trp Ala Gly Gly Ser Thr Asn Tyr Asn Ser Ala Leu Met
        50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Glu Tyr Trp Gly Gln
                100                 105                 110

Gly Thr Thr Val Thr Val Ser Ser
            115                 120
```

<210> SEQ ID NO 3
<211> LENGTH: 120
<212> TYPE: PRT
<213> ORGANISM: Artificial Sequence
<220> FEATURE:
<223> OTHER INFORMATION: Synthetic Construct

<400> SEQUENCE: 3

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr Ile Tyr
                20                  25                  30

Gly Ala His Trp Val Arg Gln Ala Pro Gly Lys Gly Leu Glu Trp Leu
            35                  40                  45

Gly Val Ile Trp Ala Gly Gly Ser Thr Asn Tyr Asn Ser Ala Leu Met
        50                  55                  60

Ser Arg Leu Ser Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Glu Tyr Trp Gly Gln
                100                 105                 110

Gly Thr Thr Val Thr Val Ser Ser
            115                 120
```

<210> SEQ ID NO 4
<211> LENGTH: 120
<212> TYPE: PRT
<213> ORGANISM: Artificial Sequence
<220> FEATURE:
<223> OTHER INFORMATION: Synthetic Construct

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr Ile Tyr
            20                  25                  30

Gly Ala His Trp Val Arg Gln Ala Pro Gly Lys Gly Leu Glu Trp Val
        35                  40                  45

Ser Val Ile Trp Ala Gly Gly Ser Thr Asn Tyr Asn Ser Ala Leu Met
    50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Glu Tyr Trp Gly Gln
            100                 105                 110

Gly Thr Thr Val Thr Val Ser Ser
        115                 120

<210> SEQ ID NO 5
<211> LENGTH: 120
<212> TYPE: PRT
<213> ORGANISM: Artificial Sequence
<220> FEATURE:
<223> OTHER INFORMATION: Synthetic Construct

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Leu
        35                  40                  45

Ser Val Ile Trp Ala Gly Gly Ser Thr Asn Tyr Asn Ser Ala Leu Met
    50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Glu Tyr Trp Gly Gln
            100                 105                 110

Gly Thr Thr Val Thr Val Ser Ser
        115                 120

<210> SEQ ID NO 6
<211> LENGTH: 120
<212> TYPE: PRT
<213> ORGANISM: Artificial Sequence
<220> FEATURE:
<223> OTHER INFORMATION: Synthetic Construct

<400> SEQUENCE: 6

Glu Val Gln Leu Val Glu Ser Gly Gly Gly Leu Val Gln Pro Gly Gly

```
                1               5                  10                 15
        Ser Leu Arg Leu Ser Cys Ala Ala Ser Gly Phe Ser Leu Thr Ile Tyr
                        20                  25                 30

Gly Ala His Trp Val Arg Gln Ala Pro Gly Lys Gly Leu Glu Trp Val
                        35                  40                 45

Gly Val Ile Trp Ala Gly Gly Ser Thr Asn Tyr Asn Ser Ala Leu Met
                        50                  55                 60

Ser Arg Phe Thr Ile Ser Lys Asp Asn Ser Lys Asn Thr Val Tyr Leu
        65                      70                  75                 80

Gln Met Asn Ser Leu Arg Ala Glu Asp Thr Ala Val Tyr Tyr Cys Ala
                        85                  90                 95

Arg Asp Gly Ser Ser Pro Tyr Tyr Tyr Ser Met Glu Tyr Trp Gly Gln
                        100                 105                110

Gly Thr Thr Val Thr Val Ser Ser
                        115                 120

<210> SEQ ID NO 7
<211> LENGTH: 120
<212> TYPE: PRT
<213> ORGANISM: Artificial Sequence
<220> FEATURE:
<223> OTHER INFORMATION: Synthetic Construct

<400> SEQUENCE: 7

Glu Val Gln Leu Val Glu Ser Gly Gly Gly Leu Val Gln Pro Gly Gly
        1               5                  10                 15

Ser Leu Arg Leu Ser Cys Ala Ala Ser Gly Phe Ser Leu Thr Ile Tyr
                        20                  25                 30

Gly Ala His Trp Val Arg Gln Ala Pro Gly Lys Gly Leu Glu Trp Val
                        35                  40                 45

Ser Val Ile Trp Ala Gly Gly Ser Thr Asn Tyr Asn Ser Ala Leu Met
                        50                  55                 60

Ser Arg Leu Thr Ile Ser Lys Asp Asn Ser Lys Asn Thr Val Tyr Leu
        65                      70                  75                 80

Gln Met Asn Ser Leu Arg Ala Glu Asp Thr Ala Val Tyr Tyr Cys Ala
                        85                  90                 95

Arg Asp Gly Ser Ser Pro Tyr Tyr Tyr Ser Met Glu Tyr Trp Gly Gln
                        100                 105                110

Gly Thr Thr Val Thr Val Ser Ser
                        115                 120

<210> SEQ ID NO 8
<211> LENGTH: 120
<212> TYPE: PRT
<213> ORGANISM: Artificial Sequence
<220> FEATURE:
<223> OTHER INFORMATION: Synthetic Construct

<400> SEQUENCE: 8

Glu Val Gln Leu Val Glu Ser Gly Gly Gly Leu Val Gln Pro Gly Gly
        1               5                  10                 15

Ser Leu Arg Leu Ser Cys Ala Ala Ser Gly Phe Ser Leu Thr Ile Tyr
                        20                  25                 30

Gly Ala His Trp Val Arg Gln Ala Pro Gly Lys Gly Leu Glu Trp Val
                        35                  40                 45

Ser Val Ile Trp Ala Gly Gly Ser Thr Asn Tyr Asn Ser Ala Leu Met
                        50                  55                 60
```

```
Ser Arg Phe Ser Ile Ser Lys Asp Asn Ser Lys Asn Thr Val Tyr Leu
 65                  70                  75                  80

Gln Met Asn Ser Leu Arg Ala Glu Asp Thr Ala Val Tyr Tyr Cys Ala
                 85                  90                  95

Arg Asp Gly Ser Ser Pro Tyr Tyr Tyr Ser Met Glu Tyr Trp Gly Gln
            100                 105                 110

Gly Thr Thr Val Thr Val Ser Ser
        115                 120

<210> SEQ ID NO 9
<211> LENGTH: 120
<212> TYPE: PRT
<213> ORGANISM: Artificial Sequence
<220> FEATURE:
<223> OTHER INFORMATION: Synthetic Construct

<400> SEQUENCE: 9

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ile Tyr
                 20                  25                  30

Gly Ala His Trp Ile Arg Gln Pro Pro Gly Lys Gly Leu Glu Trp Ile
             35                  40                  45

Gly Val Ile Trp Ala Gly Gly Ser Thr Asn Tyr Asn Ser Ala Leu Met
         50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Gly Ser Ser Pro Tyr Tyr Tyr Ser Met Glu Tyr Trp Gly Gln
            100                 105                 110

Gly Thr Leu Val Thr Val Ser Ser
        115                 120

<210> SEQ ID NO 10
<211> LENGTH: 120
<212> TYPE: PRT
<213> ORGANISM: Artificial Sequence
<220> FEATURE:
<223> OTHER INFORMATION: Synthetic Construct

<400> SEQUENCE: 10

Gln Val Gln Leu Gln Glu Ser Gly Pro Gly Leu Val Lys Pro Ser Glu
  1               5                  10                  15

Thr Leu Ser Leu Thr Cys Thr Val Ser Gly Phe Ser Leu Thr Ile Tyr
                 20                  25                  30

Gly Ala His Trp Val Arg Gln Pro Pro Gly Lys Gly Leu Glu Trp Leu
             35                  40                  45

Gly Val Ile Trp Ala Gly Gly Ser Thr Asn Tyr Asn Ser Ala Leu Met
         50                  55                  60

Ser Arg Leu Ser Ile Ser Lys Asp Asn Ser Lys Asn Gln Val Ser Leu
 65                  70                  75                  80

Lys Leu Ser Ser Val Thr Ala Ala Asp Thr Ala Val Tyr Tyr Cys Ala
                 85                  90                  95

Arg Asp Gly Ser Ser Pro Tyr Tyr Tyr Ser Met Glu Tyr Trp Gly Gln
            100                 105                 110

Gly Thr Leu Val Thr Val Ser Ser
        115                 120
```

<210> SEQ ID NO 11
<211> LENGTH: 120
<212> TYPE: PRT
<213> ORGANISM: Artificial Sequence
<220> FEATURE:
<223> OTHER INFORMATION: Synthetic Construct

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
        35                  40                  45

Gly Val Ile Trp Ala Gly Gly Ser Thr Asn Tyr Asn Ser Ala Leu Met
    50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Gly Met Glu Tyr Trp Gly Gln
            100                 105                 110

Gly Thr Thr Val Thr Val Ser Ser
        115                 120

<210> SEQ ID NO 12
<211> LENGTH: 120
<212> TYPE: PRT
<213> ORGANISM: Artificial Sequence
<220> FEATURE:
<223> OTHER INFORMATION: Synthetic Construct

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
        35                  40                  45

Gly Val Ile Trp Ala Gly Gly Ser Thr Asn Tyr Asn Ser Ala Leu Met
    50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Asp Tyr Trp Gly Gln
            100                 105                 110

Gly Thr Thr Val Thr Val Ser Ser
        115                 120

<210> SEQ ID NO 13
<211> LENGTH: 120
<212> TYPE: PRT
<213> ORGANISM: Artificial Sequence
<220> FEATURE:
<223> OTHER INFORMATION: Synthetic Construct

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
            35                  40                  45

Gly Val Ile Trp Ala Gly Gly Ser Thr Asn Tyr Asn Ser Ala Leu Met
50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
            85                  90                  95

Arg Asp Gly Ser Ser Pro Tyr Tyr Tyr Ser Met Glu Val Trp Gly Gln
            100                 105                 110

Gly Thr Thr Val Thr Val Ser Ser
            115                 120

<210> SEQ ID NO 14
<211> LENGTH: 120
<212> TYPE: PRT
<213> ORGANISM: Artificial Sequence
<220> FEATURE:
<223> OTHER INFORMATION: Synthetic Construct

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
            35                  40                  45

Gly Val Ile Trp Ala Gly Gly Ser Thr Asn Tyr Asn Ser Ala Leu Met
50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
            85                  90                  95

Arg Asp Gly Ser Ser Pro Tyr Tyr Tyr Gly Met Asp Val Trp Gly Gln
            100                 105                 110

Gly Thr Thr Val Thr Val Ser Ser
            115                 120

<210> SEQ ID NO 15
<211> LENGTH: 106
<212> TYPE: PRT
<213> ORGANISM: Artificial Sequence
<220> FEATURE:
<223> OTHER INFORMATION: Synthetic Construct

<400> SEQUENCE: 15

Gln Ile Ile Leu Thr Gln Ser Pro Ala Ile Met Ser Ala Ser Pro Gly
1               5                   10                  15

Glu Lys Val Ser Ile Thr Cys Ser Ala Thr Ser Ser Val Ser Tyr Met
            20                  25                  30

His Trp Phe Gln Gln Lys Pro Gly Thr Ser Pro Lys Leu Trp Ile Tyr
            35                  40                  45

Ser Thr Ser Asn Leu Ala Ser Gly Val Pro Val Arg Phe Ser Gly Ser
50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Phe Thr
                85                  90                  95

Phe Gly Ser Gly Thr Lys Leu Glu Ile Lys
            100                 105

<210> SEQ ID NO 16
<211> LENGTH: 106
<212> TYPE: PRT
<213> ORGANISM: Artificial Sequence
<220> FEATURE:
<223> OTHER INFORMATION: Synthetic Construct

<400> SEQUENCE: 16

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
                20                  25                  30

His Trp Phe Gln Gln Lys Pro Gly Gln Ala Pro Arg Leu Leu Ile Tyr
            35                  40                  45

Ser Thr Ser Asn Leu Ala Ser Gly Ile Pro Ala Arg Phe Ser Gly Ser
        50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
            100                 105

<210> SEQ ID NO 17
<211> LENGTH: 106
<212> TYPE: PRT
<213> ORGANISM: Artificial Sequence
<220> FEATURE:
<223> OTHER INFORMATION: Synthetic Construct

<400> SEQUENCE: 17

Glu Ile Ile Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
                20                  25                  30

His Trp Phe Gln Gln Lys Pro Gly Gln Ala Pro Arg Leu Trp Ile Tyr
            35                  40                  45

Ser Thr Ser Asn Leu Ala Ser Gly Val Pro Ala Arg Phe Ser Gly Ser
        50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
            100                 105

<210> SEQ ID NO 18
<211> LENGTH: 106
<212> TYPE: PRT
<213> ORGANISM: Artificial Sequence
<220> FEATURE:
<223> OTHER INFORMATION: Synthetic Construct

<400> SEQUENCE: 18

Glu Ile Ile Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Leu Ile Tyr
        35                  40                  45

Ser Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
            100                 105

<210> SEQ ID NO 19
<211> LENGTH: 106
<212> TYPE: PRT
<213> ORGANISM: Artificial Sequence
<220> FEATURE:
<223> OTHER INFORMATION: Synthetic Construct

<400> SEQUENCE: 19

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Trp Ile Tyr
        35                  40                  45

Ser Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
            100                 105

<210> SEQ ID NO 20
<211> LENGTH: 106
<212> TYPE: PRT
<213> ORGANISM: Artificial Sequence
<220> FEATURE:
<223> OTHER INFORMATION: Synthetic Construct

<400> SEQUENCE: 20

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Leu Ile Tyr
        35                  40                  45

Ser Thr Ser Asn Leu Ala Ser Gly Val Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
            100                 105

<210> SEQ ID NO 21
<211> LENGTH: 106
<212> TYPE: PRT
<213> ORGANISM: Artificial Sequence
<220> FEATURE:
<223> OTHER INFORMATION: Synthetic Construct

<400> SEQUENCE: 21

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Leu Ile Tyr
        35                  40                  45

Ser Thr Ser Asn Leu Ala Ser Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
            100                 105

<210> SEQ ID NO 22
<211> LENGTH: 106
<212> TYPE: PRT
<213> ORGANISM: Artificial Sequence
<220> FEATURE:
<223> OTHER INFORMATION: Synthetic Construct

<400> SEQUENCE: 22

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Tyr Gln Gln Lys Pro Gly Gln Ala Pro Arg Leu Leu Ile Tyr
        35                  40                  45

Ser Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
            100                 105

<210> SEQ ID NO 23
<211> LENGTH: 106
<212> TYPE: PRT
<213> ORGANISM: Artificial Sequence
<220> FEATURE:
<223> OTHER INFORMATION: Synthetic Construct

<400> SEQUENCE: 23

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Leu Ile Tyr
            35                  40                  45

Ser Thr Ser Asn Leu Ala Ser Gly Ile Pro Ala Arg Phe Ser Gly Ser
        50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Tyr Thr
                85                  90                  95

Phe Gly Pro Gly Thr Lys Leu Asp Ile Lys
            100                 105

<210> SEQ ID NO 24
<211> LENGTH: 106
<212> TYPE: PRT
<213> ORGANISM: Artificial Sequence
<220> FEATURE:
<223> OTHER INFORMATION: Synthetic Construct

<400> SEQUENCE: 24

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Leu Ile Tyr
            35                  40                  45

Ser Thr Ser Asn Leu Ala Ser Gly Ile Pro Ala Arg Phe Ser Gly Ser
        50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Arg Ser Ser Tyr Pro Tyr Thr
                85                  90                  95

Phe Gly Pro Gly Thr Lys Leu Asp Ile Lys
            100                 105

<210> SEQ ID NO 25
<211> LENGTH: 30
<212> TYPE: PRT
<213> ORGANISM: Artificial Sequence
<220> FEATURE:
<223> OTHER INFORMATION: Synthetic Construct

<400> SEQUENCE: 25

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr
            20                  25                  30

<210> SEQ ID NO 26
<211> LENGTH: 30
<212> TYPE: PRT
<213> ORGANISM: Artificial Sequence
<220> FEATURE:
<223> OTHER INFORMATION: Synthetic Construct

<400> SEQUENCE: 26

Glu Val Gln Leu Val Glu Ser Gly Gly Gly Leu Val Gln Pro Gly Gly

```
                1               5                   10                  15
Ser Leu Arg Leu Ser Cys Ala Ala Ser Gly Phe Ser Leu Thr
            20                  25                  30

<210> SEQ ID NO 27
<211> LENGTH: 30
<212> TYPE: PRT
<213> ORGANISM: Artificial Sequence
<220> FEATURE:
<223> OTHER INFORMATION: Synthetic Construct

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr
            20                  25                  30

<210> SEQ ID NO 28
<211> LENGTH: 30
<212> TYPE: PRT
<213> ORGANISM: Artificial Sequence
<220> FEATURE:
<223> OTHER INFORMATION: Synthetic Construct

<400> SEQUENCE: 28

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser
            20                  25                  30

<210> SEQ ID NO 29
<211> LENGTH: 30
<212> TYPE: PRT
<213> ORGANISM: Artificial Sequence
<220> FEATURE:
<223> OTHER INFORMATION: Synthetic Construct

<400> SEQUENCE: 29

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr
            20                  25                  30

<210> SEQ ID NO 30
<211> LENGTH: 14
<212> TYPE: PRT
<213> ORGANISM: Artificial Sequence
<220> FEATURE:
<223> OTHER INFORMATION: Synthetic Construct

<400> SEQUENCE: 30

Trp Val Arg Gln Pro Pro Gly Lys Gly Leu Glu Trp Leu Gly
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Synthetic Construct

<400> SEQUENCE: 31

Trp Val Arg Gln Ala Pro Gly Lys Gly Leu Glu Trp Val Ser
1               5                   10
```

```
<210> SEQ ID NO 32
<211> LENGTH: 14
<212> TYPE: PRT
<213> ORGANISM: Artificial Sequence
<220> FEATURE:
<223> OTHER INFORMATION: Synthetic Construct

<400> SEQUENCE: 32

Trp Val Arg Gln Ala Pro Gly Lys Gly Leu Glu Trp Leu Gly
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Synthetic Construct

<400> SEQUENCE: 33

Trp Val Arg Gln Ala Pro Gly Lys Gly Leu Glu Trp Leu Ser
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Synthetic Construct

<400> SEQUENCE: 34

Trp Val Arg Gln Ala Pro Gly Lys Gly Leu Glu Trp Val Gly
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Synthetic Construct

<400> SEQUENCE: 35

Trp Ile Arg Gln Pro Pro Gly Lys Gly Leu Glu Trp Ile Gly
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Synthetic Construct

<400> SEQUENCE: 36

Trp Val Arg Gln Pro Pro Gly Lys Gly Leu Glu Trp Leu Gly
1               5                   10

<210> SEQ ID NO 37
<211> LENGTH: 32
<212> TYPE: PRT
<213> ORGANISM: Artificial Sequence
<220> FEATURE:
<223> OTHER INFORMATION: Synthetic Construct

<400> SEQUENCE: 37

Arg Leu Ser Ile Ser Lys Asp Asn Ser Lys Ser Gln Val Phe Leu Lys
1               5                   10                  15

Ile Asn Ser Leu Gln Thr Asp Asp Thr Ala Leu Tyr Tyr Cys Ala Arg
```

```
<210> SEQ ID NO 38
<211> LENGTH: 32
<212> TYPE: PRT
<213> ORGANISM: Artificial Sequence
<220> FEATURE:
<223> OTHER INFORMATION: Synthetic Construct

<400> SEQUENCE: 38

Arg Phe Thr Ile Ser Lys Asp Asn Ser Lys Asn Thr Val Tyr Leu Gln
 1               5                  10                  15

Met Asn Ser Leu Arg Ala Glu Asp Thr Ala Val Tyr Tyr Cys Ala Arg
             20                  25                  30

<210> SEQ ID NO 39
<211> LENGTH: 32
<212> TYPE: PRT
<213> ORGANISM: Artificial Sequence
<220> FEATURE:
<223> OTHER INFORMATION: Synthetic Construct

<400> SEQUENCE: 39

Arg Leu Ser Ile Ser Lys Asp Asn Ser Lys Asn Thr Val Tyr Leu Gln
 1               5                  10                  15

Met Asn Ser Leu Arg Ala Glu Asp Thr Ala Val Tyr Tyr Cys Ala Arg
             20                  25                  30

<210> SEQ ID NO 40
<211> LENGTH: 32
<212> TYPE: PRT
<213> ORGANISM: Artificial Sequence
<220> FEATURE:
<223> OTHER INFORMATION: Synthetic Construct

<400> SEQUENCE: 40

Arg Leu Thr Ile Ser Lys Asp Asn Ser Lys Asn Thr Val Tyr Leu Gln
 1               5                  10                  15

Met Asn Ser Leu Arg Ala Glu Asp Thr Ala Val Tyr Tyr Cys Ala Arg
             20                  25                  30

<210> SEQ ID NO 41
<211> LENGTH: 32
<212> TYPE: PRT
<213> ORGANISM: Artificial Sequence
<220> FEATURE:
<223> OTHER INFORMATION: Synthetic Construct

<400> SEQUENCE: 41

Arg Phe Ser Ile Ser Lys Asp Asn Ser Lys Asn Thr Val Tyr Leu Gln
 1               5                  10                  15

Met Asn Ser Leu Arg Ala Glu Asp Thr Ala Val Tyr Tyr Cys Ala Arg
             20                  25                  30

<210> SEQ ID NO 42
<211> LENGTH: 32
<212> TYPE: PRT
<213> ORGANISM: Artificial Sequence
<220> FEATURE:
<223> OTHER INFORMATION: Synthetic Construct

<400> SEQUENCE: 42

Arg Val Thr Ile Ser Val Asp Thr Ser Lys Asn Gln Phe Ser Leu Lys
 1               5                  10                  15
```

```
Leu Ser Ser Val Thr Ala Ala Asp Thr Ala Val Tyr Tyr Cys Ala Arg
         20                  25                  30
```

<210> SEQ ID NO 43
<211> LENGTH: 32
<212> TYPE: PRT
<213> ORGANISM: Artificial Sequence
<220> FEATURE:
<223> OTHER INFORMATION: Synthetic Construct

<400> SEQUENCE: 43

```
Arg Leu Ser Ile Ser Lys Asp Asn Ser Lys Asn Gln Val Ser Leu Lys
1               5                   10                  15

Leu Ser Ser Val Thr Ala Ala Asp Thr Ala Val Tyr Tyr Cys Ala Arg
         20                  25                  30
```

<210> SEQ ID NO 44
<211> LENGTH: 11
<212> TYPE: PRT
<213> ORGANISM: Artificial Sequence
<220> FEATURE:
<223> OTHER INFORMATION: Synthetic Construct

<400> SEQUENCE: 44

```
Trp Gly Gln Gly Thr Ser Val Thr Val Ser Ser
1               5                   10
```

<210> SEQ ID NO 45
<211> LENGTH: 11
<212> TYPE: PRT
<213> ORGANISM: Artificial Sequence
<220> FEATURE:
<223> OTHER INFORMATION: Synthetic Construct

<400> SEQUENCE: 45

```
Trp Gly Gln Gly Thr Thr Val Thr Val Ser Ser
1               5                   10
```

<210> SEQ ID NO 46
<211> LENGTH: 11
<212> TYPE: PRT
<213> ORGANISM: Artificial Sequence
<220> FEATURE:
<223> OTHER INFORMATION: Synthetic Construct

<400> SEQUENCE: 46

```
Trp Gly Gln Gly Thr Leu Val Thr Val Ser Ser
1               5                   10
```

<210> SEQ ID NO 47
<211> LENGTH: 23
<212> TYPE: PRT
<213> ORGANISM: Artificial Sequence
<220> FEATURE:
<223> OTHER INFORMATION: Synthetic Construct

<400> SEQUENCE: 47

```
Gln Ile Ile Leu Thr Gln Ser Pro Ala Ile Met Ser Ala Ser Pro Gly
1               5                   10                  15

Glu Lys Val Ser Ile Thr Cys
         20
```

<210> SEQ ID NO 48
<211> LENGTH: 23
<212> TYPE: PRT
<213> ORGANISM: Artificial Sequence

```
<220> FEATURE:
<223> OTHER INFORMATION: Synthetic Construct

<400> SEQUENCE: 48

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 49
<211> LENGTH: 23
<212> TYPE: PRT
<213> ORGANISM: Artificial Sequence
<220> FEATURE:
<223> OTHER INFORMATION: Synthetic Construct

<400> SEQUENCE: 49

Glu Ile Ile Leu Thr Gln Ser Pro Ala Thr Leu Ser Leu Ser Pro Gly
1               5                   10                  15

Glu Arg Ala Thr Leu Ser Cys
            20

<210> SEQ ID NO 50
<211> LENGTH: 15
<212> TYPE: PRT
<213> ORGANISM: Artificial Sequence
<220> FEATURE:
<223> OTHER INFORMATION: Synthetic Construct

<400> SEQUENCE: 50

Trp Phe Gln Gln Lys Pro Gly Thr Ser Pro Lys Leu Trp Ile Tyr
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Synthetic Construct

<400> SEQUENCE: 51

Trp Phe Gln Gln Lys Pro Gly Gln Ala Pro Arg Leu Leu Ile Tyr
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Synthetic Construct

<400> SEQUENCE: 52

Trp Phe Gln Gln Lys Pro Gly Gln Ala Pro Arg Leu Trp Ile Tyr
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Synthetic Construct

<400> SEQUENCE: 53

Trp Tyr Gln Gln Lys Pro Gly Gln Ala Pro Arg Leu Leu Ile Tyr
1               5                   10                  15
```

<210> SEQ ID NO 54
<211> LENGTH: 32
<212> TYPE: PRT
<213> ORGANISM: Artificial Sequence
<220> FEATURE:
<223> OTHER INFORMATION: Synthetic Construct

<400> SEQUENCE: 54

Gly Val Pro Val Arg Phe Ser Gly Ser Gly Ser Gly Thr Ser Tyr Ser
1               5                   10                  15

Leu Thr Ile Ser Arg Met Glu Ala Glu Asp Ala Ala Thr Tyr Tyr Cys
            20                  25                  30

<210> SEQ ID NO 55
<211> LENGTH: 32
<212> TYPE: PRT
<213> ORGANISM: Artificial Sequence
<220> FEATURE:
<223> OTHER INFORMATION: Synthetic Construct

<400> SEQUENCE: 55

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 56
<211> LENGTH: 32
<212> TYPE: PRT
<213> ORGANISM: Artificial Sequence
<220> FEATURE:
<223> OTHER INFORMATION: Synthetic Construct

<400> SEQUENCE: 56

Gly Val Pro Ala Arg Phe Ser Gly Ser Gly Ser Gly Thr Asp Tyr Thr
1               5                   10                  15

Leu Thr Ile Ser Ser Leu Glu Pro Glu Asp Phe Ala Val Tyr Tyr Cys
            20                  25                  30

<210> SEQ ID NO 57
<211> LENGTH: 32
<212> TYPE: PRT
<213> ORGANISM: Artificial Sequence
<220> FEATURE:
<223> OTHER INFORMATION: Synthetic Construct

<400> SEQUENCE: 57

Gly Val Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 58
<211> LENGTH: 32
<212> TYPE: PRT
<213> ORGANISM: Artificial Sequence
<220> FEATURE:
<223> OTHER INFORMATION: Synthetic Construct

<400> SEQUENCE: 58

Gly Ile Pro Ala Arg Phe Ser Gly Ser Gly Ser Gly Thr Asp Tyr Thr
1               5                   10                  15

Leu Thr Ile Ser Ser Leu Glu Pro Glu Asp Phe Ala Val Tyr Tyr Cys
            20                  25                  30

```
<210> SEQ ID NO 59
<211> LENGTH: 10
<212> TYPE: PRT
<213> ORGANISM: Artificial Sequence
<220> FEATURE:
<223> OTHER INFORMATION: Synthetic Construct

<400> SEQUENCE: 59

Phe Gly Ser Gly Thr Lys Leu Glu Ile Lys
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Synthetic Construct

<400> SEQUENCE: 60

Phe Gly Pro Gly Thr Lys Leu Asp Ile Lys
1               5                   10

<210> SEQ ID NO 61
<211> LENGTH: 5
<212> TYPE: PRT
<213> ORGANISM: Artificial Sequence
<220> FEATURE:
<223> OTHER INFORMATION: Synthetic Construct

<400> SEQUENCE: 61

Ile Tyr Gly Ala His
1               5

<210> SEQ ID NO 62
<211> LENGTH: 16
<212> TYPE: PRT
<213> ORGANISM: Artificial Sequence
<220> FEATURE:
<223> OTHER INFORMATION: Synthetic Construct

<400> SEQUENCE: 62

Val Ile Trp Ala Gly Gly Ser Thr Asn Tyr Asn Ser Ala Leu Met Ser
1               5                   10                  15

<210> SEQ ID NO 63
<211> LENGTH: 12
<212> TYPE: PRT
<213> ORGANISM: Artificial Sequence
<220> FEATURE:
<223> OTHER INFORMATION: Synthetic Construct

<400> SEQUENCE: 63

Asp Gly Ser Ser Pro Tyr Tyr Tyr Ser Met Glu Tyr
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Synthetic Construct

<400> SEQUENCE: 64

Ser Ala Thr Ser Ser Val Ser Tyr Met His
1               5                   10
```

<210> SEQ ID NO 65
<211> LENGTH: 7
<212> TYPE: PRT
<213> ORGANISM: Artificial Sequence
<220> FEATURE:
<223> OTHER INFORMATION: Synthetic Construct

<400> SEQUENCE: 65

Ser Thr Ser Asn Leu Ala Ser
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic Construct

<400> SEQUENCE: 66

Gln Gln Arg Ser Ser Tyr Pro Phe Thr
1               5

<210> SEQ ID NO 67
<211> LENGTH: 12
<212> TYPE: PRT
<213> ORGANISM: Artificial Sequence
<220> FEATURE:
<223> OTHER INFORMATION: Synthetic Construct

<400> SEQUENCE: 67

Asp Gly Ser Ser Pro Tyr Tyr Tyr Gly Met Glu Tyr
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Synthetic Construct

<400> SEQUENCE: 68

Asp Gly Ser Ser Pro Tyr Tyr Tyr Ser Met Asp Tyr
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Synthetic Construct

<400> SEQUENCE: 69

Asp Gly Ser Ser Pro Tyr Tyr Tyr Ser Met Glu Val
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Synthetic Construct

<400> SEQUENCE: 70

Asp Gly Ser Ser Pro Tyr Tyr Tyr Gly Met Asp Val
1               5                   10

<210> SEQ ID NO 71
<211> LENGTH: 9
<212> TYPE: PRT
<213> ORGANISM: Artificial Sequence
<220> FEATURE:
<223> OTHER INFORMATION: Synthetic Construct

<400> SEQUENCE: 71

Gln Gln Arg Ser Ser Tyr Pro Tyr Thr
1               5

<210> SEQ ID NO 72
<211> LENGTH: 474
<212> TYPE: PRT
<213> ORGANISM: Homo sapiens

<400> SEQUENCE: 72

Gly Tyr Leu Leu Gln Val Gln Glu Leu Val Thr Val Gln Glu Gly Leu
1               5                   10                  15

Cys Val His Val Pro Cys Ser Phe Ser Tyr Pro Gln Asp Gly Trp Thr
            20                  25                  30

Asp Ser Asp Pro Val His Gly Tyr Trp Phe Arg Ala Gly Asp Arg Pro
        35                  40                  45

Tyr Gln Asp Ala Pro Val Ala Thr Asn Asn Pro Asp Arg Glu Val Gln
    50                  55                  60

Ala Glu Thr Gln Gly Arg Phe Gln Leu Leu Gly Asp Ile Trp Ser Asn
65                  70                  75                  80

Asp Cys Ser Leu Ser Ile Arg Asp Ala Arg Lys Arg Asp Lys Gly Ser
                85                  90                  95

Tyr Phe Phe Arg Leu Glu Arg Gly Ser Met Lys Trp Ser Tyr Lys Ser
            100                 105                 110

Gln Leu Asn Tyr Lys Thr Lys Gln Leu Ser Val Phe Val Thr Ala Leu
        115                 120                 125

Thr His Arg Pro Asp Ile Leu Ile Leu Gly Thr Leu Glu Ser Gly His
    130                 135                 140

Ser Arg Asn Leu Thr Cys Ser Val Pro Trp Ala Cys Lys Gln Gly Thr
145                 150                 155                 160

Pro Pro Met Ile Ser Trp Ile Gly Ala Ser Val Ser Pro Gly Pro
                165                 170                 175

Thr Thr Ala Arg Ser Ser Val Leu Thr Leu Thr Pro Lys Pro Gln Asp
            180                 185                 190

His Gly Thr Ser Leu Thr Cys Gln Val Thr Leu Pro Gly Thr Gly Val
        195                 200                 205

Thr Thr Thr Ser Thr Val Arg Leu Asp Val Ser Tyr Pro Pro Trp Asn
    210                 215                 220

Leu Thr Met Thr Val Phe Gln Gly Asp Ala Thr Ala Ser Thr Ala Leu
225                 230                 235                 240

Gly Asn Gly Ser Ser Leu Ser Val Leu Glu Gly Gln Ser Leu Arg Leu
                245                 250                 255

Val Cys Ala Val Asn Ser Asn Pro Pro Ala Arg Leu Ser Trp Thr Arg
            260                 265                 270

Gly Ser Leu Thr Leu Cys Pro Ser Arg Ser Ser Asn Pro Gly Leu Leu
        275                 280                 285

Glu Leu Pro Arg Val His Val Arg Asp Glu Gly Glu Phe Thr Cys Arg
    290                 295                 300

Ala Gln Asn Ala Gln Gly Ser Gln His Ile Ser Leu Ser Leu Ser Leu
305                 310                 315                 320

-continued

```
Gln Asn Glu Gly Thr Gly Thr Ser Arg Pro Val Ser Gln Val Thr Leu
            325                 330                 335

Ala Ala Val Gly Gly Ala Gly Ala Thr Ala Leu Ala Phe Leu Ser Phe
            340                 345                 350

Cys Ile Ile Phe Ile Ile Val Arg Ser Cys Arg Lys Lys Ser Ala Arg
            355                 360                 365

Pro Ala Ala Gly Val Gly Asp Thr Gly Met Glu Asp Ala Lys Ala Ile
            370                 375                 380

Arg Gly Ser Ala Ser Gln Gly Pro Leu Thr Glu Ser Trp Lys Asp Gly
385                 390                 395                 400

Asn Pro Leu Lys Lys Pro Pro Ala Val Ala Pro Ser Ser Gly Glu
                405                 410                 415

Glu Gly Glu Leu His Tyr Ala Thr Leu Ser Phe His Lys Val Lys Pro
            420                 425                 430

Gln Asp Pro Gln Gly Gln Glu Ala Thr Asp Ser Glu Tyr Ser Glu Ile
            435                 440                 445

Lys Ile His Lys Arg Glu Thr Ala Glu Thr Gln Ala Cys Leu Arg Asn
            450                 455                 460

His Asn Pro Ser Ser Lys Glu Val Arg Gly
465                 470

<210> SEQ ID NO 73
<211> LENGTH: 474
<212> TYPE: PRT
<213> ORGANISM: Homo sapiens

<400> SEQUENCE: 73

Gly Tyr Leu Leu Gln Val Gln Glu Leu Val Thr Val Gln Glu Gly Leu
1               5                   10                  15

Cys Val His Val Pro Cys Ser Phe Ser Tyr Pro Gln Asp Gly Trp Thr
            20                  25                  30

Asp Ser Asp Pro Val His Gly Tyr Trp Phe Arg Ala Gly Asp Arg Pro
        35                  40                  45

Tyr Gln Asp Ala Pro Val Ala Thr Asn Asn Pro Asp Arg Glu Val Gln
    50                  55                  60

Ala Glu Thr Gln Gly Arg Phe Gln Leu Leu Gly Asp Ile Trp Ser Asn
65                  70                  75                  80

Asp Cys Ser Leu Ser Ile Arg Asp Ala Arg Lys Arg Asp Lys Gly Ser
                85                  90                  95

Tyr Phe Phe Arg Leu Glu Arg Gly Ser Met Lys Trp Ser Tyr Lys Ser
            100                 105                 110

Gln Leu Asn Tyr Lys Thr Lys Gln Leu Ser Val Phe Val Thr Ala Leu
        115                 120                 125

Thr His Arg Pro Asp Ile Leu Ile Leu Gly Thr Leu Glu Ser Gly His
    130                 135                 140

Pro Arg Asn Leu Thr Cys Ser Val Pro Trp Ala Cys Lys Gln Gly Thr
145                 150                 155                 160

Pro Pro Met Ile Ser Trp Ile Gly Ala Ser Val Ser Ser Pro Gly Pro
                165                 170                 175

Thr Thr Ala Arg Ser Ser Val Leu Thr Leu Thr Pro Lys Pro Gln Asp
            180                 185                 190

His Gly Thr Ser Leu Thr Cys Gln Val Thr Leu Pro Gly Thr Gly Val
        195                 200                 205

Thr Thr Thr Ser Thr Val Arg Leu Asp Val Ser Tyr Pro Pro Trp Asn
```

```
Leu Thr Met Thr Val Phe Gln Gly Asp Ala Thr Ala Ser Thr Ala Leu
225                 230                 235                 240

Gly Asn Gly Ser Ser Leu Ser Val Leu Glu Gly Gln Ser Leu Arg Leu
                245                 250                 255

Val Cys Ala Val Asn Ser Asn Pro Pro Ala Arg Leu Ser Trp Thr Arg
                260                 265                 270

Gly Ser Leu Thr Leu Cys Pro Ser Arg Ser Ser Asn Pro Gly Leu Leu
            275                 280                 285

Glu Leu Pro Arg Val His Val Arg Asp Glu Gly Glu Phe Thr Cys Arg
        290                 295                 300

Ala Gln Asn Ala Gln Gly Ser Gln His Ile Ser Leu Ser Leu Ser Leu
305                 310                 315                 320

Gln Asn Glu Gly Thr Gly Thr Ser Arg Pro Val Ser Gln Val Thr Leu
                325                 330                 335

Ala Ala Val Gly Gly Ala Gly Ala Thr Ala Leu Ala Phe Leu Ser Phe
                340                 345                 350

Cys Ile Ile Phe Ile Ile Val Arg Ser Cys Arg Lys Lys Ser Ala Arg
            355                 360                 365

Pro Ala Ala Gly Val Gly Asp Thr Gly Met Glu Asp Ala Lys Ala Ile
        370                 375                 380

Arg Gly Ser Ala Ser Gln Gly Pro Leu Thr Glu Ser Trp Lys Asp Gly
385                 390                 395                 400

Asn Pro Leu Lys Lys Pro Pro Ala Val Ala Pro Ser Ser Gly Glu
                405                 410                 415

Glu Gly Glu Leu His Tyr Ala Thr Leu Ser Phe His Lys Val Lys Pro
            420                 425                 430

Gln Asp Pro Gln Gly Gln Glu Ala Thr Asp Ser Glu Tyr Ser Glu Ile
        435                 440                 445

Lys Ile His Lys Arg Glu Thr Ala Glu Thr Gln Ala Cys Leu Arg Asn
450                 455                 460

His Asn Pro Ser Ser Lys Glu Val Arg Gly
465                 470

<210> SEQ ID NO 74
<211> LENGTH: 573
<212> TYPE: PRT
<213> ORGANISM: Artificial Sequence
<220> FEATURE:
<223> OTHER INFORMATION: Synthetic Construct

<400> SEQUENCE: 74

Gly Tyr Leu Leu Gln Val Gln Glu Leu Val Thr Val Gln Glu Gly Leu
1               5                   10                  15

Cys Val His Val Pro Cys Ser Phe Ser Tyr Pro Gln Asp Gly Trp Thr
                20                  25                  30

Asp Ser Asp Pro Val His Gly Tyr Trp Phe Arg Ala Gly Asp Arg Pro
            35                  40                  45

Tyr Gln Asp Ala Pro Val Ala Thr Asn Asn Pro Asp Arg Glu Val Gln
        50                  55                  60

Ala Glu Thr Gln Gly Arg Phe Gln Leu Leu Gly Asp Ile Trp Ser Asn
65                  70                  75                  80

Asp Cys Ser Leu Ser Ile Arg Asp Ala Arg Lys Arg Asp Lys Gly Ser
                85                  90                  95

Tyr Phe Phe Arg Leu Glu Arg Gly Ser Met Lys Trp Ser Tyr Lys Ser
```

-continued

```
                100                 105                 110
Gln Leu Asn Tyr Lys Thr Lys Gln Leu Ser Val Phe Val Thr Ala Leu
            115                 120                 125

Thr His Arg Pro Asp Ile Leu Ile Leu Gly Thr Leu Glu Ser Gly His
130                 135                 140

Ser Arg Asn Leu Thr Cys Ser Val Pro Trp Ala Cys Lys Gln Gly Thr
145                 150                 155                 160

Pro Pro Met Ile Ser Trp Ile Gly Ala Ser Val Ser Ser Pro Gly Pro
                165                 170                 175

Thr Thr Ala Arg Ser Ser Val Leu Thr Leu Thr Pro Lys Pro Gln Asp
            180                 185                 190

His Gly Thr Ser Leu Thr Cys Gln Val Thr Leu Pro Gly Thr Gly Val
        195                 200                 205

Thr Thr Thr Ser Thr Val Arg Leu Asp Val Ser Tyr Pro Pro Trp Asn
210                 215                 220

Leu Thr Met Thr Val Phe Gln Gly Asp Ala Thr Ala Ser Thr Ala Leu
225                 230                 235                 240

Gly Asn Gly Ser Ser Leu Ser Val Leu Glu Gly Gln Ser Leu Arg Leu
                245                 250                 255

Val Cys Ala Val Asn Ser Asn Pro Pro Ala Arg Leu Ser Trp Thr Arg
            260                 265                 270

Gly Ser Leu Thr Leu Cys Pro Ser Arg Ser Ser Asn Pro Gly Leu Leu
        275                 280                 285

Glu Leu Pro Arg Val His Val Arg Asp Glu Gly Glu Phe Thr Cys Arg
290                 295                 300

Ala Gln Asn Ala Gln Gly Ser Gln His Ile Ser Leu Ser Leu Ser Leu
305                 310                 315                 320

Gln Asn Glu Gly Thr Gly Thr Ser Arg Pro Val Ser Gln Val Thr Leu
                325                 330                 335

Ala Ala Val Gly Gly Ile Glu Gly Arg Ser Asp Lys Thr His Thr Cys
            340                 345                 350

Pro Pro Cys Pro Ala Pro Glu Leu Leu Gly Gly Pro Ser Val Phe Leu
        355                 360                 365

Phe Pro Pro Lys Pro Lys Asp Thr Leu Met Ile Ser Arg Thr Pro Glu
370                 375                 380

Val Thr Cys Val Val Val Asp Val Ser His Glu Asp Pro Glu Val Lys
385                 390                 395                 400

Phe Asn Trp Tyr Val Asp Gly Val Glu Val His Asn Ala Lys Thr Lys
                405                 410                 415

Pro Arg Glu Glu Gln Tyr Asn Ser Thr Tyr Arg Val Val Ser Val Leu
            420                 425                 430

Thr Val Leu His Gln Asp Trp Leu Asn Gly Lys Glu Tyr Lys Cys Lys
        435                 440                 445

Val Ser Asn Lys Ala Leu Pro Ala Pro Ile Glu Lys Thr Ile Ser Lys
450                 455                 460

Ala Lys Gly Gln Pro Arg Glu Pro Gln Val Tyr Thr Leu Pro Pro Ser
465                 470                 475                 480

Arg Glu Glu Met Thr Lys Asn Gln Val Ser Leu Thr Cys Leu Val Lys
                485                 490                 495

Gly Phe Tyr Pro Ser Asp Ile Ala Val Glu Trp Glu Ser Asn Gly Gln
            500                 505                 510

Pro Glu Asn Asn Tyr Lys Thr Thr Pro Pro Val Leu Asp Ser Asp Gly
        515                 520                 525
```

Ser Phe Phe Leu Tyr Ser Lys Leu Thr Val Asp Lys Ser Arg Trp Gln
            530                 535                 540

Gln Gly Asn Val Phe Ser Cys Ser Val Met His Glu Ala Leu His Asn
545                 550                 555                 560

His Tyr Thr Gln Lys Ser Leu Ser Leu Ser Pro Gly Lys
                565                 570

<210> SEQ ID NO 75
<211> LENGTH: 449
<212> TYPE: PRT
<213> ORGANISM: Artificial Sequence
<220> FEATURE:
<223> OTHER INFORMATION: Synthetic Construct

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
        35                  40                  45

Gly Val Ile Trp Ala Gly Gly Ser Thr Asn Tyr Asn Ser Ala Leu Met
    50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Glu Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

```
Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 76
<211> LENGTH: 213
<212> TYPE: PRT
<213> ORGANISM: Artificial Sequence
<220> FEATURE:
<223> OTHER INFORMATION: Synthetic Construct

<400> SEQUENCE: 76

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Leu Ile Tyr
        35                  40                  45

Ser Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

-continued

```
<210> SEQ ID NO 77
<211> LENGTH: 213
<212> TYPE: PRT
<213> ORGANISM: Artificial Sequence
<220> FEATURE:
<223> OTHER INFORMATION: Synthetic Construct

<400> SEQUENCE: 77

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Leu Ile Tyr
        35                  40                  45

Ser Thr Ser Asn Leu Ala Ser Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 78
<211> LENGTH: 329
<212> TYPE: PRT
<213> ORGANISM: Homo sapiens

<400> SEQUENCE: 78

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
```

```
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
290                 295                 300
Val Phe Ser Cys Ser Val Met His Glu Ala Leu His Asn His Tyr Thr
305                 310                 315                 320
Gln Lys Ser Leu Ser Leu Ser Pro Gly
                325

<210> SEQ ID NO 79
<211> LENGTH: 326
<212> TYPE: PRT
<213> ORGANISM: Homo sapiens

<400> SEQUENCE: 79

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Pro Cys Pro Ala Pro
            100                 105                 110
Glu Phe Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
    130                 135                 140
```

```
Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
            165                 170                 175

Asn Ser Thr Tyr Arg Val Val Ser Val Leu Thr Val Leu His Gln Asp
        180                 185                 190

Trp Leu Asn Gly Lys Glu Tyr Lys Cys Lys Val Ser Asn Lys Gly Leu
    195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly
            325

<210> SEQ ID NO 80
<211> LENGTH: 107
<212> TYPE: PRT
<213> ORGANISM: Homo sapiens

<400> SEQUENCE: 80

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
            85                  90                  95

Pro Val Thr Lys Ser Phe Asn Arg Gly Glu Cys
        100                 105

<210> SEQ ID NO 81
<211> LENGTH: 444
<212> TYPE: PRT
<213> ORGANISM: Mus musculus

<400> SEQUENCE: 81

Gln Val Gln Leu Lys Arg Ala Ser Gly Pro Gly Leu Val Ala Pro Ser
1               5                   10                  15

Gln Ser Leu Ser Ile Thr Cys Thr Val Ser Gly Phe Ser Leu Thr Ile
            20                  25                  30
```

```
Tyr Gly Ala His Trp Val Arg Gln Pro Pro Gly Lys Gly Leu Glu Trp
             35                  40                  45

Leu Gly Val Ile Trp Ala Gly Gly Ser Thr Asn Tyr Asn Ser Ala Leu
 50                      55                  60

Met Ser Arg Leu Ser Ile Ser Lys Asp Asn Ser Lys Ser Gln Val Phe
 65                  70                  75                  80

Leu Lys Ile Asn Ser Leu Gln Thr Asp Asp Thr Ala Leu Tyr Tyr Cys
                 85                  90                  95

Ala Arg Asp Gly Ser Ser Pro Tyr Tyr Tyr Ser Met Glu Tyr Trp Gly
                100                 105                 110

Gln Gly Thr Ser Val Thr Val Ser Ser Ala Lys Thr Thr Pro Pro Ser
            115                 120                 125

Val Tyr Pro Leu Ala Pro Gly Ser Ala Ala Gln Thr Asn Ser Met Val
        130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Glu Ser Asp Leu Tyr Thr Leu Ser Ser Ser Val Thr Val Pro
                180                 185                 190

Ser Ser Pro Arg Pro Ser Glu Thr Val Thr Cys Asn Val Ala His Pro
            195                 200                 205

Ala Ser Ser Thr Lys Val Asp Lys Lys Ile Val Pro Arg Asp Cys Gly
        210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
                260                 265                 270

Phe Ser Trp Phe Val Asp Asp Val Glu Val His Thr Ala Gln Thr Gln
            275                 280                 285

Pro Arg Glu Glu Gln Phe Asn Ser Thr Phe Arg Ser Val Ser Glu Leu
        290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365

Asp Phe Phe Pro Glu Asp Ile Thr Val Glu Trp Gln Trp Asn Gly Gln
370                 375                 380

Pro Ala Glu Asn Tyr Lys Asn Thr Gln Pro Ile Met Asn Thr Asn Gly
385                 390                 395                 400

Ser Tyr Phe Val Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
                420                 425                 430

His His Thr Glu Lys Ser Leu Ser His Ser Pro Gly
            435                 440
```

-continued

```
<210> SEQ ID NO 82
<211> LENGTH: 212
<212> TYPE: PRT
<213> ORGANISM: Mus musculus

<400> SEQUENCE: 82
```

Glu Ile Ile Leu Thr Gln Ser Pro Ala Ile Met Ser Ala Ser Pro Gly
1               5                   10                  15

Glu Lys Val Ser Ile Thr Cys Ser Ala Thr Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Phe Thr
                85                  90                  95

Phe Gly Ser Gly Thr Lys Leu Glu Ile Lys Ala Asp Ala Ala Pro Thr
            100                 105                 110

Val Ser Ile Phe Pro Pro Ser Ser Glu Gln Leu Thr Ser Gly Gly Ala
        115                 120                 125

Ser Val Val Cys Phe Leu Asn Asn Phe Tyr Pro Lys Asp Ile Asn Val
    130                 135                 140

Lys Trp Lys Ile Asp Gly Ser Glu Arg Gln Asn Gly Val Leu Asn Ser
145                 150                 155                 160

Trp Thr Asp Gln Asp Ser Lys Asp Ser Thr Tyr Ser Met Ser Ser Thr
                165                 170                 175

Leu Thr Leu Thr Lys Asp Glu Tyr Glu Arg His Asn Ser Tyr Thr Cys
            180                 185                 190

Glu Ala Thr His Lys Thr Ser Thr Ser Pro Ile Val Lys Ser Phe Asn
        195                 200                 205

Arg Asn Glu Cys
    210

```
<210> SEQ ID NO 83
<211> LENGTH: 212
<212> TYPE: PRT
<213> ORGANISM: Mus musculus

<400> SEQUENCE: 83
```

Gln Ile Ile Leu Thr Gln Ser Pro Ala Ile Met Ser Ala Ser Pro Gly
1               5                   10                  15

Glu Lys Val Ser Ile Thr Cys Ser Ala Thr Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Phe Thr
                85                  90                  95

Phe Gly Ser Gly Thr Lys Leu Glu Ile Lys Ala Asp Ala Ala Pro Thr
            100                 105                 110

Val Ser Ile Phe Pro Pro Ser Ser Glu Gln Leu Thr Ser Gly Gly Ala

```
                115                 120                 125
Ser Val Val Cys Phe Leu Asn Asn Phe Tyr Pro Lys Asp Ile Asn Val
    130                 135                 140

Lys Trp Lys Ile Asp Gly Ser Glu Arg Gln Asn Gly Val Leu Asn Ser
145                 150                 155                 160

Trp Thr Asp Gln Asp Ser Lys Asp Ser Thr Tyr Ser Met Ser Ser Thr
                165                 170                 175

Leu Thr Leu Thr Lys Asp Glu Tyr Glu Arg His Asn Ser Tyr Thr Cys
            180                 185                 190

Glu Ala Thr His Lys Thr Ser Thr Ser Pro Ile Val Lys Ser Phe Asn
            195                 200                 205

Arg Asn Glu Cys
210

<210> SEQ ID NO 84
<211> LENGTH: 450
<212> TYPE: PRT
<213> ORGANISM: Artificial Sequence
<220> FEATURE:
<223> OTHER INFORMATION: Synthetic Construct

<400> SEQUENCE: 84

Gln Val Gln Leu Lys Arg Ala Ser Gly Pro Gly Leu Val Ala Pro Ser
1               5                   10                  15

Gln Ser Leu Ser Ile Thr Cys Thr Val Ser Gly Phe Ser Leu Thr Ile
                20                  25                  30

Tyr Gly Ala His Trp Val Arg Gln Pro Pro Gly Lys Gly Leu Glu Trp
            35                  40                  45

Leu Gly Val Ile Trp Ala Gly Gly Ser Thr Asn Tyr Asn Ser Ala Leu
        50                  55                  60

Met Ser Arg Leu Ser Ile Ser Lys Asp Asn Ser Lys Ser Gln Val Phe
65                  70                  75                  80

Leu Lys Ile Asn Ser Leu Gln Thr Asp Asp Thr Ala Leu Tyr Tyr Cys
                85                  90                  95

Ala Arg Asp Gly Ser Ser Pro Tyr Tyr Tyr Ser Met Glu Tyr Trp Gly
            100                 105                 110

Gln Gly Thr Ser Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
```

```
                   260                 265                 270
Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 85
<211> LENGTH: 213
<212> TYPE: PRT
<213> ORGANISM: Artificial Sequence
<220> FEATURE:
<223> OTHER INFORMATION: Synthetic Construct

<400> SEQUENCE: 85

Glu Ile Ile Leu Thr Gln Ser Pro Ala Ile Met Ser Ala Ser Pro Gly
1               5                   10                  15

Glu Lys Val Ser Ile Thr Cys Ser Ala Thr Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Phe Thr
                85                  90                  95

Phe Gly Ser Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
```

```
            165                 170                 175
Thr Leu Thr Leu Ser Lys Ala Asp Tyr Glu Lys His Lys Val Tyr Ala
        180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 86
<211> LENGTH: 213
<212> TYPE: PRT
<213> ORGANISM: Artificial Sequence
<220> FEATURE:
<223> OTHER INFORMATION: Synthetic Construct

<400> SEQUENCE: 86

Gln Ile Ile Leu Thr Gln Ser Pro Ala Ile Met Ser Ala Ser Pro Gly
1               5                   10                  15

Glu Lys Val Ser Ile Thr Cys Ser Ala Thr Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Phe Thr
                85                  90                  95

Phe Gly Ser Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 87
<211> LENGTH: 446
<212> TYPE: PRT
<213> ORGANISM: Artificial Sequence
<220> FEATURE:
<223> OTHER INFORMATION: Synthetic Construct

<400> SEQUENCE: 87

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30
```

Gly Ala His Trp Val Arg Gln Ala Pro Gly Lys Gly Leu Glu Trp Val
            35                  40                  45

Gly Val Ile Trp Ala Gly Gly Ser Thr Asn Tyr Asn Ser Ala Leu Met
 50                  55                  60

Ser Arg Phe Thr Ile Ser Lys Asp Asn Ser Lys Asn Thr Val Tyr Leu
65                   70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Glu Tyr Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
            210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
            435                 440                 445

```
<210> SEQ ID NO 88
<211> LENGTH: 5
<212> TYPE: PRT
<213> ORGANISM: Mus musculus

<400> SEQUENCE: 88

Ser Tyr Ala Met Ser
1               5

<210> SEQ ID NO 89
<211> LENGTH: 5
<212> TYPE: PRT
<213> ORGANISM: Mus musculus

<400> SEQUENCE: 89

Asp Tyr Tyr Met Tyr
1               5

<210> SEQ ID NO 90
<211> LENGTH: 5
<212> TYPE: PRT
<213> ORGANISM: Mus musculus

<400> SEQUENCE: 90

Ser Ser Trp Met Asn
1               5

<210> SEQ ID NO 91
<211> LENGTH: 17
<212> TYPE: PRT
<213> ORGANISM: Mus musculus

<400> SEQUENCE: 91

Ile Ile Ser Ser Gly Gly Ser Tyr Thr Tyr Tyr Ser Asp Ser Val Lys
1               5                   10                  15

Gly

<210> SEQ ID NO 92
<211> LENGTH: 17
<212> TYPE: PRT
<213> ORGANISM: Mus musculus

<400> SEQUENCE: 92

Arg Ile Ala Pro Glu Asp Gly Asp Thr Glu Tyr Ala Pro Lys Phe Gln
1               5                   10                  15

Gly

<210> SEQ ID NO 93
<211> LENGTH: 17
<212> TYPE: PRT
<213> ORGANISM: Mus musculus

<400> SEQUENCE: 93

Gln Ile Tyr Pro Gly Asp Asp Tyr Thr Asn Tyr Asn Gly Lys Phe Lys
1               5                   10                  15

Gly

<210> SEQ ID NO 94
<211> LENGTH: 11
<212> TYPE: PRT
<213> ORGANISM: Mus musculus

<400> SEQUENCE: 94
```

His Glu Thr Ala Gln Ala Ala Trp Phe Ala Tyr
1               5                   10

<210> SEQ ID NO 95
<211> LENGTH: 12
<212> TYPE: PRT
<213> ORGANISM: Mus musculus

<400> SEQUENCE: 95

Glu Gly Asn Tyr Tyr Gly Ser Ser Ile Leu Asp Tyr
1               5                   10

<210> SEQ ID NO 96
<211> LENGTH: 9
<212> TYPE: PRT
<213> ORGANISM: Mus musculus

<400> SEQUENCE: 96

Leu Gly Pro Tyr Gly Pro Phe Ala Asp
1               5

<210> SEQ ID NO 97
<211> LENGTH: 10
<212> TYPE: PRT
<213> ORGANISM: Mus musculus

<400> SEQUENCE: 97

Ser Ala Ser Ser Ser Val Ser Tyr Met His
1               5                   10

<210> SEQ ID NO 98
<211> LENGTH: 11
<212> TYPE: PRT
<213> ORGANISM: Mus musculus

<400> SEQUENCE: 98

Arg Ala Ser Gln Asp Ile Thr Asn Tyr Leu Asn
1               5                   10

<210> SEQ ID NO 99
<211> LENGTH: 10
<212> TYPE: PRT
<213> ORGANISM: Mus musculus

<400> SEQUENCE: 99

Ser Ala Ser Ser Ser Val Ser Tyr Met Tyr
1               5                   10

<210> SEQ ID NO 100
<211> LENGTH: 7
<212> TYPE: PRT
<213> ORGANISM: Mus musculus

<400> SEQUENCE: 100

Asp Thr Ser Lys Leu Ala Tyr
1               5

<210> SEQ ID NO 101
<211> LENGTH: 7
<212> TYPE: PRT
<213> ORGANISM: Mus musculus

<400> SEQUENCE: 101

Phe Thr Ser Arg Leu His Ser
1               5

```
<210> SEQ ID NO 102
<211> LENGTH: 7
<212> TYPE: PRT
<213> ORGANISM: Mus musculus

<400> SEQUENCE: 102

Asp Thr Ser Ser Leu Ala Ser
1               5

<210> SEQ ID NO 103
<211> LENGTH: 9
<212> TYPE: PRT
<213> ORGANISM: Mus musculus

<400> SEQUENCE: 103

Gln Gln Trp Ser Ser Asn Pro Pro Thr
1               5

<210> SEQ ID NO 104
<211> LENGTH: 9
<212> TYPE: PRT
<213> ORGANISM: Mus musculus

<400> SEQUENCE: 104

Gln Gln Gly Asn Thr Leu Pro Trp Thr
1               5

<210> SEQ ID NO 105
<211> LENGTH: 9
<212> TYPE: PRT
<213> ORGANISM: Mus musculus

<400> SEQUENCE: 105

Gln Gln Trp Asn Ser Asp Pro Tyr Thr
1               5

<210> SEQ ID NO 106
<211> LENGTH: 120
<212> TYPE: PRT
<213> ORGANISM: Mus musculus

<400> SEQUENCE: 106

Glu Val Gln Val Val Glu Ser Gly Gly Asp Leu Val Lys Ser Gly Gly
1               5                   10                  15

Ser Leu Lys Leu Ser Cys Ala Ala Ser Gly Phe Pro Phe Ser Ser Tyr
            20                  25                  30

Ala Met Ser Trp Val Arg Gln Thr Pro Asp Lys Arg Leu Glu Trp Val
        35                  40                  45

Ala Ile Ile Ser Ser Gly Gly Ser Tyr Thr Tyr Tyr Ser Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Glu Thr Ala Gln Ala Ala Trp Phe Ala Tyr Trp Gly Gln
            100                 105                 110

Gly Thr Leu Val Thr Val Ser Ala
        115                 120

<210> SEQ ID NO 107
```

```
<211> LENGTH: 121
<212> TYPE: PRT
<213> ORGANISM: Mus musculus

<400> SEQUENCE: 107

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Tyr
            20                  25                  30

Tyr Met Tyr Trp Val Lys Gln Arg Pro Glu Gln Gly Leu Glu Trp Ile
        35                  40                  45

Gly Arg Ile Ala Pro Glu Asp Gly Asp Thr Glu Tyr Ala Pro Lys Phe
    50                  55                  60

Gln Gly Lys Ala Thr Val Thr Ala Asp Thr Ser Ser Asn Thr Ala Tyr
65                  70                  75                  80

Leu His Leu Ser Ser Leu Thr Ser Glu Asp Thr Ala Val Tyr Tyr Cys
                85                  90                  95

Thr Thr Glu Gly Asn Tyr Tyr Gly Ser Ser Ile Leu Asp Tyr Trp Gly
            100                 105                 110

Gln Gly Thr Thr Leu Thr Val Ser Ser
        115                 120

<210> SEQ ID NO 108
<211> LENGTH: 118
<212> TYPE: PRT
<213> ORGANISM: Mus musculus

<400> SEQUENCE: 108

Gln Val Gln Leu Gln Gln Ser Gly Ala Glu Leu Val Lys Pro Gly Ala
1               5                   10                  15

Ser Val Lys Ile Ser Cys Lys Ala Ser Gly Tyr Ala Phe Arg Ser Ser
            20                  25                  30

Trp Met Asn Trp Val Lys Gln Arg Pro Gly Lys Gly Leu Glu Trp Ile
        35                  40                  45

Gly Gln Ile Tyr Pro Gly Asp Asp Tyr Thr Asn Tyr Asn Gly Lys Phe
    50                  55                  60

Lys Gly Lys Val Thr Leu Thr Ala Asp Arg Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Leu Gly Pro Tyr Gly Pro Phe Ala Asp Trp Gly Gln Gly Thr
            100                 105                 110

Leu Val Thr Val Ser Ala
        115

<210> SEQ ID NO 109
<211> LENGTH: 106
<212> TYPE: PRT
<213> ORGANISM: Mus musculus

<400> SEQUENCE: 109

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45
```

```
Asp Thr Ser Lys Leu Ala Tyr Gly Val Pro Ala Arg Phe Ser Gly Ser
    50              55                  60

Gly Ser Gly Thr Ser Tyr Ser Leu Thr Ile Ser Ser Met Glu Ala Glu
65              70                  75                  80

Asp Ala Ala Thr Tyr Tyr Cys Gln Gln Trp Ser Ser Asn Pro Pro Thr
                85                  90                  95

Phe Gly Gly Gly Thr Lys Leu Glu Ile Lys
            100             105

<210> SEQ ID NO 110
<211> LENGTH: 107
<212> TYPE: PRT
<213> ORGANISM: Mus musculus

<400> SEQUENCE: 110

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Thr Asn Tyr
            20                  25                  30

Leu Asn Trp Tyr Gln Gln Lys Pro Asp Gly Thr Val Lys Leu Leu Ile
        35                  40                  45

Tyr Phe Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65              70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100             105

<210> SEQ ID NO 111
<211> LENGTH: 106
<212> TYPE: PRT
<213> ORGANISM: Mus musculus

<400> SEQUENCE: 111

Gln Ile Val Leu Thr Gln Ser Pro Ala Ile Val Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Arg Pro Gly Ser Ser Pro Arg Leu Leu Ile Tyr
        35                  40                  45

Asp Thr Ser Ser Leu Ala Ser Gly Val Pro Val Arg Phe Ser Gly Ser
    50                  55                  60

Gly Ser Gly Thr Ser Tyr Ser Leu Thr Ile Ser Arg Ile Glu Ser Glu
65              70                  75                  80

Asp Ala Ala Asn Tyr Tyr Cys Gln Gln Trp Asn Ser Asp Pro Tyr Thr
                85                  90                  95

Phe Gly Gly Gly Thr Lys Leu Glu Ile Lys
            100             105
```